(12) United States Patent
Munger et al.

(10) Patent No.: US 9,029,413 B2
(45) Date of Patent: *May 12, 2015

(54) TREATMENT OF VIRAL INFECTIONS BY MODULATION OF HOST CELL METABOLIC PATHWAYS

(75) Inventors: Josh Munger, Rochester, NY (US); Bryson Bennett, Metuchen, NJ (US); Thomas Shenk, Princeton, NJ (US); Joshua Rabinowitz, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/438,616

(22) Filed: Apr. 3, 2012

(65) Prior Publication Data

US 2013/0065850 A1 Mar. 14, 2013

Related U.S. Application Data

(63) Continuation of application No. 12/156,517, filed on Jun. 2, 2008, now Pat. No. 8,158,677.

(60) Provisional application No. 60/932,769, filed on Jun. 1, 2007, provisional application No. 61/033,243, filed on Mar. 3, 2008.

(51) Int. Cl.
| | |
|---|---|
| *A61K 31/38* | (2006.01) |
| *A61K 31/34* | (2006.01) |
| *A61K 31/335* | (2006.01) |
| *A61K 31/405* | (2006.01) |
| *A61K 31/225* | (2006.01) |
| *A61K 31/435* | (2006.01) |
| *A61K 31/522* | (2006.01) |
| *A61K 31/70* | (2006.01) |
| *A61K 31/24* | (2006.01) |
| *A61K 31/35* | (2006.01) |
| *A61K 31/365* | (2006.01) |
| *A61K 31/381* | (2006.01) |
| *A61K 31/336* | (2006.01) |
| *A61K 31/341* | (2006.01) |
| *A61K 31/351* | (2006.01) |
| *A61K 31/675* | (2006.01) |
| *A61K 31/706* | (2006.01) |
| *A61K 31/44* | (2006.01) |
| *A61K 31/22* | (2006.01) |
| *A61K 31/221* | (2006.01) |
| *A61K 31/52* | (2006.01) |

(52) U.S. Cl.
CPC .......... *A61K 31/365* (2013.01); *A61K 31/351* (2013.01); *A61K 31/675* (2013.01); *A61K 31/706* (2013.01); *A61K 31/44* (2013.01); *A61K 31/22* (2013.01); *A61K 31/221* (2013.01); *A61K 31/522* (2013.01); *A61K 31/52* (2013.01); *A61K 31/405* (2013.01); *A61K 31/381* (2013.01); *A61K 31/336* (2013.01); *A61K 31/341* (2013.01)

(58) Field of Classification Search
USPC ............ 514/461, 445, 438, 471, 451, 460, 47
See application file for complete search history.

(56) References Cited

U.S. PATENT DOCUMENTS

| | | |
|---|---|---|
| 3,983,140 A | 9/1976 | Endo et al. |
| 4,231,938 A | 11/1980 | Monaghan et al. |
| 4,334,913 A | 6/1982 | Koerwer |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,598,089 A | 7/1986 | Hadvary et al. |
| 4,602,099 A | 7/1986 | Parker |
| 4,613,610 A | 9/1986 | Wareing |
| 4,647,576 A | 3/1987 | Hoefle et al. |
| 4,681,893 A | 7/1987 | Roth |

(Continued)

FOREIGN PATENT DOCUMENTS

| | | |
|---|---|---|
| EP | 0374886 | 6/1990 |
| FR | 2425432 | 12/1979 |

(Continued)

OTHER PUBLICATIONS

Shen et al., "A Mechanism for the Potent Inhibition of Eukaryotic Acetyl-Coenzyme A Carboxylase by Soraphen A, a Macrocyclic Polyketide Natural Product", Molecular Cell, 16(22):881-891.

(Continued)

*Primary Examiner* — Shengjun Wang
(74) *Attorney, Agent, or Firm* — Kenyon & Kenyon LLP

(57) ABSTRACT

Alterations of certain metabolite concentrations and fluxes that occur in response to viral infection are described. Host cell enzymes in the involved metabolic pathways are selected as targets for intervention; i.e., to restore metabolic flux to disadvantage viral replication, or to further derange metabolic flux resulting in "suicide" of viral-infected cells (but not uninfected cells) to limit viral propagation. While any of the enzymes in the relevant metabolic pathway can be selected, pivotal enzymes at key control points in these metabolic pathways are preferred as candidate antiviral drug targets. Inhibitors of these enzymes are used to reverse, or redirect, the effects of the viral infection. Drug candidates are tested for antiviral activity using screening assays in vitro and host cells, and in animal models. Animal models are then used to test efficacy of candidate compounds in preventing and treating viral infections. Antiviral activity of enzyme inhibitors is demonstrated.

31 Claims, 26 Drawing Sheets

(56) References Cited

U.S. PATENT DOCUMENTS

Figure 1A:
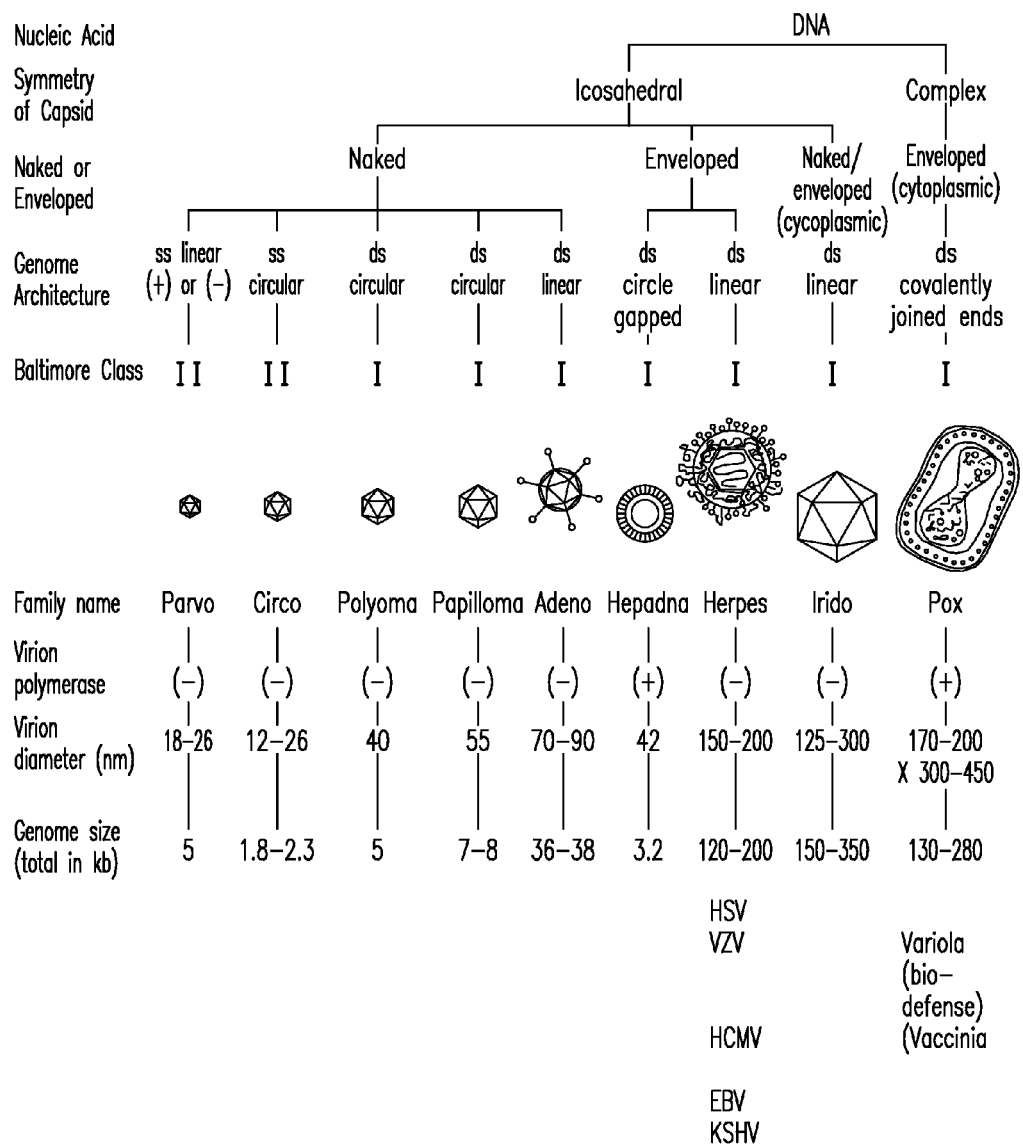

| | | | |
|---|---|---|---|
| 4,686,237 | A | 8/1987 | Anderson |
| 5,006,530 | A | 4/1991 | Angerbauer et al. |
| 5,011,930 | A | 4/1991 | Fujikawa et al. |
| 5,026,878 | A | 6/1991 | Bohlendorf et al. |
| 5,177,080 | A | 1/1993 | Angerbauer et al. |
| 5,188,830 | A | 2/1993 | Atkinson et al. |
| 5,190,969 | A | 3/1993 | Blumenstein |
| 5,260,440 | A | 11/1993 | Hirai et al. |
| 5,273,995 | A | 12/1993 | Roth |
| 5,354,772 | A | 10/1994 | Kathawala |
| 5,385,929 | A | 1/1995 | Bjorge et al. |
| 5,447,954 | A | 9/1995 | Gribble et al. |
| 5,491,123 | A | 2/1996 | Hagen et al. |
| 5,506,219 | A | 4/1996 | Robl |
| 5,614,551 | A | 3/1997 | Dick |
| 5,686,104 | A | 11/1997 | Mills et al. |
| 5,691,322 | A | 11/1997 | Robl |
| 5,753,675 | A | 5/1998 | Wattanasin |
| 6,103,664 | A | 8/2000 | Sievernich et al. |
| 6,153,589 | A | 11/2000 | Blumenstein et al. |
| 6,383,987 | B1 | 5/2002 | von der Heyde et al. |
| 6,506,559 | B1 | 1/2003 | Fire et al. |
| 6,576,636 | B2 | 6/2003 | Webb et al. |
| 6,875,781 | B2 | 4/2005 | Hong et al. |
| 7,078,543 | B2 | 7/2006 | Cernerud et al. |
| 7,211,423 | B2 | 5/2007 | Cheng et al. |
| 8,158,677 | B2 * | 4/2012 | Munger et al. ............ 514/473 |
| 2002/0086356 | A1 | 7/2002 | Tuschl et al. |
| 2002/0114784 | A1 | 8/2002 | Li et al. |
| 2003/0153570 | A1 | 8/2003 | Bhatt et al. |
| 2003/0158156 | A1 | 8/2003 | Syverson et al. |
| 2005/0009140 | A1 | 1/2005 | Mukerji et al. |
| 2005/0089981 | A1 | 4/2005 | Napier et al. |
| 2005/0119251 | A1 | 6/2005 | Fu et al. |
| 2005/0239877 | A1 | 10/2005 | Gomez et al. |
| 2006/0241177 | A1 | 10/2006 | Kuhadja et al. |
| 2008/0026363 | A1 | 1/2008 | Cheng et al. |
| 2008/0161256 | A1 | 7/2008 | Morrisey et al. |

FOREIGN PATENT DOCUMENTS

| | | |
|---|---|---|
| FR | 2457864 | 12/1980 |
| GB | 2205837 | 12/1988 |
| WO | 86/03488 | 6/1986 |
| WO | 86/07054 | 12/1986 |
| WO | 97/18806 | 5/1997 |
| WO | 02/16369 | 2/2002 |
| WO | 02/44321 | 6/2002 |
| WO | 03/006477 | 1/2003 |
| WO | WO 03/011867 | 2/2003 |
| WO | 03/072197 | 9/2003 |
| WO | 03/072557 | 9/2003 |
| WO | 2004/041189 | 5/2004 |
| WO | 2004/078754 | 9/2004 |
| WO | 2004/096797 | 11/2004 |
| WO | 2005/011655 | 2/2005 |
| WO | 2005/018534 | 3/2005 |
| WO | 2005/021519 | 3/2005 |
| WO | 2005/042708 | 5/2005 |
| WO | 2005/051296 | 6/2005 |
| WO | 2005/068444 | 7/2005 |
| WO | 2007/099236 | 9/2007 |
| WO | 2008/014219 | 1/2008 |

OTHER PUBLICATIONS

Office Action for U.S. Appl. No. 12/156,517, mailed Aug. 4, 2010, and response filed on Feb. 4, 2011.

Office Action for U.S. Appl. No. 12/156,517, mailed Apr. 13, 2011, and response filed on Oct. 11, 2011.

Stephenson "New HIV Prevention strategies urged," JAMA, 2004, vol. 202, No. 1 0, pp. 1163-1164.

Nyholm et al. "Prevention of Maternal cytomegalovirus infection current status and future prospects, International J. Women's health," 2010, pp. 23-35.

Parker et al. "5-(tetradecyloxy)-2-furancarboxylic acid and related hypolipidemic fatty acid-like alkoxyarylcarboxylic acids," J. Med. Chem. 1977, vol. 20, No. 6, pp. 781-791.

Munger, et al., "Systems-level metabolic flux profiling identifies fatty acid synthesis as a target for antiviral therapy". Nature Biotechnology (2008) vol. 26: pp. 1179-1186.

Ikuta, et al., "Inhibition of Cleavage of Moloney Murine Leukemia Virus gag and env Coded Precursor Polyproteins by Cerulenin". Virology (1986) vol. 154: pp. 195-206.

Krieger, N. et al., Enhancement of Hepatitis C Virus RNA Replication by Cell Culture-Adaptive Mutations, Journal of Virology (2001),vol. 75:10, pp. 4614-4624.

Search Report dated Jul. 14, 2010 from related European Application No. 08827478.2.

Official Communication dated Jul. 27, 2010 from related European Application No. 08827478.2.

Freiberg et al., "Discovering the Mechanism of Action of Novel Antibacterial Agents Through Transcriptional Profiling of Conditional Mutants, 2005", Antimicrob. Agents Chemother., 49(2): 749-759.

Pohlmann et al., "Pyrrolidinedione Derivatives as Antibacterial Agents with a Novel Mode of Action", 2005, Bioorg. Med. Chem. Lett. 15:1189-1192.

Clark et al., "Phenoxy Thiazole Derivatives as Potent and Selective Acetyl-CoA Carboxylase 2 Inhibitors: Modulation of Isozyme Selectivity by Incorporation of Phenyl Ring Substituents," 2007, Bioorg. Med. Chem. Lett. 17:1961-1965.

Gu et al., "Synthesis and Structure-Activity Relationships of N-{3-[2-(4-Alkoxyphenoxy) Thiazol-5-y]-1-Methylprop-2-ynyl} Carboxy Derviatives as Selective Acetyl-CoA Carboxylase 2 Inhibitors," 2006, J. Med. Chem. 49:3770-3773.

Camps et al., "Blockade of PI3K (Suppresses Joint Inflammation and Damage in Mouse Models of Rheumatoid Arthritis," 2005, Nat. Med. 11(9):936-943.

Petiot et al., "Distinct Classes of Phosphatidylinositol 3p-Kinases are Involved in Signaling Pathways That Control Macroautophagy in H-29 Cells," 2000, J. Biol. Chem. 275(2):992-998.

Couzin, "Small RNAs Make Big Splash," 2002, Science 298:2296-2297.

McManus et al., "Gene Silencing in Mammals by Small Interfering RNAs," 2002, Nat. Rev. Genet. 3:737-747.

Hannon, "RNA Interference," 2002, Nature 418:244-251.

Paddison et al., "RNA Interference: The New Somatic Cell Genetics?," 2002, Cancer Cell 2:17-23.

Elbashir et al., "Functional Anatomy of siRNAs for Mediating Efficient RNAi in *Drosophila melanogaster* Embryo Lysate," 2001, The EMBO Journal, 20(23):6877-6888.

Tuschl et al., "Targeted mRNA Degradation by Double-Stranded RNA in Vitro," 1999, Genes Dev. 13:3191-3197.

Hutvagner et al., "A microRNA in a Multiple-turnover RNAi Enzyme Complex," Science 297:2056-2060.

Lee et al., "The *C. elegans* Heterochronic Gene lin-4 Encodes Small RNAs with Antisense Complementairty to lin-14," 1993, Cell 75:843-854.

Reinhart et al., The 21-Nucleotide let-7 RNA Regulates Developmental Timing in *Caenorhaditis elegans*, 2000, Nature 403:901-906.

Lee et al., "An Extensive Class of Small RNAs in *Caenorhabditis elegans*," 2001 Science 294:862-864.

Lau et al., "An Abundant Class of Tiny RNAs with Probable Regulatory Roles in *Caenorhabiditis elegans*," 2001, Science 294:858-862.

Hutvagner et al., "A Cellular Function for the RNA-Interference Enzyme Dicer in the Maturation of the let-7 Small Temporal RNA," 2001, Science 293:834-838.

Zeng et al., "Both Natural and Designed Micro RNAs Can Inhibit the Expression of Cognate mRNAs When Expressed in Human Cells," 2002, Molec. Cell 9:1327-1333.

Wang et al., "Characterization of HSCD5, a Novel Human Stearoyl-CoA Desaturase Unique to Primates," 2005, Biochem. Biophys. Res. Comm. 332:735-742.

Pizer et al., Inhibition of Fatty Acid Synthesis Induces Programmed Cell Death in Human Breast Cancer Cells, 1996, Cancer Res. 56:2745-2747.

(56) References Cited

OTHER PUBLICATIONS

Pizer et al., "Pharmacological Inhibitors of Mammalian Fatty Acid Synthase Suppress DNA Replication and Induce Apoptosis in Tumor Cell Lines," 1998, Cancer Res. 58:4611-4615.
Pizer et al., "Malonyl-Coenzyme-A is a Potential Mediator of Cytotoxicity Induced by Fatty-Acid Synthase Inhibition in Human Breast Cancer Cells and Xenografts," 2000, Cancer Res. 60:213-218.
Rassmann et al., "The Human Fatty Acid Synthase: A New Therapeutic Target for Coxsackievirus B3-Induced Diseases?," 2007, Antiviral Res. 76:150-158.
Gibson et al., "Toxicity and Teratogenicity Studies with the Hypolipidemic Drug RMI 14,514 in Rats," 1981, Fundamental Appl. Toxicol., 1:19-25.
Peschko et al., "First Total Synthesis of the Marine Alkaloids Purpurone and Ningalin C," 2000, Tetrahedron Letters 41:9477-9481.
Saxty et al., "Synthesis and Evaluation of (+) and (−)-2,2-Difluorocitrate as Inhibitors of Rat-Liver ATP-Citrate Lyase and Porcine-Heart Aconitase," 1992, Eur. J. Biochem. 202:889-896.
Dolle et al., "Synthesis of Novel Thiol-Containing Citric Acid Analogues. Kinetic Evaluation of These and Other Potential Active-Site-Directed and Mechanism-Based Inhibitors of APT Citrate Lyase," 1995, J. Med. Chem. 38:537-543.
Usher et al., "A Very Short Hydrogen Bond Provides Only Moderate Stabilization of an Enzyme-Inhibitor Complex of Citrate Synthase," 1994, Biochemistry 33:7753-7759.
Charlier et al., "Inactivation of 3-Hydroxl-3-Methylglutaryl-CoA Synthase and Other Acyl-CoA-Utilizing Enzymes by 3-Oxobutylsulfoxyl-CoA," 1997, Biochemistry 36:1551-1558.
Lawrence et al., "Structure-Activity Studies of Cerulenin Analogues as Protein Palmitoylation Inhibitors," 1999, J. Med. Chem. 42:4932-4941.
Parker et al., "5-(Tetradecyloxy)-2-Furancarboxylic Acid and Related Hypolipidemic Fatty Acid-Like Alkyloxyarylcarboxylic Acids," 1977, J. Med. Chem. 20:(6):781-791.
Liu et al., "Discovery of Potent, Selective, Orally Bioavailabe Stearoyl-CoA Desaturase 1 Inhibitors," 2007, J. Med. Chem. 50:3086-3100.
Freiberg et al., "Identification and Characterization of the First Class of Potent Bacterial Acetyl-CoA Carboxylase Inhibitors with Antibacterial Activity," 2004, J. Biol. Chem. 279(25):26066-26073.
Wightman et al., "Posttranscriptional Regulation of the Heterochronic Gene lin-14 by lin-14 Mediates Temporal Pattern Formation in C. elegans," 1993, Cell 75:855-862.
Grishok et al., "Genes and Mechanisms Related to RNA Interference Regulate Expression of the Small Temporal RNAs that Control C. elegans Development Timing," 2001, Cell 106:23-34.
Ketting et al., "Dicer Functions in RNA Interference and in Synthesis of Small RNA Involved in Development Timing in C. elegans," 2001, Genes Dev. 15:2654-2659.
Williams et al., "Argonaute1 is Required for Efficient RNA Interference in Drosophila Embryos," 2002, proc. Natl. Acad. Sci. USA 99(10):6889-6894.
Hammond et al., "Argonaute2, a Link Between Genetic and Biochemical Analysis of RNAi," 2001, Science 293:1146-1150.
Mourelatos et al., "miRNPs: A Novel Class of Ribonucleoproteins Containing Numerous microRNAs," 2002, Genes Dev. 16:720-728.
Chen et al., "Inhibition of Hepatitis B Virus Replication by Stably Expressed shRNA," 2003, Biochem. Biophys. Res. Commun. 311:398-404.
Yuan et al., "Mammalian Pol III Promoter H1 Can Transcribe shRNA Inducing RNAi in Chicken Cells," 2006, Mol. Bio. Rep. 33:33-41.
Scherer et al., "Rapid Assessment of Anti-HIV siRNA Efficacy Using PCR-Derived Pol III shRNA Cassettes," 2004, Mol. Ther. 10(3):597-603.
Amarzguioui et al., "Approaches for Chemically Synthesized siRNA and Vector-Mediated RNAi," 2005, FEBS Letters 579:5974-5981.

Zecherle et al., "Purines are Required at the $5_7$Ends of Newly Initiated RNAs for Optimal RNA Polymerase III Gene Expression," 1996, Mol. Cell. Biol. 16(10):5801-5810.
Fruscoloni et al., "Mutational Analysis of the Transcription Start Site of the Yeast tRNA$^{LEU}_3$ Gene," 1995, Nucleic Acids Research, 23(15):2914-2918.
Mattaj et al., "Changing the RNA Polymerase Specificity of U snRNA Gene Promoters," 1988, Cell 55:435-442.
McCaffrey et al., "RNA Interference in Adult Mice," 2002, Nature 418:38-39.
Xia et al., "siRNA-Mediated Gene Silencing in Vitro and in Vivo," 2002, Nat. Biotech. 20:1006-1010.
Lewis et al., "Efficient Delivery of siRNA for Inhibition of Gene Expression in Postnatal Mice," 2002, Nat. Genetic 32:107-108.
Rubinson et al., "A Lentivirus-Based Systems to Functionally Silence Genes in Primary Mammalian Cells and Transgenic Mice by RNA Interference," 2003, Nat. Genetic 33(3):401-406 (Abstract).
Tiscornia et al., "A General Method for Gene Knockdown in Mice by Using Lentiviral Vectors Expressing Small Interfering RNA," 2003, Proc. Natl. Acad. Sci. USA 100(4):1844-1848.
Martinez et al., "Synthetic Small Inhibiting RNAs: Efficient Tools to Inactivate Oncogenic Mutations and Restore p53 Pathways," 2002, Proc. Natl. Acad. Sci. USA 99(23): 14849-14854.
Wilda et al., "Killing of Leukemic Cells with a BCR/ABL Fusion Gene by RNA Interference (RNAi)," 2002, Oncogene 21:5716-5724.
Aza-Blanc et al., "Identification of Modulators of Trail-Induced Apoptosis via RNAi-Based Phenotypic Screening," 2003, Mol. Cell 12:627-637.
Munger et al., "Dynamics of the Cellular Metabolome During Human Cytomegalovirus Infection," 2006, PLoS Pathogens 2(12):1165-1175.
Yuan et al., "Kinetic Flux Profiling of Nitrogen Assimilation in *Escherichia coli*," 2006, Nat. Chem. Biol. 2(10):529-530.
Sagan et al., "The Influence of Cholesterol and Lipid Metabolism on Host Cell Structure and Hepatitis C Virus Replication," 2006, Biochem. Cell. Biol. 84:67-79.
Kapadia et al., Hepatitis C Virus RNA Replication is Regulated by Host Geranylgeranylation and Fatty Acids, 2005, PNAS 102(7):2561-2566.
Potenta et al., "Hydroxymethyl-Glutaryl Coenzyme A Reductase Inhibition Limits Cytomegalovirus Infection in Human Endothelial Cells," 2004, Circulation 109:532-536.
Lin et al., "Cholesterol Requirement of Hepatitis B Surface Antigen (HBsAg) Secretion," 2003, Virology 314:253-260.
Hak et al., "16$^{th}$ European Congress of Clinical Microbiology and Infectious Diseases," Nice, France, Abstract, 2006, www.blackwellpublishing.com/eccmid16/abstract.asp?id=49073.
Zhu et al., "Inhibition of Cyclooxygenase 2 Blocks Human Cytomegalovirus Replication," 2002, PNAS 99(6):3932-3937.
Harwood et al., "Isozyme-Nonselective N-Substituted Bipiperidylcarboxamide Acetyl-CoA Carboxylase Inhibitors Reduce Tissue Malonyl-CoA Concentrations, Inhibit Fatty Acid Synthesis, and Increase Fatty Acid Oxidation in Cultured Cells and in Experimental Animals," 2003, J. Biol. Chem. 278(39):37099-37111.
Kapadia et al., "Initiation of Hepatitis C Virus Infection is Dependent on Cholesterol and Cooperativity between CD81 and Scavenger Receptor B Type I," Jan. 2007, Journal of Virology, 81(1): 374-383.
Kariya et al., "Inhibition of Fatty Acid Synthesis by RMI 14,514(5-tetradecyloxy-2-furoic acid)," Feb. 1978, Biochemical and Biophysical Research Communications, 80(4):1022-1024.
Landini, "Early Enhanced Glucose Uptake in Human Cytomegalovirus-Infected Cells," 1984, Journal of General Virology, 65:1229-1232.
Bacon, "Clinical Case: Management of Patients with Chronic Hepatitis C from the book Management of Patients with Viral Hepatitis," Marcellin ed., Nouvelle Imprimerie Laballery, Clamecy, France, Jan. 2007, p. 143-7.

* cited by examiner

Integrated metabolimic and fluxomic analysis of cellular response to viral infection

Goals:
1. Measure the metabolome of primary fibroblasts during human cytomegalovirus (HCMV) infection
2. Determine the major flux changes induced by the virus
3. Compare metabolic changes to transcriptional ones
4. Use the data to identify new ways to treat viral infections

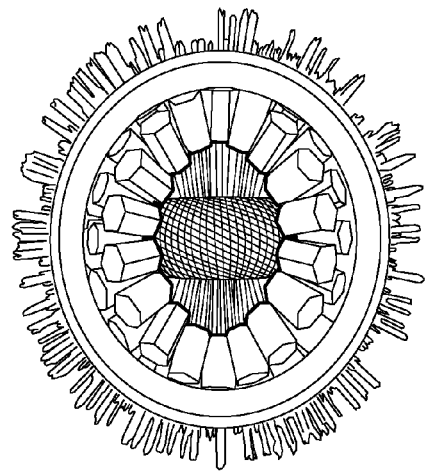

How do we measure metabolites?
LC-ESI-triple quadrupole MS/MS

Step 1: Separate by polarity
Step 2: Ionize
Step 3: Separate and identify by molecular weight
Step 4: Quantify

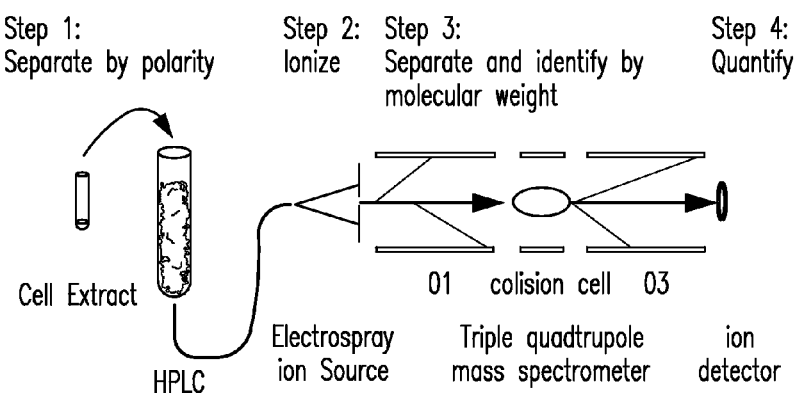

FIG. 12A

How does the virus impact glycolysis?
Both concentrations and fluxes increase

The pentose phosphate pathway?
Overall flux unchanged, but more outflow to nucleotides

Dual ACC1/ACC2 inhibitors

CP-640186
IC50 ~ 50 nM *in vitro*
IC50 ~ 10 mg/kg in rodents 50X effect

CP-610431
IC50 ~ 50 nM *in vitro*
IC50 ~ 20 mg/kg in rodents 50X effect

Compound 8a
IC50 ~ 50 nM *in vitro*

> 100X effect

SEQUENCE LISTING

```
<160> NUMBER OF SEQ ID NOS: 56

<210> SEQ ID NO 1
<211> LENGTH: 21
<212> TYPE: DNA
<213> ORGANISM: Artificial Sequence
<220> FEATURE:
<223> OTHER INFORMATION: ACC1 Target Sequence 1

<400> SEQUENCE: 1
aatcactttg cccgtgtggc g                                            21

<210> SEQ ID NO 2
<211> LENGTH: 21
<212> TYPE: RNA
<213> ORGANISM: Artificial Sequence
<220> FEATURE:
<223> OTHER INFORMATION: Sense Strand siRNA 1

<400> SEQUENCE: 2
ucacuuugcc cguguggcgu u                                            21

<210> SEQ ID NO 3
<211> LENGTH: 21
<212> TYPE: RNA
<213> ORGANISM: Artificial Sequence
<220> FEATURE:
<223> OTHER INFORMATION: Antisense Strand siRNA 1
```

```
<400> SEQUENCE: 3
cgccacacgg gcaaagugau u                                              21

<210> SEQ ID NO 4
<211> LENGTH: 21
<212> TYPE: DNA
<213> ORGANISM: Artificial Sequence
<220> FEATURE:
<223> OTHER INFORMATION: ACC1 Target Sequence 2

<400> SEQUENCE: 4
aacgttccca tctccacccc t                                              21

<210> SEQ ID NO 5
<211> LENGTH: 21
<212> TYPE: RNA
<213> ORGANISM: Artificial Sequence
<220> FEATURE:
<223> OTHER INFORMATION: Sense Strand siRNA 2

<400> SEQUENCE: 5
cguucccauc uccaccccuu u                                              21

<210> SEQ ID NO 6
<211> LENGTH: 21
<212> TYPE: RNA
<213> ORGANISM: Artificial Sequence
<220> FEATURE:
<223> OTHER INFORMATION: Antisense Strand siRNA 2

<400> SEQUENCE: 6
agggguggag augggaacgu u                                              21

<210> SEQ ID NO 7
<211> LENGTH: 21
<212> TYPE: DNA
<213> ORGANISM: Artificial Sequence
<220> FEATURE:
<223> OTHER INFORMATION: ACC1 Target Sequence 3

<400> SEQUENCE: 7
aagggaaatt gaggctgagg g                                              21

<210> SEQ ID NO 8
<211> LENGTH: 21
<212> TYPE: RNA
<213> ORGANISM: Artificial Sequence
<220> FEATURE:
<223> OTHER INFORMATION: Sense strand siRNA 2

<400> SEQUENCE: 8
gggaaauuga ggcugagggu u                                              21

<210> SEQ ID NO 9
<211> LENGTH: 21
<212> TYPE: RNA
<213> ORGANISM: Artificial Sequence
<220> FEATURE:
<223> OTHER INFORMATION: Antisense strand siRNA 2

<400> SEQUENCE: 9
cccucagccu caauuucccu u                                              21

<210> SEQ ID NO 10
<211> LENGTH: 21
```

```
<212> TYPE: DNA
<213> ORGANISM: Artificial Sequence
<220> FEATURE:
<223> OTHER INFORMATION: ACC1 Target Sequence 4

<400> SEQUENCE: 10
aaattgaggc tgagggaact g                                              21

<210> SEQ ID NO 11
<211> LENGTH: 21
<212> TYPE: RNA
<213> ORGANISM: Artificial Sequence
<220> FEATURE:
<223> OTHER INFORMATION: Sense Strand siRNA 4

<400> SEQUENCE: 11
auugaggcug agggaacugu u                                              21

<210> SEQ ID NO 12
<211> LENGTH: 21
<212> TYPE: RNA
<213> ORGANISM: Artificial Sequence
<220> FEATURE:
<223> OTHER INFORMATION: Antisense Strand siRNA 4

<400> SEQUENCE: 12
caguucccuc agccucaauu u                                              21

<210> SEQ ID NO 13
<211> LENGTH: 21
<212> TYPE: DNA
<213> ORGANISM: Artificial Sequence
<220> FEATURE:
<223> OTHER INFORMATION: ACC1 Target Sequence 5

<400> SEQUENCE: 13
aactgggccc agggacggcg a                                              21

<210> SEQ ID NO 14
<211> LENGTH: 21
<212> TYPE: RNA
<213> ORGANISM: Artificial Sequence
<220> FEATURE:
<223> OTHER INFORMATION: Sense Strand siRNA 5

<400> SEQUENCE: 14
cugggcccag ggacggcgau u                                              21

<210> SEQ ID NO 15
<211> LENGTH: 21
<212> TYPE: RNA
<213> ORGANISM: Artificial Sequence
<220> FEATURE:
<223> OTHER INFORMATION: Antisense Strand siRNA 5

<400> SEQUENCE: 15
ucgccguccc ugggcccagu u                                              21

<210> SEQ ID NO 16
<211> LENGTH: 21
<212> TYPE: DNA
<213> ORGANISM: Artificial Sequence
<220> FEATURE:
<223> OTHER INFORMATION: ACC1 Target Sequence 6

<400> SEQUENCE: 16
```
aagggctgct cgtggatgaa c                                              21

<210> SEQ ID NO 17
<211> LENGTH: 21
<212> TYPE: RNA
<213> ORGANISM: Artificial Sequence
<220> FEATURE:
<223> OTHER INFORMATION: Sense Strand siRNA 6

<400> SEQUENCE: 17
gggcugcucg uggaugaacu u                                              21

<210> SEQ ID NO 18
<211> LENGTH: 21
<212> TYPE: RNA
<213> ORGANISM: Artificial Sequence
<220> FEATURE:
<223> OTHER INFORMATION: Antisense Strand siRNA 6

<400> SEQUENCE: 18
guucauccac gagcagcccu u                                              21

<210> SEQ ID NO 19
<211> LENGTH: 21
<212> TYPE: DNA
<213> ORGANISM: Artificial Sequence
<220> FEATURE:
<223> OTHER INFORMATION: ACC1 Target Sequence 7

<400> SEQUENCE: 19
aatcagatgc ttctggaacg t                                              21

<210> SEQ ID NO 20
<211> LENGTH: 21
<212> TYPE: RNA
<213> ORGANISM: Artificial Sequence
<220> FEATURE:
<223> OTHER INFORMATION: Sense Strand siRNA 7

<400> SEQUENCE: 20
ucagaugcuu cuggaacguu u                                              21

<210> SEQ ID NO 21
<211> LENGTH: 21
<212> TYPE: RNA
<213> ORGANISM: Artificial Sequence
<220> FEATURE:
<223> OTHER INFORMATION: Antisense Strand siRNA 7

<400> SEQUENCE: 21
acguuccaga agcaucugau u                                              21

<210> SEQ ID NO 22
<211> LENGTH: 21
<212> TYPE: DNA
<213> ORGANISM: Artificial Sequence
<220> FEATURE:
<223> OTHER INFORMATION: ACC1 Target Sequence 8

<400> SEQUENCE: 22
aataatggat gaaccatctc c                                              21

<210> SEQ ID NO 23
<211> LENGTH: 21
<212> TYPE: RNA
<213> ORGANISM: Artificial Sequence

```
<220> FEATURE:
<223> OTHER INFORMATION: Sense Strand siRNA 8

<400> SEQUENCE: 23
uaauggauga accaucuccu u                                              21

<210> SEQ ID NO 24
<211> LENGTH: 21
<212> TYPE: RNA
<213> ORGANISM: Artificial Sequence
<220> FEATURE:
<223> OTHER INFORMATION: Antisense Strand siRNA 8

<400> SEQUENCE: 24
ggagaugguu cauccauuau u                                              21

<210> SEQ ID NO 25
<211> LENGTH: 21
<212> TYPE: DNA
<213> ORGANISM: Artificial Sequence
<220> FEATURE:
<223> OTHER INFORMATION: ACC1 Target Sequence 9

<400> SEQUENCE: 25
aatggatgaa ccatctccct t                                              21

<210> SEQ ID NO 26
<211> LENGTH: 21
<212> TYPE: RNA
<213> ORGANISM: Artificial Sequence
<220> FEATURE:
<223> OTHER INFORMATION: Sense Strand siRNA 9

<400> SEQUENCE: 26
uggaugaacc aucuccuuu u                                               21

<210> SEQ ID NO 27
<211> LENGTH: 21
<212> TYPE: RNA
<213> ORGANISM: Artificial Sequence
<220> FEATURE:
<223> OTHER INFORMATION: Antisense Strand siRNA 9

<400> SEQUENCE: 27
aagggagaug guucauccau u                                              21

<210> SEQ ID NO 28
<211> LENGTH: 21
<212> TYPE: DNA
<213> ORGANISM: Artificial Sequence
<220> FEATURE:
<223> OTHER INFORMATION: ACC2 Target Sequence 1

<400> SEQUENCE: 28
aatggtcttg cttctttgtc t                                              21

<210> SEQ ID NO 29
<211> LENGTH: 21
<212> TYPE: RNA
<213> ORGANISM: Artificial Sequence
<220> FEATURE:
<223> OTHER INFORMATION: Sense Strand siRNA 1

<400> SEQUENCE: 29
uggucuugcu ucuuugucuu u                                              21
```

```
<210> SEQ ID NO 30
<211> LENGTH: 21
<212> TYPE: RNA
<213> ORGANISM: Artificial Sequence
<220> FEATURE:
<223> OTHER INFORMATION: Antisense Strand siRNA 1

<400> SEQUENCE: 30
agacaaagaa gcaagaccau u                                            21

<210> SEQ ID NO 31
<211> LENGTH: 21
<212> TYPE: DNA
<213> ORGANISM: Artificial Sequence
<220> FEATURE:
<223> OTHER INFORMATION: ACC2 Target Sequence 2

<400> SEQUENCE: 31
aagccgatca ccaagagtaa a                                            21

<210> SEQ ID NO 32
<211> LENGTH: 21
<212> TYPE: RNA
<213> ORGANISM: Artificial Sequence
<220> FEATURE:
<223> OTHER INFORMATION: Sense Strand siRNA 2

<400> SEQUENCE: 32
gccgaucacc aagaguaaau u                                            21

<210> SEQ ID NO 33
<211> LENGTH: 21
<212> TYPE: RNA
<213> ORGANISM: Artificial Sequence
<220> FEATURE:
<223> OTHER INFORMATION: Antisense Strand siRNA 2

<400> SEQUENCE: 33
uuuacucuug gugaucggcu u                                            21

<210> SEQ ID NO 34
<211> LENGTH: 21
<212> TYPE: DNA
<213> ORGANISM: Artificial Sequence
<220> FEATURE:
<223> OTHER INFORMATION: ACC2 Target Sequence 3

<400> SEQUENCE: 34
aagaaacccc ctttcttcca g                                            21

<210> SEQ ID NO 35
<211> LENGTH: 21
<212> TYPE: RNA
<213> ORGANISM: Artificial Sequence
<220> FEATURE:
<223> OTHER INFORMATION: Sense Strand siRNA 3

<400> SEQUENCE: 35
gaaacccccu uucuuccagu u                                            21

<210> SEQ ID NO 36
<211> LENGTH: 21
<212> TYPE: RNA
<213> ORGANISM: Artificial Sequence
<220> FEATURE:
<223> OTHER INFORMATION: Antisense Strand siRNA 3
```

```
<400> SEQUENCE: 36
cuggaagaaa ggggguuucu u                                              21

<210> SEQ ID NO 37
<211> LENGTH: 21
<212> TYPE: DNA
<213> ORGANISM: Artificial Sequence
<220> FEATURE:
<223> OTHER INFORMATION: ACC2 Target Sequence 4

<400> SEQUENCE: 37
aaagaagaca agaagcaggc a                                              21

<210> SEQ ID NO 38
<211> LENGTH: 21
<212> TYPE: RNA
<213> ORGANISM: Artificial Sequence
<220> FEATURE:
<223> OTHER INFORMATION: Sense Strand siRNA 4

<400> SEQUENCE: 38
agaagacaag aagcaggcau u                                              21

<210> SEQ ID NO 39
<211> LENGTH: 21
<212> TYPE: RNA
<213> ORGANISM: Artificial Sequence
<220> FEATURE:
<223> OTHER INFORMATION: Antisense Strand siRNA 4

<400> SEQUENCE: 39
ugccugcuuc uugucuucuu u                                              21

<210> SEQ ID NO 40
<211> LENGTH: 21
<212> TYPE: DNA
<213> ORGANISM: Artificial Sequence
<220> FEATURE:
<223> OTHER INFORMATION: ACC2 Target Sequence 5

<400> SEQUENCE: 40
aaggtgctta ttgccaacaa c                                              21

<210> SEQ ID NO 41
<211> LENGTH: 21
<212> TYPE: RNA
<213> ORGANISM: Artificial Sequence
<220> FEATURE:
<223> OTHER INFORMATION: Sense Strand siRNA 5

<400> SEQUENCE: 41
ggugcuuauu gccaacaacu u                                              21

<210> SEQ ID NO 42
<211> LENGTH: 21
<212> TYPE: RNA
<213> ORGANISM: Artificial Sequence
<220> FEATURE:
<223> OTHER INFORMATION: Antisense Strand siRNA 5

<400> SEQUENCE: 42
guuguuggca auaagcaccu u                                              21

<210> SEQ ID NO 43
```

```
<211> LENGTH: 21
<212> TYPE: DNA
<213> ORGANISM: Artificial Sequence
<220> FEATURE:
<223> OTHER INFORMATION: ACC2 Target Sequence 6

<400> SEQUENCE: 43
aatcagtgtc ccagaagatg t                                              21

<210> SEQ ID NO 44
<211> LENGTH: 21
<212> TYPE: RNA
<213> ORGANISM: Artificial Sequence
<220> FEATURE:
<223> OTHER INFORMATION: Sense Strand siRNA 6

<400> SEQUENCE: 44
ucaguguccc agaagauguu u                                              21

<210> SEQ ID NO 45
<211> LENGTH: 21
<212> TYPE: RNA
<213> ORGANISM: Artificial Sequence
<220> FEATURE:
<223> OTHER INFORMATION: Antisense Strand siRNA 6

<400> SEQUENCE: 45
acaucuucug ggacacugau u                                              21

<210> SEQ ID NO 46
<211> LENGTH: 21
<212> TYPE: DNA
<213> ORGANISM: Artificial Sequence
<220> FEATURE:
<223> OTHER INFORMATION: ACC2 Target Sequence 7

<400> SEQUENCE: 46
aatttccgga gcagcaagaa c                                              21

<210> SEQ ID NO 47
<211> LENGTH: 21
<212> TYPE: RNA
<213> ORGANISM: Artificial Sequence
<220> FEATURE:
<223> OTHER INFORMATION: Sense Strand siRNA 7

<400> SEQUENCE: 47
uuuccggagc agcaagaacu u                                              21

<210> SEQ ID NO 48
<211> LENGTH: 21
<212> TYPE: RNA
<213> ORGANISM: Artificial Sequence
<220> FEATURE:
<223> OTHER INFORMATION: Antisense Strand siRNA 7

<400> SEQUENCE: 48
guucuugcug cuccggaaau u                                              21

<210> SEQ ID NO 49
<211> LENGTH: 21
<212> TYPE: DNA
<213> ORGANISM: Artificial Sequence
<220> FEATURE:
<223> OTHER INFORMATION: ACC2 Target Sequence 8

<400> SEQUENCE: 49
```

```
aatttgggca ctgcttctcc t                                                21
```

<210> SEQ ID NO 50
<211> LENGTH: 21
<212> TYPE: RNA
<213> ORGANISM: Artificial Sequence
<220> FEATURE:
<223> OTHER INFORMATION: Sense Strand siRNA 8

<400> SEQUENCE: 50

```
uuugggcacu gcuucuccuu u                                                21
```

<210> SEQ ID NO 51
<211> LENGTH: 21
<212> TYPE: RNA
<213> ORGANISM: Artificial Sequence
<220> FEATURE:
<223> OTHER INFORMATION: Antisense Strand siRNA 8

<400> SEQUENCE: 51

```
aggagaagca gugcccaaau u                                                21
```

<210> SEQ ID NO 52
<211> LENGTH: 21
<212> TYPE: DNA
<213> ORGANISM: Artificial Sequence
<220> FEATURE:
<223> OTHER INFORMATION: ACC2 Target Sequence 9

<400> SEQUENCE: 52

```
aatacctcat taacctcctg g                                                21
```

<210> SEQ ID NO 53
<211> LENGTH: 21
<212> TYPE: RNA
<213> ORGANISM: Artificial Sequence
<220> FEATURE:
<223> OTHER INFORMATION: Sense Strand siRNA 9

<400> SEQUENCE: 53

```
uaccucauua accuccuggu u                                                21
```

<210> SEQ ID NO 54
<211> LENGTH: 21
<212> TYPE: RNA
<213> ORGANISM: Artificial Sequence
<220> FEATURE:
<223> OTHER INFORMATION: Antisense Strand siRNA 9

<400> SEQUENCE: 54

```
ccaggagguu aaugagguau u                                                21
```

<210> SEQ ID NO 55
<211> LENGTH: 4
<212> TYPE: PRT
<213> ORGANISM: Artificial Sequence
<220> FEATURE:
<223> OTHER INFORMATION: FYVE domain

<400> SEQUENCE: 55

Phe Tyr Val Glu
 1

<210> SEQ ID NO 56
<211> LENGTH: 11

```
<212> TYPE: PRT
<213> ORGANISM: Artificial Sequence
<220> FEATURE:
<223> OTHER INFORMATION: HIV-1 Tat

<400> SEQUENCE: 56

Tyr Gly Arg Lys Lys Arg Arg Gln Arg Arg
 1               5                  10
```

TREATMENT OF VIRAL INFECTIONS BY MODULATION OF HOST CELL METABOLIC PATHWAYS

This application is a continuation of U.S. patent application Ser. No. 12/156,517, filed Jun. 2, 2008, now U.S. Pat. No. 8,158,677, which claims priority benefit under 35 U.S.C.§119(e) to U.S. Provisional Application No. 60/932,769, filed Jun. 1, 2007, and to U.S. Provisional Application No. 61/033,243, filed Mar. 3, 2008, each of which is incorporated by reference herein in its entirety.

GOVERNMENT RIGHTS

This invention was made with government support under Grants #CA082396, CA085786, and GM071508 awarded by the National Institutes of Health. The government has certain rights in this invention.

1. INTRODUCTION

This application relates to antiviral therapies and antiviral drug design.

2. BACKGROUND OF THE INVENTION

Strategies for antiviral drug design have typically focused on identifying compounds that attack the virus itself. As such, the most common antiviral targets have been viral proteins—the structural components of the virion, as well as viral genome-encoded enzymes which are necessary for propagation of the virus. Thus, antiviral compounds have been designed and developed to interfere with viral proteins involved in attachment of the virus to the host cell membrane and entry into the cell, replication, transcription and translation of the viral genes, propagation of the virion inside the cell, and/or release of progeny virions from the cell.

Nevertheless, the approach of targeting viral proteins has several limitations: 1) the limited number of viral targets; 2) viral targets tend to be highly specific to a particular virus or even strain of virus; and 3) the ability of viruses to rapidly alter their genetic composition to develop resistance to antiviral drugs.

Another approach in antiviral drug development is to design drugs to strengthen the host's immune system to fight the viral infection, rather than to fight the viral infection itself. Using this strategy, drugs are designed to boost the host's immune system to allow the host to better fight off infection by the virus.

On the other hand, cellular targets have traditionally been considered less desirable candidates for antiviral therapy. Relatively few antiviral drugs have been directed at host enzymes for several reasons, the most prominent being the high risk of toxicity to the host itself. Although host cell factors play a key role in facilitating viral growth and propagation, strategies for attacking such host factors remain elusive.

A major challenge to antiviral drug development is finding new strategies for combating viral infection.

3. SUMMARY OF THE INVENTION

The present invention relates to antiviral compounds, methods of screening for such compounds, methods for treating viral infections using such compounds, and antiviral therapies directed at host cell enzymes.

Propagation of viruses during the process of viral infection requires energy and macromolecular precursors derived from the metabolic network of the host cell. Viruses alter cellular metabolic activity through a variety of routes to meet the needs of the virus. Changes induced in metabolic flux are likely to be critical to viral survival and propagation. Until recently however, adequate technology for evaluating the effect of viral infection on host metabolism was not available.

The invention is based, in part, on the applicants' development of an integrated approach, referred to herein as "kinetic flux profiling" for profiling metabolic fluxes. Using this approach, the applicants discovered alterations of certain metabolite concentrations and fluxes in response to viral infection. Based on these discoveries, the applicants selected host cell enzymes in the involved metabolic pathways as targets for intervention; i.e., to restore metabolic flux to disadvantage viral replication, or to further derange metabolic flux resulting in death, e.g., "suicide" of viral-infected cells (but not uninfected cells) in order to limit viral propagation. While any of the enzymes in the relevant metabolic pathway can be selected, pivotal enzymes at key control points in these metabolic pathways are preferred as candidate antiviral drug targets. Inhibitors of these enzymes are used to reverse, or redirect, the effects of the viral infection. Drug candidates are tested for antiviral activity using screening assays in vitro and host cells, as well as in animal models. Animal models are then used to test efficacy of candidate compounds in preventing and treating viral infections.

The kinetic flux profiling approach described herein has led to the unexpected discovery that enveloped viruses alter metabolic flux profiles, suggesting enveloped viruses may use common mechanisms for redirecting host metabolic pathways to achieve their energy needs. In the working examples of the present invention, the Applicants have shown that, upon infection of its host cells, human cytomegalovirus (HCMV) increases flux from glucose into the fatty acid biosynthesis pathway to produce fatty acids and/or from glucose to glycerol by glucose-3 phosphate dehydrogenase. Thus, enzymes in the fatty acid biosynthetic pathway constitute key antiviral drug targets. In various embodiments, the virus may be enveloped or naked (i.e., a non-enveloped virus). Proof of this principle is demonstrated in the working examples which show that inhibitors of host enzymes in these metabolic pathways inhibit production of progeny virus by at least 2 logs. In particular, elongases and/or related enzymes of fatty acid elongation, fatty acid desaturation enzymes, and enzymes that modulate cholesterol metabolism and/or lipid-related processes may also constitute key antiviral drug targets.

Without being bound by any particular theory, such candidate antiviral compounds identified by this approach may function by blocking the virus from using host enzymes to achieve its own metabolic needs, and thereby restoring at least in part the normal metabolic activity of the host cell. Thus, the invention also relates to a method for redirecting metabolic flux altered by viral infection in a human subject, comprising administering an effective amount of a preselected compound to a human subject in need thereof, in which said preselected compound is an inhibitor of a cellular enzyme, and reverses or redirects metabolic flux in cultured cells infected with the virus.

3.1 Terminology

As used herein, the term "metabolome" the total set of metabolites in a cell at a given time.

As used herein, the term "about" or "approximately" when used in conjunction with a number refers to any number within 1, 5 or 10% of the referenced number.

As used herein, the term "Compound" refers to any agent that is being tested for its ability to inhibit the activity of a target enzyme or has been identified as inhibiting the activity of a target enzyme, including the particular structures provided herein or incorporated by reference herein, and solvates, hydrates, prodrugs, stereoisomers and pharmaceutically acceptable salts thereof. Compounds include, but are not limited to, proteinaceous molecules, including, but not limited to, peptides (including dimers and multimers of such peptides), polypeptides, proteins, including post-translationally modified proteins, conjugates, antibodies, antibody fragments etc.; small molecules, including inorganic or organic compounds; nucleic acid molecules including, but not limited to, double-stranded or single-stranded DNA, or double-stranded or single-stranded RNA, antisense RNA, RNA interference (RNAi) molecules (e.g., small interfering RNA (siRNA), micro-RNA (miRNA), short hairpin RNA (shRNA), etc.), intron sequences, triple helix nucleic acid molecules and aptamers; carbohydrates; and lipids. In one embodiment, a Compound is of structure (I)-(XLIV). In one embodiment, a Compound is purified.

As used herein, the term "purified," in the context of a Compound that is chemically synthesized, refers to a Compound that is substantially free of chemical precursors or other chemicals when chemically synthesized. In a specific embodiment, the Compound is 60%, preferably 65%, 70%, 75%, 80%, 85%, 90%, or 99% free of other, different compounds.

An "isolated" or "purified", nucleic acid sequence or nucleotide sequence, such as an RNAi molecule (e.g., siRNA, miRNA, shRNA, etc.) or a vector construct for producing an RNAi molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

As used herein, the terms "purified" and "isolated" when used in the context of a Compound (including proteinaceous agents such as peptides) that can be obtained from a natural source, e.g., cells, refers to a compound or agent which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound or agent that has been separated from the material (e.g., cellular components of the cells) from which it is isolated. Thus, a Compound that is isolated includes preparations of a compound or agent having less than about 30%, 20%, 10%, 5%, 2%, or 1% (by dry weight) of cellular materials and/or contaminating materials.

Definitions of the more commonly recited chemical groups are set forth below. Certain variables in classes of Compounds disclosed herein recite other chemical groups. Chemical groups recited herein, but not specifically defined, have their ordinary meaning as would be known by a chemist skilled in the art.

A "C1-xalkyl" group is a saturated straight chain or branched non-cyclic hydrocarbon having from 1 to x carbon atoms. Representative —(C1-8alkyls) include -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. A —(C1-xalkyl) group can be substituted or unsubstituted.

The terms "halogen" and "halo" mean fluorine, chlorine, bromine and iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "heteroaryl" group is an aryl ring system having one to four heteroatoms as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include aromatic groups selected from the following:

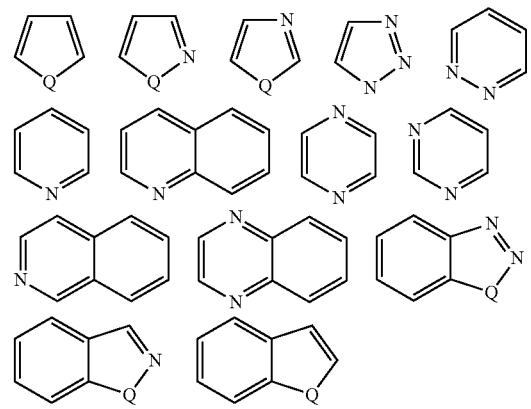

wherein Q is CH2, CH=CH, O, S or NH. Further representative examples of heteroaryl groups include, but are not limited to, benzofuranyl, benzothienyl, indolyl, benzopyrazolyl, coumarinyl, furanyl, isothiazolyl, imidazolyl, isoxazolyl, thiazolyl, triazolyl, tetrazolyl, thiophenyl, pyrimidinyl, isoquinolinyl, quinolinyl, pyridinyl, pyrrolyl, pyrazolyl, 1H-indolyl, 1H-indazolyl, benzo[d]thiazolyl and pyrazinyl. Heteroaryls can be bonded at any ring atom (i.e., at any carbon atom or heteroatom of the heteroaryl ring) A heteroaryl group can be substituted or unsubstituted. In one embodiment, the heteroaryl group is a C3-10heteroaryl.

A "cycloalkyl" group is a saturated or unsaturated non-aromatic carbocyclic ring. Representative cycloalkyl groups include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl. A cycloalkyl group can be substituted or unsubstituted. In one embodiment, the cycloalkyl group is a C3-8cycloalkyl group.

A "heterocycloalkyl" group is a non-aromatic cycloalkyl in which one to four of the ring carbon atoms are independently replaced with a heteroatom from the group consisting of O, S and N. Representative examples of a heterocycloalkyl group include, but are not limited to, morpholinyl, pyrrolyl, pyrrolidinyl, thienyl, furanyl, thiazolyl, imidazolyl, pyrazolyl, triazolyl, piperizinyl, isothiazolyl, isoxazolyl, (1,4)-dioxane, (1,3)-dioxolane, 4,5-dihydro-1H-imidazolyl and tetrazolyl. Heterocycloalkyls can also be bonded at any ring atom (i.e., at any carbon atom or heteroatom of the Heteroaryl ring). A heterocycloalkyl group can be substituted or unsubstituted. In one embodiment, the heterocycloalkyl is a 3-7 membered heterocycloalkyl.

In one embodiment, when groups described herein are said to be "substituted," they may be substituted with any suitable substituent or substituents. Illustrative examples of substituents include those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; CO2CH3; CONH2; OCH2CONH2; NH2; SO2NH2; OCHF2; CF3; OCF3.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, See for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a compound, or a salt thereof, that further includes a stoichiometric or non-stoichiometric amount of water bound by non-covalent intermolecular forces.

As used herein and unless otherwise indicated, the term "solvate" means a Compound, or a salt thereof, that further includes a stoichiometric or non-stoichiometric amount of a solvent bound by non-covalent intermolecular forces.

As used herein and unless otherwise indicated, the term "prodrug" means a Compound derivative that can hydrolyze, oxidize, or otherwise react under biological conditions (in vitro or in vivo) to provide Compound. Examples of prodrugs include, but are not limited to, derivatives and metabolites of a Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of Compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a Compound, in the context of an organic or inorganic molecule, that is substantially free of other stereoisomers of that Compound. For example, a stereomerically pure Compound having one chiral center will be substantially free of the opposite enantiomer of the Compound. A stereomerically pure Compound having two chiral centers will be substantially free of other diastereomers of the Compound. A typical stereomerically pure Compound comprises greater than about 80% by weight of one stereoisomer of the compound and less than about 20% by weight of other stereoisomers of the Compound, greater than about 90% by weight of one stereoisomer of the Compound and less than about 10% by weight of the other stereoisomers of the Compound, greater than about 95% by weight of one stereoisomer of the Compound and less than about 5% by weight of the other stereoisomers of the Compound, or greater than about 97% by weight of one stereoisomer of the Compound and less than about 3% by weight of the other stereoisomers of the Compound. The Compounds can have chiral centers and can occur as racemates, individual enantiomers or diastereomers, and mixtures thereof. All such isomeric forms are included within the embodiments disclosed herein, including mixtures thereof.

Various Compounds contain one or more chiral centers, and can exist as racemic mixtures of enantiomers, mixtures of diastereomers or enantiomerically or optically pure Compounds. The use of stereomerically pure forms of such Compounds, as well as the use of mixtures of those forms are encompassed by the embodiments disclosed herein. For example, mixtures comprising equal or unequal amounts of the enantiomers of a particular Compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, N.Y., 1962); and Wilen, S. H., Tables of Resolving Agents and Optical Resolutions p. 268 (E. L. Eliel, Ed., Univ. of Notre Dame Press, Notre Dame, 1N, 1972).

It should also be noted that Compounds, in the context of organic and inorganic molecules, can include E and Z isomers, or a mixture thereof, and cis and trans isomers or a mixture thereof. In certain embodiments, Compounds are isolated as either the E or Z isomer. In other embodiments, Compounds are a mixture of the E and Z isomers.

As used herein, the term "effective amount" in the context of administering a therapy to a subject refers to the amount of a therapy which is sufficient to achieve one, two, three, four, or more of the following effects: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a viral infection or a symptom associated therewith; (vi) prevent the recurrence of a viral infection or a symptom associated therewith; (vii) reduce or prevent the spread of a virus from one cell to another cell, or one tissue to another tissue; (ix) prevent or reduce the spread of a virus from one subject to another subject; (x) reduce organ failure associated with a viral infection; (xi) reduce hospitalization of a subject; (xii) reduce hospitalization length; (xiii) increase the survival of a subject with a viral infection; (xiv) eliminate a virus infection; and/or (xv) enhance or improve the prophylactic or therapeutic effect(s) of another therapy.

As used herein, the term "effective amount" in the context of a Compound for use in cell culture-related products refers to an amount of a Compound which is sufficient to reduce the viral titer in cell culture or prevent the replication of a virus in cell culture.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject with a viral infection. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a viral infection.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In one embodiment, an infection refers to the pathological state resulting from the presence of the virus in a cell or a subject, or by the invasion of a cell or subject by the virus.

As used herein, the term "library" refers to a plurality of compounds. A library can be a combinatorial library, e.g., a collection of compounds synthesized using combinatorial chemistry techniques, or a collection of unique chemicals of low molecular weight (less than 1000 daltons).

As used herein, the terms "manage," "managing," and "management," in the context of the administration of a therapy to a subject, refer to the beneficial effects that a subject derives from a therapy, which does not result in a cure of a viral infection. In certain embodiments, a subject is administered one or more therapies to "manage" a disease so as to prevent the progression or worsening of the viral infection.

As used herein, the phrase "multiplicity of infection" or "MOI" is the average number of virus per infected cell. The MOI is determined by dividing the number of virus added (ml added×PFU) by the number of cells added (ml added×cells/ml).

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the terms "prevent," "preventing" and "prevention" in the context of the administration of a therapy(ies) to a subject to prevent a viral infection refer to one or more of the following effects resulting from the administration of a therapy or a combination of therapies: (i) the inhibition of the development or onset of a viral infection and/or a symptom associated therewith; and (ii) the inhibition of the recurrence of a viral infection and/or a symptom associated therewith.

As used herein, the terms "prophylactic agent" and "prophylactic agents" refer to any agent(s) which can be used in the prevention of a viral infection or a symptom associated therewith. Preferably, a prophylactic agent is an agent which is known to be useful to or has been or is currently being used to prevent or impede the onset, development, progression and/or severity of a viral infection or a symptom associated therewith.

As used herein, the term "prophylactically effective amount" refers to the amount of a therapy (e.g., prophylactic agent) which is sufficient to prevent a viral infection or a symptom thereof in a subject.

As used herein, the term "small molecules" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

As used herein, the terms "subject" or "patient" are used interchangeably. As used herein, the terms "subject" and "subjects" refer to an animal (e.g., birds, reptiles, and mammals), preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the terms "therapies" and "therapy" can refer to any protocol(s), method(s), compositions, formulations, and/or agent(s) that can be used in the prevention, treatment, management, or amelioration of a viral infection or a symptom associated therewith. In certain embodiments, the terms "therapies" and "therapy" refer to biological therapy, supportive therapy, and/or other therapies useful in treatment, management, prevention, or amelioration of a viral infection or a symptom associated therewith known to one of skill in the art.

As used herein, the term "synergistic," in the context of the effect of therapies, refers to a combination of therapies which is more effective than the additive effects of any two or more single therapies. In a specific embodiment, a synergistic effect of a combination of therapies permits the use of lower dosages of one or more of therapies and/or less frequent administration of said therapies to a subject with a viral infection. In certain embodiments, the ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a viral infection. In some embodiments, a synergistic effect results in improved efficacy of therapies (e.g., prophylactic or therapeutic agents) in the prevention, management and/or treatment of a viral infection. In some embodiments, a synergistic effect of a combination of therapies (e.g., prophylactic or therapeutic agents) avoids or reduces adverse or unwanted side effects associated with the use of any single therapy.

As used herein, the term "therapeutically effective amount" refers to the amount of a therapy, which is sufficient to treat and/or manage a viral infection. As used herein, the terms "therapeutic agent" and "therapeutic agents" refer to any agent(s) which can be used in the prevention, treatment and/or management of a viral infection or a symptom associated therewith. Preferably, a therapeutic agent is an agent which is known to be useful for, or has been or is currently being used for the prevention, treatment, and/or management of a viral infection or a symptom associated therewith.

As used herein, the terms "treat," "treatment," and "treating" refer in the context of administration of a therapy(ies) to a subject to treat a viral infection refer to one, two, three, four, five or more of the following effects resulting from the administration of a therapy or a combination of therapies: (i) the reduction or amelioration of the severity of a viral infection and/or a symptom associated therewith; (ii) the reduction in the duration of a viral infection and/or a symptom associated therewith; (iii) the regression of a viral infection and/or a symptom associated therewith; (iv) the reduction of the titer of a virus; (v) the reduction in organ failure associated with a viral infection; (vi) the reduction in hospitalization of a subject; (vii) the reduction in hospitalization length; (viii) the increase in the survival of a subject; (ix) the elimination of a virus infection; (x) the inhibition of the progression of a viral infection and/or a symptom associated therewith; (xi) the prevention of the spread of a virus from a cell, tissue or subject to another cell, tissue or subject; and/or (xii) the enhancement or improvement the therapeutic effect of another therapy.

4. DESCRIPTION OF THE FIGURES

Figure 1B:
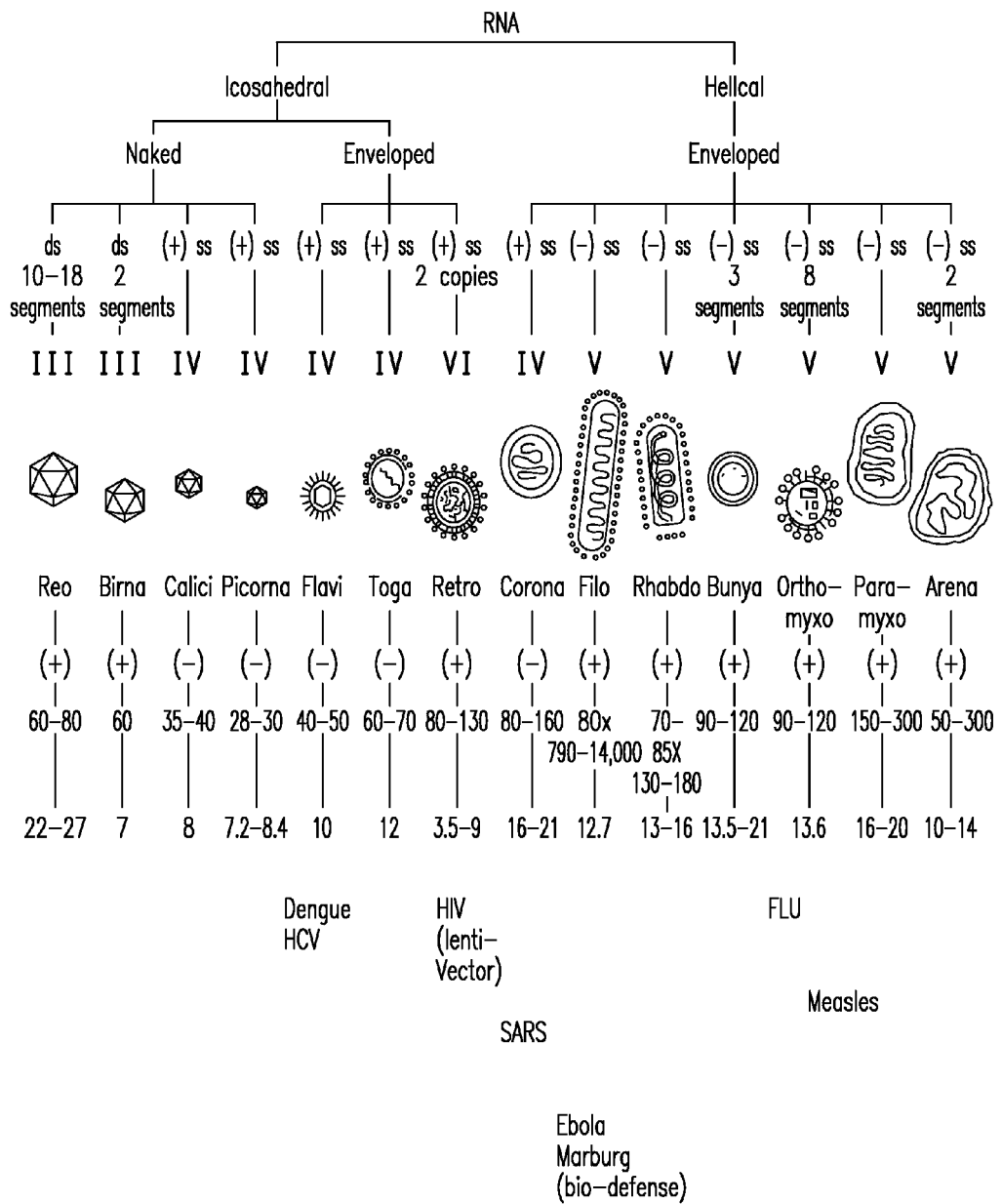

FIG. 1. Schematic Diagram of Virus Classification.

FIG. 1 shows the classification of families of viruses and their structural characteristics. FIG. 1 is a modified figure from Flint et al., Principles of Virology: Molecular Biology, Pathogenesis and Control of Animal Virus. 2nd edition, ASM Press, 2003. A subset of viruses against which Compounds can be assessed for antiviral activity are shown.

FIG. 2. CMV infection directs glycolytic outflow into fatty acid biosynthesis.

Figure 2A:
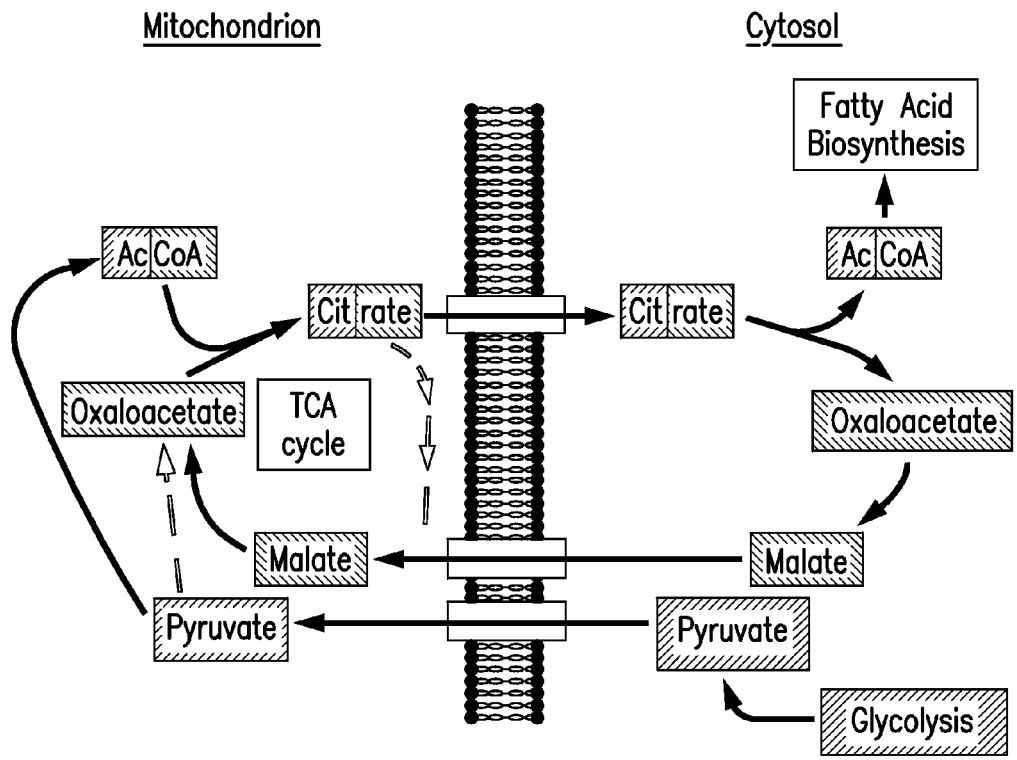
Figure 2B:
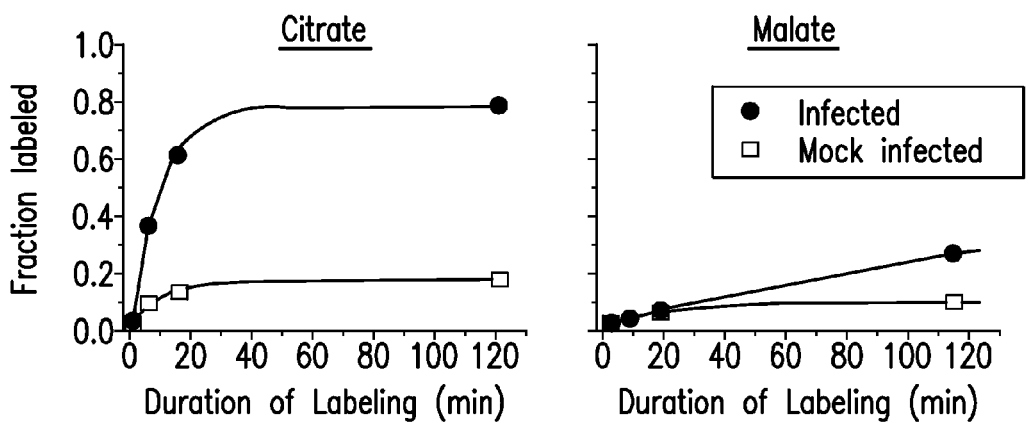

FIG. 2A summarizes the results of kinetic flux profiling (KFP) experiments in which metabolite labeling patterns in CMV infected cells were observed following their transfer from unlabeled into uniformly 13C-glucose. Compounds found to be rapidly fully labeled are shown in dark gray, partially labeled in mixed dark gray/light gray, and unlabeled in light gray alone. Labeling of Acetyl CoenzymeA (AcCoA) was restricted to the acetyl moiety, and labeling of citrate was limited to the two C-atoms coming directly from AcCoA. The pathways consistent with the observed labeling pattern are shown in solid lines, and lead from pyruvate into fatty acid biosynthesis. The dashed lines indicate major metabolic pathways that appear to be largely inactive, as their activity would result in substantially different labeling patterns from those observed. FIG. 2B shows exemplary kinetic data used to generate FIG. 2A. The kinetics of citrate versus malate labeling provide pivotal information, as they distinguish use of citrate for lipid biosynthesis (which does not result in malate labeling) from use of citrate to drive to the tricarboxylic acid (TCA) cycle (which would result in malate being labeled with similar kinetics to citrate, and eventually generation of more thoroughly labeled citrate). See Example 2.

Figure 3:
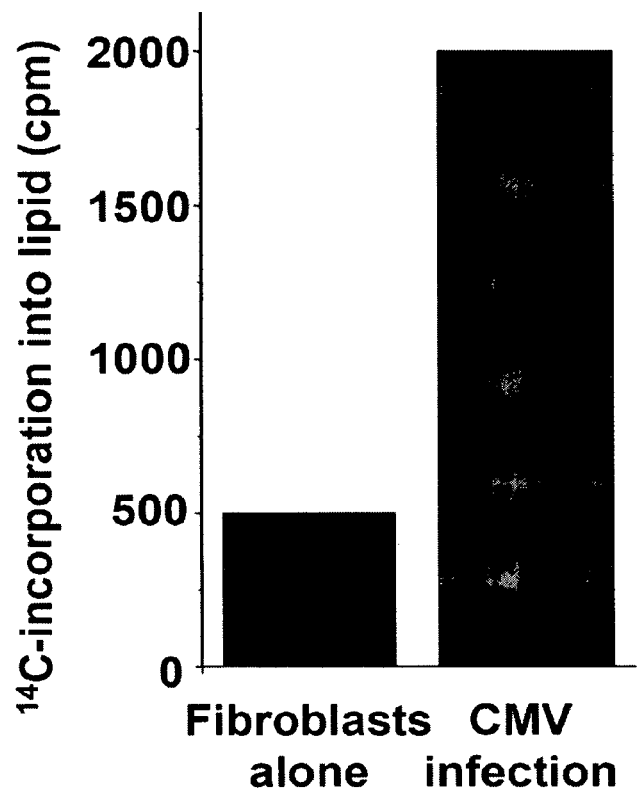

FIG. 3. CMV infection induces de novo synthesis of lipids from $^{14}$C-glucose.

See Example 4.

Figure 4:
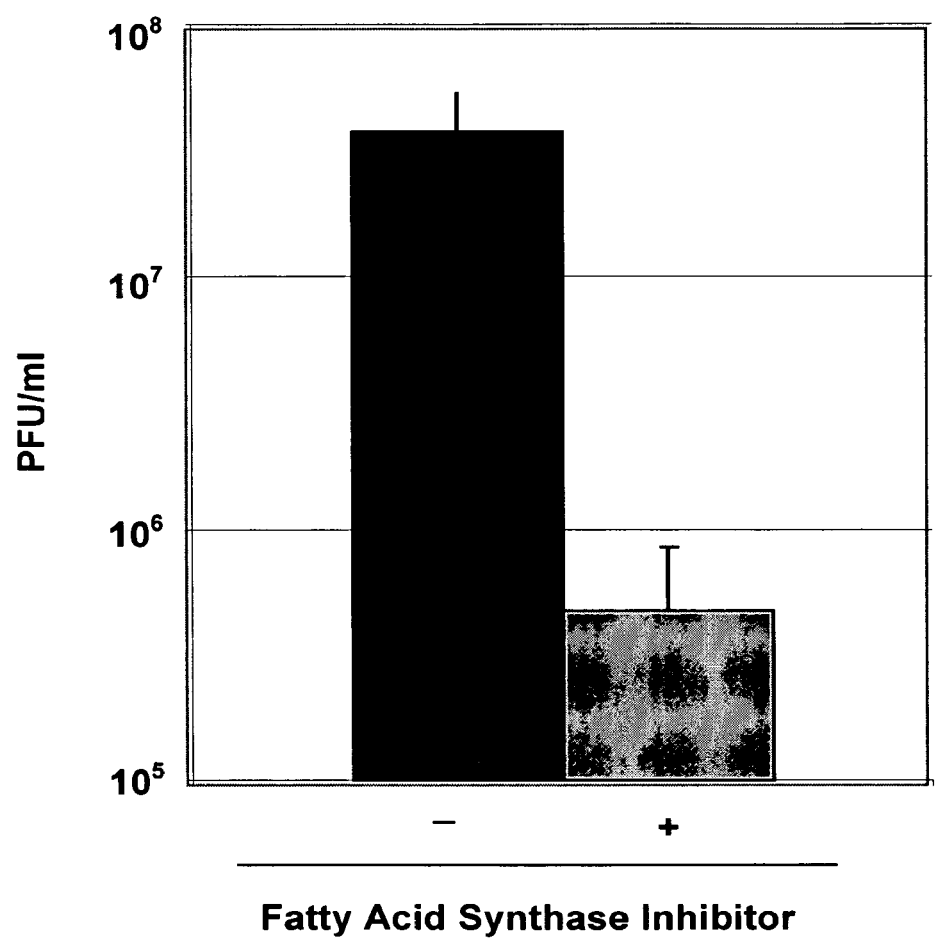

FIG. 4. C75 Inhibits HSV Viral Replication.

FIG. 4 shows that C75 effectively inhibited the replication of HSV following infection of primary fibroblasts MRC-5 cells. C75 reduced HSV viral replication by more than 2 logs. See Example 8.

Figure 5:
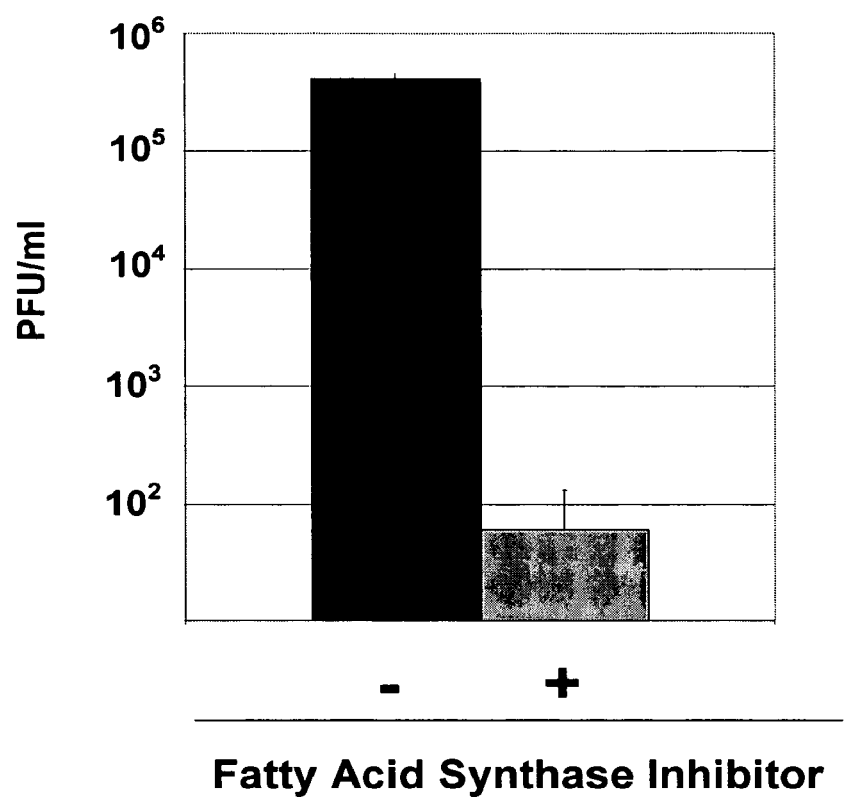

FIG. 5. C75 Inhibits HCMV Viral Replication.

FIG. 5 shows that C75 effectively inhibited the replication of HCMV following infection of primary fibroblasts MRC-5 cells. C75 reduced HCMV viral replication by more than 3 logs. See Example 8.

Figure 6:
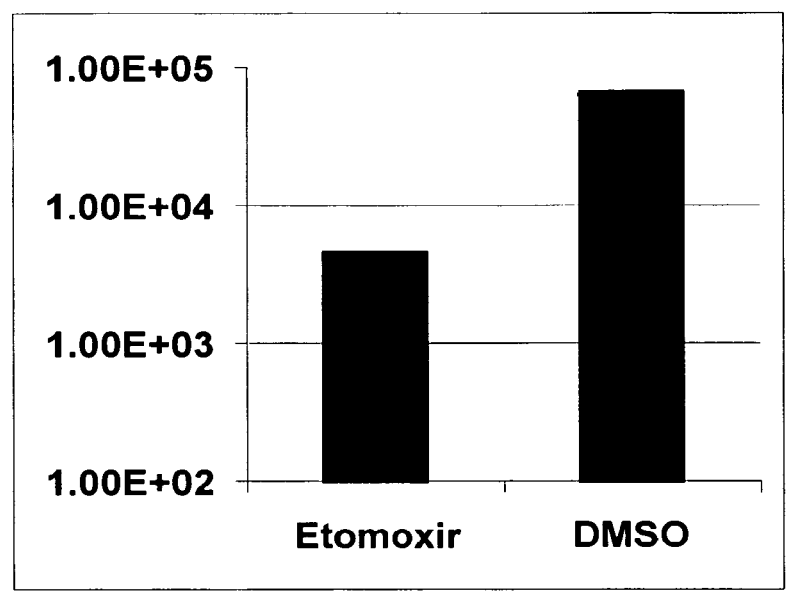

FIG. 6. Etomoxir Inhibits HCMV Viral Replication.

FIG. 6 shows that Etomoxir effectively inhibited the replication of HCMV following infection of primary fibroblasts. Etomoxir reduced HCMV viral replication by more than 1 log. See Example 8.

FIGS. 7A and 7B. CMV infection directs metabolic flux of glycolytic and related compounds.

FIGS. 7A and 7B show the labeling kinetics of glycolytic and related compounds in mock-infected and CMV-infected human fibroblasts, respectively. See Example 9, Section 6.9.1.

Figure 8:
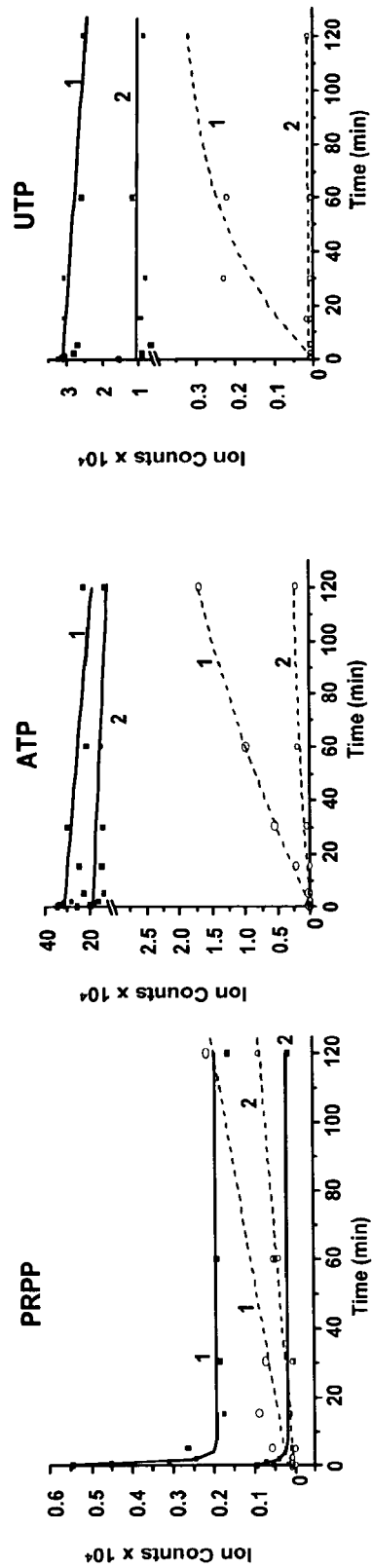

FIG. 8. CMV infection directs metabolic flux of nucleotide triphosphates and their precursor PRPP.

FIG. 8 shows the labeling kinetics of nucleotide triphosphates and their precursor PRPP in mock-infected (labeled "2") and CMV-infected human fibroblasts (labeled "1"). See Example 9, Section 6.9.2.

FIGS. 9A and 9B. CMV infection directs metabolic flux of TCA cycle compounds: glucose labeling.

FIGS. 9A and 9B show the labeling kinetics of TCA cycle compounds and the fractional labeling of these compounds, respectively. See Example 9, Section 6.9.3.

FIGS. 10A and 10B. CMV infection directs metabolic flux of TCA cycle compounds: Glutamine labeling.

FIGS. 10A and 10B show the labeling kinetics of TCA cycle compounds and the fractional labeling of these compounds, respectively. See Example 9, Section 6.9.4.

Figure 11:
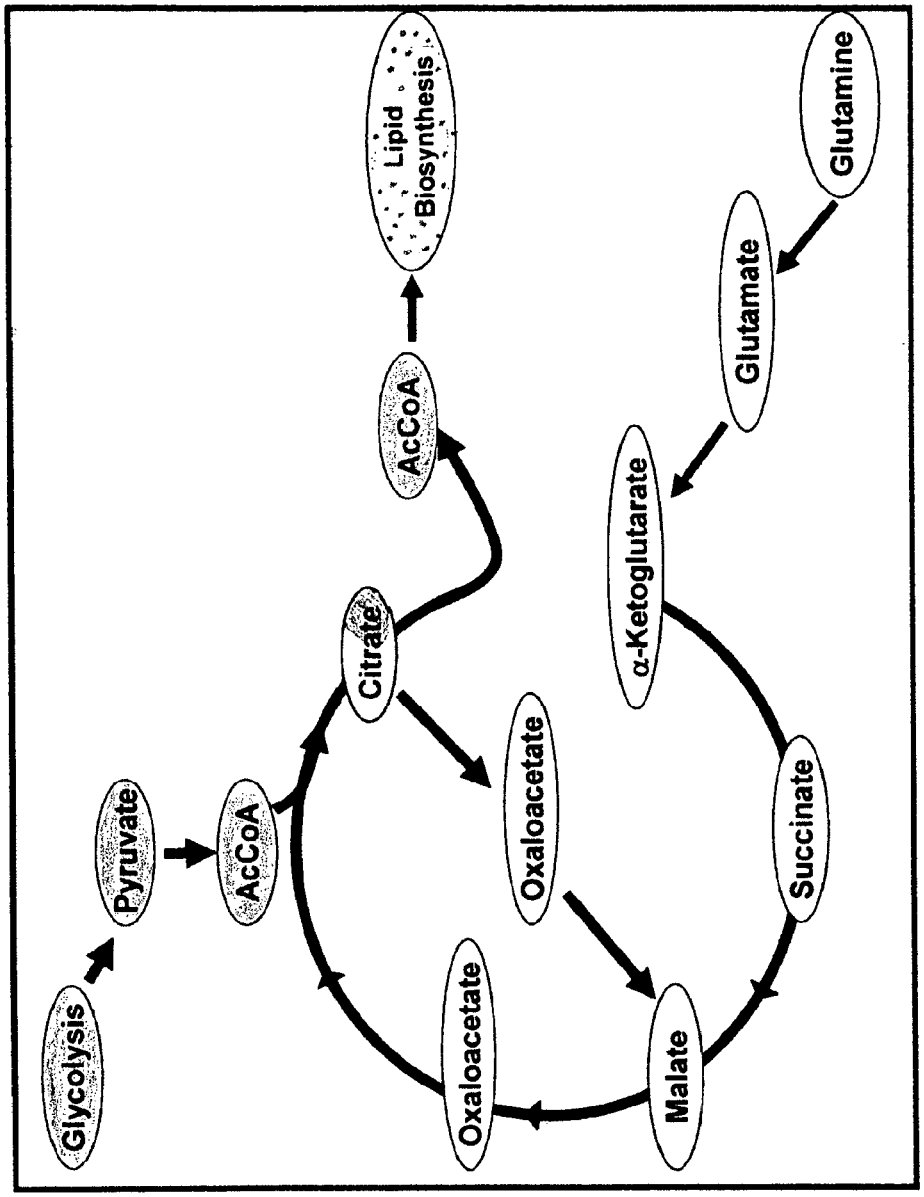
Figure 12B:
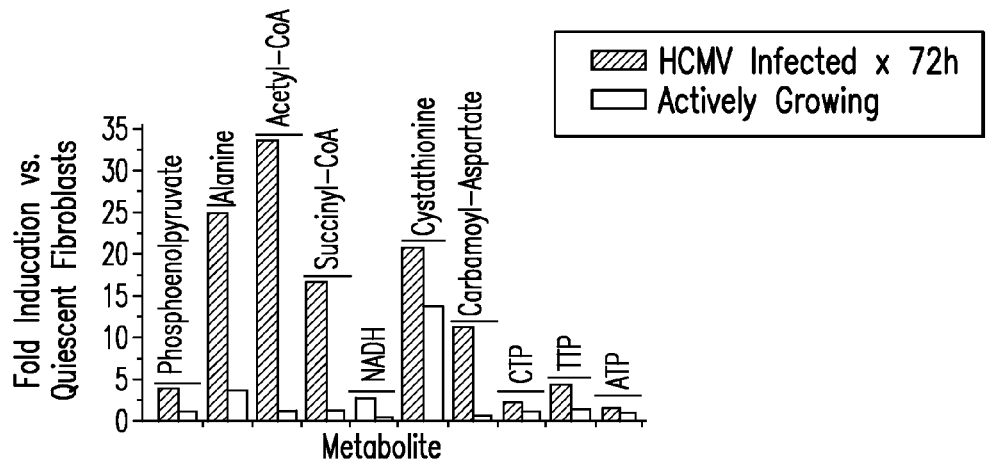
Figure 12B:
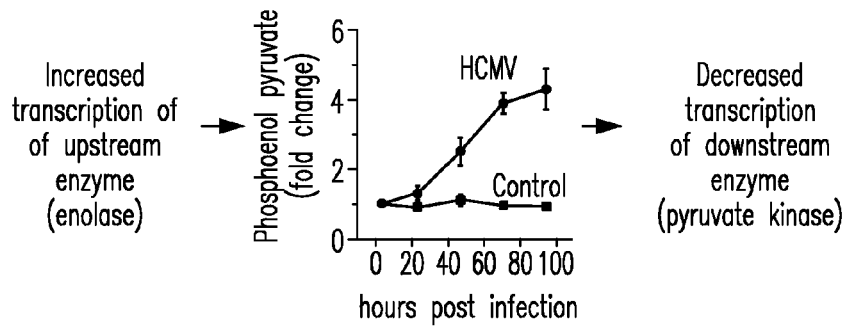
Figure 12B:
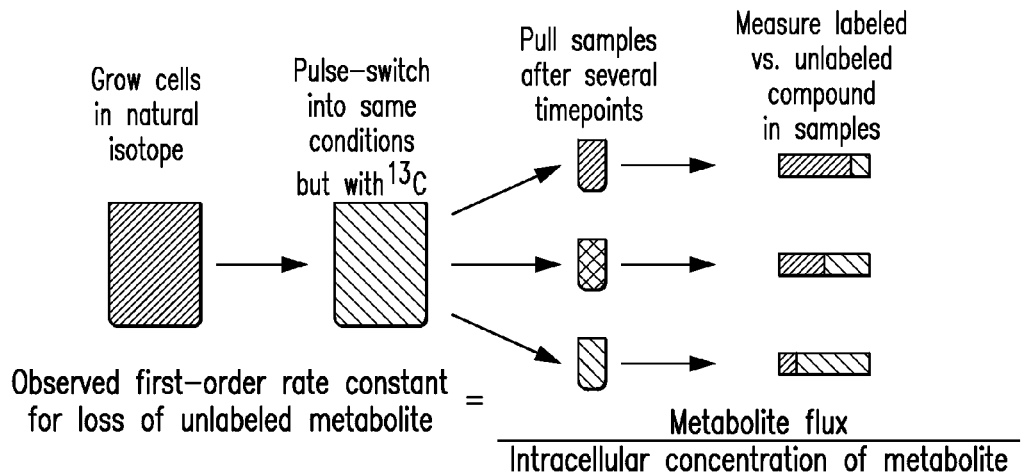
Figure 12C:
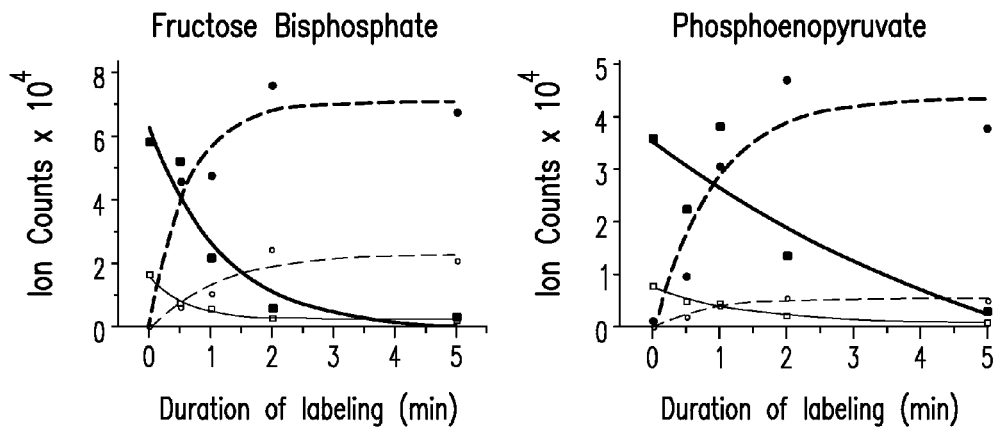
Figure 12C:
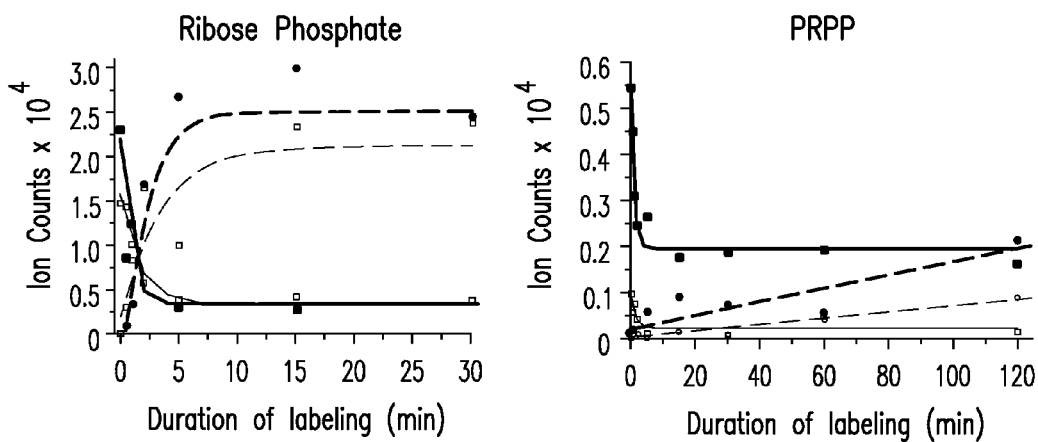
Figure 12D:
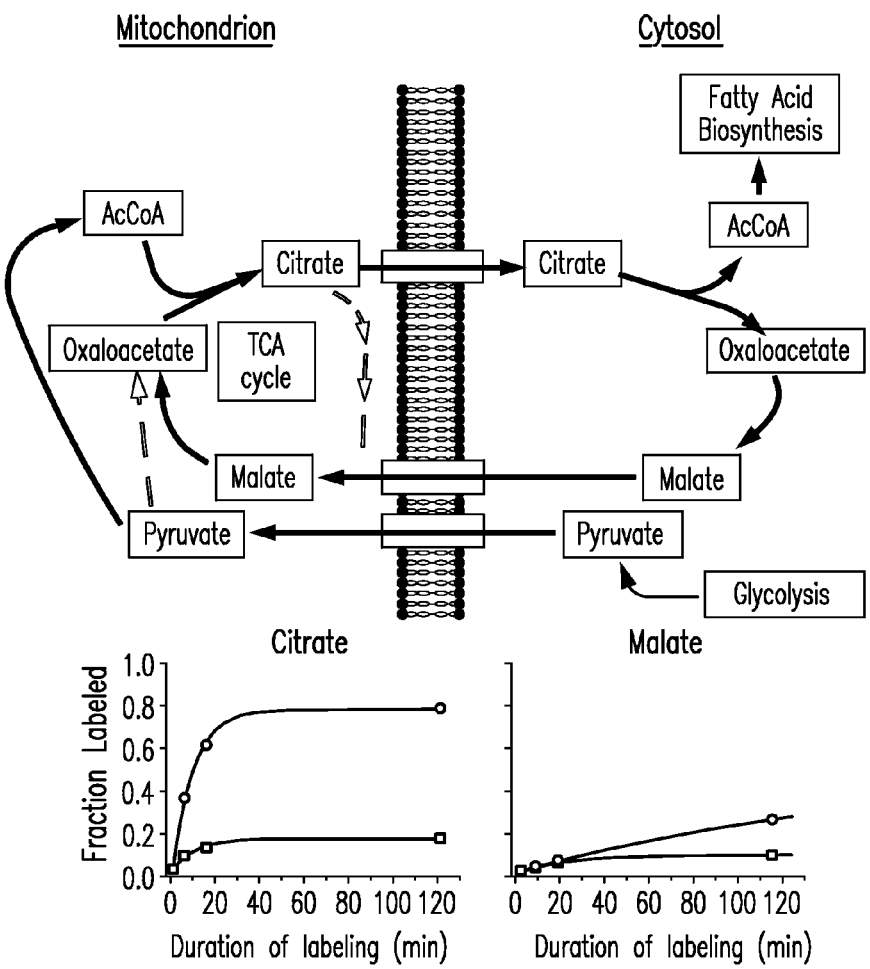
Figure 12D:
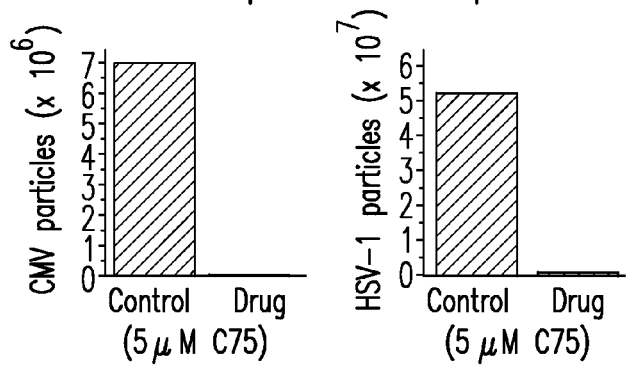

FIG. 11. Schematic of central carbon metabolic flows in CMV infected cells.

FIG. 11 shows a schematic of central carbon metabolic flows in virally infected cells. Glucose and metabolites formed from glucose are represented by shaded areas, and glutamine and metabolites formed from glutamine are represented by unshaded areas. See Example 9, Section 6.9.5.

FIG. 12. Integrated metabolomic and fluxomic analysis of cellular response to viral infection.

FIG. 12 provides an overview of the integrated metabolomic and fluxomic analysis of cellular response to viral infection described in further detail in section 6.

Figure 13:
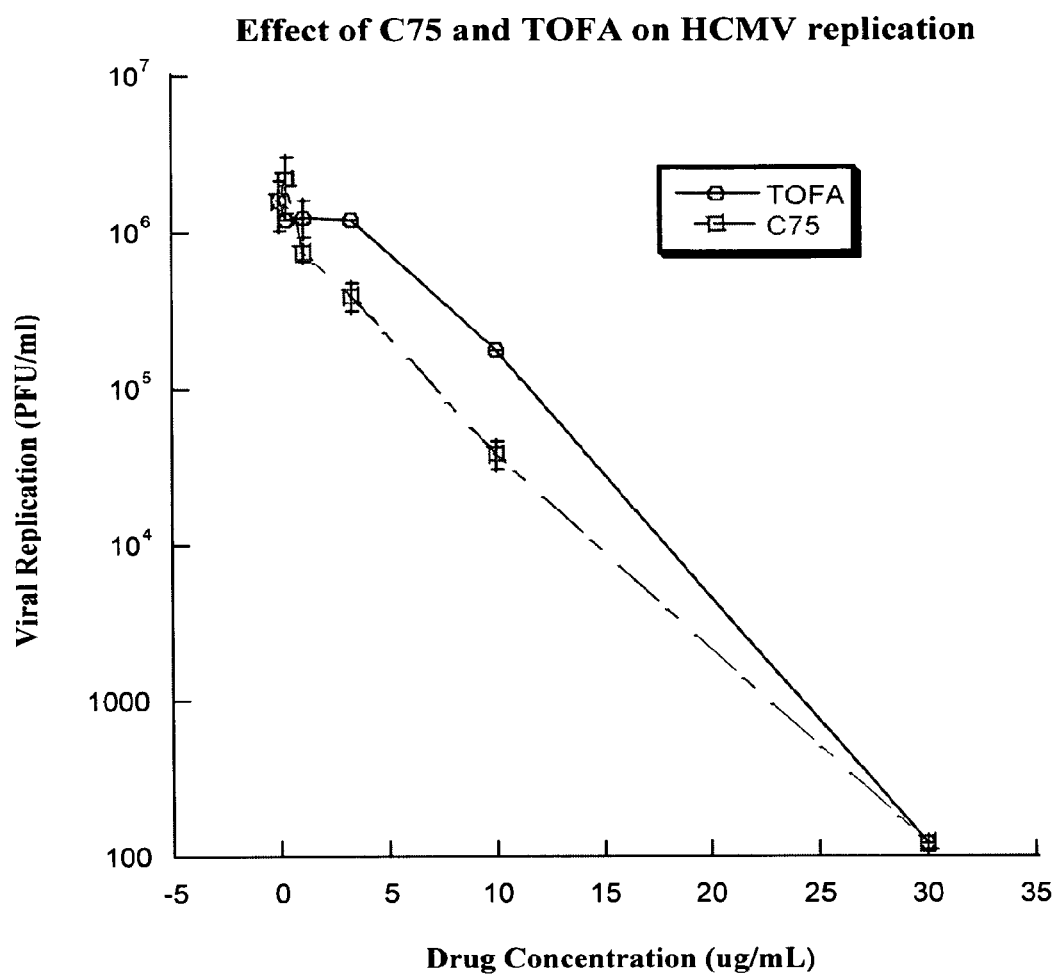

FIG. 13. Dose Response of C75 and TOFA in Inhibition of HCMV Replication.

FIG. 13 shows that 10 μg/mL of both C75 and TOFA was adequate to produce a roughly one-log decrease in viral replication in primary fibroblasts infected with HCMV. Error bars show the standard deviation of duplicate measurements. See Example 11.

Figure 14:
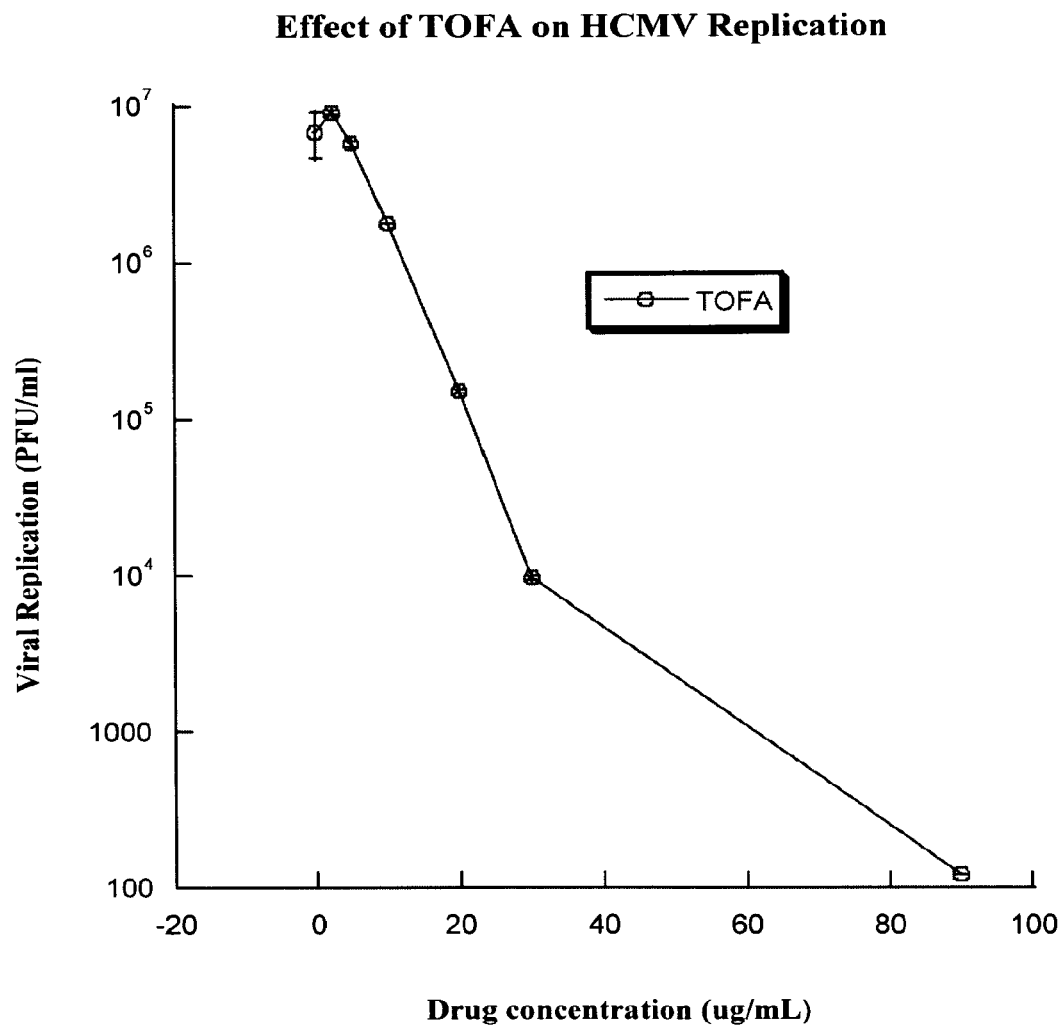

FIG. 14. Dose Response of TOFA in Inhibition of HCMV Replication.

FIG. 14 shows that 20 μg/mL of TOFA produced a roughly two-log decrease in viral replication in primary fibroblasts infected with HCMV. Error bars show the standard deviation of duplicate measurements. See Example 12.

Figure 15:
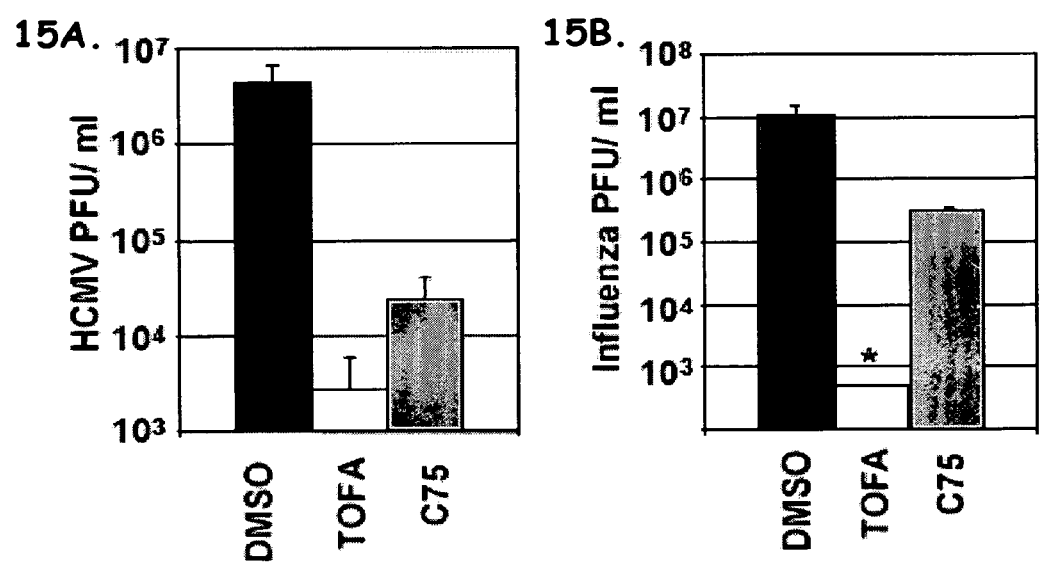

FIGS. 15A-B. Effect of C75 and TOFA on HCMV and Influenza A Virus Replication.

FIG. 15A shows that 10 μg/mL of both C75 and TOFA produced a greater than 100-fold and 1000-fold decrease, respectively, in viral production (PFU/ml) of infectious HCMV virions 96 hours after infection (high multiplicity of infection (MOI)=3.0). FIG. 15B shows that 10 μg/mL of C75 and TOFA produced a greater than 10-fold and 1000-fold decrease, respectively, in viral replication of infectious influenza A virions 24 hours after infection (MOI=0.1). See Example 13.

Figure 16:
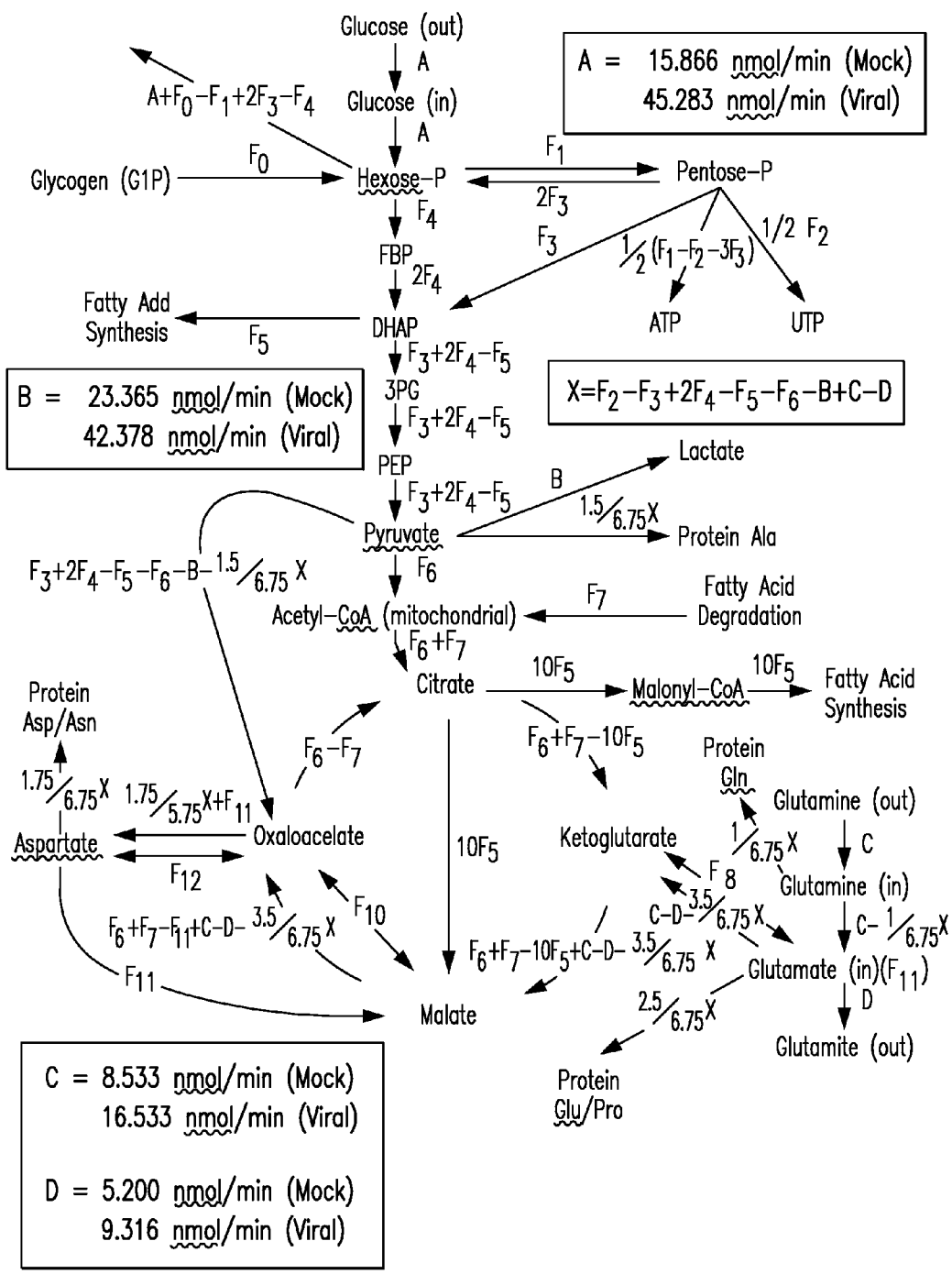

FIG. 16. Network Diagram of Central Metabolism and its connections to biosynthesis.

FIG. 16 shows a network diagram of central metabolism and its connection to biosynthesis, which diagram was used as the basis to construct an ordinary differential equation (ODE) model as described in Example 14.

Figure 17:
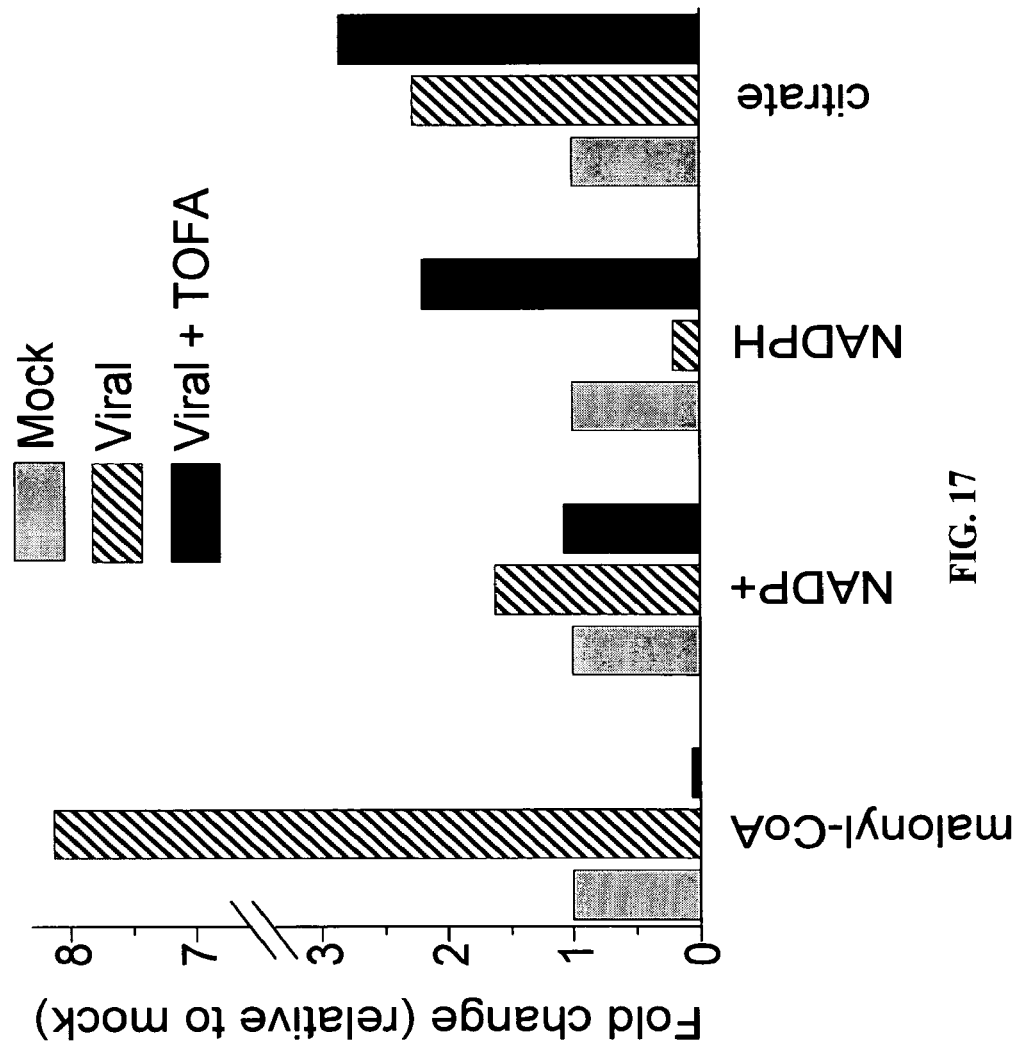

FIG. 17. Effect of TOFA on Metabolome of HCMV-infected Fibroblasts.

FIG. 17 shows the fold change (relative to mock) in malonyl-CoA, $NADP^+$, NADPH, and citrate in mock-infected fibroblasts (gray bars), HCMV-infected fibroblasts (striped bars), and HCMV-infected fibroblasts cultured in medium containing TOFA (solid black bars). The virus-induced elevation in malonyl-CoA and depletion of cellular NADPH (elevation of $NADP^+$) are blocked by TOFA. See Example 22.

Figure 18:
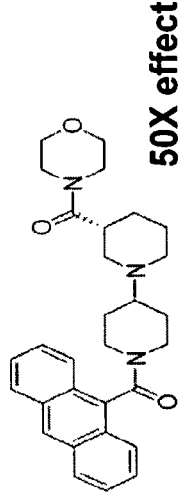
Figure 18:
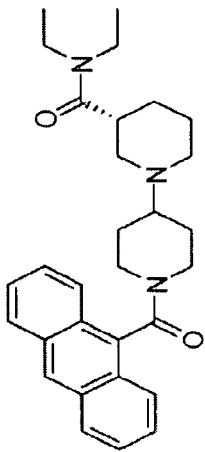
Figure 18:
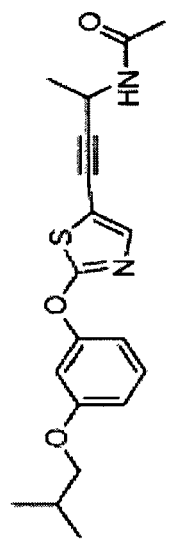

FIG. 18. Dual ACC1/ACC2 Inhibitors Having Anti-HCMV Activity.

FIG. 18 shows the structures of dual ACC1/ACC2 inhibitor compounds, their respective IC50 values in vitro and in rodents, and the anti-HCMV effect of each compound in inhibiting viral replication. See Example 23.

Figure 19:
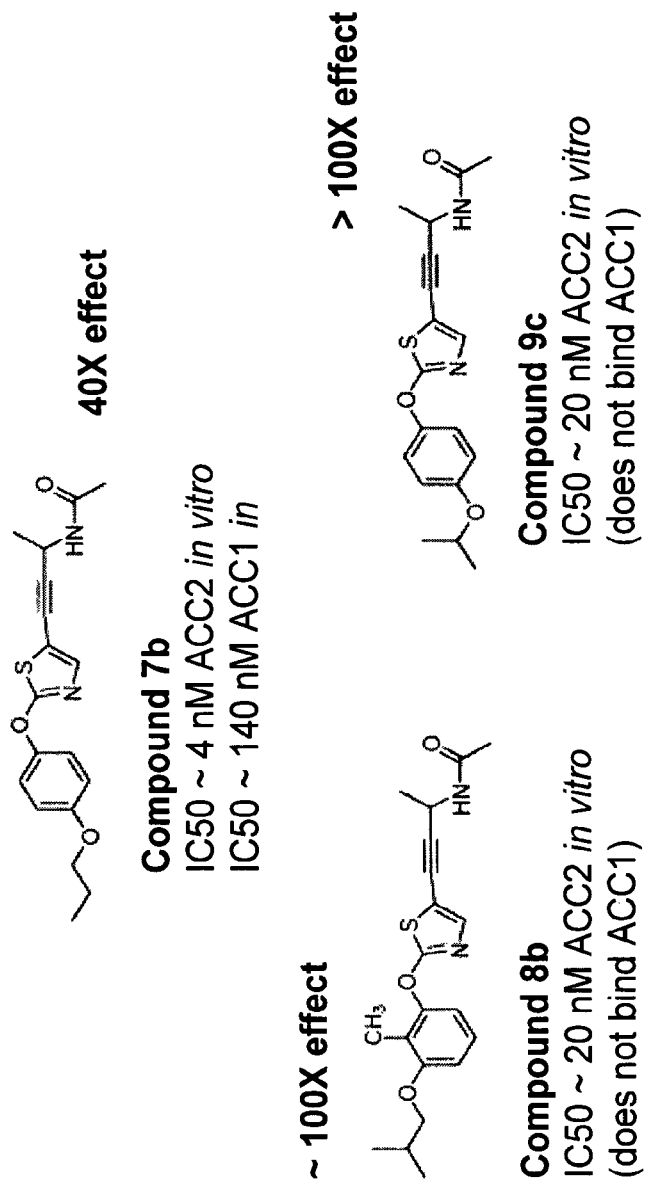

FIG. 19. Selective ACC2 Inhibitors Having Anti-HCMV Activity.

FIG. 19 shows the structures of selective ACC2 inhibitor compounds, their respective IC50 values in vitro for inhibition of ACC2 and ACC1, and the anti-HCMV effect of each compound in inhibiting viral replication. See Example 23.

Figure 20:
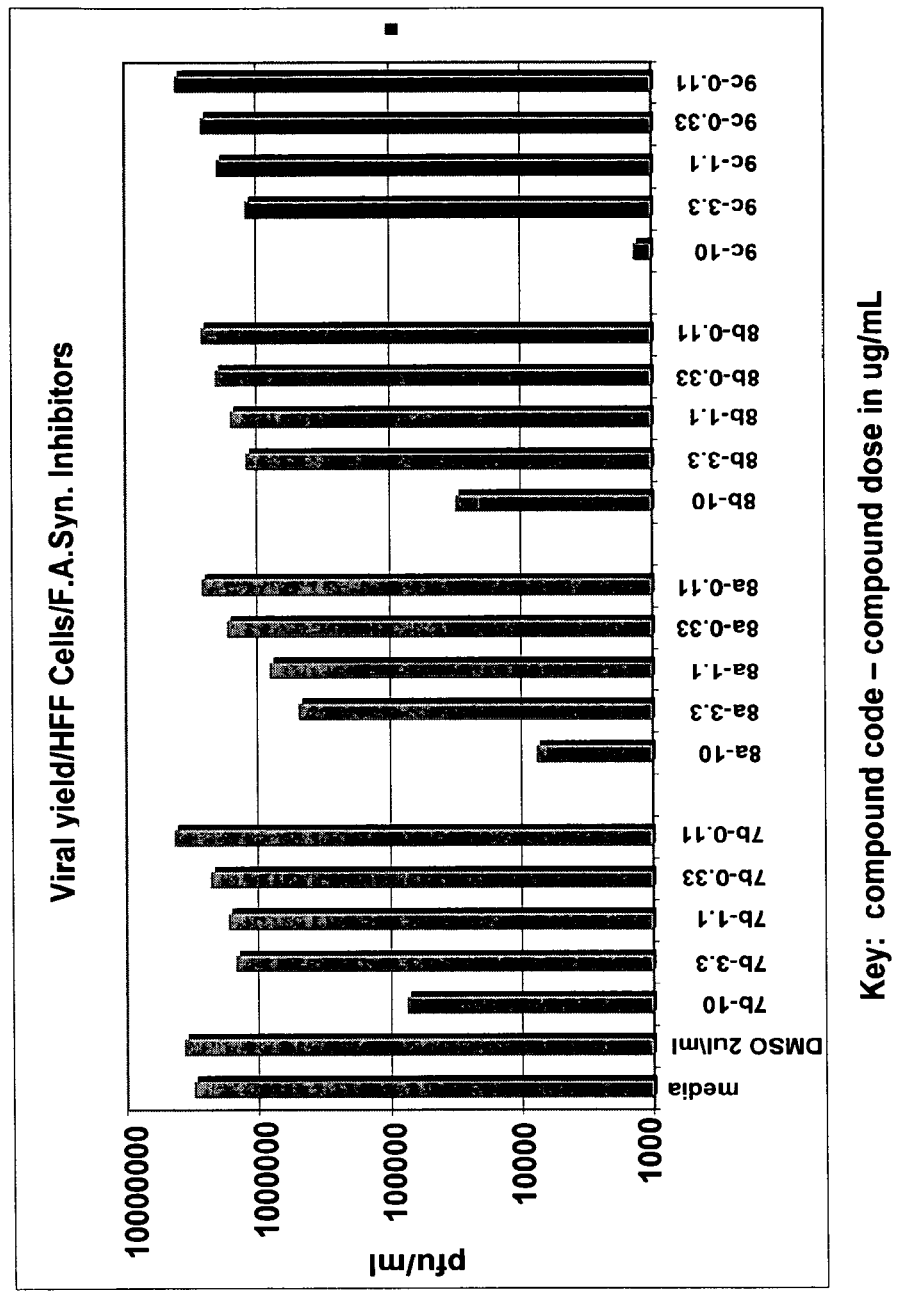

FIG. 20. Antiviral Effect of ACC Inhibitors.

FIG. 20 shows a bar graph plotting the effect of the indicated ACC inhibitor compounds on viral yield (pfu/ml). The bar graph corresponds to the raw data presented in Table 13. See Example 23.

Figure 21:
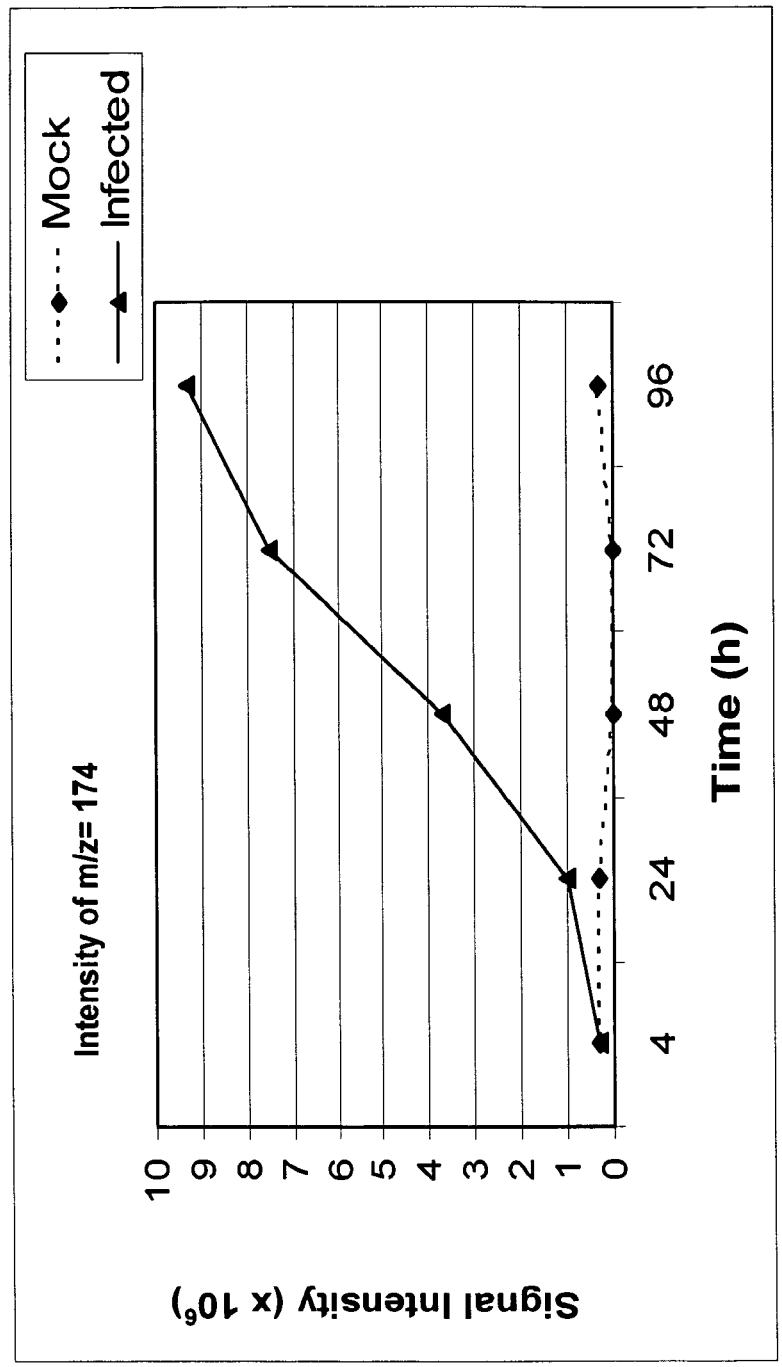

FIG. 21. Using High Resolution Mass Spectrometry to IdentifyMetabolic Pathways Up-Regulated by Viral Infection.

FIG. 21 shows data from an experiment analyzing extracts from cells mock infected or infected with HCMV by liquid chromatography-high mass-resolution mass spectrometry in full scan mode on an Orbitrap instrument. The graph plots the signal intensity versus time of extracts from cells mock infected or infected with HCMV. The experiment identified N-acetyl-aspartate (NAA) as a metabolite whose production increased in HCMV-infected cells. See Example 24.

Figure 22:
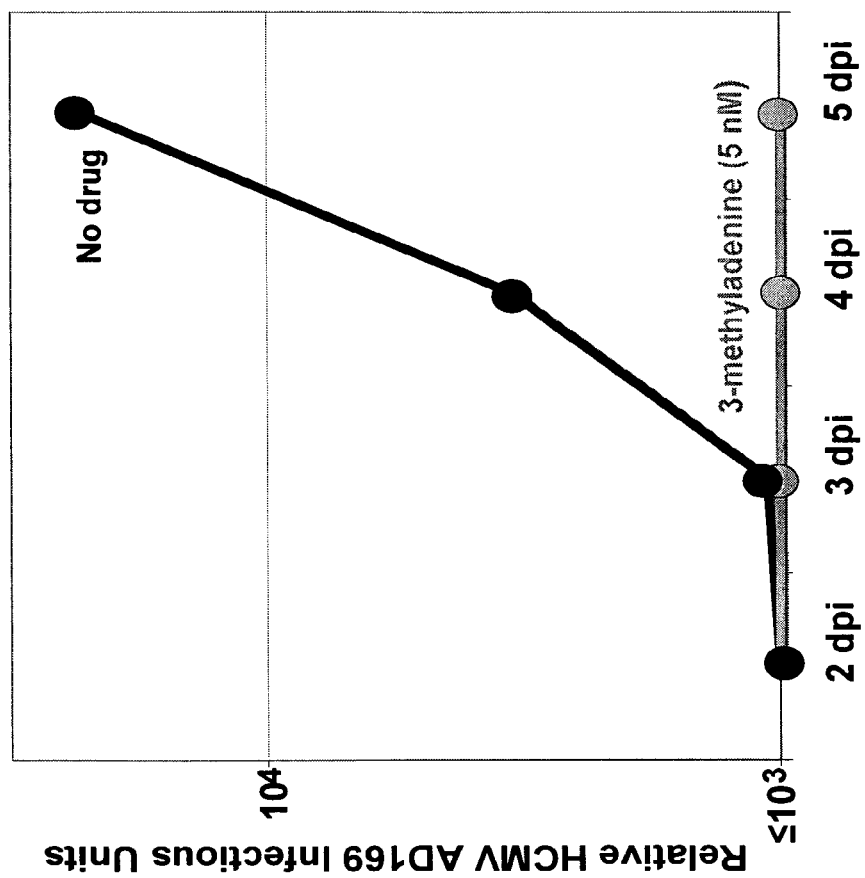

FIG. 22. 3-Methyladenine Inhibits Viral Replication of HCMV.

FIG. 22 shows a graph that plots the relative HCMV infectious units versus days post infection (dpi). The graph shows that 3-methyladenine, an inhibitor of class III PI(3) kinase, has antiviral activities. See Example 25.

5. DETAILED DESCRIPTION

Viral replication requires energy and macromolecular precursors derived from the metabolic network of the host cell. Using an integrated approach to profiling metabolic flux, the inventors discovered alterations of certain metabolite concentrations and fluxes in response to viral infection. Based on these discoveries, certain enzymes in the various metabolic pathways, especially those which serve as key "switches," were selected for intervention; i.e., as targets for redirecting the metabolic flux to disadvantage viral replication and restore normal metabolic flux profiles, thus serving as targets for antiviral therapies. Enzymes involved in initial steps in a metabolic pathway are preferred enzyme targets. In addition, enzymes that catalyze "irreversible" reactions or committed steps in metabolic pathways can be advantageously used as enzyme targets for antiviral therapy.

For example, viral infections that direct glycolytic outflow into fatty acid biosynthesis can be treated by blockade of fatty acid synthesis. While any enzyme involved in fatty acid biosynthesis can be used as the target, the enzymes involved in the committed steps for converting glucose into fatty acid are preferred; e.g., these include, but are not limited to acetyl CoA carboxylase (ACC), its upstream regulator AMP-activated protein kinase (AMPK), or ATP citrate lyase.

Elongases and/or related enzymes of fatty acid elongation, fatty acid desaturation enzymes, including but not limited to, stearoyl-CoA desaturases (SCDs), delta-6-desaturase, delta-5-desaturase, and enzymes that modulate cholesterol metabolism and/or lipid-related processes may also constitute key antiviral drug targets.

As another example, viral infections may alter nitrogen fluxes that direct ammonia incorporation. Enzyme targets of this metabolic pathway, including, without limitation, glutamate dehydrogenase and glutaminase, may be used to redirect nitrogen flow in virally infected cells.

The subsections below describe in more detail the target enzymes of the invention, compounds that inhibit such target enzymes and can thus be used as antiviral compounds, screening assays for identifying and characterizing new antiviral compounds, and methods for their use as antiviral therapeutics to treat and prevent viral infections.

5.1 Host Cell Target Enzymes

Any enzyme of a cellular metabolic pathway in which metabolite concentration and/or flux are modulated in response to viral infection is contemplated as a target for antiviral intervention. In particular embodiments, host enzymes involved in fatty acid biosynthesis and metabolism are targets for antiviral intervention. Based on the discovery that viruses modulate host metabolic fluxes and thereby interfere with the host cell's normal flow of energy, e.g., from glucose to lipid, host enzymes involved in such pathways have been identified as antiviral drug targets. Non-limiting examples of such enzymes which are targets for antiviral intervention are presented in Table 1.

The observed increase in acetyl-CoA flux (especially flux through cytosolic acetyl-CoA) and associated increase in de novo fatty acid biosynthesis, serve a number of functions for viruses, especially for enveloped viruses. For example, de novo fatty acid synthesis provides precursors for synthesis of phospholipid, and phospholipid contributes to the formation of the viral envelope, among other functions. Importantly, newly synthesized fatty acid and phospholipid may be required by the virus for purposes including control of envelope chemical composition and physical properties (e.g., phospholipid fatty acyl chain length and/or desaturation, and associated envelope fluidity). Pre-existing cellular phospholipid may be inadequate in absolute quantity, chemical composition, or physical properties to support viral growth and replication.

As such, inhibitors of any step of phospholipid biosynthesis may constitute antiviral agents. This includes steps linking initial fatty acid biosynthesis to the synthesis of fatty acyl-CoA compounds appropriate for synthesis of viral phospholipids. These steps include, but are not limited to, fatty acid elongation and desaturation. Fatty acid elongation takes the terminal product of fatty acid synthase (FAS), palmitoyl-CoA (a C16-fatty acid), and extends it further by additional two carbon units (to form, e.g., C18 and longer fatty acids). The enzyme involved is elongase. As formation of C18 and longer fatty acids is required for control of viral envelope chemical composition and physical properties, as well as for other viral functions, inhibitors of elongase may serve as inhibitors of viral growth and/or replication. Thus, in addition to Compounds for treatment of viral infection by inhibition of de novo fatty acid biosynthesis enzymes (e.g., acetyl-CoA carboxylase and fatty acid synthase), the present invention also includes Compounds for treatment of viral infection by inhibition of elongase and/or related enzymes of fatty acid elongation. Elongases, including, but not limited to alpha-linolenic acid specific elongase, have been described in the art, e.g., see U.S. Patent Application Publication Nos. US 2005/0089981 A1 and US 2005/00009140 A1, each of which is incorporated by reference herein in its entirety.

The principle pathway of production of monounsaturated fatty acids in mammals uses as major substrates palmitoyl-CoA (the product of FAS, whose production requires carboxylation of cytosolic acetyl-CoA by acetyl-CoA carboxylase [ACC]) and stearoyl-CoA (the first product of elongase). The major enzymes are Stearoyl-CoA Desaturases (SCD) 1-5 (also known generically as Fatty Acid Desaturase 1 or delta-9-desaturase). SCD isozymes 1 and 5 are expressed in primates including humans (Wang et al., Biochem. Biophys. Res. Comm. 332:735-42, 2005), and are accordingly targets for treatment of viral infection in human patients in need thereof. Other isozymes are expressed in other mammals and are accordingly targets for treatment of viral infection in species in which they are expressed. Thus, in addition to Compounds for treatment of viral infection by inhibition of de novo fatty acid biosynthesis enzymes (e.g., acetyl-CoA carboxylase and fatty acid synthase), the present invention also includes Compounds for treatment of viral infection by inhibition of fatty acid desaturation enzymes (e.g., SCD1, SCD5, as well as enzymes involved in formation of highly unsaturated fatty acids, e.g., delta-6-desaturase, delta-5-desaturase). Exemplary inhibitors of SCD are described in section 5.2.

As discussed above, control of lipid-related processes is essential to viral growth, replication, and/or other elements of infection. The importance of these processes derives in part from the need for viruses to control cellular membrane composition and/or physical properties (i.e., of the plasma membrane or intracellular membranous structures like endoplasmic reticulum), and in part from the need for enveloped viruses to control their envelope composition and/or physical properties. The previously unrecognized importance of this control was revealed in part via the observation of dramatically increased flux through metabolites involved in cholesterol biosynthesis, such as cytosolic acetyl-CoA, via the metabolomic and flux profiling experiments described herein. A key component of mammalian cell membranes is cholesterol (and its derivatives). Cholesterol, like fatty acyl chain length and desaturation, plays a key role in controlling membrane/envelope physical properties like fluidity, freezing point, etc. Cholesterol percentage, like the details of phospholipid composition, can also impact the properties of membrane proteins and/or the functioning of lipid signaling. As some or all of these events play a key role in viral infection, inhibitors or other modulators of cholesterol metabolism may serve as antiviral agents. For example, inhibitors of the enzymes acetyl-CoA acetyltransferase, HMG-CoA synthase, HMG-CoA reductase, mevalonate kinase, phosphomevalonate kinase, isopentyldiphosphate isomerase, geranyldiphosphate synthase, farnesyl-diphosphate synthase, farnesyl-diphosphate farnesyltransferase, squalene monooxigenase, lanosterol synthase, and associated demethylases, oxidases, reductase, isomerases, and desaturases of the sterol family may serve as antiviral agents. HMG-CoA reductase inhibitors and their structures are well known in the art. Exemplary HMG-CoA reductase inhibitors are described in section 5.2.

While inhibitors of fatty acid biosynthetic enzymes generally have utility in the treatment of viral infection, acetyl-CoA carboxylase (ACC) has specific properties that render it an especially valuable target for the treatment of viral infection. Notably, ACC is uniquely situated to control flux through fatty acid biosynthesis. The upstream enzymes (e.g., pyruvate dehydrogenase, citrate synthase, ATP-citrate lyase, acetyl-CoA synthetase), while potential antiviral targets, generate products that are involved in multiple reaction pathways, whereas ACC generates malonyl-CoA, which is a committed substrate of the fatty acid pathway. Acetyl-CoA synthetase and ATP-citrate lyase both have the potential to generate cytosolic acetyl-CoA. Accordingly, one may, in some circumstances, partially substitute for the other. In contrast, there is no adequate alternative reaction pathway to malonyl-CoA other than carboxylation of acetyl-CoA (the ACC reaction). In this respect, targeting of ACC more completely and specifically controls fatty acid biosynthesis than targeting of upstream reactions.

As an alternative to or in addition to targeting ACC, targeting FAS also enables adequate control of fatty acid de novo biosynthesis as a whole. A key difference between targeting of ACC versus targeting of FAS, is that the substrate of ACC (acetyl-CoA) is used in numerous pathways. Accordingly, targeting ACC does not necessarily lead to marked buildup of acetyl-CoA because other pathways can consume it. In contrast, the substrate of FAS (malonyl-CoA) is used largely by FAS. Accordingly, targeting of FAS tends to lead to marked buildup of malonyl-CoA. While such buildup may in some cases have utility in the treatment of viral infection, it may in other cases contribute to side effects. Such side effects are of particular concern given (1) the important signaling and metabolism-modulating functions of malonyl-CoA and (2) lack of current FAS inhibitors with minimal in vivo side effects in mammals. The inhibition of FAS with resulting elevation in intracellular malonyl-CoA can cause cell cycle arrest with a block to cellular DNA replication and onset of apoptosis (Pizer et al., Cancer Res. 56:2745-7, 1996; Pizer et al., Cancer Res. 58:4611-5, 1998; Pizer et al., Cancer Res. 60:213-8, 2000), and it has been suggested that this toxic response can potentially account for inhibition of virus replication by FAS inhibitors (Rassmann et al., Antiviral Res. 76:150-8, 2007). In contrast, ACC inhibitors such as TOFA are remarkably benign in mammals, see e.g., Gibson et al., Toxicity and teratogenicity studies with the hypolipidemic drug RMI 14,514 in rats. *Fundam. Appl. Toxicol.* 1981 January-Feburary; 1(1):19-25. For example, in rats, the oral LD50 of TOFA can be greater than 5,000 mg/kg and no adverse effects are observed at 100 mg/kg/day for 6 months. In addition, TOFA is not teratogenic in rats at 150 mg/kg/day. Non-limiting examples of ACC inhibitors are provided in section 5.2.

Of note, ACC exists as two isozymes in humans, ACC1 and ACC2. Compounds described herein include, but are not limited to isozyme specific inhibitors of ACC. Compounds that are isozymes selective are described in section 5.2.

Depending on the specific viral infection and the specific infection site (e.g., brain, peripheral nervous system, skin, connective tissue, liver, heart, adipose, etc.), targeting of only a single isozymes of ACC may optimize the therapeutic antiviral benefit of ACC inhibitor therapy relative to its risk (which will presumably be reduced by use of an isozymes-specific agent). In general, the preferred isozyme to target will be (1) the dominant isozymes in the particular infected tissue(s) of greatest concern and/or (2) the isozyme whose activity is more strongly upregulated by the particular virus of interest.

In particular embodiments, host enzymes involved in the glycolysis pathway are targets for antiviral intervention. In one embodiment, host enzymes of the tricarboxylic acid (TCA) cycle are targeted for antiviral intervention. In one embodiment, host enzymes involved in fatty acid metabolism and biosynthesis are targets for antiviral intervention. In one embodiment, host enzymes involved in fatty acid oxidation are targets for antiviral intervention. In some embodiments, host enzymes involved in fatty acid biosynthesis are targets for antiviral intervention. In one embodiment, host enzymes involved in cholesterol biosynthesis and metabolism are targets for antiviral intervention. In an embodiment, host enzymes involved in glucose transport are targets for antiviral intervention. In one embodiment, cellular components that are involved in ion homeostasis and energy transport across barriers, such as the proton ATPase, are viable targets for antiviral intervention in accordance with our discovery that viruses modulate host metabolic fluxes. Exemplary target enzymes of the invention are listed in Table 1. Other enzymes in these or other pathways related to cellular metabolism are also potential targets of the compounds of the invention. In some embodiments, the enzyme is not an enzyme of fatty acid biosynthesis. In some embodiments of the invention, the target enzyme is not an enzyme involved in fatty acid breakdown. In certain embodiments, the enzyme target is not involved in cholesterol biosynthesis or metabolism. In some embodiments, the enzyme to be targeted in not part of the glycolysis pathway. In particular embodiments, the enzyme is not part of the TCA cycle. In some embodiments, the enzyme target is not fatty acid synthase. In some embodiments, the enzyme is not ATP citrate lyase. In some embodiments, the enzyme target is not acetyl-CoA carboxylase. In some embodiments, the target is not AMP-activated protein kinase. In some embodiments, the enzyme is not Carnitine Palmitoyl transferase (CPT I). In some embodiments, the enzyme is not Malonyl-CoA decarboxylase. In some embodiments, the enzyme is not methylmalonyl-CoA mutase. In some embodiments, the enzyme is not Glutamate Dehydrogenase. In some embodiments, the enzyme is not HMG-CoA synthase. In some embodiments, the enzyme to be targeted for antiviral intervention is not lysophosphatidic acid acetyltransferase or lysophosphatidic acid acyltransferase. In other embodiments, the enzyme is not a stearoyl-CoA desaturase (SCD). In certain embodiments, the enzyme is not delta-6-desaturase. In some embodiments, the enzyme is not delta-5-desaturase.

In certain embodiments, host enzymes involved in the production phopholipids and/or the regulation of phospholipid activities are targets for antiviral intervention. Phospholipid species occur with a diversity of head groups (e.g., choline, serine, inositol, etc.). Production of these species depends on the availability of fatty acid, glycerol, and the head group. Accordingly, inhibition of assimilation or biosynthesis of any of these chemical moieties in virally infected cells (or in cells that serve to feed virally infected cells) can have antiviral effects. Furthermore, inhibition of the condensation of these components to produce phospholipid, or inhibition of subsequent metabolism of the resulting phospholipid product, can also have antiviral effects.

Among the various phospholipid species, those with inositol-containing head groups are of particular importance during viral infection. Metabolomic data indicate that inositol is specifically depleted by HCMV infection of human fibroblasts. This depletion is particularly striking given that inositol is present in the media used to grow the fibroblasts. In light of the other data contained herein, this depletion of inositol likely indicates its virally-induced consumption for synthesis of inositol-phospholipid species. The inventors have recently found that certain inositol-containing species play an essential role in the replication of HCMV. These include phosphatidylinositol and phosphatidylinositol (3)-phosphate. Accordingly, in certain embodiments, Compounds described herein are inhibitors of viral replication that target one or more steps of the assimilation or metabolism of inositol or inositol-containing metabolites and/or phospholipids. See Example 25, section 6.25.1. In some embodiments, methods of treating viral infection described herein comprise administering a Compound to a subject suffering from a viral infection. In specific embodiments the methods of treating viral infection in a subject suffering from a viral infection comprise inhibiting a class III PI(3)K with the Compound. In other embodiments, Compounds described herein are inhibitors of viral replication that sequester inositol-containing chemical species and thereby block their normal essential role during viral infection. See Example 25, section 6.25.2. In certain embodiments, the methods of treating viral infection in a subject suffering from a viral infection comprise sequestering PI(3)P with the Compound.

Phosphoinnositide 3-kinases (PI(3)Ks) are nonlimiting examples of targets of one or more steps of the assimilation or metabolism of inositol or inositol-containing metabolites and/or phospholipids. PI(3)Ks are a family of kinases that phosphorylate the inositol ring of phosphoinositides (see, e.g., Toker and Cantley, Nature 387:673-676, 1997). PI3Ks are classified into three classes on the basis of their structural characteristics and substrate specificities. Class I enzymes are heterodimers comprising a p110 catalytic subunit and a p85 or p101 regulatory subunit, and are activated by tyrosine kinase-based signaling pathways or heterotrimeric G protein-based signaling pathways. Class II enzymes are large enzymes (>200 kDa) characterized by a C2 domain in their C terminus. Class III enzymes that are homologous to Vps34p of *Saccharomyces cerevisiae* have a substrate specificity restricted to PtdIns and produce PtdIns(3)P (see, e.g., Schu et al., Science 260:88-91, 1993). Class III PI(3)K, also known as human vaculolar protein sorting 34 [hVps34], phosphorylates the 3'-hydroxyl group on the inositol ring of PI to produce PI(3)P. In specific embodiments, the target is a class III PI(3)K (also known as human vaculolar protein sorting 34 (hVps34)).

In some embodiments, the target is not a phosphoinnositide 3-kinase. In other embodiments, the target is not a class III PI(3)K.

As discussed above, lipid-related processes are essential to viral growth, replication and/or other elements of infection. Consequently, it is likely that multiple cellular enzymes that function in lipid metabolism are needed for successful infection, and it is possible that simultaneous inhibition of multiple enzymes (e.g., two or more different enzymes) will produce a synergistic inhibition of infection or allow the use of lower doses of each Compound to achieve a desirable therapeutic effect. Accordingly, the present invention relates to the prevention and treatment of viral infection in a mammal in need thereof, via administering to the mammal two or more Compounds described herein, wherein each Compound targets one or more different enzymes described herein. In some embodiments, such combination therapy is sequential; in other embodiments, it is simultaneous. In some embodiments, the two or more agents are formulated together to create a composition comprising two or more Compounds for the prevention and/or treatment of viral infection via modulation of host cell lipid and/or cholesterol metabolism. In some embodiments, the dose of one of the Compounds is substantially less, e.g., 1.5, 2, 3, 5, 7, or 10-fold less, than required when used independently for the prevention and/or treatment of viral infection. In some embodiments, the dose of both agents is reduced by 1.5, 2, 3, 5, 7, or 10-fold or more.

Exemplary pairs of enzymes to inhibit in combination include, but are not limited to, ACC and citrate lyase; ACC and FAS; ACC and elongase; ACC and SCD; ACC and HMG-CoA reductase; FAS and HMG-CoA reductase; elongase and HMG-CoA reductase; SCD and HMG-CoA reductase; elongase and SCD; and acetyl-CoA synthetase and ATP-citrate lyase.

Exemplary host cell pathways and target enzymes are listed in Table 1.

TABLE 1

Host Cell Pathways and Target Enzymes

| Pathways | Enzyme |
|---|---|
| Fatty Acid Biosynthesis | ATP citrate lyase |
| | ATP citrate lyase I |
| | HMG-CoA synthase |
| | Acetyl-CoA carboxylase (ACC) |
| | Fatty acid synthase |
| | Fatty acid synthase keto-acyl synthase domain |
| | Fatty acid synthase thioesterase domain |
| | Lysophosphatidic acid acyltransferase-beta |
| | Lysophosphatidic acid acetyltransferase-beta |
| | Lysophosphatidic acid acyltransferase |
| | Malonyl-CoA decarboxylase |
| | AMP-activated protein kinase (AMPK) |
| | Fatty acid elongases or ELOVL (elongation of very long chain fatty acid) |
| | Stearoyl - CoA desaturases 1-5 |
| | Delta-6-desaturase |
| | Delta-5-desaturase |
| Fatty Acid Metabolism | methylmalonyl Coenzyme A mutase |
| | acetyl-Coenzyme A carboxylase beta |
| | acyl-Coenzyme A oxidase 2, branched chain |
| | putative acyl-CoA dehydrogenase |
| | acyl-Coenzyme A dehydrogenase, short/branched chain |

TABLE 1-continued

Host Cell Pathways and Target Enzymes

| Pathways | Enzyme |
|---|---|
| | putative acyl-CoA dehydrogenase |
| | xenobiotic/medium-chain fatty acid:CoA ligase |
| | enoyl Coenzyme A hydratase domain containing 3 |
| | phospholipid scramblase 1 |
| | phospholipid scramblase 2 |
| | phospholipid scramblase 4 |
| | fatty acid desaturase 1 |
| | Carnitine Palmitoyl transferase (CPT) |
| | fatty acid binding protein 5 (psoriasis-associated) |
| | fatty acid binding protein 5 (psoriasis-associated) |
| | fatty acid binding protein 5 (psoriasis-associated) |
| | fatty acid binding protein 5 (psoriasis-associated) |
| | fatty acid binding protein 3, muscle and heart (mammary-derived growth inhibitor) |
| Glucose Transport | GLUT4 |
| Glycolysis | glucose phosphate isomerase |
| | triosephosphate isomerase 1 |
| | phosphoglycerate kinase 1 |
| | enolase 1, (alpha) |
| | pyruvate kinase, muscle |
| | AMP-activated protein kinase (AMPK) |
| TCA | aconitase |
| | isocitrate dehydrogenase |
| | succinate-CoA ligase |
| | succinate dehydrogenase |
| | malate dehydrogenase |
| | malic enzyme |
| Proton ATPase | F0 complex, subunit b, isoform 1 |
| | F0 complex, subunit c (subunit 9) isoform 3 |
| | F0 complex, subunit c (subunit 9), isoform 1 |
| | F0 complex, subunit e |
| | F0 complex, subunit F6 |
| | F0 complex, subunit g |
| | F1 complex, alpha subunit, isoform 1 |
| | F1 complex, beta polypeptide |
| | F1 complex, epsilon subunit |
| | F1 complex, O subunit |
| Cholesterol Synthesis/ Metabolism | acetyl-CoA acetyltransferase |
| | HMG-CoA Synthase |
| | HMG-CoA Reductase |
| | isopentyldiphosphate isomerase |
| | mevalonate kinase |
| | phosphomevalonate kinase |
| | geranyl-diphosphate synthase |
| | farnesyl-diphosphate synthase |
| | farnesyl-diphosphate farnesyltransferase |
| | squalene monooxygenase |
| | lanosterol synthase |
| | Squalene epoxidase |
| | Squalene Oxidocyclase |
| Miscellaneous | lactate dehydrogenase B |
| | dicarbonyl/L-xylulose reductase |
| | hydroxyprostaglandin dehydrogenase 15-(NAD) |
| | ribulose-5-phosphate-3-epimerase |
| | glutamate dehydrogenase |
| | glutaminase |
| | phospholipase A2 |
| | cyclooxygenase 1 |
| | cyclooxygenase 2 |
| | phosphoinositide 3-kinases |

5.2 Compounds

Compounds that can be used in the methods described herein for treatment or prevention of a virus infection, include, but are not limited to, organic and inorganic molecules, peptides and peptide analogs, small molecules, and nucleic acid molecules (e.g., RNA interference (RNAi) molecules, including small interfering RNA (siRNA), micro-RNA (miRNA), short hairpin RNA (shRNA), etc.).

Illustrative Compounds are set forth below.

In one embodiment, a Compound has the following structure (I) (Structure identifiers are also referred to herein alternatively as "Formulas"):

(I)

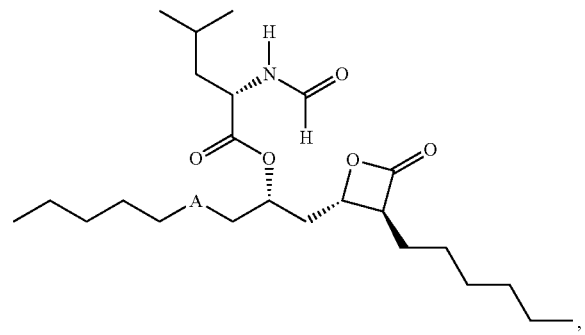

where A is —(CH$_2$)$_x$— or

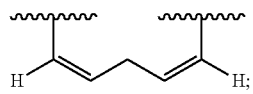

where x is from 0 to 6.

Compounds of structure (I) can be made using organic synthesis techniques known to those skilled in the art, as well as by the methods described by Hadvary et. al. (U.S. Pat. No. 4,958,089), which is incorporated herein by reference in its entirety (particularly at column 8, line 1 to page 11, line 10). Further, specific examples of these compounds can be found in this publication.

A specific example of a Compound of structure (I) is:

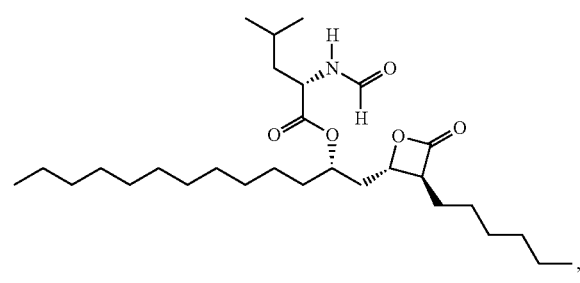 [SMILES: CCCCCCCCCCC[C@@H](C[C@@H]1OC(=O)[C@H]1CCCCCC)OC(=O)[C@H](CC(C)C)NC=O]

which is also identified as orlistat.

In another embodiment a Compound of structure (I) is:

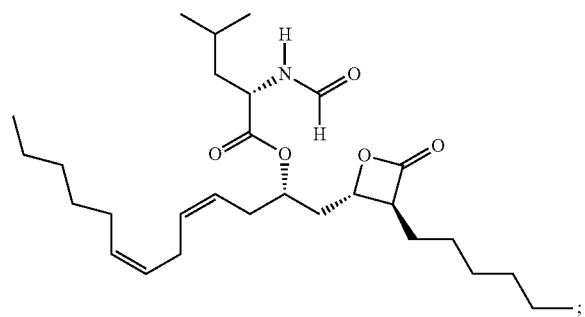

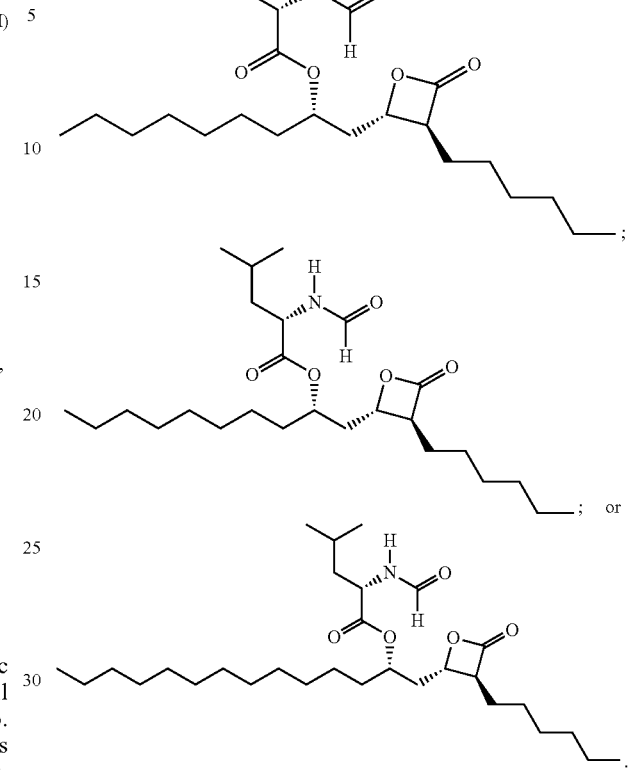

In one embodiment, the Compound of structure (I) is not Orlistat.

In one embodiment, a Compound has the following structure (II):

(II)

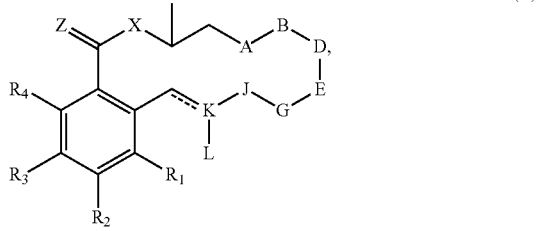

wherein the dotted line represents a bond, whereby a double bond is present, or the dotted line is absent, whereby a single bond is present;

$R_1$ is hydrogen, halogen, an aliphatic, heteroaliphatic, aryl, heteroaryl, alkylaryl, or alkylheteroaryl moiety, or $N(R_A)_2$, wherein each occurrence of $R_A$ is independently hydrogen, a protecting group, or an aliphatic, heteroaliphatic, aryl, heteroaryl, alkylaryl, or alkylheteroaryl moiety;

$R_2$ is hydrogen, halogen, cyano, —$OR_B$, —$N(R_B)_2$, —$SR_B$, —$O(C=O)R_B$, —$N(R_B)(C=O)(R_B)$, —$C(O)R_B$, —$C(O)OR_B$, —$CON(R_B)_2$, —$OCO_2R_B$, or an aliphatic, heteroaliphatic, aryl, heteroaryl, alkylaryl, or alkylheteroaryl moiety, wherein each occurrence of $R_B$ is independently hydrogen, a protecting group or an aliphatic, heteroaliphatic, aryl, heteroaryl, alkylaryl, or alkylheteroaryl moiety;

$R_3$ is hydrogen, halogen, an aliphatic, heteroaliphatic, aryl, heteroaryl, alkylaryl, or alkylheteroaryl moiety, or —N($R_C$)$_2$, wherein each occurrence of R is independently hydrogen, a protecting group, or an aliphatic, heteroaliphatic, aryl, heteroaryl, alkylaryl, or alkylheteroaryl moiety;

$R_4$ is hydrogen, halogen, cyano, —O$R_D$, —N($R_D$)$_2$, —S$R_D$, —O(C=O)$R_D$, —N($R_D$)(C=O)($R_D$), —C(O)$R_D$, —C(O)O$R_D$, —CON($R_D$)$_2$, —OCO$_2R_D$, or an aliphatic, heteroaliphatic, aryl, heteroaryl, alkylaryl, or alkylheteroaryl moiety, wherein each occurrence of RD is independently hydrogen, a protecting group or an aliphatic, heteroaliphatic, aryl, heteroaryl, alkylaryl, or alkylheteroaryl moiety;

Z is O, S or N$R_E$, wherein $R_E$ is hydrogen, a protecting group, an aliphatic, heteroaliphatic, aryl, heteroaryl, alkylaryl, or alkylheteroaryl moiety, or O$R_F$, wherein $R_F$ is hydrogen, a protecting group, an aliphatic, heteroaliphatic, aryl, heteroaryl, alkylaryl, or alkylheteroaryl moiety;

X is O, S or N$R_G$, wherein $R_G$ is hydrogen or lower alkyl;

A and B together represent

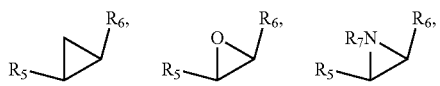

—CH$R_5$—CH$R_6$—, —C$R_5$=C$R_6$—, wherein $R_5$ and $R_6$ are each independently hydrogen, halogen, cyano, —O$R_J$, —N($R_J$)$_2$, —S$R_J$, —O(C=O)$R_J$, —O(S=O)$R_J$, —N($R_J$)(C=O)($R_J$), —C(=O)$R_J$, —C(=O)O$R_B$, —CON($R_J$)$_2$, —OCO$_2R_J$, —OS(=O)O$R_J$ or an aliphatic, heteroaliphatic, aryl, heteroaryl, alkylaryl, or alkylheteroaryl moiety, wherein each occurrence of $R_J$ is independently hydrogen, a protecting group, or an aliphatic, heteroaliphatic, aryl, heteroaryl, alkylaryl, or alkylheteroaryl moiety, and wherein $R_7$ is hydrogen, a protecting group, —O$R_K$, —S$R_K$, —C(O)O$R_K$, —C(O)N$R_K$, —S(O)$_2R_K$, —O(C=O)$R_K$, —N($R_K$)(C=O)($R_K$), —C(O)$R_K$, —C(O)O$R_K$, —CON($R_K$)$_2$, —OCO$_2R_K$, or an aliphatic, heteroaliphatic, aryl, heteroaryl, alkylaryl, or alkylheteroaryl moiety, wherein each occurrence of $R_K$ is independently hydrogen, a protecting group or an aliphatic, heteroaliphatic, aryl, heteroaryl, alkylaryl, or alkylheteroaryl moiety, or when A and B together represent-CH$R_5$—CH$R_6$—, $R_5$ and $R_6$ taken together represent a substituted or unsubstituted 3-7 membered aliphatic, heteroaliphatic, aryl or heteroaryl ring, D and E together represent-CH$R_8$—CH$R_9$—, —C$R_8$=C$R_9$—, wherein $R_8$ and $R_9$ are each independently hydrogen or lower alkyl;

G and J together represent —CH$R_{10}$—CH$R_{11}$—, —C$R_{10}$=C$R_{11}$, wherein $R_{10}$ and $R_{11}$ are each independently hydrogen or lower alkyl;

K and L together represent C=O, C=S, CH—CH$_3$, CH—CH($R_L$)$_2$, C=C ($R_L$)$_2$, —CH$_2$—, —C(=S(CH$_2$)$_3$S—)—, CH—O$R_L$, CH—S$R_L$, CH—N($R_L$)$_2$, CH—N($R_L$)(C=O)($R_L$), C=N—O—$R_L$, CH—N=O, C=C($R_L$)—N($R_L$)$_2$, C=N—$R_L$, C=N—N—($R_L$)$_2$, or, if the dotted line - - - represents a bond, whereby a double bond is present, then K and L together represent C—N($R_L$)$_2$, wherein each occurrence of $R_L$ is independently hydrogen, a protecting group, an aliphatic, heteroaliphatic, aryl, heteroaryl, alkylaryl, or alkylheteroaryl moiety, or two occurrences of $R_L$ taken together represent a 3 to 7 membered cyclic aliphatic, heteroaliphatic, aromatic or heteroaromatic moiety; whereby each of the foregoing aliphatic and heteroaliphatic moieties may independently be substituted or unsubstituted, cyclic or acyclic, or branched or unbranched, and each aryl, heteroaryl, alkylaryl, and alkylheteroaryl moiety may be substituted or unsubstituted; wherein one or any two of $R_1$, $R_A$, $R_2$, $R_B$, $R_3$, $R_C$, $R_4$, $R_D$, $R_S$, $R_6$, $R_J$ or $R_L$ are optionally a linker covalently bonded to a compound selected from the group consisting of radicicol, monocillin, analogues of radicicol, monocillin, geldanamycin, analogues of geldanamycin, and steroids; and pharmaceutically acceptable derivatives thereof.

Compounds of structure (II) can be made using organic synthesis techniques known to those skilled in the art, as well as by the methods described in Danishefsky et. al. (International Publication No. WO 02/16369), which is incorporated herein by reference in its entirety (particularly at page 69, line 25 to page 87, line 28). Further, specific examples of these compounds can be found in this publication.

A specific example of a Compound of structure (II) is:

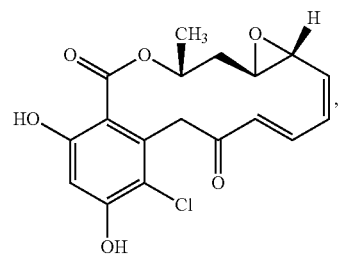 [SMILES: C[C@@H]1C[C@H]2O[C@@H]2/C=C\C=C\C(=O)Cc2c(Cl)c(O)cc(O)c2C(=O)O1]

which is identified as radicicol and monorden.

In another embodiment, the Compound of structure (II) is:

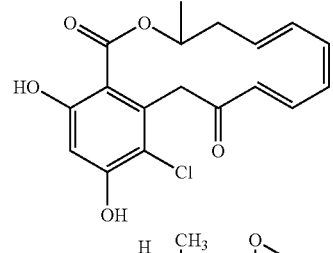

;

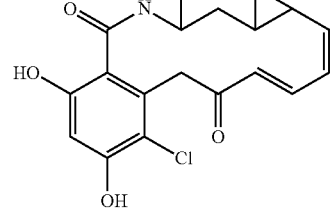

;

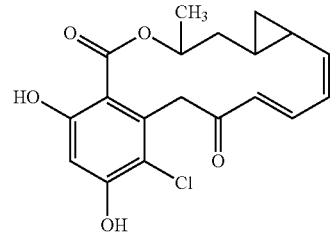

;

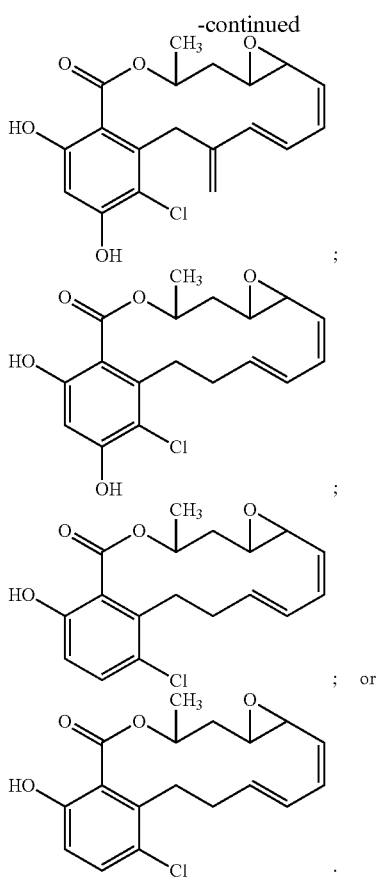

In one embodiment, the Compound of structure (II) is not radicicol.

In one embodiment, a Compound has the following structure (III):

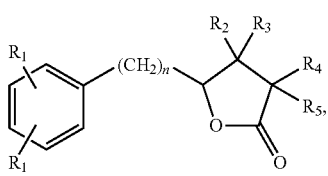
(III)

in which, each group $R_1$ is independently a lipophilic and/or electron withdrawing group;

n is 5 to 8; and either $R_2$ and $R_3$ are both hydrogen, $R_4$ is hydrogen or hydroxy and $R_5$ is $CH(R_6)R_7$ in which $R_6$ is hydrogen or hydroxy and $R_7$ is a carboxyl group or a carboxylic acid ester group hydrolysable to a carboxyl group; or $R_4$ is hydrogen and $R_5$ is hydrogen or hydroxy, $R_2$ is hydroxy and $R_3$ is a carboxyl group or a carboxylic acid ester group hydrolysable to a carboxyl group; or $R_2$ and $R_3$ are hydrogen and $R_4$ and $R_5$ together form a group $=C(R_6)R_7$ in which $R_6$ and $R_7$ are as defined above, and salts thereof.

Compounds of structure (III) can be made using organic synthesis techniques known to those skilled in the art, as well as by the methods described in Gribble et. al. (U.S. Pat. No. 5,447,954), which is incorporated herein by reference in its entirety (particularly at column 10, line 37 to column 24, line 50). Further, specific examples of these compounds can be found in this publication.

A specific example of a Compound of structure III is:

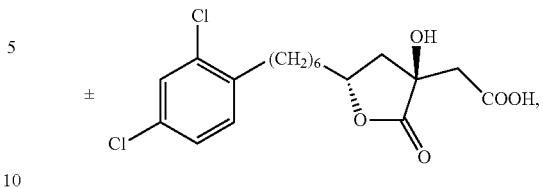

which is identified by the compound name SB-204990.

In another embodiment the compound of structure (III) is:

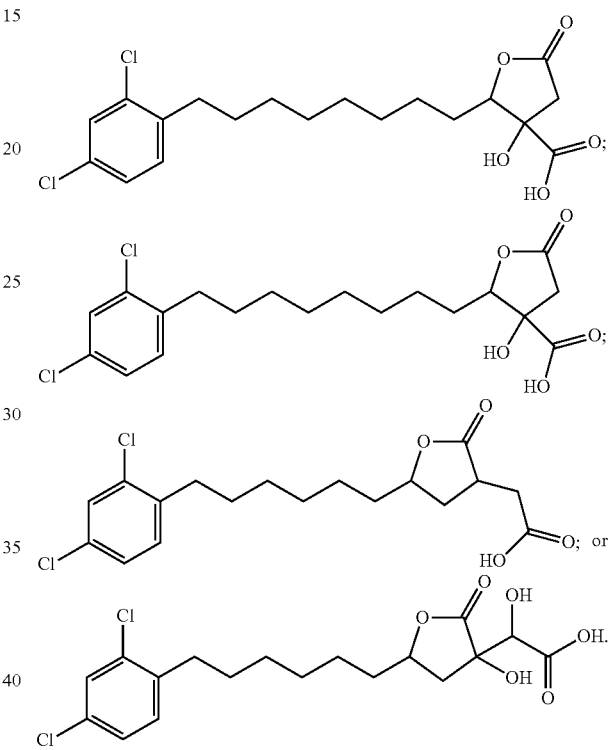

In one embodiment, the Compound of structure (III) is not SB-204990.

In one embodiment the compound has a structure (IV):

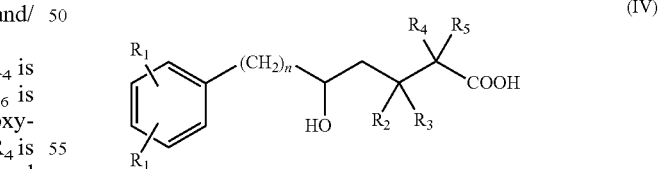
(IV)

in which each group $R_1$ is independently a lipophilic and/or electron withdrawing group;

where n is 5 to 8; and either $R_2$ and $R_3$ are both hydrogen, $R_4$ is hydrogen or hydroxy and $R_5$ is $CH(R_6)COOH$ in which $R_6$ is hydrogen or hydroxy; or $R_4$ is hydrogen and $R_5$ is hydrogen or hydroxy, $R_2$ is hydroxy and $R_3$ COOH; or $R_2$ and $R_3$ are hydrogen and $R_4$ and $R_5$ together form a group $=C(R_6)COOH$ in which $R_6$ is as defined above, and pharmaceutically acceptable salts thereof.

Compounds of structure (IV) can be made using organic synthesis techniques known to those skilled in the art, as well as by the methods described in Gribble et. al. (U.S. Pat. No. 5,447,954), which is incorporated herein by reference in its entirety (particularly at column 10, line 37 to column 24, line 50). Further, specific examples of these compounds can be found in this publication.

A specific example of a Compound of structure (IV) is:

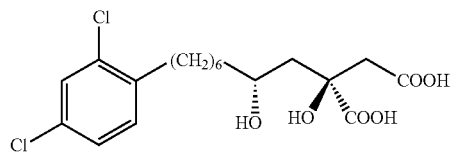

which is identified by the compound name SB-201076.

In another embodiment a Compound of structure (IV) is:

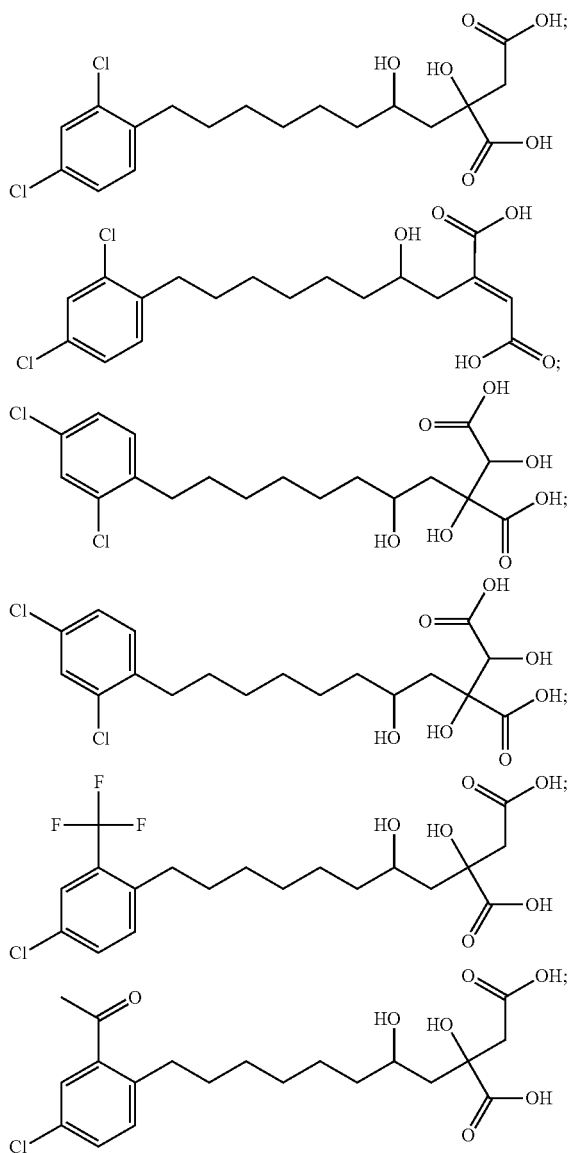

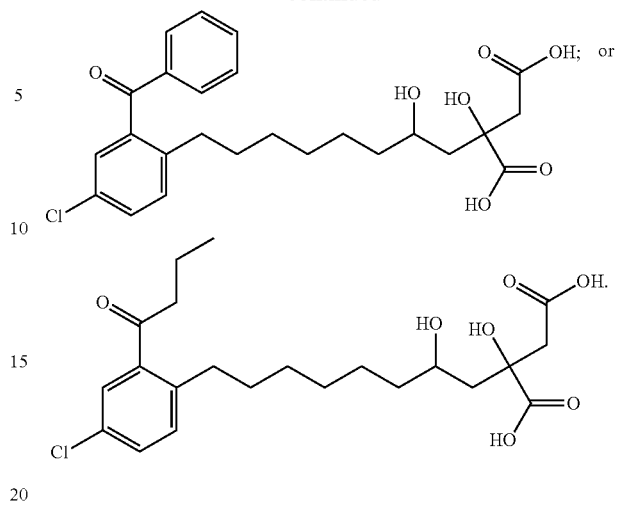

In one embodiment, the Compound of structure (IV) is not SB-201076.

In one embodiment, a Compound has the following structure (V):

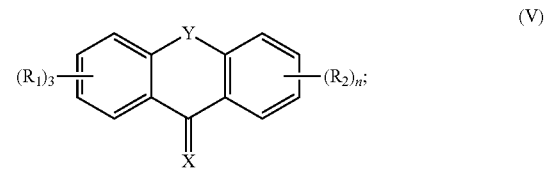

(V)

wherein: Y is selected from the group consisting of CH, $CH_2$, N, C=O, O, S, and $NR_3$, wherein $R_3$ is selected from the group consisting of H, alkyl, alkenyl, alkynyl, aryl, alkoxyl, and Y can be present or absent;

X is O, S, and $NR_4$, wherein each $R_4$ is independently selected from the group consisting of H, alkyl, alkenyl, alkynyl, aryl, and alkoxyl.

$R_1$ is selected from the group consisting of alkyl, halo, hydroxyl, alkoxy, aryloxyl, and alkoxy;

$R_2$ is selected from the group consisting of H, alkyl, halo, hydroxyl, alkoxy, aryloxyl, and alkoxy;

n is an integer from 0-3.

Compounds of structure (V) can be made using organic synthesis techniques known to those skilled in the art, as well as by the methods described in (International Patent Publication WO 2005/051296), which is incorporated herein by reference in its entirety (particularly at page 38, line 4 to page 49, line 11). Further, specific examples of these compounds can be found in this publication.

A specific example of a Compound of structure V is:

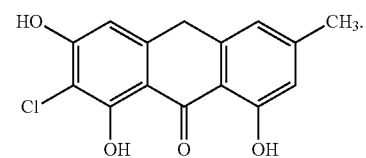

In another embodiment a Compound of structure (V) is:

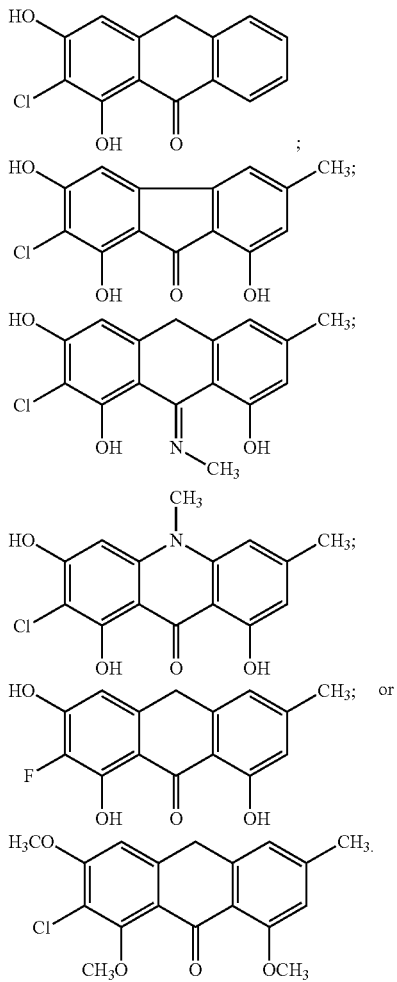

In one embodiment, the Compound of structure (V) is not:

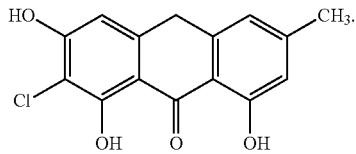 [SMILES: Cc1cc(O)c2c(c1)Cc1cc(O)c(Cl)c(O)c1C2=O]

In one embodiment, a Compound has the following structure (VI):

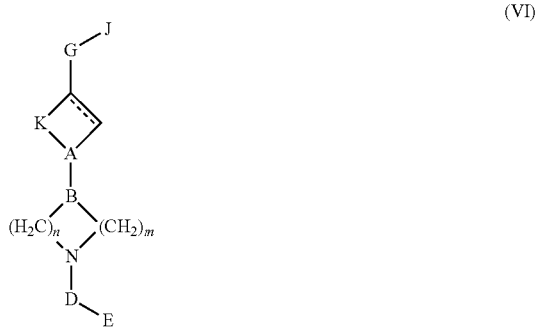

(VI)

wherein A-B is N—CH or CH—N; K is (CH$_2$)r wherein r is 2, 3 or 4; m and n are each independently 1, 2 or 3 when A-B is N—CH or m and n are each independently 2 or 3 when A-B is CH—N; the dashed line represents the presence of an optional double bond;

D is carbonyl or sulfonyl;

E is either a) a bicyclic ring consisting of two fused fully unsaturated five to seven membered rings, taken independently, each of said rings optionally having one to four heteroatoms selected independently from oxygen, sulfur and nitrogen, or b) a tricyclic ring consisting of two fused fully unsaturated five to seven membered rings, taken independently, each of said rings optionally having one to four heteroatoms selected independently from oxygen, sulfur and nitrogen, said two fused rings fused to a third partially saturated, fully unsaturated or fully saturated five to seven membered ring, said third ring optionally having one to four heteroatoms selected independently from oxygen, sulfur and nitrogen; or c) a tetracyclic ring comprising a bicyclic ring consisting of two fused fully unsaturated five to seven membered rings, taken independently, each of said rings optionally having one to four heteroatoms selected independently from oxygen, sulfur and nitrogen, said bicyclic ring fused to two fully saturated, partially saturated or fully unsaturated five to seven membered monocyclic rings taken independently, each of said rings optionally having one to four heteroatoms selected independently from oxygen, sulfur and nitrogen or said bicyclic ring fused to a second bicyclic ring consisting of two fused fully saturated, partially saturated or fully unsaturated five to seven membered rings, taken independently, each of said rings optionally having one to four heteroatoms selected independently from oxygen, sulfur and nitrogen; or d) a teraryl ring comprising a fully unsaturated five to seven membered ring, said ring optionally having one to four heteroatoms selected independently from oxygen, sulfur and nitrogen, and said ring di-substituted independently with a fully unsaturated five to seven membered ring to form a teraryl nonfused ring system, each of said substituent rings optionally having one to four heteroatoms selected independently from oxygen, sulfur and nitrogen, wherein said E bi-, tri- or tetra cyclic ring or teraryl ring is optionally mono-, di- or tri-substituted independently on each ring used to form the bi-, tri- or tetra cyclic ring or teraryl ring with halo, hydroxy, amino, cyano, nitro, oxo, carboxy, (C$_1$-C$_6$) alkyl, (C$_2$-C$_6$) alkenyl, (C$_2$-C$_6$) alkynyl, (C$_1$-C$_6$) alkoxy, (C$_1$-C$_4$) alkylthio, (C$_1$-C$_6$) alkoxycarbonyl, wherein said E bi-, tri- or tetra-cyclic-ring or teraryl ring is optionally mono-substituted with a partially saturated, fully saturated or fully unsaturated three to eight membered ring R$_{10}$ optionally having one to four heteroatoms selected independently from oxygen, sulfur and nitrogen or a bicyclic ring R" consisting of two fused partially saturated, fully saturated or fully unsaturated three to eight membered rings, taken independently, each of said rings optionally having one to four heteroatoms selected independently from oxygen, sulfur and nitrogen, said R$_{10}$ and R" rings optionally additionally bridged and said R$_{10}$ and R" rings optionally linked through a fully saturated, partially unsaturated or fully unsaturated one to four membered straight or branched carbon chain wherein the carbon (s) may optionally be replaced with one or two heteroatoms selected independently from oxygen, nitrogen and sulfur, provided said E bicyclic ring has at least one substituent and the E bicyclic ring atom bonded to D is carbon; wherein said R$_{10}$ or R"ring is optionally mono-, di- or tri-substituted independently with halo, hydroxy, amino, cyano, nitro, oxo, carboxy, (C$_1$-C$_6$) alkyl, (C$_2$-C$_6$) alkenyl, (C$_2$-C$_6$) alkynyl, (C$_1$-C$_6$) alkoxy, (C$_1$-C$_4$)alkylthio, (C$_1$-C$_6$) alkoxycarbonyl, (C$_1$-C$_6$) alkylcarbonyl, (C$_1$-C$_6$) alkylcarbonylamino, or mono-N- or di-N,N—(C$_1$-C$_6$) alkylamino or mono-N- or di-N,N—($C_1$-$C_6$) alkylaminocarbonyl wherein said ($C_1$-$C_6$) alkyl and ($C_1$-$C_6$) alkoxy substituents are also optionally mono-, di- or tri-substituted independently with halo, hydroxy, ($C_1$-$C_6$) alkoxy, amino, mono-N- or di-N,N—($C_1$-$C_6$) alkylamino or from one to nine fluorines;

G is carbonyl, sulfonyl or $CR_7R_8$; wherein $R_7$ and $R_8$ are each independently H, ($C_1$-$C_6$) alkyl, ($C_2$-$C_6$) alkenyl or ($C_2$-$C_6$) alkynyl or a five to seven membered partially saturated, fully saturated or fully unsaturated ring optionally having one heteroatom selected from oxygen, sulfur and nitrogen; J is OR', $NR_2R_3$ or $CR_4R_5R_6$; wherein R', $R_2$ and $R_3$ are each independently H, Q, or a ($C_1$-$C_{10}$) alkyl, ($C_3$-$C_{10}$) alkenyl or ($C_3$-$C_{10}$) alkynyl substituent wherein said carbon(s) may optionally be replaced with one or two heteroatoms selected independently from oxygen, nitrogen and sulfur and wherein said sulfur is optionally mono- or di-substituted with oxo, said carbon (s) is optionally mono-substituted with oxo, said nitrogen is optionally di-substituted with oxo, said carbon (s) is optionally mono-, di- or tri-substituted independently with halo, hydroxy, amino, nitro, cyano, carboxy, ($C_1$-$C_4$) alkylthio, ($C_1$-$C_6$)alkyloxycarbonyl, mono-N- or di-N,N—($C_1$-$C_6$) alkylamino or mono-N- or di-N,N—($C_1$-$C_6$)alkylaminocarbonyl; and said chain is optionally mono-substituted with $Q_1$; wherein Q and $Q_1$ are each independently a partially saturated, fully saturated or fully unsaturated three to eight membered ring optionally having one to three heteroatoms selected independently from oxygen, sulfur and nitrogen or a bicyclic ring consisting of two fused or spirocyclic partially saturated, fully saturated or fully unsaturated three to six membered rings, taken independently, said bicyclic ring optionally having one to three heteroatoms selected independently from oxygen, sulfur and nitrogen, said mono or bicyclic ring optionally additionally bridged with ($C_1$-$C_3$) alkylen wherein said ($C_1$-$C_3$) alkylen carbons are optionally replaced with one to two heteroatoms selected independently from oxygen, sulfur and nitrogen; wherein said Q and $Q_1$ ring are each independently optionally mono-, di-, tri-, or tetra-substituted independently with halo, hydroxy, amino, nitro, cyano, oxo, carboxy, ($C_1$-$C_6$)alkyl, ($C_2$-$C_6$) alkenyl, ($C_2$-$C_6$) alkynyl, ($C_1$-$C_6$) alkoxy, ($C_1$-$C_4$) alkylthio, ($C_1$-$C_6$) alkylcarbonyl, ($C_1$-$C_6$) alkylcarbonylamino, ($C_1$-$C_6$)alkyloxycarbonyl, mono-N- or di-N,N—($C_1$-$C_6$) alkylamino, mono-N- or di-N,N—($C_1$-$C_6$)alkylaminosulfonyl, mono-N- or di-N,N—($C_1$-$C_6$) alkylaminocarbonyl, wherein said ($C_1$-$C_6$) alkyl substituent is optionally mono-, di- or tri-substituted independently with halo, hydroxy, amino, nitro, cyano, oxo, carboxy, ($C_1$-$C_6$)alkoxy, ($C_1$-$C_4$) alkylthio, ($C_1$-$C_6$)alkyloxycarbonyl or mono-N- or di-N,N—($C_1$-$C_6$)alkylamino wherein said ($C_1$-$C_6$) alkyl substituent is also optionally substituted with from one to nine fluorines;

or wherein $R_2$ and $R_3$ can be taken together with the nitrogen atom to which they are attached to form a partially saturated, fully saturated or fully unsaturated three to eight membered ring optionally having one to three additional heteroatoms selected independently from oxygen, sulfur and nitrogen or a bicyclic ring consisting of two fused, bridged or spirocyclic partially saturated, fully saturated or fully unsaturated three to six membered rings, taken independently, said bicyclic ring optionally having one to three additional heteroatoms selected independently from oxygen, sulfur and nitrogen or a tricyclic ring consisting of three fused, bridged or spirocyclic partially saturated, fully saturated or fully unsaturated three to six membered rings, taken independently, said tricyclic ring optionally having one to three additional heteroatoms selected independently from oxygen, sulfur and nitrogen; wherein said $NR_2R_3$ ring is optionally mono-, di-, tri- or tetra-substituted independently with R15, halo, hydroxy, amino, nitro, cyano, oxo, carboxy, ($C_1$-$C_6$) alkyl, ($C_2$-$C_6$) alkenyl, ($C_2$-$C_6$) alkynyl, ($C_1$-$C_6$) alkoxy, ($C_1$-$C_4$) alkylthio, ($C_1$-$C_6$) alkylcarbonylamino or mono-N- or di-N,N—($C_1$-$C_6$) alkylamino, wherein said ($C_1$-$C_6$) alkyl substituent is optionally mono-, di- or tri-substituted independently with halo, hydroxy, amino, nitro, cyano, oxo, carboxy, ($C_1$-$C_6$) alkoxy, ($C_1$-$C_4$) alkylthio, ($C_1$-$C_6$) alkyloxycarbonyl, mono-N- or di-N,N—($C_1$-$C_6$) alkylamino, said ($C_1$-$C_6$) alkyl substituent is also optionally substituted with from one to nine fluorines;

wherein three heteroatoms selected independently from oxygen, sulfur and nitrogen wherein said ring is optionally mono-, di- or tri-substituted with halo, hydroxy, amino, nitro, cyano, oxo, carboxy, ($C_1$-$C_6$) alkyl, ($C_2$-$C_6$) alkenyl, ($C_2$-$C_6$) alkynyl, ($C_1$-$C_4$)alkylthio, ($C_1$-$C_6$) alkoxy, ($C_1$-$C_6$)alkylcarbonylamino, mono-N- or di-N, N—($C_1$-$C_6$) alkylamino; wherein said $NR_2R_3$ ring is optionally substituted with a partially saturated, fully saturated or fully unsaturated three to eight membered ring optionally having one to three heteroatoms selected independently from oxygen, sulfur and nitrogen or a bicyclic ring consisting of two fused partially saturated, fully saturated or fully unsaturated three to six membered rings, taken independently, said bicyclic ring optionally having one to three heteroatoms selected independently from oxygen, sulfur and nitrogen, said mono or bicyclic ring optionally additionally bridged said ring optionally having one to three heteroatoms selected independently from oxygen, sulfur and nitrogen, wherein said ($C_1$-$C_6$) alkyl and said ring are optionally mono-, di- or tri-substituted with halo, hydroxy, amino, nitro, cyano, oxo, carboxy, ($C_2$-$C_6$) alkenyl, ($C_3$-$C_6$) alkynyl, ($C_1$-$C_6$) alkylcarbonylamino, hydroxy, ($C_1$-$C_6$) alkoxy, ($C_1$-$C_4$) alkylthio, ($C_1$-$C_6$) alkoxy, mono-N- or di-N,N—($C_1$-$C_6$) alkylamino; wherein $R_4$, $R_5$ and $R_6$ are independently H, halo, hydroxy, ($C_1$-$C_6$) alkyl or $R_4$ and $R_5$ are taken together to form a partially saturated, fully saturated or fully unsaturated three to eight membered ring, said ring optionally having one to three heteroatoms selected independently from oxygen, sulfur and nitrogen, wherein said ($C_1$-$C_6$) alkyl and said ring are optionally mono-, di- or tri-substituted with halo, hydroxy, amino, nitro, cyano, oxo, carboxy, ($C_2$-$C_6$) alkenyl, ($C_3$-$C_6$) alkynyl, ($C_1$-$C_6$) alkylcarbonylamino, hydroxy, ($C_1$-$C_6$)alkoxy, ($C_1$-$C_4$)alkylthio, ($C_1$-$C_6$)alkoxy, mono-N- or di-N,N—($C_1$-$C_6$)alkylamino with the proviso that 1'-(anthracene-9-carbonyl)-[1,4']bipiperidinyl-3-carboxylic acid diethylamide; 1'-(1-oxa-2,3-diaza-cyclopenta[a]naphthalene-5-sulfonyl)-[1,4']bipiperidinyl-3 carboxylic acid diethylamide; 1'-(5-dimethylamino-naphthalene-1-sulfonyl)-[1,4']bipiperidinyl-3-carboxylic acid diethylamide; 1'-(9,10,10-trioxo-9,10-dihydro-thioxanthene-3-carbonyl)-[1-4']bipiperidinyl-3-carboxylic acid diethylamide; and 1'-(2-Oxo-2H-chromen-3-carbonyl)-[1-4']bipiperidinyl-3-carboxylic acid diethylamide are not included.

Compounds of structure (VI) can be made using organic synthesis techniques known to those skilled in the art, as well as by the methods described in (International Patent Publication WO 03/072197), which is incorporated herein by reference in its entirety (particularly at page 103, line 14 to page 160, line 17). Further, specific examples of these compounds can be found in this publication.

Other specific examples of Compounds of structure (VI) are:

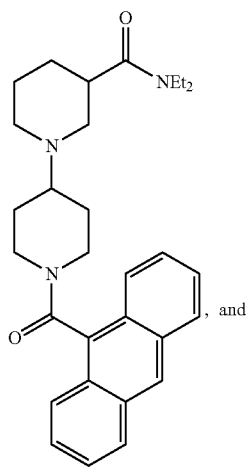
, and
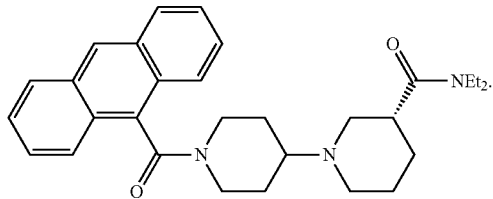
also known as CP-610431.
Other specific examples of Compounds of structure (VI) are:
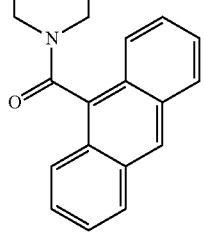, and
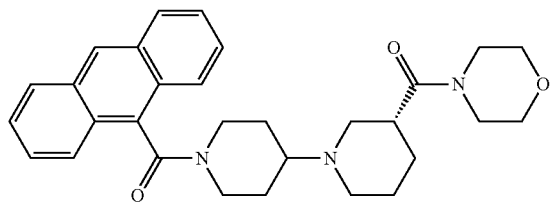
also known as CP-640186.
In another embodiment a Compound of structure (VI) is:
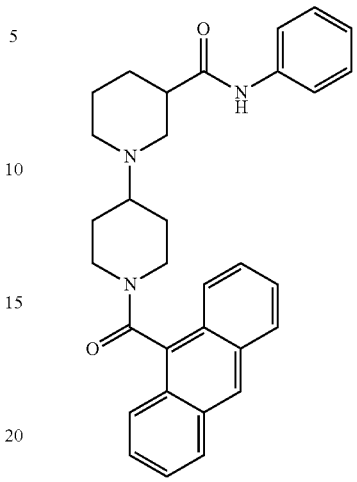
;
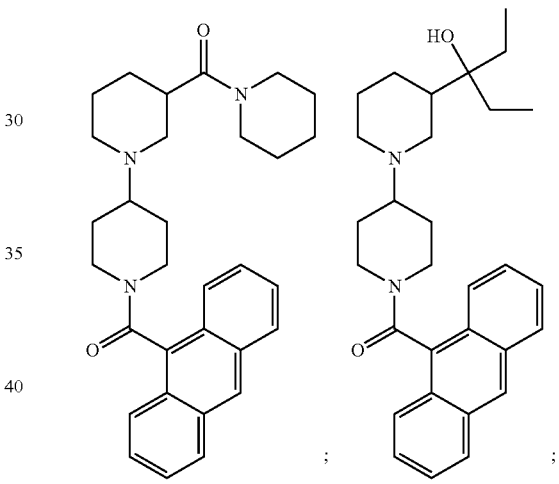
;     ;
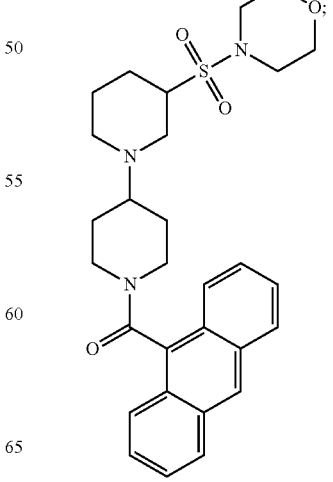
;

-continued

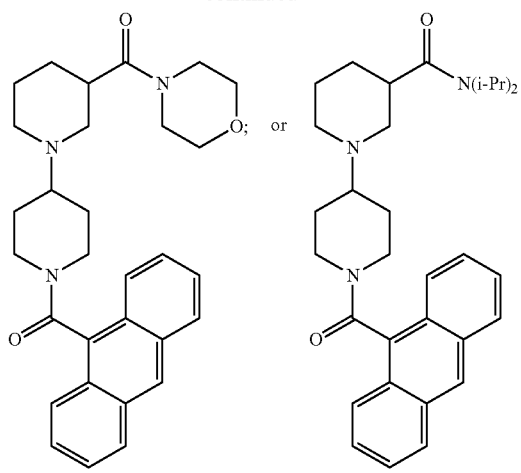

In one embodiment, the Compound of structure (VI) is not CP-610431.

In another embodiment, the Compound of structure (VI) is not CP-640186.

In one embodiment, a Compound has the following structure (VII):

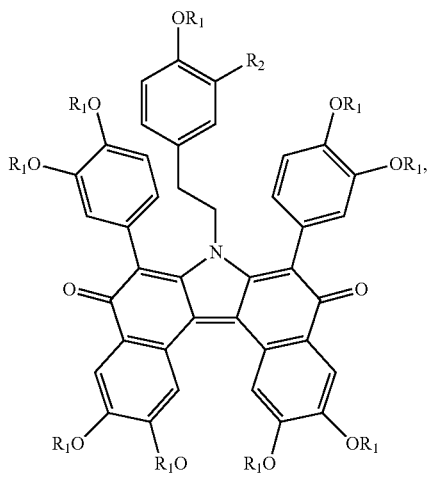

(VII)

wherein each $R_1$ is independently hydrogen, $(C_1-C_6)$alkyl, $(C_1-C_6)$alkenyl, $(C_1-C_6)$alkynyl, phenyl, benzyl, or $C(O)R_3$;

$R_2$ is —H or $OR_1$;

$R_3$ is $(C_1-C_6)$alkyl, $(C_1-C_6)$alkenyl, $(C_1-C_6)$alkynyl, $NR_4$, or phenyl;

$R_4$ is $(C_1-C_6)$alkyl, $(C_1-C_6)$alkenyl, $(C_1-C_6)$alkynyl, or phenyl.

Compounds of structure (VII) can be made using organic synthesis techniques known to those skilled in the art, as well as by the methods described in (Peschko et. al., Tetrahedron Letters, 41: 9477-9481, 2000), which is incorporated herein by reference in its entirety. Further, specific examples of these compounds can be found in this publication.

A specific example of a Compound of structure (VII) is:

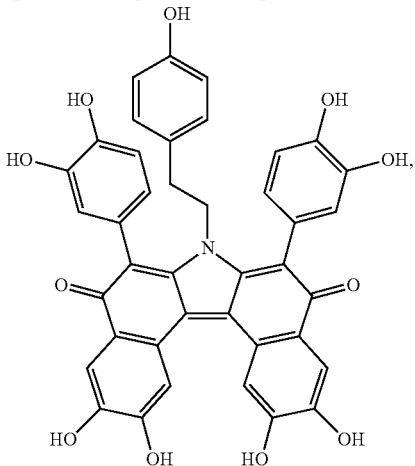 [SMILES: O=C1C(c2ccc(O)c(O)c2)=c2c(c3c(n2CCc2ccc(O)cc2)=C(c2ccc(O)c(O)c2)C(=O)c2cc(O)c(O)cc2-3)-c2cc(O)c(O)cc21]

which is also known as Pupurone.

In a particular embodiment a Compound of structure (VII) is:

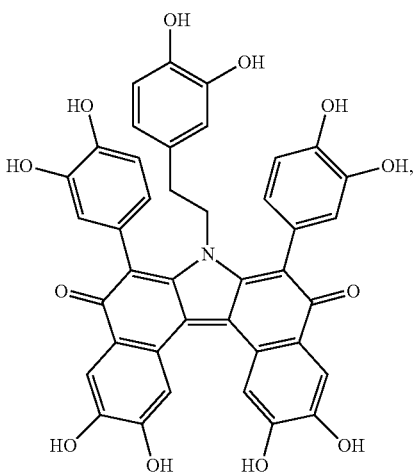 [SMILES: O=C1C(c2ccc(O)c(O)c2)=c2c(c3c(n2CCc2ccc(O)c(O)c2)=C(c2ccc(O)c(O)c2)C(=O)c2cc(O)c(O)cc2-3)-c2cc(O)c(O)cc21]

which is also known as ningalin D.

In a particular embodiment a Compound of structure (VII) is:

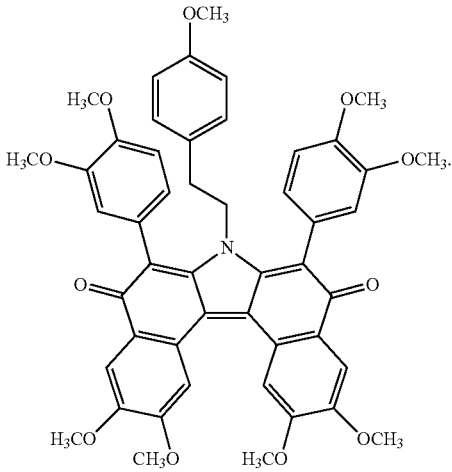

In one embodiment, the Compound of structure (VII) is not Puporone.

In another embodiment, the Compound of structure (VII) is not ningalin D.

In one embodiment, a Compound has the following structure (VIII):

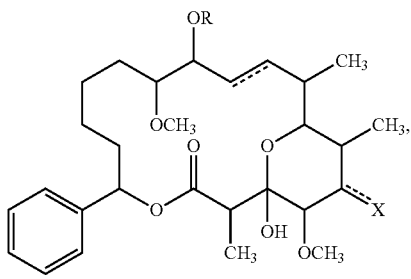
(VIII)

In this formula, the dotted lines are independently a saturated bond or a double bond, alternatively, while R is hydrogen, $CH_3$ or —C(O)A, where A is hydrogen, $(C_3-C_6)$cycloalkyl or $(C_1-C_6)$alkyl which is unsubstituted or substituted by halogen or $(C_1-C_3)$alkoxy, and X is —OH if the bond is saturated, or =O, =N—OY or =N—N($R_1$)($R_2$) if there is an unsaturated bond, where Y is hydrogen, $(C_1-C_6)$alkyl, $(C_3-C_6)$alkenyl, $(C_3-C_6)$alkynyl or an acyl group —C(O)—Z in which Z is phenyl, or a $(C_1-C_6)$alkyl group which is substituted by halogen or $(C_1-C_4)$alkoxy, or is hydrogen, $(C_1-C_6)$alkyl, $(C_2-C_6)$alkenyl or $(C_2-C_6)$alkynyl;

$R_1$ is hydrogen or $(C_1-C_6)$alkyl and $R_2$ is hydrogen, $(C_1-C_6)$alkyl, phenyl, carbamoyl ($CONH_2$), —COA or —$SO_2$—$R_3$, where $R_3$ is $(C_1-C_6)$ alkyl, or is phenyl which is unsubstituted or substituted by $(C_1-C_4)$alkyl.

Compounds of structure (VIII) can be made using organic synthesis techniques known to those skilled in the art, as well as by the methods described in Böhlendorf et. al. (U.S. Pat. No. 5,026,878), which is incorporated herein by reference in its entirety (particularly at column 10, line 25 to column 16, line 14). Further, specific examples of these compounds can be found in this publication.

A specific example of a Compound of structure (VIII) is:

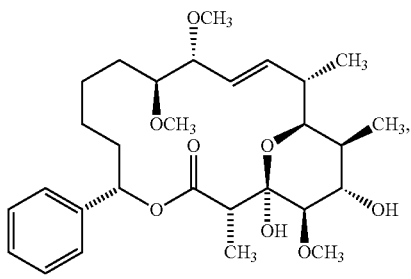

which is also known as Soraphen A.

In a particular embodiment a Compound of structure (VIII) is:

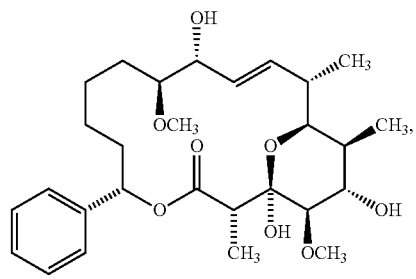

which is also known as Soraphen B.

In another embodiment a Compound of structure (VIII) is:

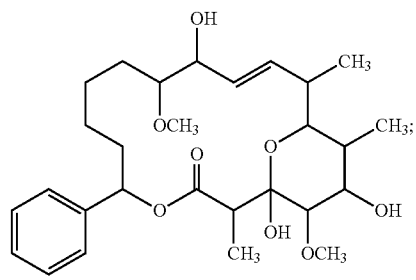

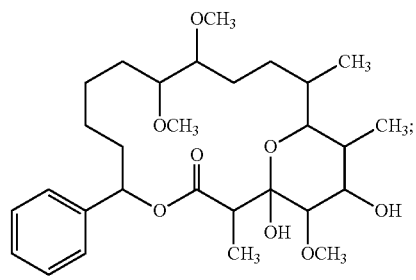

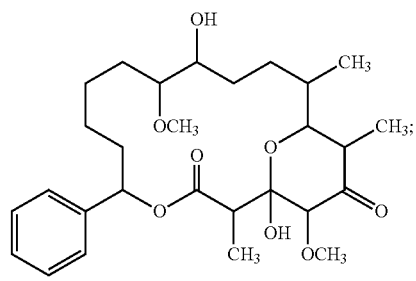

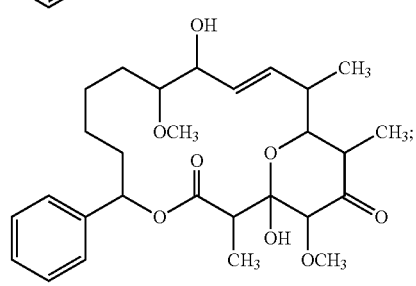

In one embodiment, the Compound of structure (VIII) is not Soraphen A.

In one embodiment, the Compound of structure (VIII) is not Soraphen B.

In one embodiment, a Compound has the following structure (IX):

wherein T is oxygen or sulfur;
X is Cl, Br or CF$_3$;
Y is H, Cl, Br or CF$_3$, provided at least one of X and Y is CF$_3$;
Z is —C(O)OR$_1$, —C(O)NR$_2$R$_3$, —C(O)O$^-$M$^+$, —C(O)SR$_4$, —CNR$_1$ is H, (C$_1$-C$_8$)alkyl, benzyl, chlorobenzyl or C$_3$-C$_6$ alkoxyalkyl;
R$_4$ is (C$_1$-C$_4$)alkyl;
R$_5$ is H or (C$_1$-C$_4$) alkyl;
R$_6$ is (C$_1$-C$_7$) alkyl;
M is NHR$_2$R$_3$R$_7$, Na, K, Mg or Ca;
R$_2$ and R$_3$ are each independently selected from R$_7$ or —OCH$_3$, provided both R$_2$ and R$_3$ cannot be simultaneously —OCH$_3$ and neither is —OCH$_3$ in —NHR$_2$R$_3$R$_7$; and
R$_7$ is H, (C$_1$-C$_4$)alkyl or (C$_2$-C$_3$)hydroxyalkyl.

A specific example of a Compound of structure (IX) is:

which is also known as haloxyfop.

In another embodiment a Compound of structure (IX) is:

In one embodiment, the Compound of structure (IX) is not haloxyfop.

In one embodiment, a Compound has the following structure (X):

$$\text{(X)}$$

wherein when the dashed line is a bond, R$_2$ and R$_3$ are not present;
R$_1$ is H, OR$_4$, NR$_4$R$_5$, SR$_6$, halo, C(O)OR$_4$ or 0 shared with R$_3$ to form an epoxide ring;
R$_2$ is H or halo;
R$_3$ is H, SR$_6$, or O shared with R$_1$ to form an epoxide ring;
R$_4$ is H, (C$_1$-C$_6$)alkyl, (C$_2$-C$_6$)alkenyl, (C$_2$-C$_6$)alkynyl, aryl, or benzyl;
R$_5$ is H, (C$_1$-C$_6$)alkyl, or OR$_4$;
R$_6$ is H, (C$_1$-C$_6$)alkyl, SH, or S—(C$_1$-C$_6$)alkyl;
Provided that when R$_1$ is OR$_4$ or 0 shared with R$_3$ to form an epoxide ring, R$_2$ can not be halo.

Compounds of structure (X) can be made using organic synthesis techniques known to those skilled in the art, as well as by the methods described in (Saxty et. al. 1992 Eur. J. Biochem. 202:889-896. and Dolle et. al. 1995 Journal of Medicinal Chemistry 38(3):537-543), which are incorporated herein by reference in their entirety. Further, specific examples of these compounds can be found in these publications.

A specific example of a Compound of structure (X) is:

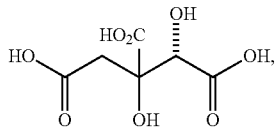

also known as 2S-hydroxycitrate.

In a particular embodiment a Compound of structure (X) is:

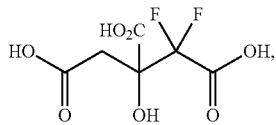

also known as 2,2-difluorocitrate.

In a particular embodiment a Compound of structure (X) is:

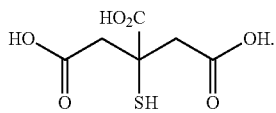 [SMILES: O=C(O)CC(S)(CC(=O)O)C(=O)O]

In a particular embodiment a Compound of structure (X) is:

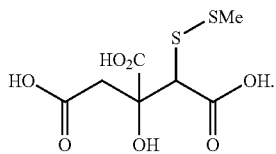

In a particular embodiment a Compound of structure (X) is:

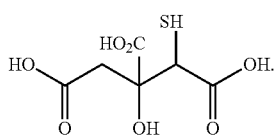 [SMILES: O=C(O)CC(O)(C(=O)O)C(S)C(=O)O]

In a particular embodiment a Compound of structure (X) is:

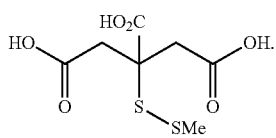 [SMILES: CSSC(CC(=O)O)(CC(=O)O)C(=O)O]

In another embodiment a Compound of structure (X) is:

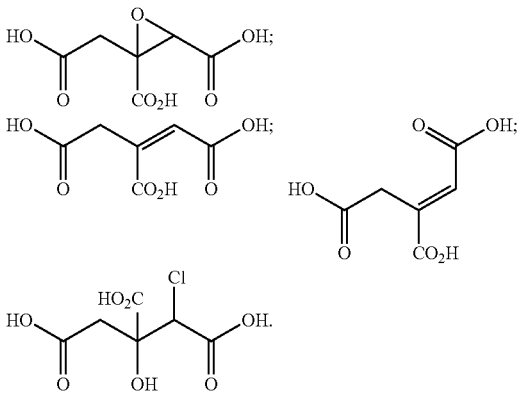

In one embodiment, a Compound has the following structure (XI):

(XI)

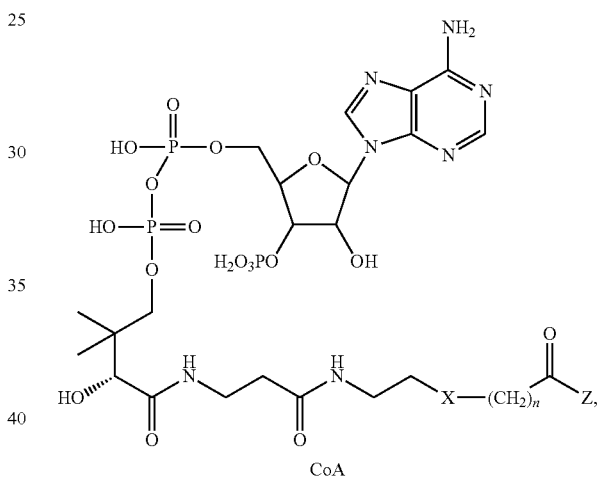

wherein X is S, S=O or —$CH_2$—;
n is from 0 to 6;
Z is ($C_1$-$C_6$)alkyl, ($C_1$-$C_6$)alkyl-COOH, $OR_1$, or $NR_1R_2$;
$R_1$ is H, ($C_1$-$C_6$)alkyl, ($C_2$-$C_6$)alkenyl, ($C_2$-$C_6$)alkynyl, phenyl, or benzyl;
$R_2$ is H, ($C_1$-$C_6$)alkyl, ($C_2$-$C_6$)alkenyl, ($C_2$-$C_6$)alkynyl, phenyl, or benzyl.

Compounds of structure (XI) can be made using organic synthesis techniques known to those skilled in the art, as well as by the methods described in (Usher et. al. 1994 Biochemistry 33: 7753-7759. and Charlier et. al. 1997 Biochemistry 36: 1551-1558), which are incorporated herein by reference in their entirety. Further, specific examples of these compounds can be found in these publications.

A specific example of a Compound of structure (XI) is:

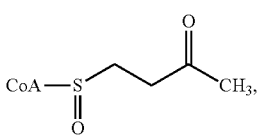

which is also known as 3-Oxobutyl-CoA.

In another embodiment a Compound of structure (XI) is:

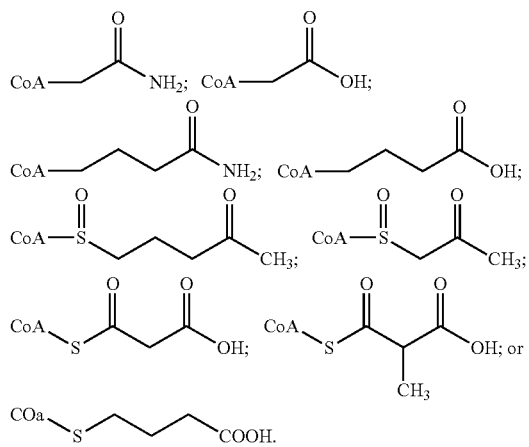

In one embodiment, the Compound of structure (XI) is not -Oxobutyl-CoA.

In one embodiment, a Compound has the following structure (XII):

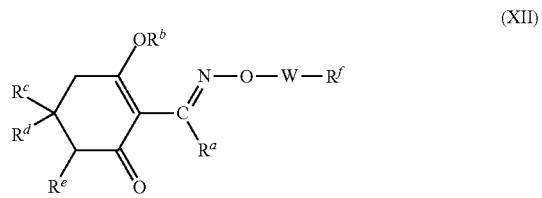

wherein:

$R^a$ is $C_1$-$C_6$-alkyl;

$R^b$ is hydrogen, one equivalent of an agriculturally useful cation, $C_2$-$C_8$-alkylcarbonyloxy, $C_1$-$C_{10}$-alkylsulfonyl, $C_1$-$C_{10}$-alkylphosphonyl or benzoyl, benzenesulfonyl or benzenephosphonyl, where the three last-mentioned groups may furthermore each carry from one to five halogen atoms;

$R^c$ is hydrogen, cyano, formyl, $C_1$-$C_6$-alkyl, $C_1$-$C_4$-alkoxy-$C_1$-$C_6$-alkyl or $C_1$-$C_4$-alkylthio-$C_1$-$C_6$-alkyl, phenoxy-$C_1$-$C_6$-alkyl, phenylthio-$C_1$-$C_6$-alkyl, pyridyloxy-$C_1$-$C_6$-alkyl or pyridylthio-$C_1$-$C_6$-alkyl, where the phenyl and pyridyl rings may each furthermore carry from one to three radicals selected from the group consisting of nitro, cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_3$-$C_6$-alkenyl, $C_3$-$C_6$-alkenyloxy, $C_3$-$C_6$-alkynyl, $C_3$-$C_6$-alkynyloxy and —NR$^g$R$^h$, where $R^g$ is hydrogen, $C_1$-$C_4$-alkyl, $C_3$-$C_6$-alkenyl, $C_3$-$C_6$-alkynyl, $C_1$-$C_6$-acyl or benzoyl which may carry from one to three radicals selected from the group consisting of nitro, cyano, halogen, $C_1$-$C_4$-alkyl, partially or completely halogenated $C_1$-$C_4$-alkyl, $C_1$-$C_4$-alkoxy and $C_1$-$C_4$-alkylthio and $R^h$ is hydrogen, $C_1$-$C_4$-alkyl, $C_3$-$C_6$-alkenyl or $C_3$-$C_6$-alkynyl; $C_3$-$C_7$-cycloalkyl or $C_5$-$C_7$-cycloalkenyl, where these groups may furthermore carry from one to three radicals selected from the group consisting of hydroxyl, halogen, $C_1$-$C_4$-alkyl, partially or completely halogenated $C_1$-$C_4$-alkyl, $C_1$-$C_4$-alkoxy, $C_1$-$C_4$-alkylthio, benzylthio, $C_1$-$C_4$-alkylsulfonyl, $C_1$-$C_4$-alkylsulfenyl and $C_1$-$C_4$-alkylsulfinyl, a 5-membered saturated heterocyclic structure which contains one or two oxygen or sulfur atoms or one oxygen and one sulfur atom as hetero atoms and which may furthermore carry from one to three radicals selected from the group consisting of $C_1$-$C_4$-alkyl, partially or completely halogenated $C_1$-$C_4$-alkyl, $C_1$-$C_4$-alkoxy and $C_1$-$C_4$-alkylthio, a 6-membered or 7-membered saturated heterocyclic structure or mono- or diunsaturated heterocyclic structure which contains one or two oxygen or sulfur atoms or one oxygen and one sulfur atom as hetero atoms and which may furthermore carry from one to three radicals selected from the group consisting of hydroxyl, halogen, $C_1$-$C_4$-alkyl, partially or completely halogenated $C_1$-$C_4$-alkyl, $C_1$-$C_4$-alkoxy and $C_1$-$C_4$-alkylthio, a 5-membered heteroaromatic structure containing from one to three hetero atoms selected from the group consisting of one or two nitrogen atoms and one oxygen or sulfur atom, where the heteroaromatic structure may furthermore carry from one to three radicals selected from a group consisting of cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_2$-$C_6$-alkenyl, $C_2$-$C_6$-alkenyloxy, $C_3$-$C_6$-alkynyloxy and $C_1$-$C_4$-alkoxy-$C_1$-$C_4$-alkyl, phenyl or pyridyl, each of which may furthermore carry from one to three radicals selected from the group consisting of nitro, cyano, formyl, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio, $C_3$-$C_6$-alkenyl, $C_3$-$C_6$-alkenyloxy, $C_3$-$C_6$-alkynyl, $C_3$-$C_6$-alkynyloxy and —NR$^g$R$^h$, where $R^g$ and $R^h$ have the above-mentioned meanings;

$R^d$ is hydrogen, hydroxyl or $C_1$-$C_6$-alkyl;

$R^o$ is hydrogen, halogen, cyano, a $C_1$-$C_4$-alkoxycarbonyl or a $C_1$-$C_4$-alkylketoxime group;

W is a $C_1$-$C_6$-alkylene, $C_3$-$C_6$-alkenylene or $C_3$-$C_6$-alkynylene chain, each of which may furthermore carry from one to three radicals selected from the group consisting of three $C_3$-$C_6$-alkyl substituents, three halogen atoms and one methylene substituent; a $C_3$-$C_6$-alkylene or $C_4$-$C_6$-alkenylene chain, both of which may furthermore carry from one to three $C_3$-$C_6$-alkyl radicals, where in each case one methylene group of the chains may be replaced by an oxygen or sulfur atom, a sulfoxyl or sulfonyl group or a group —N(R$^i$)—, where R$^i$ is hydrogen, $C_1$-$C_4$-alkyl, $C_3$-$C_6$-alkenyl or $C_3$-$C_6$-alkynyl;

$R^f$ is hydrogen; $C_1$-$C_6$-alkyl; vinyl; a group —CH=CH—Z, where Z is cyano, halogen, $C_1$-$C_4$-alkyl, partially or completely halogenated $C_1$-$C_4$-alkyl, $C_3$-$C_6$-cycloalkyl, which, if desired, in turn may carry from one to three substituents selected from the group consisting of hydroxyl, halogen, $C_1$-$C_4$-alkyl, partially or completely halogenated $C_1$-$C_4$-alkyl and $C_1$-$C_4$-alkoxy; carboxyl, $C_1$-$C_8$-alkoxycarbonyl, benzyloxycarbonyl, phenyl, thienyl or pyridyl, where these three aromatic radicals may be unsubstituted or may carry from one to three substituents selected from the group consisting of nitro, cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy, $C_1$-$C_4$-alkylthio and $C_3$-$C_6$-cycloalkyl, where the cycloalkyl substituent may be unsubstituted or in turn may furthermore carry from one to three radicals selected from the group consisting of halogen, $C_1$-$C_4$-alkyl, partially or completely halogenated $C_1$-$C_4$-alkyl and $C_1$-$C_4$-alkoxy; ethynyl which may carry one of the following radicals: $C_1$-$C_4$-alkyl, $C_3$-$C_6$-cycloalkyl, which, if desired, may carry from one to three substituents selected from the group consisting of hydroxy, halogen, $C_1$-$C_4$-alkyl, partially or completely halogenated $C_1$-$C_4$-alkyl and $C_1$-$C_4$-alkoxy, or phenyl, thienyl or pyridyl, where these aromatic radicals may be unsubstituted or may each furthermore carry from one to three substituents selected from the group consisting of nitro, cyano, halogen, $C_1$-$C_4$-alkyl, partially or completely halogenated $C_1$-$C_4$-alkyl, $C_1$-$C_4$-alkoxy, partially or completely halogenated $C_1$-$C_4$-alkoxy and $C_1$-$C_4$-alkylthio; phenyl, halophenyl, dihalophenyl, a 5-membered heteroaromatic group having from one to three hetero atoms, selected from the group consisting of from one to three nitrogen atoms and one oxygen or sulfur atom, or a 6-membered heteroaromatic group having from one to four nitrogen atoms, all of which may not be adjacent to one another at the same time, where the phenyl and hetaryl groups may, if desired, furthermore carry from one to three radicals selected from the group consisting of nitro, $C_1$-$C_4$-alkoxy, $C_1$-$C_4$-alkylthio, partially or completely halogenated $C_1$-$C_4$-alkoxy, radicals Z and —$NR^kR^l$, where $R^k$ is hydrogen, $C_1$-$C_4$-alkyl, $C_3$-$C_6$-alkenyl or $C_3$-$C_6$-alkynyl; and $R^l$ is hydrogen, $C_1$-$C_4$-alkyl, $C_3$-$C_6$-alkenyl, $C_3$-$C_6$-alkynyl, $C_1$-$C_6$-acyl or benzoyl which, if desired, may furthermore carry from one to three substituents selected from the group consisting of nitro, cyano, halogen, $C_1$-$C_4$-alkyl, partially or completely halogenated $C_1$-$C_4$-alkyl, $C_1$-$C_4$-alkoxy and $C_1$-$C_4$-alkylthio.

Compounds of structure (XII) can be made using organic synthesis techniques known to those skilled in the art, as well as by the methods described in U.S. Pat. No. 5,491,123, issued Feb. 13, 1996, which is incorporated herein by reference in its entirety (particularly at column 11, line 62 to column 13, line 5). Further, specific examples of these Compounds can be found in this patent. Additional examples of Compounds of structure (XII) are found in U.S. Pat. No. 6,383,987, issued May 7, 2002; U.S. Pat. No. 6,103,664, issued Aug. 15, 2000; and U.S. Pat. No. 4,334,913, issued Jun. 15, 1982, each being incorporated herein by reference in its entirety.

A specific example of a Compound of structure (XII) is:

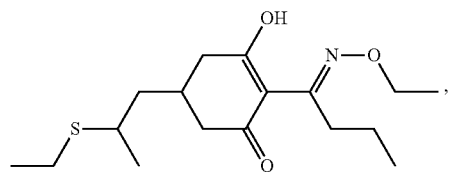 [SMILES: CCC/C(=N\OCC)C1=C(O)CC(CC(C)SCC)CC1=O]

which is also identified as sethoxydim.

In another embodiment, the Compound of structure (XII) is:

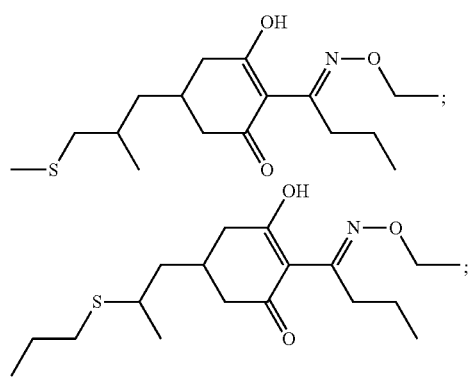

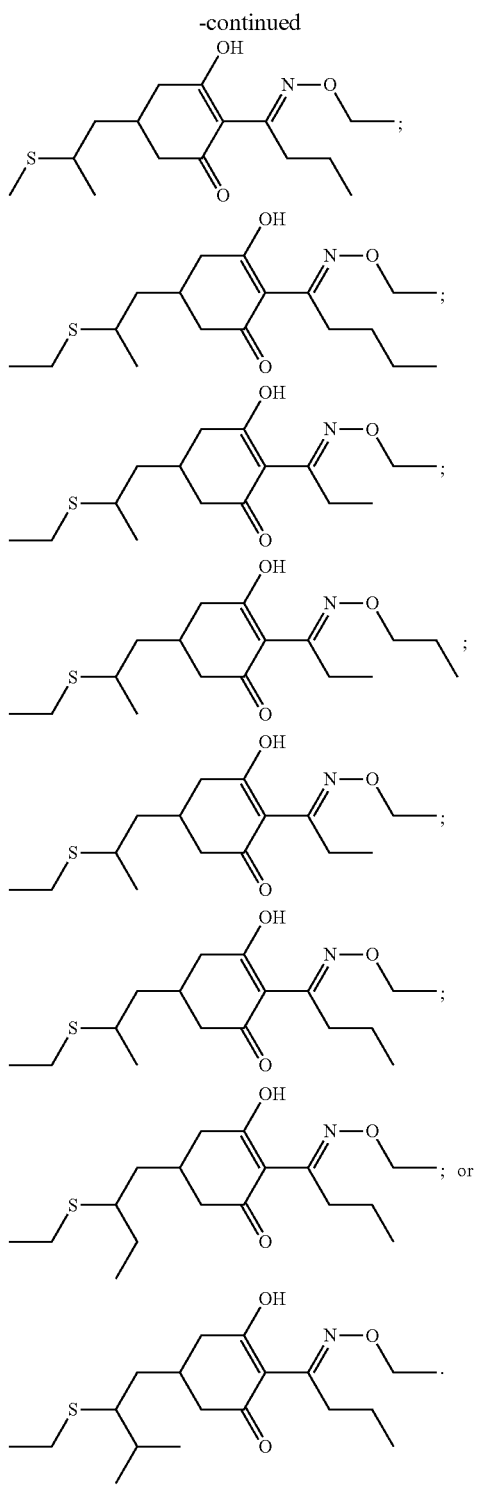

In one embodiment, the Compound of structure (XII) is not sethoxydim.

In one embodiment, a Compound has the following structure (XIII):

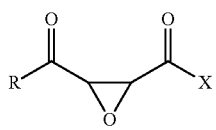
(XIII)

wherein:

R is $C_{1-10}$alkyl, $C_{2-10}$alkenyl, aryl or aralkyl;

X is $NHR^1$ or $OR^2$; and $R^1$ and $R^2$ are H or $C_{1-6}$alkyl.

Compounds of structure (XIII) can be made using organic synthesis techniques known to those skilled in the art, as well as by the methods described in U.S. Pat. No. 5,188,830, issued Feb. 23, 1993, which is incorporated herein by reference in its entirety (particularly at column 5, line 1 to column 6, line 62). Further, specific examples of these Compounds can be found in this patent. Additional examples of Compounds of structure (XIII) are found in U.S. Patent Application Publication No. 2003/0158156, published Aug. 21, 2005; FR 2425432, published Jan. 11, 1980; FR 2457864, published Dec. 26, 1908; and Lawrence et al., 1999, *J. Med. Chem.* 42:4932-4941, each being incorporated herein by reference in its entirety.

In one embodiment, a Compound of structure (XIII) is that wherein R is $C_{2-10}$alkenyl.

A specific example of a Compound of structure (XIII) is:

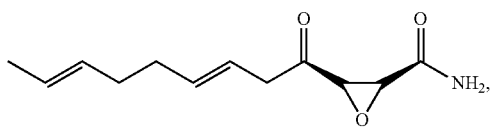

which is also identified as cerulenin.

In another embodiment, the Compound of structure (XIII) is:

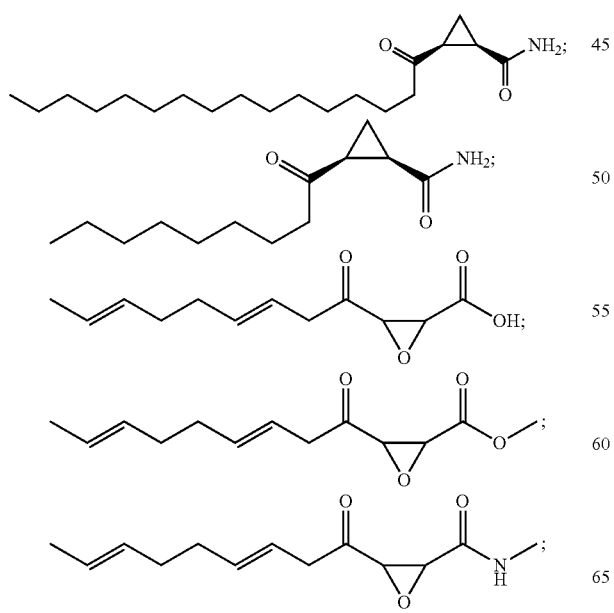

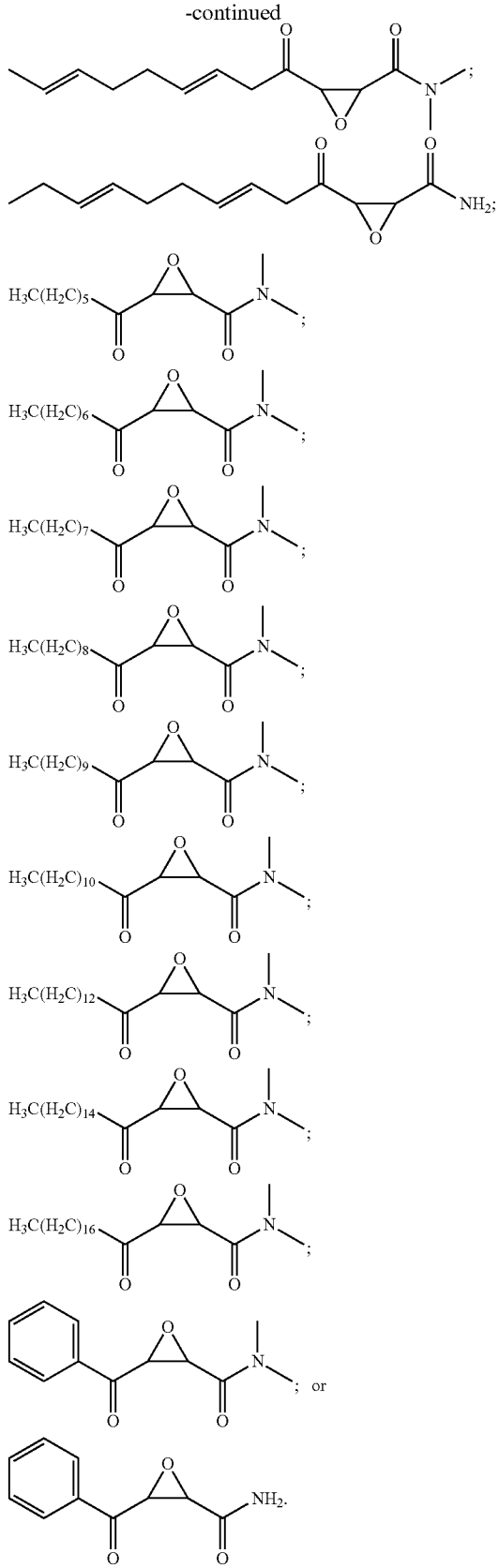

In one embodiment, the Compound of structure (XIII) is not cerulinin.

In one embodiment, a Compound has the following structure (XIV):

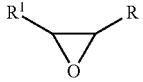
(XIV)

wherein:

R is selected from —CH$_2$OH, —CO$_2$R$^2$, —CONR$^3$R$^4$ or COR$^5$, wherein R$^2$ is hydrogen or a lower alkyl group, R$^3$ and R$^4$ are each independently hydrogen or a lower alkyl group, R$^5$ is an amino acid residue bound via a terminal nitrogen on said amino acid or a peptide having at least two amino acid residues; and wherein R$^1$ is aralkyl, aralkyl(lower alkyl)ether or C$_5$-C$_{13}$ alkyl(lower alkyl)ether.

Compounds of structure (XIV) can be made using organic synthesis techniques known to those skilled in the art, as well as by the methods described in U.S. Pat. No. 6,153,589, issued Nov. 28, 2000, which is incorporated herein by reference in its entirety (particularly at column 4, line 21 to column 17, line 24). Further, specific examples of these Compounds can be found in this patent.

In one embodiment, the Compounds of structure (XIV) do not have activity against a retrovirus.

In another embodiment, the Compounds of structure (XIV) do not have activity against a virus which encodes for a protease.

In another embodiment, the Compounds of structure (XIV) do not have activity against Type C retroviruses, Type D retroviruses, HTLV-1, HTLV-2, HIV-1, HIV-2, murine leukemia virus, murine mammary tumor virus, feline leukemia virus, bovine leukemia virus, equine infectious anemia virus, or avian sarcoma viruses such as rous sarcoma virus.

In another embodiment, the Compound of structure (XIV) is:

2R-cis-Nonyloxirane methanol, 2S-cis-Nonyloxirane methanol, 2R-cis-Heptyloxirane methanol, 2S-cis-Heptyloxirane methanol, 2R-cis-(Heptyloxymethyl) oxirane, methanol, 2S-cis-(Heptyloxymethyl) oxirane, methanol, 2-cis-Undecyloxirane methanol, 2R-cis-(Benzyloxymethyl) oxirane, methanol, 2S-cis-(Benzyloxymethyl) oxirane methanol, cis-2-Epoxydecene, 2R-trans-Nonyloxirane methanol, 2S-trans-Nonyloxirane methanol, 2R-trans-Heptyloxirane methanol, 2S-trans-Heptyloxirane methanol, 2R-trans-Undecyloxirane methanol, 2S-trans-Undecyloxirane methanol, 2-trans-Undecyloxirane methanol, 2R-cis-Nonyloxiranecarboxylic acid, 2S-cis-Nonyloxiranecarboxylic acid, 2R-cis-Heptyloxiranecarboxylic acid, 2S-cis-Heptyloxiranecarboxylic acid, 2-cis-Undecyloxiranecarboxylic acid, 2R-trans-Nonyloxiranecarboxylic acid, 2S-trans-Nonyloxiranecarboxylic acid, 2R-trans-Undecyloxiranecarboxylic acid, 2S-trans-Undecyloxirane carboxylic acid, 2R-cis-Nonyloxiranecarboxy amide, 2S-cis-Nonyloxiranecarboxy amide, N,N-Diethyl-2R-Cis-nonloxiranecarboxy amide, or N-(2R-cis-Nonyloxiraneacyl)-L-proline methyl ester.

In one embodiment, a Compound has the following structure (XV):

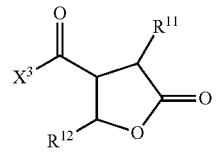
(XV)

wherein:

R$^{11}$ is H, or C$_1$-C$_{20}$ alkyl, cycloalkyl, alkenyl, aryl, aralkyl, or alkylaryl, =CHR$^{13}$, —C(O)OR$^{13}$, —C(O)R$^{13}$, —CH$_2$C(O)OR$^{13}$, —CH$_2$C(O)NHR$^{13}$, where R$^{13}$ is H or C$_1$-C$_{10}$ alkyl, cycloalkyl, or alkenyl;

R$_{12}$ is C$_1$-C$_{20}$alkyl, cycloalkyl, alkenyl, aryl, arylalkyl, or alkylaryl;

X$^3$ is OR$^{14}$ or NHR$^{14}$, where R$^{14}$ is H, C$_1$-C$_{20}$ alkyl, hydroxyalkyl, cycloalkyl, alkenyl, aryl, arylalkyl, or alkylaryl, the R$^{14}$ group optionally containing a carbonyl group, a carboxyl group, a carboxyamide group, an alcohol group, or an ether group, the R$^{14}$ group further optionally containing one or more halogen atoms.

Compounds of structure (XV) can be made using organic synthesis techniques known to those skilled in the art, as well as by the methods described in U.S. Patent Application Publication No. 2006/0241177, published Oct. 26, 2006, which is incorporated herein by reference in its entirety (particularly at pages 7-10 and FIGS. 1 and 2). Further, specific examples of these Compounds can be found in this publication. Additional examples of Compounds of structure (XV) are found in International Patent Publication No. WO 2004/041189, published May 21, 2004; International Patent Publication No. WO 97/18806, published May 29, 1997; and U.S. Patent Application Publication No. 2005/0239877, published Oct. 27, 2005, each being incorporated herein by reference in its entirety.

A specific example of a Compound of structure (XV) is:

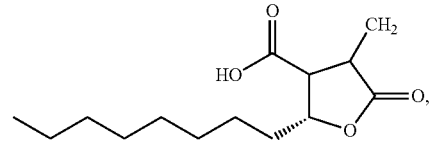 [SMILES: CCCCCCCC[C@H]1OC(=O)C(C)C1C(=O)O]

which is also identified as C75 (trans-4-carboxy-5-octyl-3-methylene-butyrolactone).

In another embodiment, the Compound of structure (XV) is:

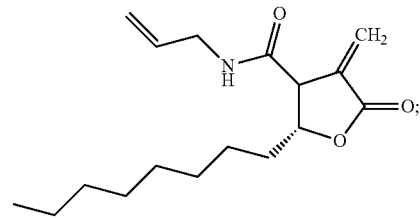

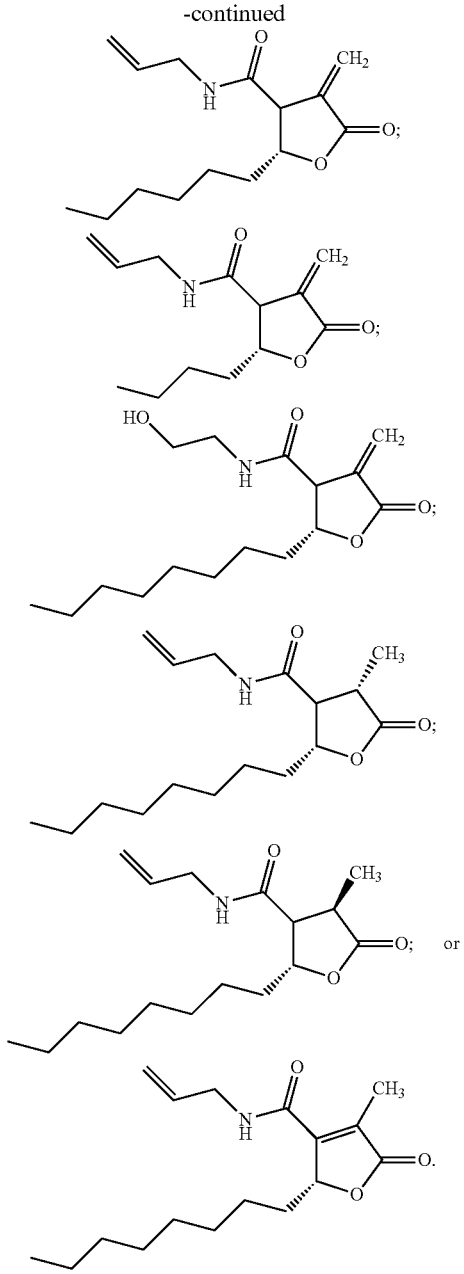

In one embodiment, the Compound of structure (XV) is not C75.

In one embodiment, a Compound has the following structure (XVI):

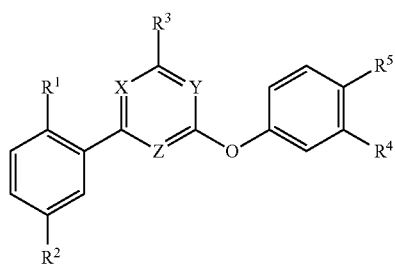

wherein:

$R^1$-$R^5$ are independently H, OH, alkyl, alkoxy, halogen, $NH_2$, NHR, $NR_2$, or $CR_3$, where R at each occurrence independently H, halogen or alkyl;

Q is a NH, O or S;

and two of X, Y and Z are N with the third being N or CH.

Compounds of structure (XVI) can be made using organic synthesis techniques known to those skilled in the art, as well as by the methods described in U.S. Patent Application Publication No. 2003/0153570, published Aug. 14, 2003, which is incorporated herein by reference in its entirety (particularly at pages 8-41, Examples 1-90). Further, specific examples of these Compounds can be found in this publication. Additional examples of Compounds of structure (XVI) are found in U.S. Pat. No. 6,875,781, issued Apr. 5, 2005, incorporated herein by reference in its entirety.

A specific example of a Compound of structure (XVI) is:

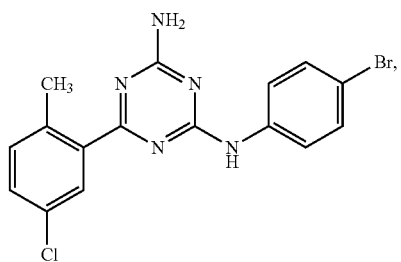

which is also identified as CT-32228.

In another embodiment, the Compound of structure (XVI) is:

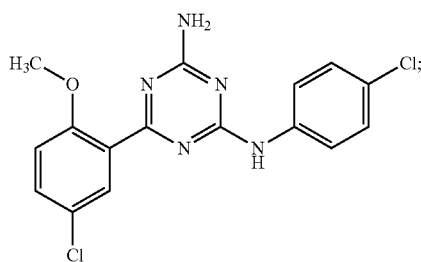

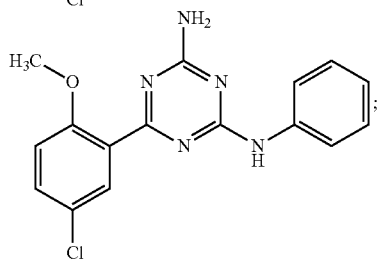

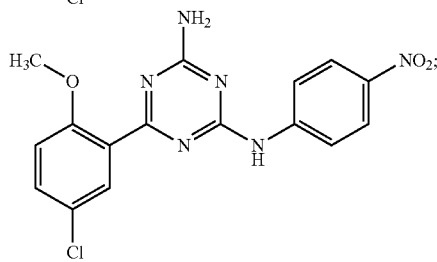

-continued
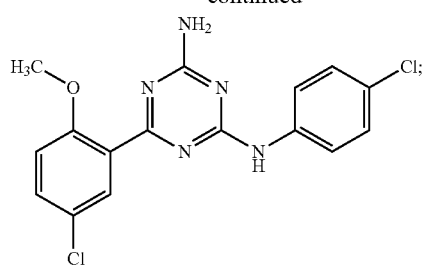
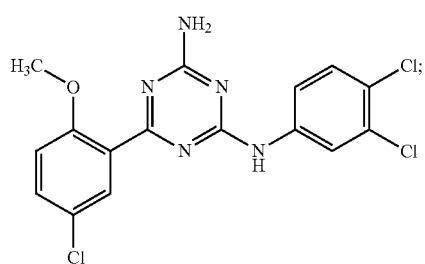
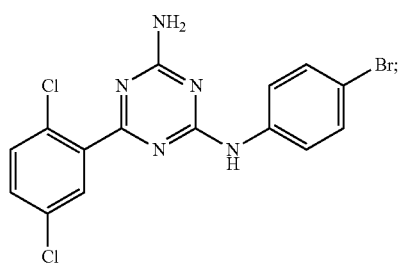 [SMILES: Cc1ccc(Cl)cc1-c1nc(N)nc(Nc2ccc(Br)cc2)n1]
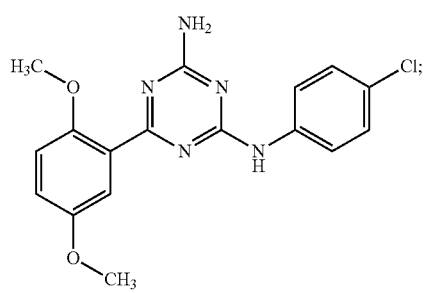
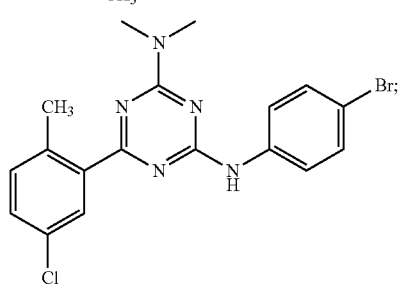
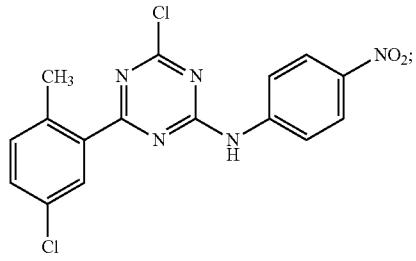
-continued
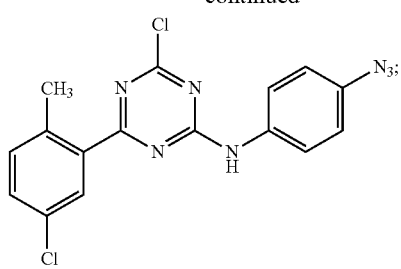
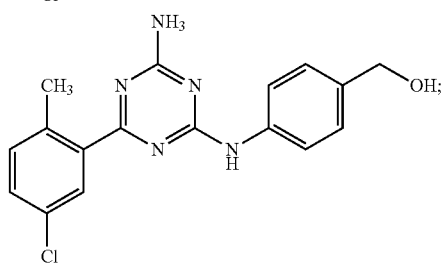
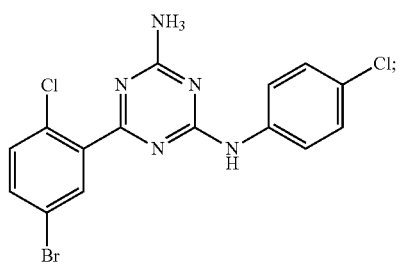
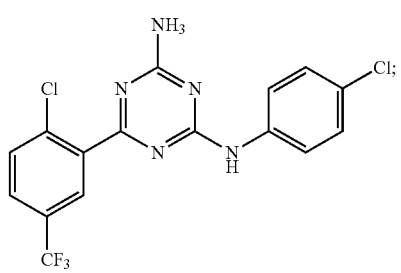
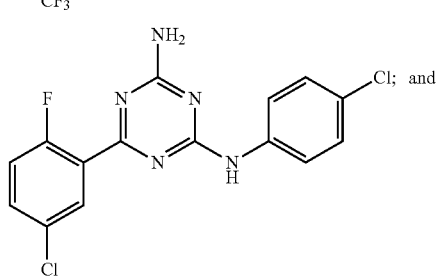
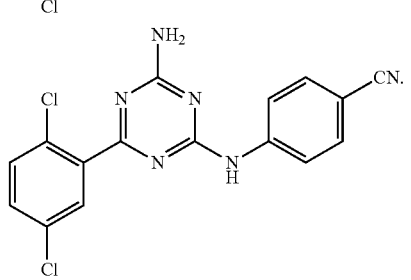
In one embodiment, the Compound of structure (XVI) is not CT32228.
In one embodiment, a Compound has the following structure (XVII):

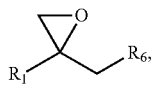

(XVII)

wherein:

R₁ is a straight-chain or branched mono-, poly- or unsubstituted alkyl group, a straight-chain or branched mono-, poly- or unsubstituted alkylene group, a straight-chain or branched mono-, poly- or unsubstituted aralkyl, alkylaryl or aryl group;

R6 is selected from the group consisting of OH, O-M+, O-M2+, where M is an alkali metal, an alkaline earth metal or an earth metal or a cation of an organic nitrogen base, and OR, where R is a substituted or unsubstituted alkyl or alkylene radical having 1 to 15 carbon atoms.

Compounds of structure (XVII) can be made using organic synthesis techniques known to those skilled in the art, as well as by the methods described by Cernerud et. al. (U.S. Pat. No. 7,078,543), which is incorporated herein by reference in its entirety. Further, specific examples of these compounds can be found in this publication.

A specific example of a Compound of structure (XVII) is:

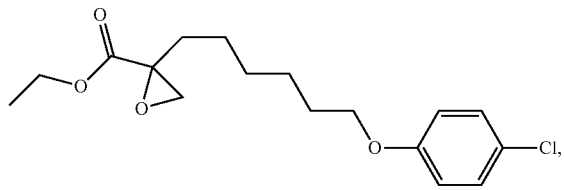 [SMILES: CCOC(=O)C1(CCCCCCOc2ccc(Cl)cc2)CO1]

which is also identified as Etomoxir.

In one embodiment, the Compound of structure (XVII) is not Etomoxir.

In one embodiment, a Compound has the following structure (XVIII):

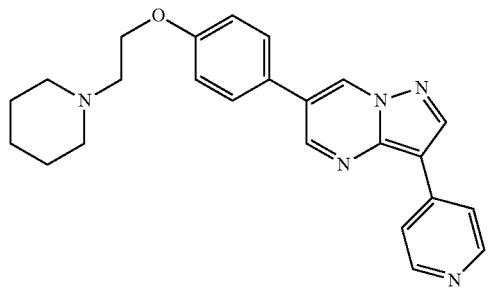 [SMILES: c1cc(-c2cnn3cc(-c4ccc(OCCN5CCCCC5)cc4)cnc23)ccn1]

which has the chemical name 6-[4-(2-Piperidin-1-yl-ethoxy)-phenyl)]-3-pyridin-4-yl-pyrrazolo[1,5-a]-pyrimidine.

In one embodiment, a Compound has the following structure (XIX):

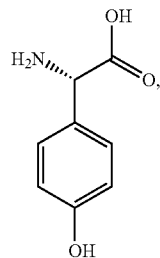

which is also referred to as oxfenicine.

In one embodiment, a Compound has the following structure (XX):

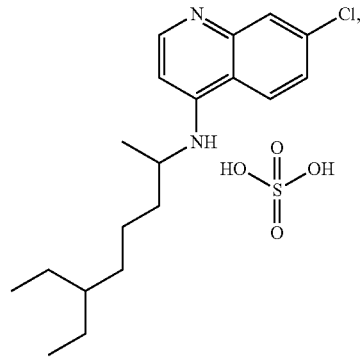

which is also referred to as chloroquine.

In one embodiment, a Compound has the following structure (XXI):

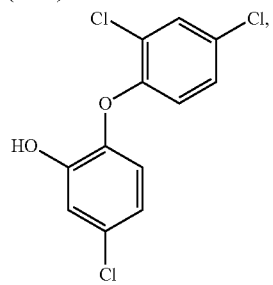

which is also referred to as triclosan.

In one embodiment, a Compound has the following structure (XXII):

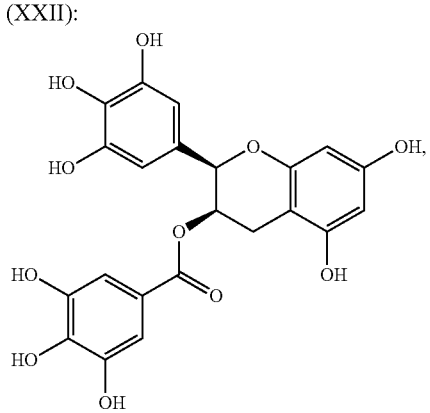

which is also referred to as epigallocatechin-3-gallate.

In one embodiment, a Compound is a naturally occurring flavonoid.

In a particular embodiment, a Compound is one of the following naturally occurring flavonoids:

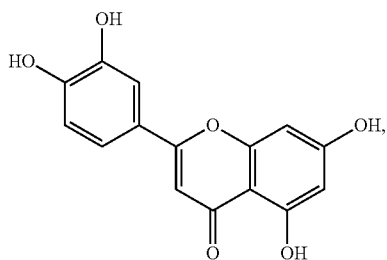 [SMILES: O=c1cc(-c2ccc(O)c(O)c2)oc2cc(O)cc(O)c12]

which is also referred to as luteolin;

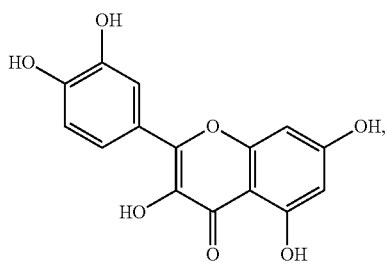 [SMILES: O=c1c(O)c(-c2ccc(O)c(O)c2)oc2cc(O)cc(O)c12]

which is also referred to as quercetin; or

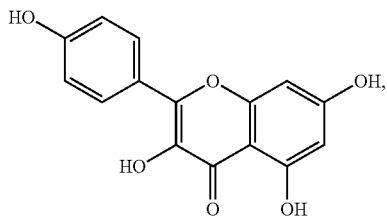 [SMILES: O=c1c(O)c(-c2ccc(O)cc2)oc2cc(O)cc(O)c12]

which is also referred to as kaempferol.

In one embodiment, a Compound is CBM-301106.
In one embodiment, a Compound has the following structure (XXIV):

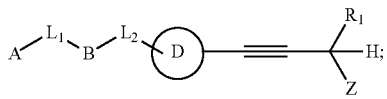

or therapeutically suitable salt, ester or prodrug, thereof, wherein:

A is selected from the group consisting of alkenyl, alkoxyalkyl, alkyl, aryl, arylalkyl, cycloalkyl, cycloalkylalkyl, haloalkyl, heteroaryl, heteroarylalkyl, heterocycle, and heterocyclealkyl;

B is selected from the group consisting of an aryl ring and a heteroaryl ring, which may optionally be substituted with halo, -halo, —OH, —NO$_2$, NHC(O)—(C$_{1-6}$)alkyl, CHO, vinyl, allyl, (C$_{1-6}$)hydroxyalkyl, NH$_2$, NH(C$_{1-6}$)alkyl, N[(C$_{1-6}$) alkyl]$_2$ CH=NOH, CH$_2$N[(C$_{1-6}$)alkyl]$_2$ or CN;

D is selected from the group consisting of an aryl ring and a heteroaryl ring;

L$_1$ is absent or is selected from the group consisting of hydroxyalkylene, —C(R$_a$R$_b$)—, —C(O)—, —C(O)O—, —C(O)NH—, —NR$_c$CH$_2$—, —NR$_c$C(O)—, —NR$_c$C(O)—O—, —NH—N=CH—, —NR$_c$S(O)$_2$—, —O—, —OC(O)NH—, —OC(O)—, —O—N=CH—, —S—, —S(O)$_2$—, —S(O)$_2$NH—;

L$_2$ is selected from the group consisting of —C(R$_d$R$_e$)—, —(CH$_2$)$_n$—, —NH—, —O—, and —S—;

n is 1, 2 or 3;

Z is a member selected from the group consisting of alkoxy, hydroxy, hydroxyalkyl, R$_g$—O— and R$_j$—NH—;

R$_1$ is hydrogen, (C$_{1-6}$)haloalkyl or (C$_{1-6}$)alkyl; R$_a$ and R$_b$ are each individually selected from the group consisting of hydrogen, alkyl, haloalkyl and hydroxy or R$_a$ and R$_b$ taken together with the atom to which they are attached form R$_f$—N=;

R$_c$ is selected from the group consisting of hydrogen, alkyl, aryl, haloalkyl, and heteroaryl;

R$_d$ is selected from the group consisting of alkyl, haloalkyl, hydroxy and halo;

R$_e$ is selected from the group consisting of hydrogen, alkyl, haloalkyl, hydroxy and halo, or R$_d$ and R$_e$ taken together with the atom to which they are attached form oxo;

R$_f$ is selected from the group consisting of alkoxy, aryloxy, heteroaryloxy and hydroxy;

R$_g$ is H$_2$N—C(O)— or (C$_{1-6}$)alkylHN—C—(O)—; and R$_j$ is a member selected from the group consisting of alkylcarbonyl, alkyl-NH—C(O)—, alkoxyalkyl, alkoxyalkylcarbonyl, alkoxycarbonyl, alkoxycarbonyl-NH-alkyl-NHC(O)—, alkoxy-NH—C(O)—, cyanoalkylcarbonyl, hydroxy, HONH—C(O)—, H$_2$NC(O)—, H$_2$NC(=NH)—, H$_2$NC(O)alkyl-NHC(O)—, H$_2$N—O—C(O)—, heteroaryl, heteroarylcarbonyl, heterocycle, and heterocyclecarbonyl.

An embodiment of structure (XXIV), is structure (XXIVa):

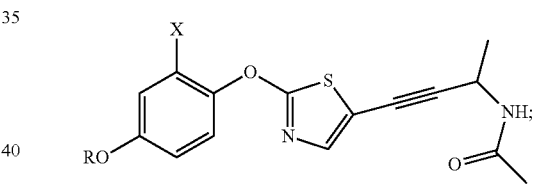

wherein

R is (C$_{1-6}$)alkyl, (C$_{1-6}$)alkyl-cycloalkyl, (C$_{1-6}$)alkyl-heteroaryl, (C$_{1-6}$) alkyl-heterocycloalkyl; and wherein X is -halo, —OH, —NO$_2$, NHC(O)—(C$_{1-6}$)alkyl, CHO, vinyl, allyl, (C$_{1-6}$)hydroxyalkyl, NH$_2$, NH(C$_{1-6}$)alkyl, N[(C$_{1-6}$) alkyl]$_2$ CH=NOH, CH$_2$N[(C$_{1-6}$)alkyl]$_2$ or CN;

Specific embodiments of structure (XXIVa) are presented in the table below:

| Compound | R | X |
|---|---|---|
| XIVa1 | i-Pr | H |
| XIVa2 | i-Bu | H |
| XIVa3 | Pr | H |
| XIVa4 | CH$_2$(cyclopropyl) | H |
| XIVa5 | Cyclohexyl | H |

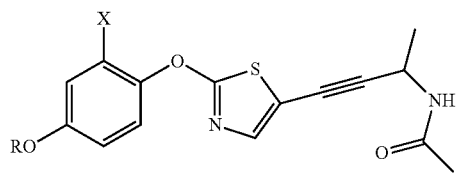

| Compound | R | X |
|---|---|---|
| XIVa6 | CH₂(cyclohexyl) | H |
| XIVa7 | CH₂(Tetrahydrofuran-3-yl) | H |
| XIVa8 | i-Pr | Cl |
| XIVa9 | i-Bu | Cl |
| XIVa10 | Pr | Cl |
| XIVa11 | CH₂(cyclopropyl) | Cl |
| XIVa12 | Cyclohexyl | Cl |
| XIVa13 | CH₂(cyclohexyl) | Cl |
| XIVa14 | CH₂(Tetrahydrofuran-3-yl) | Cl |
| XIVa15 | i-Bu | F |
| XIVa16 | i-Bu | Br |
| XIVa17 | i-Bu | Me |
| XIVa18 | i-Bu | NO₂ |
| XIVa19 | i-Bu | NH₂ |
| XIVa20 | i-Bu | NHCOMe |
| XIVa21 | i-Bu | CHO |
| XIVa22 | i-Bu | CH=NOH |
| XIVa23 | i-Bu | CN |
| XIVa24 | i-Bu | Vinyl |
| XIVa25 | i-Bu | CH₂OH |
| XIVa26 | i-Bu | CH₂NMe₂ |

Another embodiment of structure (XXIV), is structure (XXIVb):

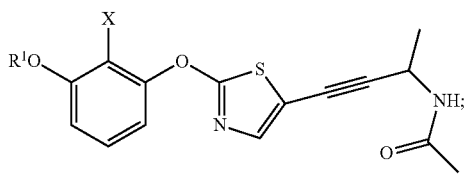

wherein:

R is $(C_{1-6})$alkyl, $(C_{1-6})$alkyl-cycloalkyl, $(C_{1-6})$alkyl-heteroaryl, $(C_{1-6})$ alkyl-heterocycloalkyl; and wherein X is -halo, —OH, —NO₂, NHC(O)—$(C_{1-6})$alkyl, CHO, vinyl, allyl, $(C_{1-6})$hydroxyalkyl, NH₂, NH$(C_{1-6})$alkyl, N[$C_{1-6}$ alkyl]₂ CH=NOH, CH₂N[$(C_{1-6})$alkyl]₂ or CN;

In a specific embodiment, the compound of structure (XXIVb) is:

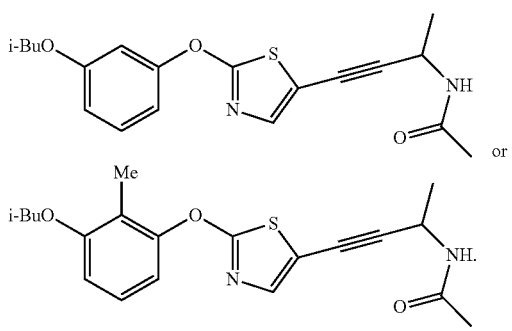

In specific embodiment, the compound of structure (XXIV) is:

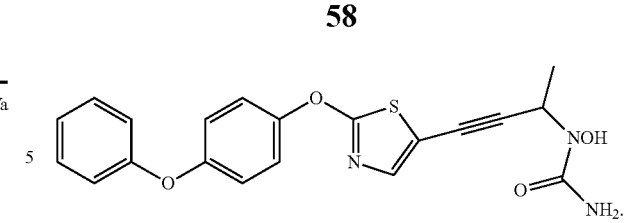

In specific embodiment, the compound of structure (XXIV) is not:

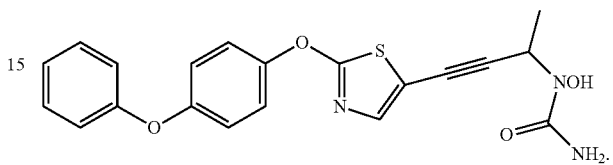

In one embodiment, a Compound has the following structure (XXV):

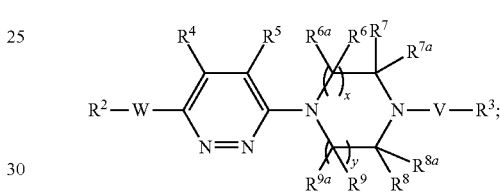

wherein:
x and y are each independently 1, 2 or 3;
W is —C(O)N($R^1$)—, —C(O)N[C(O)$R^{1a}$]—, —N($R^1$)C(O)N($R^{1a}$)— or —N($R^1$)C(O)—;
V is —C(O)—, —C(S)—, —C($R^{10}$)H, —O— or —CH₂—;
each $R^1$ is independently selected from the group consisting of hydrogen; $(C_1-C_6)$alkyl optionally substituted with one or more substituents selected from the group consisting of halo, methyl or trifluoromethyl; and $(C_2-C_6)$alkyl optionally substituted with one or more substituents selected from the group consisting of methoxy and hydroxyl;
$R^{1a}$ is selected from the group consisting of hydrogen, $(C_1-C_6)$alkyl and cycloalkyl;
$R^2$ is selected from the group consisting of $(C_1-C_6)$alkyl, $(C_2-C_{12})$alkenyl, $(C_2-C_{12})$hydroxyalkyl, $(C_2-C_{12})$hydroxyalkenyl, $(C_2-C_{12})$alkoxy, $(C_2-C_{12})$alkoxyalkyl, $(C_3-C_{12})$cycloalkyl, $(C_4-C_{12})$cycloalkylalkyl, aryl, $(C_7-C_{12})$aralkyl, $(C_3-C_{12})$heterocyclyl, $(C_3-C_{12})$heterocyclylalkyl, $(C_3-C_{12})$heteroaryl, and $(C_3-C_{12})$heteroarylalkyl; or
$R^2$ is a multi-ring structure having 2 to 4 rings wherein the rings are independently selected from the group consisting of cycloalkyl, heterocyclyl, aryl and heteroaryl and where some or all of the rings may be fused to each other;
$R^3$ is selected from the group consisting of $(C_1-C_6)$alkyl, $(C_2-C_{12})$alkenyl, $(C_2-C_{12})$hydroxyalkyl, $(C_2-C_{12})$hydroxyalkenyl, $(C_2-C_{12})$alkoxy, $(C_2-C_{12})$alkoxyalkyl, $(C_3-C_{12})$cycloalkyl, $(C_4-C_{12})$cycloalkylalkyl, substituted aryl, substituted $(C_7-C_{12})$aralkyl, $(C_3-C_{12})$heterocyclyl, $(C_3-C_{12})$heterocyclylalkyl, $(C_3-C_{12})$heteroaryl, and $(C_3-C_{12})$heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or $-N(R^{12})_2$;

$R^6$, $R^{6a}$, $R^7$, $R^{7a}$, $R^8$, $R^{8a}$, $R^9$, and $R^{9a}$ are each independently selected from hydrogen or $(C_1-C_3)$alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is $-C(O)-$, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or $(C_3-C_2)$alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $(C_3-C_{12})$alkyl;

$R^{10}$ is hydrogen or $(C_3-C_{12})$alkyl; and
each $R^{12}$ is independently selected from hydrogen or $(C_1-C_6)$ alkyl;

a stereoisomer, enantiomer or tautomer thereof, a pharmaceutically acceptable salt thereof, a pharmaceutical composition thereof or a prodrug thereof.

In a specific embodiment, the compound of structure (XXV) is:

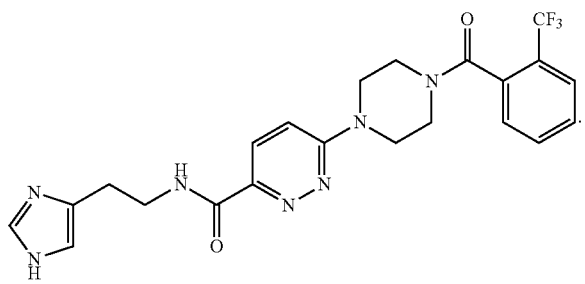

wherein
Ar is 2-trifluoromethylphenyl, phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2-chlorophenyl or 2,5-dichlorophenyl.

Another specific embodiment of structure (XXV) is:

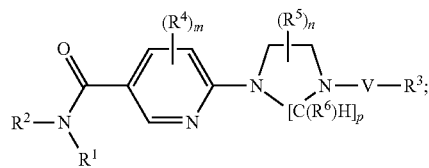

In one embodiment, a Compound has the following structure (XXVI):

wherein:
m is 1, 2 or 3;
n is 1, 2, 3 or 4;
p is 2, 3 or 4;
V is $-C(O)-$, $-S(O)-$ or $-S(O)_2$, $-O-$ or $-CH_2-$;
$R^1$ is hydrogen, alkyl, alkenyl, aryl, heteroaryl, aralkyl, aralkenyl or cycloalkyl;
$R^2$ is selected from the group consisting of hydrogen, $-R^7-OR^8$, $-R^7-N(R^8)_2$, $-R^7-S(O)_tR^{10}$ (where t is 0, 1 or 2), alkyl, alkenyl, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl and optionally substituted heteroarylalkenyl;
$R^3$ is selected from the group consisting of hydrogen, $-R^9-OR^8$, $-R^9-N(R^8)_2$, alkyl, alkenyl, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl and optionally substituted heteroarylalkenyl;
each $R^4$ is independently hydrogen, alkyl, alkenyl, halo, haloalkyl, aryl, cyano, nitro, $-R^9-OR^8$, $-R^9-N(R^8)_2$ or $-S(O)_t-R^{10}$ (where t is 0, 1 or 2);
each $R^5$ and $R^6$ is independently hydrogen, oxo, alkyl, alkenyl, halo, haloalkyl or aryl; or
one $R^5$ and one $R^6$ may together form an straight or branched alkylene bridge;
each $R^7$ is independently a straight or branched alkylene or alkenylene chain;
each $R^8$ is independently hydrogen, alkyl, alkenyl, haloalkyl, cycloalkyl, cycloalkylalkyl, aryl, aralkyl, heterocyclyl, heterocylylalkyl, heteroaryl or heteroarylalkyl;

each $R^9$ is independently a direct bond or a straight or branched alkylene or alkenylene chain; and $R^{10}$ is alkyl, alkenyl, haloalkyl, cycloalkyl, cycloalkylalkyl, aryl, aralkyl, heterocyclyl, heterocylylalkyl, heteroaryl or heteroarylalkyl; as a single stereoisomer, a mixture of stereoisomers, a racemic mixture thereof of stereoisomers, or as a tautomer; or as a, pharmaceutically acceptable salt, prodrug, solvate or polymorph thereof.

A specific embodiment of structure (XXVI) is:

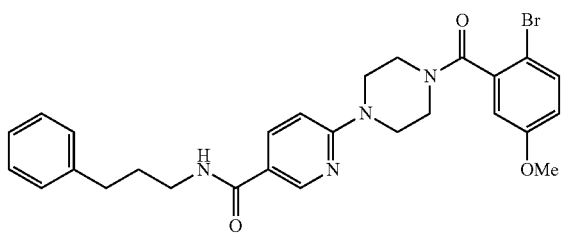

In one embodiment, a Compound has the following structure (XXVII):

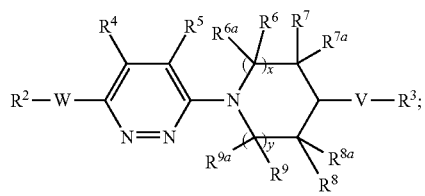

wherein:

x and y are each independently 1, 2 or 3;

W is —C(O)N($R^1$)—, —C(O)N[C(O)$R^{1a}$]—, —N($R^1$)C(O) N($R^{1a}$)— or —N($R^1$)C(O)—;

V is —C(O)—, —C(S)—, —C($R^{10}$)H—, —O— or —CH$_2$—;

each $R^1$ is independently selected from the group consisting of hydrogen; ($C_1$-$C_6$)alkyl optionally substituted with one or more substituents selected from the group consisting of halo, methyl or trifluoromethyl; and ($C_2$-$C_6$)alkyl optionally substituted with one or more substituents selected from the group consisting of methoxy and hydroxyl;

$R^{1a}$ is selected from the group consisting of hydrogen, ($C_1$-$C_6$)alkyl and cycloalkyl;

$R^2$ is selected from the group consisting of ($C_1$-$C_6$)alkyl, ($C_2$-$C_{12}$)alkenyl, ($C_2$-$C_{12}$)hydroxyalkyl, ($C_2$-$C_{12}$)hydroxyalkenyl, ($C_2$-$C_{12}$)alkoxy, ($C_2$-$C_{12}$)alkoxyalkyl, ($C_3$-$C_{12}$)cycloalkyl, ($C_4$-$C_{12}$)cycloalkylalkyl, aryl, ($C_7$-$C_{12}$)aralkyl, ($C_3$-$C_{12}$)heterocyclyl, ($C_3$-$C_{12}$)heterocyclylalkyl, ($C_3$-$C_{12}$) heteroaryl, and ($C_3$-$C_{12}$)heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of ($C_1$-$C_6$)alkyl, ($C_2$-$C_{12}$)alkenyl, ($C_2$-$C_{12}$)hydroxyalkyl, ($C_2$-$C_{12}$)hydroxyalkenyl, ($C_2$-$C_{12}$)alkoxy, ($C_2$-$C_{12}$)alkoxyalkyl, ($C_3$-$C_{12}$)cycloalkyl, ($C_4$-$C_{12}$)cycloalkylalkyl, substituted aryl, substituted ($C_7$-$C_{12}$)aralkyl, ($C_3$-$C_{12}$)heterocyclyl, ($C_3$-$C_{12}$) heterocyclylalkyl, ($C_3$-$C_{12}$)heteroaryl, and ($C_3$-$C_{12}$) heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —N($R^{12}$)$_2$;

$R^6$, $R^{6a}$, $R^7$, $R^{7a}$, $R^8$, $R^{8a}$, $R^9$, and $R^{9a}$ are each independently selected from hydrogen or ($C_1$-$C_3$)alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$ and $R^{9a}$ are each independently selected from hydrogen or ($C_3$-$C_{12}$)alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or ($C_3$-$C_{12}$)alkyl;

$R^{10}$ is hydrogen or ($C_3$-$C_{12}$)alkyl; and each $R^{12}$ is independently selected from hydrogen or ($C_1$-$C_6$)alkyl;

a stereo isomer, enantiomer or tautomer thereof, a pharmaceutically acceptable salt thereof, a pharmaceutical composition thereof or a prodrug thereof.

One embodiment of structure (XXVII) is (XXVIIa):

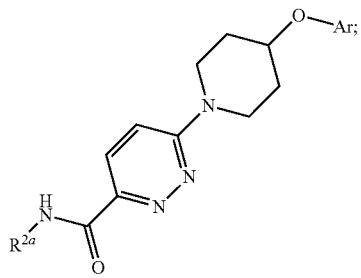

wherein $R^{2a}$ is —H, CH$_3$, HOCH$_2$CH$_2$,

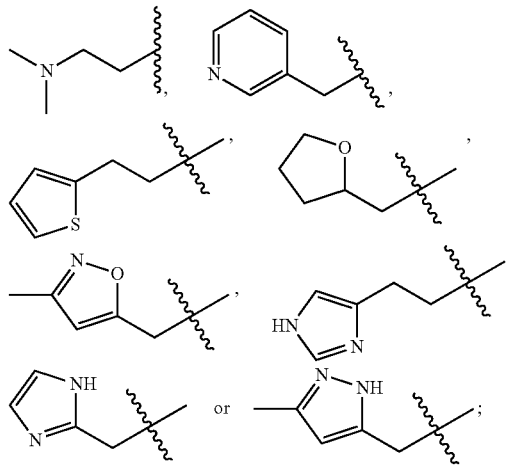

and wherein Ar is 2-fluorophenyl, 2-chlorophenyl, 2-bromophenyl, 2-cyanophenyl or 2-chloro-5-fluorophenyl.

In one embodiment, a Compound has the following structure (XXVIII):

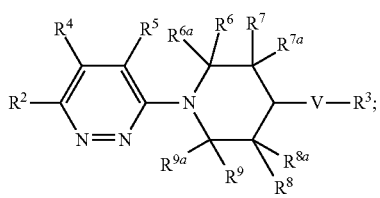

wherein:

x and y are each independently 1, 2 or 3;

V is —C(O)—, —C(S)—, —C($R^{10}$)H, —O— or —$CH_2$—;

each $R^1$ is independently selected from the group consisting of hydrogen; ($C_1$-$C_6$)alkyl optionally substituted with one or more substituents selected from the group consisting of halo, methyl or trifluoromethyl; and ($C_2$-$C_6$)alkyl optionally substituted with one or more substituents selected from the group consisting of methoxy and hydroxyl;

$R^{1a}$ is selected from the group consisting of hydrogen, ($C_1$-$C_6$)alkyl and cycloalkyl;

$R^2$ is selected from the group consisting of ($C_1$-$C_6$)alkyl, ($C_2$-$C_{12}$)alkenyl, ($C_2$-$C_{12}$)hydroxyalkyl, ($C_2$-$C_{12}$)hydroxyalkenyl, ($C_2$-$C_{12}$)alkoxy, ($C_2$-$C_{12}$)alkoxyalkyl, ($C_3$-$C_{12}$)cycloalkyl, ($C_4$-$C_{12}$)cycloalkylalkyl, aryl, ($C_7$-$C_{12}$)aralkyl, ($C_3$-$C_{12}$)heterocyclyl, ($C_3$-$C_{12}$)heterocyclylalkyl, ($C_3$-$C_{12}$)heteroaryl, and ($C_3$-$C_{12}$)heteroarylalkyl; or $R^2$ is a multi-ring structure having 2 to 4 rings wherein the rings are independently selected from the group consisting of cycloalkyl, heterocyclyl, aryl and heteroaryl and where some or all of the rings may be fused to each other; $R^3$ is selected from the group consisting of ($C_1$-$C_6$)alkyl, ($C_2$-$C_{12}$)alkenyl, ($C_2$-$C_{12}$)hydroxyalkyl, ($C_2$-$C_{12}$)hydroxyalkenyl, ($C_2$-$C_{12}$)alkoxy, ($C_2$-$C_{12}$)alkoxyalkyl, ($C_3$-$C_{12}$)cycloalkyl, ($C_4$-$C_{12}$)cycloalkylalkyl, substituted aryl, substituted ($C_7$-$C_{12}$)aralkyl, ($C_3$-$C_{12}$)heterocyclyl, ($C_3$-$C_{12}$)heterocyclylalkyl, ($C_3$-$C_{12}$)heteroaryl, and ($C_3$-$C_{12}$)heteroarylalkyl; or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —N($R^{12}$)$_2$;

$R^6$, $R^{6a}$, $R^7$, $R^{7a}$, $R^8$, $R^{8a}$, $R^9$, and $R^{9a}$ are each independently selected from hydrogen or ($C_1$-$C_3$)alkyl; or $R^6$ and $R^{6a}$ together, or $R^7$ and $R^{7a}$ together, or $R^8$ and $R^{8a}$ together, or $R^9$ and $R^{9a}$ together are an oxo group, provided that when V is —C(O)—, $R^7$ and $R^{7a}$ together or $R^8$ and $R^{8a}$ together do not form an oxo group, while the remaining $R^6$, $R^{6a}$, $R^7$, $R^{7a}$, $R^8$, $R^{8a}$, $R^9$, and $R^{9a}$ are each independently selected from hydrogen or ($C_3$-$C_{12}$)alkyl; or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or ($C_3$-$C_{12}$)alkyl;

$R^{10}$ is hydrogen or ($C_3$-$C_{12}$)alkyl; and each $R^{12}$ is independently selected from hydrogen or ($C_1$-$C_6$)alkyl; a stereoisomer, enantiomer or tautomer thereof, a pharmaceutically acceptable salt thereof, a pharmaceutical composition thereof or a prodrug thereof.

In one embodiment, the Compound of structure (XVIII) is:

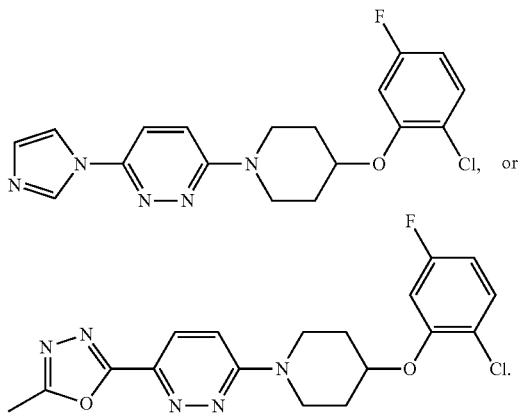

One specific embodiment of structure (XXVIII) is (XXVIIIa) as follows:

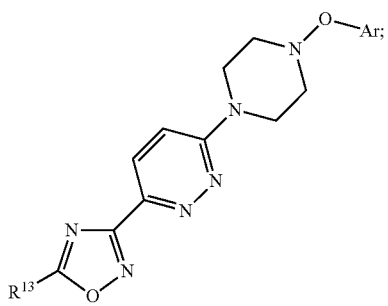

wherein $R^{13}$ is —$CH_3$, —$CF_3$, n-Pr or —$CH_2$Ph; and wherein

Ar is phenyl, 2-chlorophenyl, 2-fluorophenyl, 2-methylphenyl or 2-chloro-5-fluorophenyl.

Another specific embodiment of structure (XXVIII) is (XVIIIb) as follows:

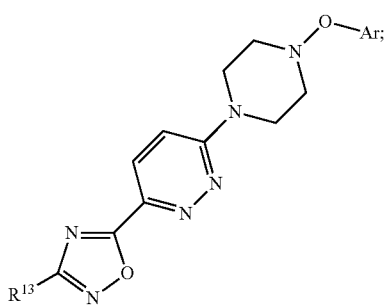

wherein $R^{13}$ is —$CH_3$, —$CF_3$, n-Pr or —$CH_2$Ph;

and wherein Ar is phenyl, 2-chlorophenyl, 2-fluorophenyl, 2-methylphenyl or 2-chloro-5-fluorophenyl.

Another specific embodiment of structure (XXVIII) is (XXVIIIc) as follows:

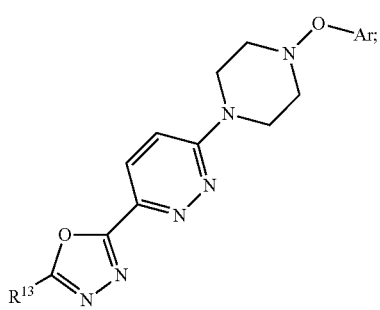

wherein R[13] is —CH$_3$, —CF$_3$, n-Pr or —CH$_2$Ph;
and wherein Ar is phenyl, 2-chlorophenyl, 2-fluorophenyl, 2-methylphenyl or 2-chloro-5-fluorophenyl.

Yet another specific embodiment of structure (XXVIII) is (XXVIIId) as follows:

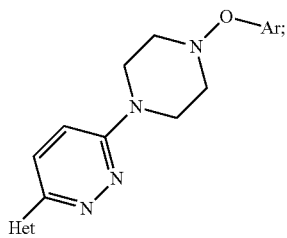

wherein Het is:

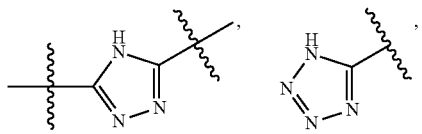

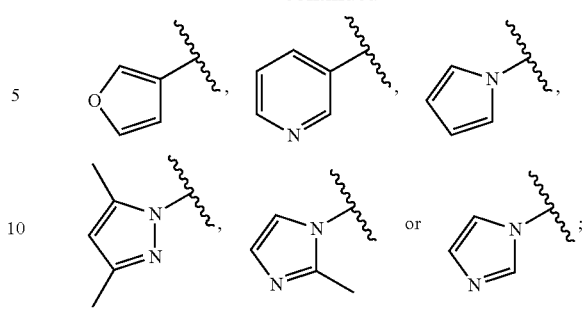

and wherein Ar is phenyl, 2-chlorophenyl, 2-fluorophenyl, 2-methylphenyl or 2-chloro-5-fluorophenyl.

In one embodiment, a Compound has the following structure (XXIX):

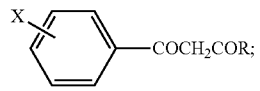

wherein:

X is —(C$_5$-C$_{20}$)alkyl, —O—(C$_5$-C$_{20}$)alkyl or —(C$_5$-C$_{20}$)alkoxy; R is —O—(C$_1$-C$_6$)alkyl, (C$_1$-C$_6$)alkoxy, O—(C$_1$-C$_6$)alkyl-NHC(O)—(C$_1$-C$_6$)alkyl, —NH$_2$ or —NH—(C$_1$-C$_6$)alkyl;

a stereoisomer, enantiomer or tautomer thereof, a pharmaceutically acceptable salt thereof, a metal chelate thereof, a pharmaceutical composition thereof or a prodrug thereof.

In a specific embodiment, a compound of structure (XXIX) is;

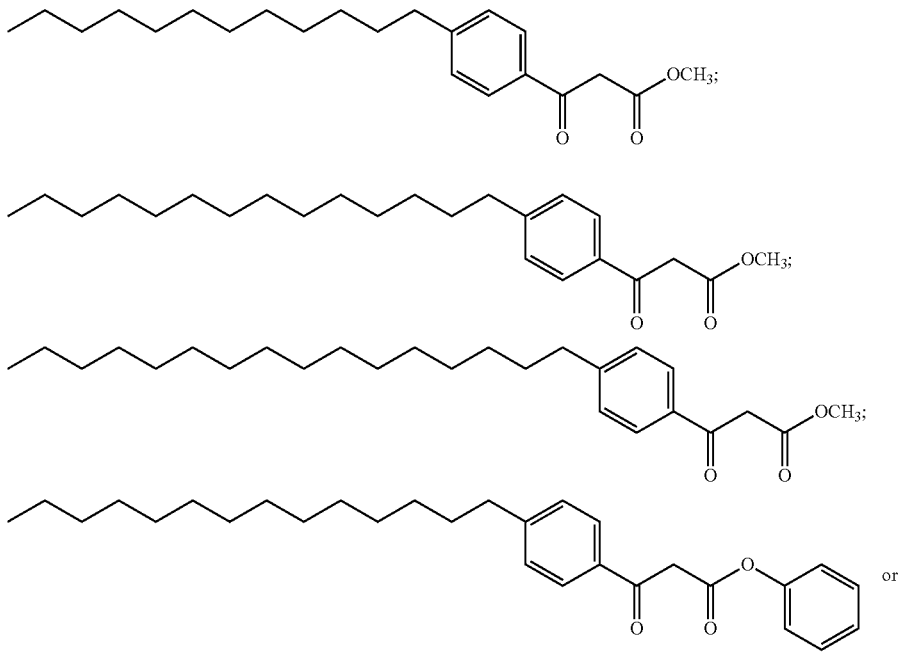

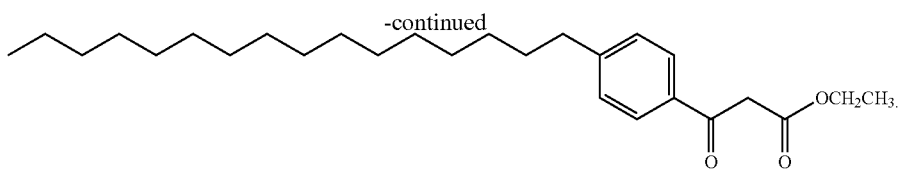

In one embodiment, a Compound has the following structure (XXX):

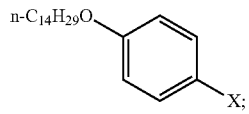

wherein:

X is —($C_1$-$C_6$)alkyl, —($C_1$-$C_6$)alkoxy, —($C_1$-$C_6$)alkenoxy, —($C_1$-$C_6$)hydroxyalkyl, aryl, heterocyclyl, heteroaryl, —CN, —CHO, —CO($C_1$-$C_6$)alkyl, —S($C_1$-$C_6$)alkyl, —CON[($C_1$-$C_6$)alkyl]$_2$, —CONH$_2$, —($C_1$-$C_6$)alkylCOO($C_1$-$C_6$)alkyl, —($C_1$-$C_6$)alkylOCOO($C_1$-$C_6$)alkyl, —($C_1$-$C_6$)alkenylCOO($C_1$-$C_6$)alkyl, —CO($C_1$-$C_6$)alkylCOO($C_1$-$C_6$)alkyl, CO($C_1$-$C_6$)alkylCOOH, —O($C_1$-$C_6$)alkylCOO($C_1$-$C_6$)alkyl or —S($C_1$-$C_6$)alkylCOO($C_1$-$C_6$)alkyl.

In a specific embodiment, the compound of structure (XXX) is:

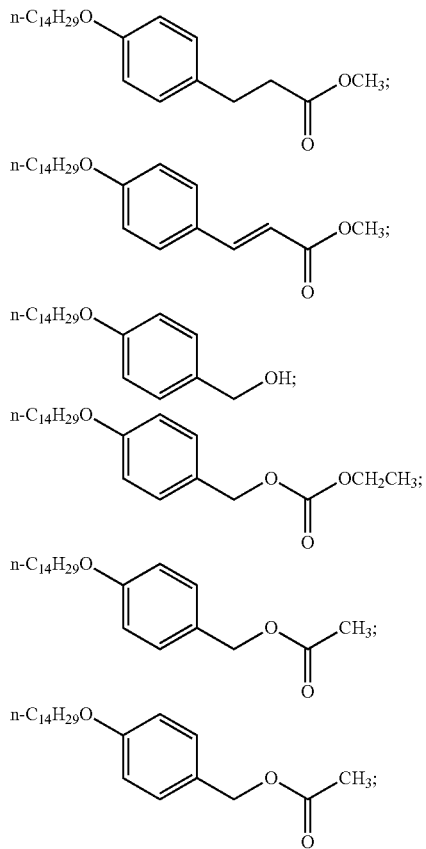

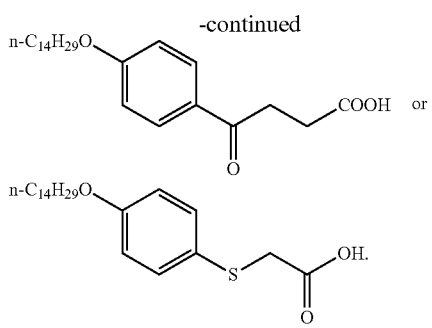

In one embodiment, a Compound has the following structure (XXXI):

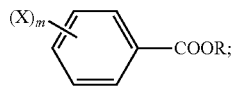

wherein:

X is —($C_5$-$C_{20}$)alkyl, —O($C_5$-$C_{20}$)alkyl or —($C_5$-$C_{20}$)alkoxy, —($C_5$-$C_{20}$)haloalkyl, —O—($C_5$-$C_{20}$)haloalkyl or —($C_5$-$C_{20}$)haloalkoxy, -halo, —OH, —($C_5$-$C_{20}$)alkenyl, —($C_5$-$C_{20}$)alkynyl, —($C_5$-$C_{20}$)alkoxy-alkenyl, —($C_5$-$C_{20}$)hydroxyalkyl, —O($C_1$-$C_6$)alkyl, —CO$_2$($C_1$-$C_6$)alkyl, —O($C_5$-$C_{20}$)alkenyl, —O($C_5$-$C_{20}$)alkynyl, —O($C_5$-$C_{20}$)cycloalkyl; —S($C_5$-$C_{20}$)alkyl, —NH($C_5$-$C_{20}$)alkyl, —NHCO($C_5$-$C_{20}$)alkyl, —N($C_1$-$C_6$)alkylCO($C_5$-$C_{20}$)alkyl or —O($C_5$-$C_{20}$)alkoxy;

R is —H or —($C_1$-$C_6$)alkyl;

m is 1, 2 or 3.

In a specific embodiment, the compound of structure (XXXI) is:

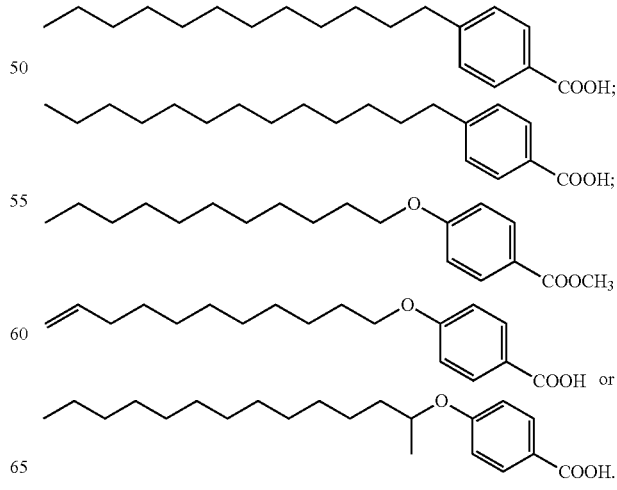

In one embodiment, a Compound has the following structure (XXXIII):

wherein:

Y is O or S; —NH or N(C-1-C6)alkyl,

X is —COOH, —CO$_2$(C$_1$-C$_6$)alkyl, —CONH$_2$, —H, —CO(C$_1$-C$_6$)alkyl, —COC(halo)$_3$,

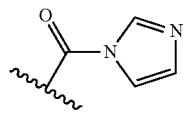 [SMILES: *C(=O)n1ccnc1]

or a moiety that can form an adduct with coenzyme A; and

Z is —(C$_5$-C$_{20}$)alkyl, —O(C$_5$-C$_{20}$)alkyl or —(C$_5$-C$_{20}$) alkoxy, —(C$_5$-C$_{20}$)haloalkyl, —O—(C$_5$-C$_{20}$)haloalkyl or —(C$_5$-C$_{20}$)haloalkoxy, -halo, —OH, —(C$_5$-C$_{20}$)alkenyl, —(C$_5$-C$_{20}$)alkynyl, —(C$_5$-C$_{20}$)alkoxy-alkenyl, —(C$_5$-C$_{20}$) hydroxyalkyl, —O(C$_1$-C$_6$)alkyl, —CO$_2$(C$_1$-C$_6$)alkyl, —O(C$_5$-C$_{20}$)alkenyl, —O(C$_5$-C$_{20}$)alkynyl, —O(C$_5$-C$_{20}$)cycloalkyl; —S(C$_5$-C$_{20}$)alkyl, —NH(C$_5$-C$_{20}$)alkyl, —NHCO (C$_5$-C$_{20}$)alkyl, —N(C$_1$-C$_6$)alkylCO(C$_5$-C$_{20}$)alkyl or —O(C$_5$-C$_{20}$)alkoxy.

In one embodiment, compounds of structure (XXXIII) are those wherein Y is O.

In another embodiment, compounds of structure (XXXIII) are those wherein X is —COOH.

In another embodiment, compounds of structure (XXXIII) are those wherein Z is —O(C$_5$-C$_{20}$)alkyl, —O(C$_5$-C$_{20}$)haloalkyl, —O(C$_5$-C$_{20}$)alkenyl, —O(C$_5$-C$_{20}$)alkynyl or —O(C$_5$-C$_{20}$)alkoxy.

In another embodiment, compounds of structure (XXXIII) are those wherein Y is O, X is —COOH and Z is —O(C$_5$-C$_{20}$)alkyl, —O(C$_5$-C$_{20}$)haloalkyl, —O(C$_5$-C$_{20}$)alkenyl, —O(C$_5$-C$_{20}$)alkynyl or —O(C$_5$-C$_{20}$)alkoxy.

In another embodiment, compounds of structure (XXXIII) are those wherein X is a moiety that can form an ester linkage with coenzyme A. For example, X can be a moiety that allows for the formation of compounds of the structure:

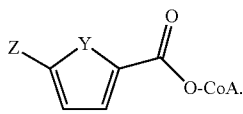

In a specific embodiment, a compound of structure (XXXIII) is:

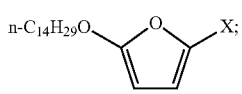

wherein:

X is —COOH, —CO$_2$(C$_1$-C$_6$)alkyl, —CONH$_2$, —H, —CO(C$_1$-C$_6$)alkyl, —COC(halo)$_3$,

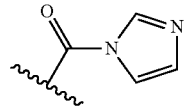 [SMILES: *C(=O)n1ccnc1]

or a moiety that can form an adduct with coenzyme A.

In another specific embodiment, a compound of structure (XXXIII) is:

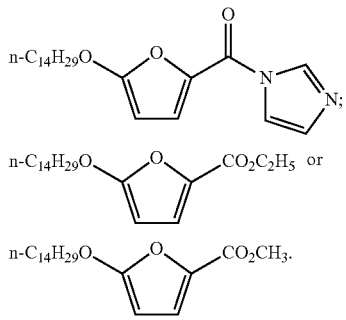

In a specific embodiment, the compounds of structure (XXXIII) are the compounds disclosed in Parker et al., *J. Med. Chem.* 1977, 20, 781-791, which is herein incorporated by reference in its entirety.

In one embodiment, a Compound has the following structure (XXXII):

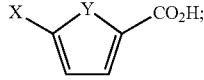

wherein:

X is —(C$_5$-C$_{20}$)alkyl, —O(C$_5$-C$_{20}$)alkyl or —(C$_5$-C$_{20}$) alkoxy, —(C$_5$-C$_{20}$)haloalkyl, —O(C$_5$-C$_{20}$)haloalkyl or —(C$_5$-C$_{20}$)haloalkoxy, -halo, —OH, —(C$_5$-C$_{20}$)alkenyl, —(C$_5$-C$_{20}$)alkynyl, —(C$_5$-C$_{20}$)alkoxy-alkenyl, —(C$_5$-C$_{20}$) hydroxyalkyl, —O(C$_1$-C$_6$)alkyl, —CO$_2$(C$_1$-C$_6$)alkyl, —O(C$_5$-C$_{20}$)alkenyl, —O(C$_5$-C$_{20}$)alkynyl, —O(C$_5$-C$_{20}$)cycloalkyl, —S(C$_5$-C$_{20}$)alkyl, —NH(C$_5$-C$_{20}$)alkyl, —NHCO (C$_5$-C$_{20}$)alkyl, —N(C$_1$-C$_6$)alkylCO(C$_5$-C$_{20}$)alkyl or —O(C$_5$-C$_{20}$)alkoxy;

Y is O, S, —NH or N(C$_1$-C$_6$)alkyl.

In a specific embodiment, a compound of structure (XXXII) is:

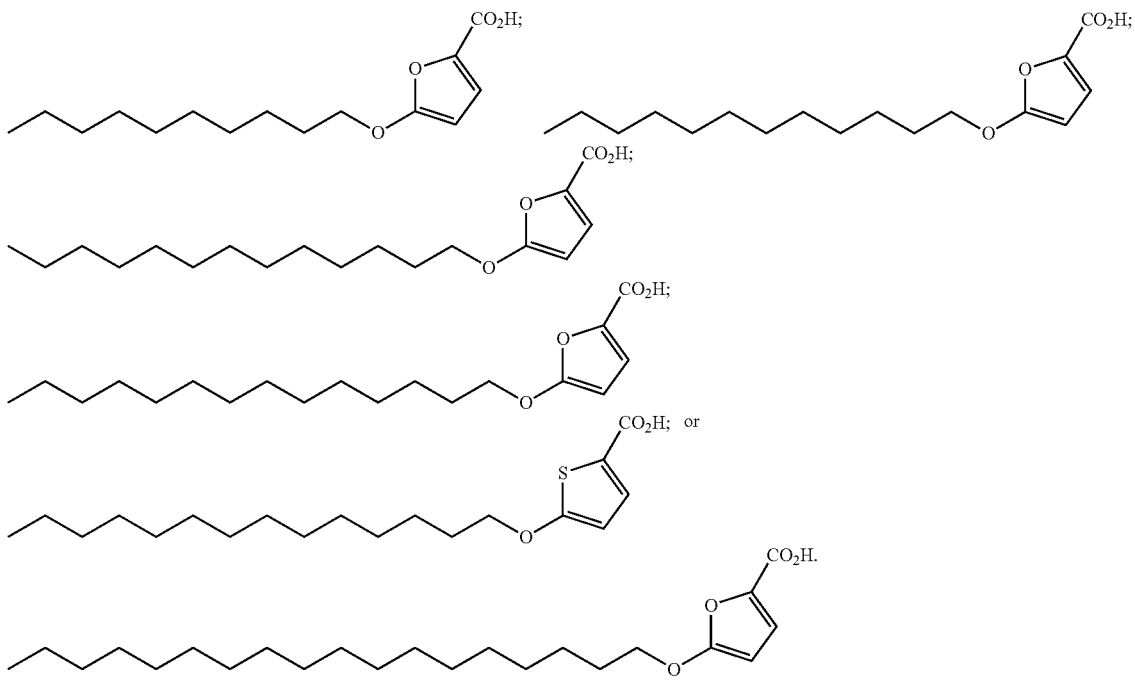

In a specific embodiment, the compounds of structure (XXXII) are the compounds disclosed in Parker et al., *J. Med. Chem.* 1977, 20, 781-791, which is herein incorporated by reference in its entirety.

In one embodiment, a compound of structure (XXXIII) is:

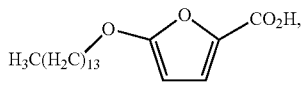

[structure (XXIII)], which is also referred to as TOFA and has the chemical name 5-(tetradecyloxy)-2-furoic acid.

In a specific embodiment, a compound of structure (XXXIII) is not TOFA, which is also depicted as the following structure:

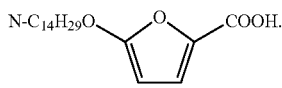

In one embodiment, a Compound has the following structure (XXXIV):

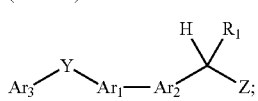

wherein:

$R_1$ is selected from the group consisting of hydrogen, cycloalkyl, alkyl and haloalkyl;

Y is selected from the group consisting of —$(CR_{4a}R_{4b})_m$—, —C(O)—, —O—, —N(H)—, —N(alkyl)- and —S—; wherein m is 1, 2 or 3;

each of $R_{4a}$, $R_{4b}$, at each occurrence, is independently selected from the group consisting of hydrogen, alkyl, hydroxyalkyl, and haloalkyl when m is 1, 2 or 3;

alternatively, $R_{4a}$ and $R_{4b}$ together with the carbon to which they are attached form a monocyclic cycloalkyl or heterocycle ring when m is 1;

$Ar_3$ is phenyl or monocyclic heteroaryl; wherein $Ar_3$ is substituted with 1, 2 or 3 or 4 substituents independently selected from the group consisting of alkyl, alkenyl, —CN, —$NO_2$, halogen, —$OR_5$, —O—N=CH($R_2$), —OC(O)$R_2$, —OC(O)N($R_3$)($R_5$), —OC(O)O$R_2$, —OS(O)$_2R_5$, —$SR_2$, —S(O)$R_2$, —S(O)$_2R_5$, —S(O)$_2OR_5$, —S(O)$_2$N($R_3$)($R_5$), —C(O)$R_5$, —C(O)N($R_3$)($R_5$), —C(O)O$R_5$, —C(O)N($R_3$)($R_5$), —N($R_3$)($R_5$), —N(H)—N=CH($R_2$), —N($R_3$)C(O)$R_2$, —N($R_3$)C(O)O$R_5$, —N($R_3$)S(O)$_2R_5$, —N($R_3$)S(O)$_2$N($R_3$)($R_5$), —$R_8$, haloalkyl, cyanoalkyl, nitroalkyl, hydroxyalkyl, alkoxyalkyl, haloalkoxyalkyl, -alkylenyl-OC(O)$R_2$, -alkylenyl-OC(O)N($R_3$)($R_5$), -alkylenyl-OC(O)O$R_2$, -alkylenyl-OS(O)$_2R_5$, -alkylenyl-$SR_2$, -alkylenyl-S(O)$R_2$, -alkylenyl-S(O)$_2R_5$, -alkylenyl-S(O)$_2$OR$_5$, -alkylenyl-S(O)$_2$N($R_3$)($R_5$), -alkylenyl-C(O)$R_5$, -alkylenyl-C(O)N($R_3$)($R_5$), -alkylenyl-C(O)O$R_5$, -alkylenyl-C(O)N($R_3$)($R_5$), -alkylenyl-N($R_3$)($R_5$), -alkylenyl-N($R_3$)C(O)$R_2$, -alkylenyl-N($R_2$)C(O)O$R_5$, -alkylenyl-N($R_3$)S(O)$_2R_5$, -alkylenyl-N($R_3$)C(O)N($R_3$)($R_5$), -alkylenyl-N($R_3$)S(O)$_2$N($R_3$)($R_5$), an alkylenyl-$R_8$;

$R_2$, at each occurrence, is independently selected from the group consisting of alkyl, alkenyl, haloalkyl, alkoxyalkyl, haloalkoxyalkyl, —$R_8$, and -alkylenyl-$R_8$;

$R_3$, at each occurrence, is independently selected from the group consisting of hydrogen, alkyl, arylalkyl, haloalkyl, and heteroarylalkyl;

$R_5$, at each occurrence, is independently selected from the group consisting of hydrogen, alkyl, alkenyl, haloalkyl, alkoxyalkyl, haloalkoxyalkyl, —$R_8$, and -alkylenyl-$R_8$;

$Ar_1$ is selected from the group consisting of phenyl and a monocyclic, five or six-membered heteroaryl;

Ar₂ is a monocyclic five membered heteroaryl, wherein each Ar₂ is independently unsubstituted or substituted with 1 or 2 substituents selected from the group consisting of alkyl, alkenyl, halogen, —CN, —NO₂, hydroxy, alkoxy, —NH₂, —N(H)(alkyl), —N(alkyl)₂, —C(O)OH, —C(O)Oalkyl, —C(O)H, —C(O)alkyl, and haloalkyl;

Z is selected from the group consisting of —OR$_{9a}$, -alkylenyl-OR$_{9a}$, —NR₆R$_{9b}$ and -alkylenyl-NR₆R$_{9b}$;

R₆, at each occurrence, is independently selected from the group consisting of hydrogen, alkyl and haloalkyl;

R$_{9a}$, at each occurrence, is independently selected from the group consisting of hydrogen, alkyl, haloalkyl, R₈, —C(O)OR₁₀, —S(O)₂R₁₀, —C(O)NR₇R₁₁, —S(O)₂NR₇R₁₁, —C(O)R₁₀, -alkylenyl-OR₁₀, -alkylenyl-NR₇R₁₁, -alkylenyl-N(R₇)C(O)OR₁₀, -alkylenyl-N(R₇)C(O)R₁₀, -alkylenyl-C(O)OR₁₀, -alkylenyl-S(O)₂R₁₀, -alkylenyl-S(O)₂NR₇R₁₁, -alkylenyl-C(O)NR₇R₁₁, -alkylenyl-C(O)R₁₀, and -alkylenyl-R₈, R$_{9b}$, at each occurrence, is independently selected from the group consisting of hydrogen, alkyl, hydroxy, alkoxy, R₈, —C(=NH)NH₂, —C(O)OR₁₀, —S(O)₂R₁₀, —C(O)NR₇R₁₂, —C(O)ONH₂, —S(O)₂NR₇R₁₂, —C(O)R₁₀, —C(O)CH₂C(O)R₁₀, haloalkyl, -alkylenyl-NR₇R₁₂, -alkylenyl-N(R₇)C(O)OR₁₀, -alkylenyl-N(R₇)C(O)R₁₀, -alkylenyl-C(O)OR₁₀, -alkylenyl-S(O)₂R₁₀, -alkylenyl-S(O)₂NR₇R₁₂, -alkylenyl-C(O)NR₇R₁₂, -alkylenyl-C(O)R₁₀, and -alkylenyl-R₈, R₇, at each occurrence, are each independently selected from the group consisting of hydrogen, alkyl and haloalkyl;

R₁₀, at each occurrence, is independently selected from the group consisting of hydrogen, alkyl, alkoxyalkyl, cyanoalkyl, haloalkyl, —R₈, and alkylenyl-R₈;

R₁₁, at each occurrence, is independently selected from the group consisting of hydrogen, alkyl, hydroxy, alkoxy, alkoxyalkyl, cyanoalkyl, haloalkyl, —R₈, and -alkylenyl-R₈;

R₁₂, at each occurrence, is independently selected from the group consisting of hydrogen, alkyl, hydroxy, alkoxy, —R₈, alkoxyalkyl, cyanoalkyl, haloalkyl, -alkylenyl-C(O)NH₂, -alkylenyl-C(O)N(H)(alkyl), -alkylenyl-C(O)N(alkyl)₂, -alkylenyl-N(H)C(O)Oalkyl, -alkylenyl-N(alkyl)C(O)Oalkyl, and -alkylenyl-R₈; and R₈, at each occurrence, is independently selected from the group consisting of aryl, heteroaryl, heterocycle, cycloalkyl and cycloalkenyl; and the phenyl, cycloalkyl, cycloalkenyl, aryl, heteroaryl, heterocycle, aryl moiety of the arylalkyl, and the heteroaryl moiety of the heteroarylalkyl represented by Ar₁, R₃ and R₈, are each independently unsubstituted or substituted with 1, 2, 3 or 4 substituents independently selected from the group consisting of alkyl, alkenyl, —CN, —NO₂, halogen, ethylenedioxy, methylenedioxy, oxo, —OR$_a$, —OC(O)R$_a$, —OC(O)OR$_a$, —OS(O)₂R$_a$, —S(alkyl), —S(O)alkyl, —S(O)₂alkyl, —S(O)₂OR$_a$, —S(O)₂NR$_a$R$_b$, —C(O)OR$_a$, —C(O)NR$_a$R$_a$, —C(O)OR$_a$, —C(O)NR$_a$R$_b$, —NR$_a$R$_b$, —NOR$_a$, —N(R$_b$)C(O)R$_a$, —N(R$_b$)C(O)OR$_a$, —N(R$_b$)S(O)₂R$_a$, —N(R$_b$)C(O)NR$_a$R$_b$, —N(R$_b$)S(O)₂NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)₂alkyl, -alkylenyl-S(alkyl), -alkylenyl-S(O)alkyl, -alkylenyl-S(O)₂alkyl, -alkylenyl-S(O)₂OR$_a$, -alkylenyl-S(O)₂NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)₂R$_a$, -alkylenyl-N(R$_b$)C(O)NR$_a$R$_b$, and -alkylenyl-N(R$_b$)S(O)₂NR$_a$R$_b$; wherein R$_a$ at each occurrence is independently selected from the group consisting of hydrogen, alkyl, alkenyl and haloalkyl, and R$_b$ at each occurrence is independently selected from the group consisting of hydrogen and alkyl.

In a specific embodiment, a compound of structure (XXXIV) is:

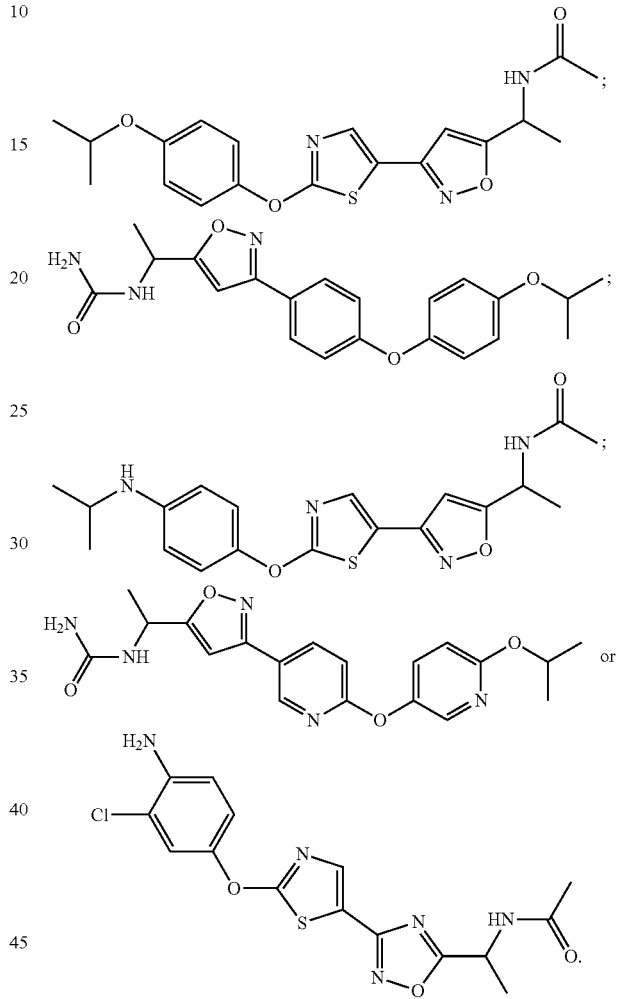

In one embodiment, a Compound has the following structure (XXXV):

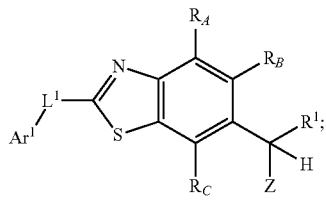

wherein:

R¹ is hydrogen, alkyl, haloalkyl, or cycloalkyl;

L¹ is —CR$_x$R$_y$—, —C(O)—, —O—, —S—, —N(alkyl)-, or —N(H)—; wherein each of R$_x$ and R$_y$ is independently selected from the group consisting of hydrogen, alkyl, hydroxyalkyl and haloalkyl; or R$_x$, and R$_y$ together with the carbon to which they are attached form a three to six-membered monocyclic ring selected from the group consisting of cycloalkyl and heterocycle ring;

$R_A$, $R_B$ and $R_C$ are each independently hydrogen, alkyl, halogen or haloalkyl;

Z is —CN, —$OR^2$, -alkylenyl-$OR^2$, —$N(R^3)(R^4)$ or -alkylenyl-$N(R^3)(R^4)$;

$R^2$, at each occurrence, is independently selected from the group consisting of hydrogen, alkyl, haloalkyl, —C(O)$OR_a$, —S(O)$_2R_a$, —C(O)N($R_a$)($R_b$), —S(O)$_2$N($R_a$)($R_b$), —C(O)$R_a$, -alkylenyl-$OR_a$, -alkylenyl-N($R_a$)($R_b$), -alkylenyl—N($R_b$)C(O)$OR_a$, -alkylenyl-N($R_b$)C(O)N($R_a$)($R_b$), -alkylenyl-N($R_b$)C(O)$R_a$, -alkylenyl-N($R_b$)S(O)$_2R_a$, -alkylenyl-C(O)$OR_a$, -alkylenyl-S(O)$_2R_a$, -alkylenyl-S(O)$_2OR_a$, -alkylenyl-S(O)$_2$N($R_a$)($R_b$), -alkylenyl-C(O)N($R_a$)($R_b$) and -alkylenyl-C(O)$R_a$;

$R^3$, at each occurrence, is independently selected from the group consisting of hydrogen, alkyl and haloalkyl;

$R^4$, at each occurrence, is independently selected from the group consisting of hydrogen, alkyl, hydroxy, alkoxy, —C(=NH)NH$_2$, —C(O)$OR_a$, —S(O)$_2R_a$, —C(O)N($R_a$)($R_b$), —S(O)$_2$N($R_a$)($R_b$), —C(O)$R_a$, —C(O)CH$_2$C(O)$R_a$, haloalkyl, -alkylenyl-$OR_a$, -alkylenyl-N($R_a$)($R_b$), -alkylenyl-N($R_b$)C(O)$OR_a$, -alkylenyl-N($R_b$)C(O)N($R_a$)($R_b$), -alkylenyl-N($R_b$)S(O)S$_2R_a$, -alkylenyl-N($R_b$)C(O)$R_a$, -alkylenyl-C(O)$OR_a$, -alkylenyl-S(O)$_2R_a$, -alkylenyl-S(O)$_2OR_a$, -alkylenyl-S(O)$_2$N($R_a$)($R_b$), -alkylenyl-C(O)N($R_a$)($R_b$) and -alkylenyl-C(O)$R_a$;

$Ar^1$ is phenyl or monocyclic heteroaryl, each of which is optionally fused to a phenyl or a monocyclic, five- or six-membered ring selected from the group consisting of cycloalkyl, cycloalkenyl, heterocycle and heteroaryl, and each $Ar^1$ is independently unsubstituted or substituted with 1, 2, 3 or 4 substituents independently selected from the group consisting of alkyl, alkenyl, —CN, —NO$_2$, halogen, —$OR^6$, —O—N=CH($R^5$), —OC(O)$R^5$, —OC(O)N($R^7$)($R^6$), —OC(O)$OR^5$, —OS(O)$_2R^5$, —$SR^6$, —S(O)$R^5$, —S(O)$_2R^5$, —S(O)$_2OR^6$, —S(O)$_2$N($R^7$)($R^6$), —C(O)$R^6$, —C(O)N($R^7$)($R^6$), —C(O)$OR^6$, —C(O)N($R^7$)($R^6$), —N($R^7$)($R^6$), —N(H)—N=CH($R^5$), —N($R^7$)C(O)$R^6$, —N($R^7$)C(O)$OR^6$, —N($R^7$)S(O)$_2R^6$, —N($R^7$)C(O)N($R^7$)($R^6$), —N($R^7$)S(O)$_2$N($R^7$)($R^6$), —$R^8$, haloalkyl, cyanoalkyl, nitroalkyl, hydroxyalkyl, alkoxyalkyl, haloalkoxyalkyl, -alkylenyl-OC(O)$R_5$, -alkylenyl-OC(O)N($R^7$)($R^6$), -alkylenyl-OC(O)$OR^5$, -alkylenyl-OS(O)$_2R^5$, -alkylenyl-$SR^6$, -alkylenyl-S(O)$R^5$, -alkylenyl-S(O)$_2R^5$, -alkylenyl-S(O)$_2OR^6$, -alkylenyl-S(O)$_2$N($R^7$)($R^6$), -alkylenyl-C(O)$R^6$, -alkylenyl-C(O)N($R^7$)($R^6$), -alkylenyl-C(O)$OR^6$, -alkylenyl-C(O)N($R^7$)($R^6$), -alkylenyl-N($R^7$)($R^6$), -alkylenyl-N($R^7$)C(O)$R^5$, -alkylenyl-N($R^7$)C(O)$OR^5$, -alkylenyl-N($R^7$)S(O)$_2R^5$, -alkylenyl-N($R^7$)C(O)N($R^7$)($R^6$), -alkylenyl-N($R^7$)S(O)$_2$N($R^7$)($R^6$), and -alkylenyl-$R^8$;

$R^5$, at each occurrence, is independently selected from the group consisting of alkyl, alkenyl, haloalkyl, alkoxyalkyl, haloalkoxyalkyl, —$R^8$, and alkylenyl-$R^8$;

$R^6$, at each occurrence, is independently selected from the group consisting of hydrogen, alkyl, alkenyl, haloalkyl, alkoxyalkyl, haloalkoxyalkyl, —$R^8$, and -alkylenyl-$R^8$;

$R^7$, at each occurrence, is independently selected from the group consisting of hydrogen, alkyl, arylalkyl, haloalkyl, and heteroarylalkyl;

$R^8$, at each occurrence, is independently selected from the group consisting of aryl, heteroaryl, heterocycle, cycloalkyl and cycloalkenyl; the phenyl, cycloalkyl, cycloalkenyl, aryl, heteroaryl, heterocycle, aryl moiety of the arylalkyl, and the heteroaryl moiety of the heteroarylalkyl represented by $R^7$ and $R^8$, are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —$OR_a$, —OC(O)$R_a$, —OC(O)$OR_a$, —OS(O)$_2R_a$, —S(alkyl), —S(O)alkyl, —S(O)$_2$alkyl, —S(O)$_2OR_a$, —S(O)$_2$N$R_aR_b$, —C(O)$R_a$, —C(O)N$R_aR_b$, C(O)$OR_a$, —C(O)N$R_aR_b$, —N$R_aR_b$, —NO$R_a$, —N($R_b$)C(O)$R_a$, —N($R_b$)C(O)$OR_a$, —N($R_b$)S(O)$_2R_a$, N($R_b$)C(O)N$R_aR_b$, —N($R_b$)S(O)$_2$N$R_aR_b$, haloalkyl, cyanoalkyl, nitroalkyl, hydroxyalkyl, alkoxyalkyl, haloalkoxyalkyl, -alkylenyl-OC(O)$R_a$, -alkylenyl-OC(O)$OR_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2OR_a$, -alkylenyl-S(O)$_2$N$R_aR_a$, -alkylenyl-C(O)$R_a$, -alkylenyl-C(O)N$R_aR_b$, -alkylenyl-C(O)$OR_a$, -alkylenyl-C(O)N$R_aR_b$, -alkylenyl-N$R_aR_b$, -alkylenyl-N($R_b$)C(O)$R_a$, -alkylenyl-N($R_b$)C(O)$OR_a$, -alkylenyl-N($R_b$)S(O)$_2R_a$, -alkylenyl-N($R_a$)C(O)N$R_aR_b$, and -alkylenyl-N($R_b$)S(O)$_2$N$R_aR_b$;

$R_a$, at each occurrence is independently selected from the group consisting of hydrogen, alkyl, alkenyl and haloalkyl, and $R_b$ at each occurrence is independently selected from the group consisting of hydrogen and alkyl.

In a specific embodiment, a compound of structure (XXXV) is:

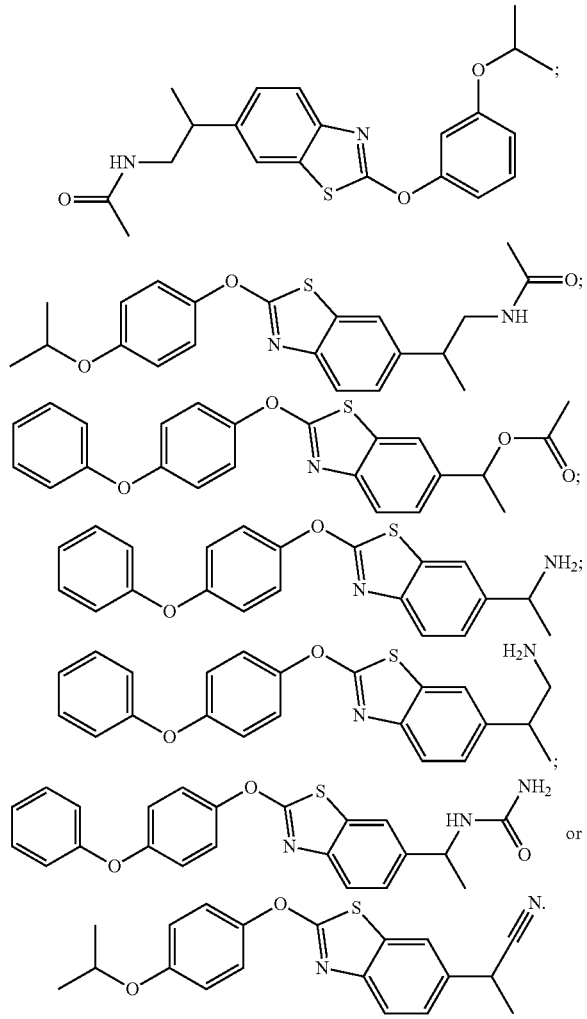

In one embodiment, a Compound has the following structure (XXXVI):

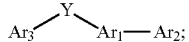

or a pharmaceutically acceptable salt, prodrug, salt of a prodrug, or combination thereof, wherein Y is selected from the group consisting of —$CR_xR_y$—, —C(O)—, —O—, —N(H)—, —N(alkyl)- and —S—; wherein each of $R_x$ and $R_y$ is independently selected from the group consisting of hydrogen, alkyl, hydroxyalkyl, and haloalkyl; or $R_x$ and $R_y$ together with the carbon to which they are attached form a monocyclic cycloalkyl or heterocycle ring;

$Ar_1$ is selected from the group consisting of phenyl and a monocyclic, five or six-membered heteroaryl;

$Ar_3$ is phenyl or monocyclic heteroaryl; wherein $Ar_3$ is substituted with 1, 2, 3 or 4 substituents independently selected from the group consisting of alkyl, alkenyl, —CN, —$NO_2$, halogen, —$OR_2$, —O—N=CH($R_1$), —OC(O)$R_1$, —OC(O)N($R_3$)($R_2$), —OC(O)$OR_1$, —OS(O)$_2R_1$, —$SR_2$, —S(O)$R_1$, —S(O)$_2R_2$, —S(O)$_2OR_2$, —S(O)$_2$N($R_3$)($R_2$), —C(O)R—, —C(O)N($R_3$)($R_2$), —C(O)$OR_2$, —C(O)N($R_3$)($R_2$), —N($R_3$)($R_2$), —N(H)—N=CH($R_1$), —N($R_3$)C(O)$R_2$, —N($R_3$)C(O)$OR_2$, —N($R_3$)S(O)$_2R_1$, —N($R_3$)C(O)N($R_3$)($R_2$), —N($R_3$)S(O)$_2$N($R_3$)($R_2$), —$R_4$, haloalkyl, cyanoalkyl, nitroalkyl, hydroxyalkyl, alkoxyalkyl, haloalkoxyalkyl, -alkylenyl—OC(O)$R_1$, -alkylenyl-OC(O)N($R_3$)($R_2$), -alkylenyl-OC(O)$OR_1$, -alkylenyl-OS(O)$R_1$, -alkylenyl-$SR_2$, -alkylenyl-S(O)$R_1$, -alkylenyl-S(O)$_2R_1$, -alkylenyl-S(O)$_2OR_2$, -alkylenyl-S(O)$_2$N($R_3$)($R_2$), -alkylenyl-C(O)$R_2$, -alkylenyl-C(O)N($R_3$)($R_2$), -alkylenyl-C(O)$OR_2$, -alkylenyl-C(O)N($R_2$)($R_2$), -alkylenyl-N($R_3$)($R_2$), -alkylenyl-N($R_3$)C(O)$R_2$, -alkylenyl-N($R_3$)C(O)$OR_2$, -alkylenyl-N($R_3$)S(O)$_2R_1$, -alkylenyl-N($R_3$)C(O)N($R_3$)($R_2$), -alkylenyl-N($R_3$)S(O)$_2$N($R_3$)($R_2$), and -alkylenyl-$R_4$;

$R_1$, at each occurrence, is independently selected from the group consisting of alkyl, alkenyl, haloalkyl, alkoxyalkyl, haloalkoxyalkyl, —$R_4$, and -alkylenyl-$R_4$;

$R_2$, at each occurrence, is independently selected from the group consisting of hydrogen, alkyl, alkenyl, haloalkyl, alkoxyalkyl, haloalkoxyalkyl, —$R_4$, and -alkylenyl-$R_4$;

$R_3$, at each occurrence, is independently selected from the group consisting of hydrogen, alkyl, arylalkyl, haloalkyl, and heteroarylalkyl;

R4, at each occurrence, is independently selected from the group consisting of aryl, heteroaryl, heterocycle, cycloalkyl and cycloalkenyl;

Ar2 is a group of formula (a), (b), (c), (d), or (e);

(a)
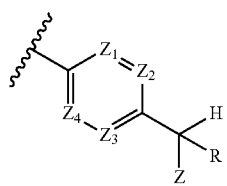

(b)
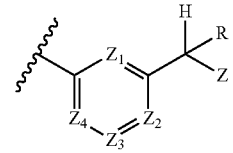

(c)
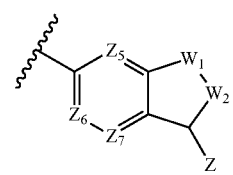

(d)
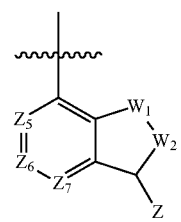

(e)
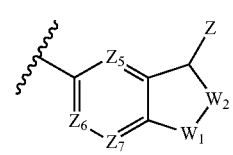

wherein

R is hydrogen, cycloalkyl, alkyl or haloalkyl;

$Z_1$, $Z_2$, $Z_3$ and $Z_4$ are C($R_{101}$), or one or two of $Z_1$, $Z_2$, $Z_3$ and $Z_4$ is N and the others are C($R_{101}$);

$Z_5$, $Z_6$ and $Z_7$ are C($R_{102}$), or one or two of $Z_5$, $Z_6$ and $Z_7$ are N; and the others are C($R_{102}$); $R_{101}$ and $R_{102}$, at each occurrence, are each independently hydrogen, alkyl, alkenyl, halogen, —CN, —$NO_2$, hydroxy, alkoxy, —$NH_2$, —N(H)(alkyl), —N(alkyl)$_2$, —C(O)OH, —C(O)Oalkyl, —C(O)H, —C(O)alkyl, or haloalkyl;

$W_1$ is $CH_2$, and $W_2$ is $CH_2$, $CH_2$—$CH_2$, or X—$CH_2$; wherein X is connected to $W_1$, and X is N($R_z$), O or S; or $W_1$ is N($R_z$), O or S, and $W_2$ is $CH_2$—$CH_2$;

$R_z$ at each occurrence is independently hydrogen, alkyl, haloalkyl, —C(O)Oalkyl, —C(O)alkyl, —C(O)$NH_2$), —C(O)N(H)(alkyl), —C(O)N(alkyl)$_2$, —S(O)$_2$N(H)$_2$, —S(O)$_2$N(H)(alkyl) or —S(O)$_2$N(alkyl)$_2$;

Z is selected from the group consisting of —$OR_5$, -alkylenyl-$OR_5$, —N($R_6$)($R_7$) and -alkylenyl-N($R_6$)($R_7$);

$R_5$, at each occurrence, is independently selected from the group consisting of hydrogen, alkyl, haloalkyl, $R_4$, —C(O)$OR_8$, —S(O)$_2R_9$, —C(O)N($R_9$)($R_{10}$), S(O)$_2$N($R_9$)($R_9$), —C(O)$R_8$, -alkylenyl-$OR_8$, -alkylenyl-N($R_9$)($R_{10}$), -alkylenyl-N($R_9$)C(O)$OR_8$, -alkylenyl-N($R_9$)C(O)$R_8$, -alkylenyl-C(O)$OR_9$, -alkylenyl-S(O)$_2R_8$, -alkylenyl-S(O)$_2$N($R_9$)($R_{10}$), -alkylenyl-C(O)N($R_9$)($R_{10}$), -alkylenyl-C(O)$R_8$, and -alkylenyl-$R_4$, $R_6$, at each occurrence, is independently selected from the group consisting of hydrogen, alkyl and haloalkyl;

$R_7$, at each occurrence, is independently selected from the group consisting of hydrogen, alkyl, hydroxy, alkoxy, $R_4$, —C(=NH)$NH_2$, —C(O)$OR_8$, —S(O)$_2R_8$, —C(O)N($R_9$)($R_{11}$), —C(O)ON($R_9$)($R_{11}$), —S(O)$_2$N($R_9$)($R_{11}$), —C(O)$R_8$, —C(O)$CH_2$C(O)$R_5$, haloalkyl, -alkylenyl-$OR_8$, -alkylenyl-N($R_9$)($R_{11}$), -alkylenyl-N($R_9$)C(O)$OR_8$, -alkylenyl-N($R_9$)C (O)R$_9$, -alkylenyl-C(O)OR$_8$, -alkylenyl-S(O)$_2$R$_8$, -alkylenyl-S(O)$_2$N(R$_9$)(R$_{11}$), -alkylenyl-C(O)N(R$_9$)(R$_{11}$), -alkylenyl-C(O)R$_8$, and -alkylenyl-R$_4$, R$_8$, at each occurrence, is independently selected from the group consisting of hydrogen, alkyl, alkoxyalkyl, cyanolakyl, haloalkyl, —R$_4$, and -alkylenyl-R$_4$;

R$_9$, at each occurrence, are each independently selected from the group consisting of hydrogen, alkyl and haloalkyl;

R$_{10}$, at each occurrence, is independently selected from the group consisting of hydrogen, alkyl, hydroxy, alkoxy, alkoxyalkyl, cyanolakyl, haloalkyl, —R$_4$, and -alkylenyl-R$_4$;

R$_{11}$, at each occurrence, is independently selected from the group consisting of hydrogen, alkyl, hydroxy, alkoxy, —R$_4$, alkoxyalkyl, cyanoalkyl, haloalkyl, -alkylenyl-C(O)NH$_2$, -alkylenyl-C(O)N(H)(allyl), -alkylenyl-C(O)N(alkyl)$_2$, -alkylenyl-N(H)C(O)Oalkyl, -alkylenyl-N(alkyl)C(O)Oalkyl, and -alkylenyl-R$_4$; and the phenyl, cycloalkyl, cycloalkenyl, aryl, heteroaryl, heterocycle, aryl moiety of the arylalkyl, and the heteroaryl moiety of the heteroarylalkyl represented by Ar$_1$, R$_3$ and R$_4$, are each independently unsubstituted or substituted with 1, 2, 3 or 4 substituents independently selected from the group consisting of alkyl, alkenyl, —CN, —NO$_2$, halogen, ethylenedioxy, methylenedioxy, oxo, —OR$_a$, —OC(O)R$_a$, —OC(O)OR$_a$, —OS(O)$_2$R$_a$, —S(alkyl), —S(O)alkyl, —S(O)$_2$alkyl, —S(O)$_2$OR$_a$, —S(O)$_2$NR$_a$R$_b$, —C(O)R$_a$, —C(O)NR$_a$R$_b$, —C(O)OR$_a$R$_b$, —C(O)NR$_a$R$_b$, —NR$_a$R$_b$, —NOR$_a$, N(R$_b$)C(O)R$_a$, —N(R$_b$)C(O)OR$_a$, —N(R$_b$)S(O)$_2$R$_a$, —N(R$_b$)C(O)NR$_a$R$_b$, —N(R$_b$)S(O)$_2$NR$_a$R$_b$, haloalkyl, cyanoalkyl, nitroalkyl, hydroxyalkyl, alkoxyalkyl, haloalkoxyalkyl, -alkylenyl-OC(O)R$_a$, -alkylenyl-OC(O)OR$_a$, -alkylenyl-OS(O)$_2$alkyl, -alkylenyl-S(alkyl), -alkylenyl-S(O)alkyl, -alkylenyl-S(O)$_2$alkyl, -alkylenyl-S(O)$_2$OR$_a$, -alkylenyl-S(O)$_2$NR$_a$R$_b$, -alkylenyl-C(O)R$_a$, -alkylenyl-C(O)NR$_a$R$_b$, -alkylenyl-C(O)OR$_a$, -alkylenyl-C(O)NR$_a$R$_b$, -alkylenyl-NR$_a$R$_b$, -alkylenyl-N(R$_b$)C(O)R$_a$, -alkylenyl-N(R$_b$)C(O)OR$_a$, -alkylenyl-N(R$_b$)S(O)$_2$R$_a$, -alkylenyl-N(R$_b$)C(O)NR$_a$R$_b$, and -alkylenyl-N(R$_b$)S(O)$_2$NR$_a$R$_b$; wherein R$_a$, at each occurrence is independently selected from the group consisting of hydrogen, alkyl, alkenyl and haloalkyl, and R$_b$ at each occurrence is independently selected from the group consisting of hydrogen and alkyl.

In a specific embodiment, a compounds of structure (XXXVI) is:

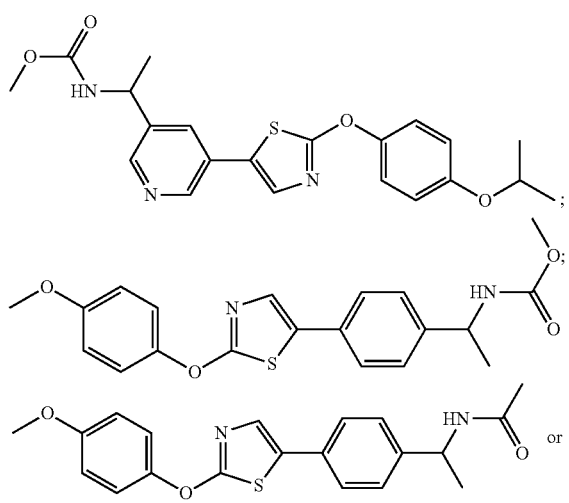

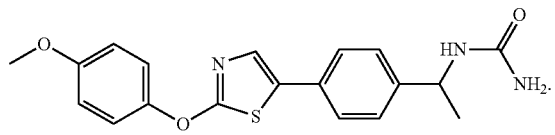

In one embodiment, a Compound has the following structure (XXXVII):

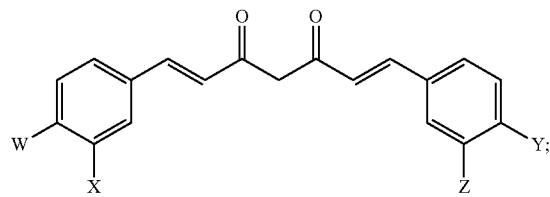

wherein

W is —OH, —O(C$_1$-C$_6$)alkyl, —NH$_2$, N((C$_1$-C$_6$)alkyl)$_2$, —NH(C$_1$-C$_6$)alkyl, —SH, —S(C$_1$-C$_6$)alkyl, halo, —CN, —H or —(C$_1$-C$_6$)alkyl;

X is —OH, —O(C$_1$-C$_6$)alkyl, —NH$_2$, N((C$_1$-C$_6$)alkyl)$_2$, —NH(C$_1$-C$_6$)alkyl, —SH, —S(C$_1$-C$_6$)alkyl, halo, —CN, —H or —(C$_1$-C$_6$)alkyl;

Y is —OH, —O(C$_1$-C$_6$)alkyl, —NH$_2$, N((C$_1$-C$_6$)alkyl)$_2$, —NH(C$_1$-C$_6$)alkyl, —SH, —S(C$_1$-C$_6$)alkyl, halo, —CN, —H or —(C$_1$-C$_6$)alkyl;

Z is —OH, —O(C$_1$-C$_6$)alkyl, —NH$_2$, N((C$_1$-C$_6$)alkyl)$_2$, —NH(C$_1$-C$_6$)alkyl, —SH, —S(C$_1$-C$_6$)alkyl, halo, —CN, —H or —(C$_1$-C$_6$)alkyl;

In a specific embodiment, a compound of structure (XXXVII) is:

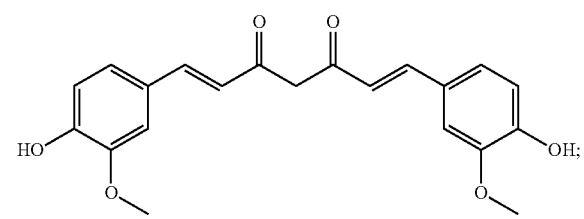 [SMILES: COc1cc(/C=C/C(=O)CC(=O)/C=C/c2ccc(O)c(OC)c2)ccc1O]

also referred to as curcumin.

In a specific embodiment, a compound of structure (XXXVII) is not curcumin.

In another specific embodiment, a compound of structure (XXXVII) is:

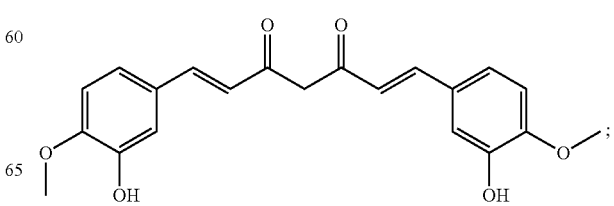

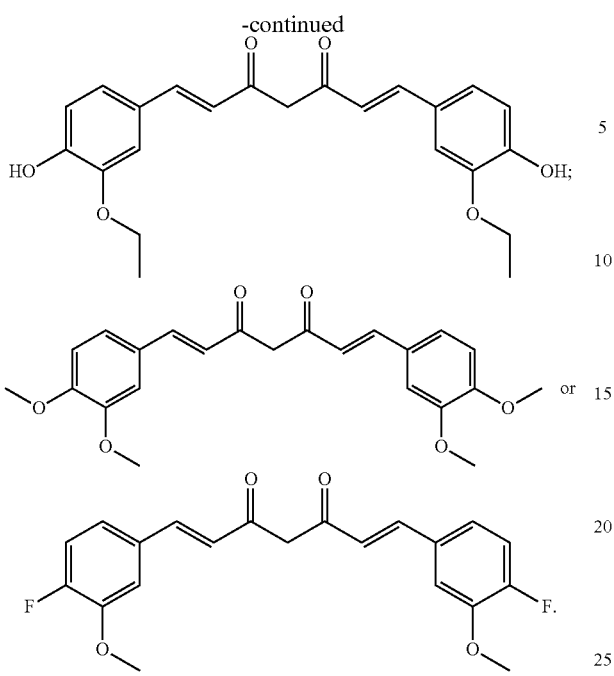

In one embodiment, a Compound has the following structure (XXXVIII):

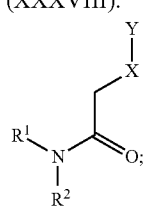

wherein

R¹ is —H, —(C₁-C₆)alkyl, —(C₁-C₆)alkenyl, —(C₁-C₆)alkynyl or —(C₁-C₆)alkoxy;

R² is —H, —(C₁-C₆)alkyl, -(C₁-C₆)alkenyl, —(C₁-C₆)alkynyl, —(C₃-C₆)cycloalkyl or a phenyl which may be optionally substituted with one or more halo, —(C₁-C₆)alkyl, —(C₁-C₆)alkenyl- and/or (C₁-C₆)alkynyl groups;

X is —CH₂O, —CH₂S, O, —S, —NH, —N(C₁-C₆)alkyl, —CH₂—,

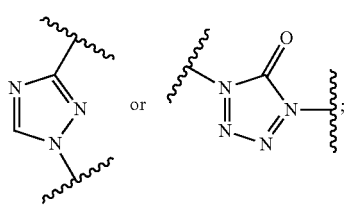

Y is -halo,

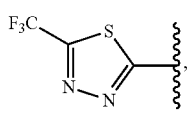

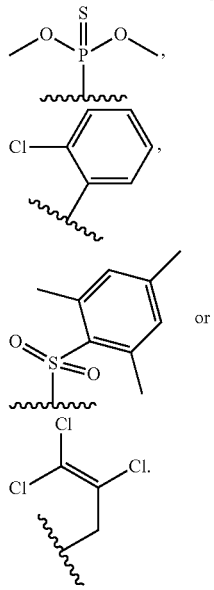

In a specific embodiment, a compound of structure (XXXVIII) is:

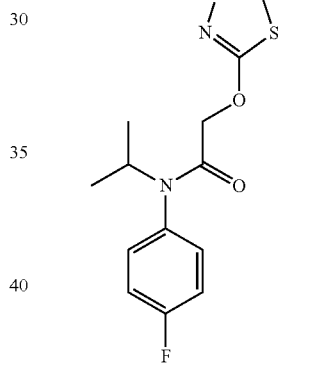

also referred to as flufenacet.

In a specific embodiment, a compound of structure (XXXVIII) is not flufenacet.

In a specific embodiment, a compound of structure (XXXVIII) is:

also referred to as anilofos.

In a specific embodiment, a compound of structure (XXX-VIII) is not anilofos.

In a specific embodiment, a compound of structure (XXX-VIII) is:

[Chemical structure: fentrazamide]

also referred to as fentrazamide.

In a specific embodiment, a compound of structure (XXX-VIII) is not fentrazamide.

In a specific embodiment, a compound of structure (XXX-VIII) is:

[Chemical structure: cafenstrole]

also referred to as cafenstrole.

In a specific embodiment, a compound of structure (XXX-VIII) is not cafenstrole.

In a specific embodiment, a compound of structure (XXX-VIII) is:

[Chemical structure: alachlor]

also referred to as alachlor.

In a specific embodiment, a compound of structure (XXX-VIII) is not alachlor.

In a specific embodiment, a compound of structure (XXX-VIII) is:

[Chemical structure: allidochlor]

also referred to as allidochlor.

In a specific embodiment, a compound of structure (XXX-VIII) is not allidochlor.

In a specific embodiment, a compound of structure (XXX-VIII) is:

[Chemical structure: triallate]

also referred to as triallate.

In a specific embodiment, a compound of structure (XXX-VIII) is not triallate.

In one embodiment, a Compound has the following structure (XXXIX):

[Chemical structure XXXIX]

wherein $R^1$ is —C(halo)$_3$, or

[Chemical structure]

$R^{2a}$ and $R^{2b}$ may combine to form an oxirane ring or (=CH$_2$);

X is -halo;

Y is halo;

m is 0, 1 or 2; and n is 0, 1 or 2.

In a specific embodiment, a compound of structure (XXXIX) is:

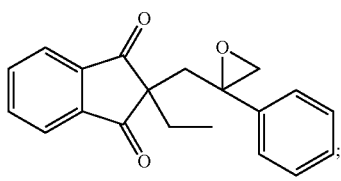 [SMILES: CCC1(CC2(c3ccccc3)CO2)C(=O)c2ccccc2C1=O]

which is also referred to as indanofan.

In a specific embodiment, a compound of structure (XXXIX) is S-indanofan.

In a specific embodiment, a compound of structure (XXXIX) is R-indanofan.

In a specific embodiment, a compound of structure (XXXIX) is not indanofan.

In a specific embodiment, a compound of structure (XXXIX) is not S-indanofan.

In a specific embodiment, a compound of structure (XXXIX) is not R-indanofan.

In a specific embodiment, a compound of structure (XXXIX) is:

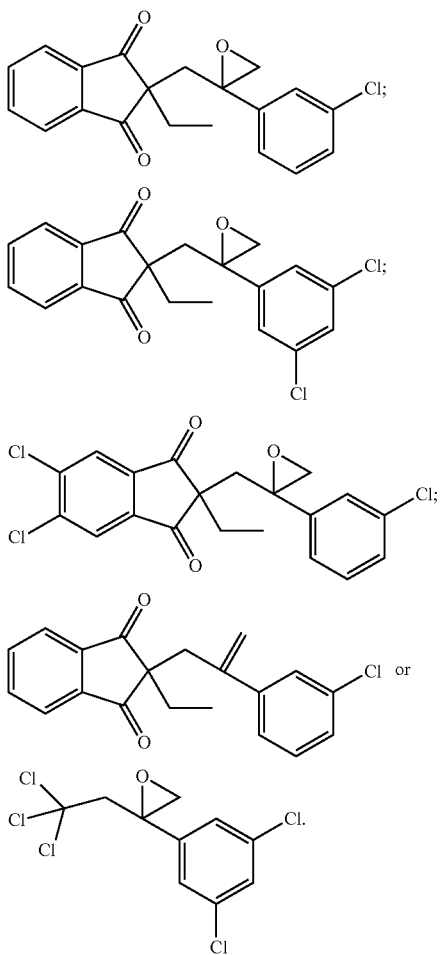

In one embodiment, a Compound has the following structure (XL):

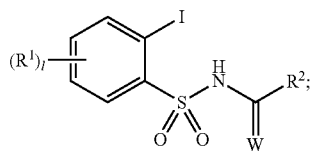

wherein

R is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or R is a heterocyclyl radical or heterocyclyloxy radical which is unsubstituted or substituted or R is a hydrogen atom, halogen or a radical $C(O)R^3$, $OC(O)R^3$, $S(O)_nR^3$, $OS(O)_nR^3$, OH, CN, $NO_2$, $NH_2$, $SF_5$, $NR_4R^5$ or $Si(R^6)_3$, where n is 0, 1 or 2;

$R^1$ independently at each occurrence is halogen, OH, SH, a carbon-free, nitrogen-containing radical or a carbon-containing radical having 1 to 30 carbon atoms, preferably 1 to 20 carbon atoms;

l is 0, 1, 2 or 3, preferably 0, 1 or 2, more preferably 0 to 1, very preferably 0;

$R^2$ is a substituted or unsubstituted heterocyclyl radical having 5 ring members, of which preferably at least one is oxygen, sulfur or nitrogen and one to four further ring members may be nitrogen;

$R^3$ is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or $R^3$ is a heterocyclyl radical or heterocyclyloxy radical which is unsubstituted substituted, or $R^3$ is a hydrogen atom, CN or $NR^4R^5$;

$R^4$ is a group of the formula $R^0\text{-}Q^0\text{-}$, in which $R^0$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, and $Q^0$ is a direct bond or a divalent group of the formula —O— or —N($R^\#$)—, $R^\#$ being a hydrogen atom, an acyl radical or a hydrocarbon radical and the last-mentioned radical being unsubstituted or substituted and inclusive of substituents having 1 to 30 carbon atoms, preferably 1 to 20 carbon atoms, or $R^0$ and $R^\#$ form with one another a nitrogen-containing heterocyclic ring;

$R^5$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, or $R^4$ and $R^5$ form with one another a nitrogen-containing heterocyclic ring;

$R^6$ is a hydrocarbon radical which is unsubstituted or substituted and inclusive of substituents has 1 to 30 carbon atoms, preferably 1 to 20 carbon atoms, preferably ($C_1$-$C_4$)alkyl or ($C_6$-$C_{10}$)aryl; and W is an oxygen atom or a sulfur atom.

In a specific embodiment, a compound of structure (XL) is:

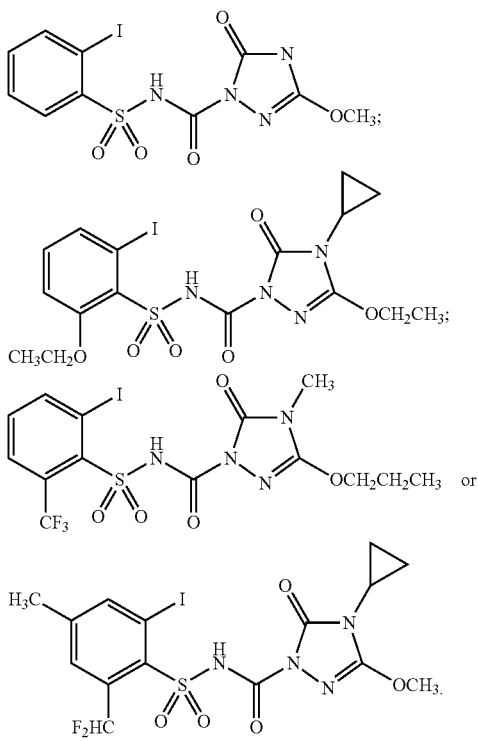

In one embodiment, a Compound has the following structure (XLI):

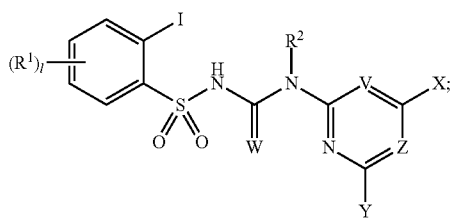

wherein

R is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or R is a heterocyclyl radical or heterocyclyloxy radical which is unsubstituted or substituted or R is a hydrogen atom, halogen or a radical $C(O)R^3$, $OC(O)R^3$, $S(O)_nR^3$, $OS(O)_nR^3$, OH, CN, $NO_2$, $NH_2$, $SF_5$, $NR_4R^5$ or $Si(R^6)_3$, where n is 0, 1 or 2; $R^1$ independently at each occurrence is halogen, OH, SH, a carbon-free, nitrogen-containing radical or a carbon-containing radical having 1 to 30 carbon atoms, preferably 1 to 20 carbon atoms;

l is 0, 1, 2 or 3, preferably 0, 1 or 2, more preferably 0 to 1, very preferably 0;

$R^2$ is a hydrogen atom or a hydrocarbon radical which is unsubstituted or substituted and inclusive of substituents has 1 to 20 carbon atoms, preferably 1 to 10 carbon atoms, e.g., unsubstituted or substituted $(C_1-C_4)$alkyl, preferably H or $CH_3$;

$R^3$ is a hydrocarbon radical or hydrocarbonoxy radical, preferably a radical from the group consisting of alkyl, alkenyl, alkynyl, cycloalkyl, cycloalkenyl, cycloalkynyl, alkoxy, alkenyloxy, alkynyloxy, cycloalkyloxy, cycloalkenyloxy, aryl and aryloxy, which is unsubstituted or substituted and inclusive of substituents has 1 to 30 carbon atoms, preferably 1 to 20 carbon atoms, or $R^3$ is a heterocyclyl radical or heterocyclyloxy radical which is unsubstituted substituted, or $R^3$ is a hydrogen atom, CN or $NR^4R^5$;

$R^4$ is a group of the formula $R^0$-$Q^0$, in which $R^0$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, and $Q^0$ is a direct bond or a divalent group of the formula —O— or —N($R^\#$)—, $R^\#$ being a hydrogen atom, an acyl radical or a hydrocarbon radical and the last-mentioned radical being unsubstituted or substituted and inclusive of substituents having 1 to 30 carbon atoms, preferably 1 to 20 carbon atoms, or $R^0$ and $R^\#$ form with one another a nitrogen-containing heterocyclic ring;

$R^5$ is a hydrogen atom, an acyl radical, a hydrocarbon radical or a heterocyclyl radical, each of the last-mentioned two radicals being unsubstituted or substituted and inclusive of substituents having 1 to 30 carbon atoms, preferably 1 to 20 carbon atoms, or $R^4$ and $R^5$ form with one another a nitrogen-containing heterocyclic ring; $R^6$ is a hydrocarbon radical which is unsubstituted or substituted and inclusive of substituents has 1 to 30 carbon atoms, preferably 1 to 20 carbon atoms, preferably $(C_1-C_4)$alkyl or $(C_6-C_{10})$aryl;

W is an oxygen atom or a sulfur atom;

X and Y independently of one another are each a hydrogen atom, halogen, $(C_1-C_6)$alkyl, $(C_1-C_6)$alkoxy or $(C_1-C_6)$alkylthio, each of the last-mentioned three radicals being unsubstituted or substituted by one or more radicals from the group consisting of halogen, $(C_1-C_4)$alkoxy, and $(C_1-C_4)$alkylthio, or are mono- or di[$(C_1-C_6)$alkyl]amino, $(C_2-C_6)$alkenyl, $(C_2-C_6)$alkynyl, $(C_3-C_6)$alkenyloxy or $(C_3-C_6)$alkynyloxy; and V and Z independently of one another are each CH or N.

In a specific embodiment, a compound of structure (XLI) is:

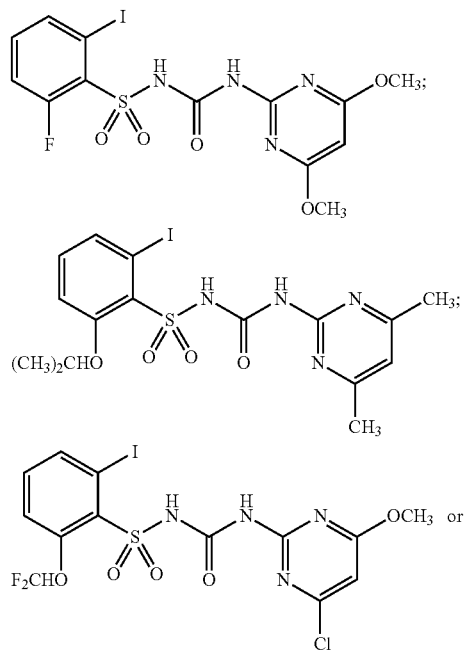

-continued

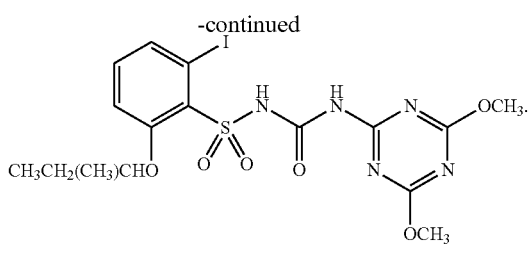

In one embodiment, a Compound has the following structure (XLII):

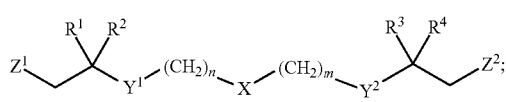

and pharmaceutically acceptable salts, solvates, hydrates, clathrates, or prodrugs thereof, wherein:

$Z^1$ and $Z^2$ are independently —OH, —OPO$_3$H, —OP$_2$O$_6$H$_2$, —OPO$_2$-(nucleotide), —OP$_2$O$_6$(H)-(nucleotide);

$R^1$ and $R^3$ are independently hydrogen, methyl, or phenyl;

$R^2$ and $R^4$ are independently methyl or phenyl;

m and n are independently 0, 1, 2, 3, 4, 5, or 6;

$Y^1$ and $Y^2$ are independently —CH$_2$,

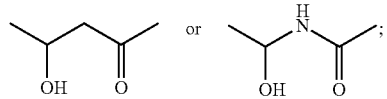

and

X is O, S, Se, C(O), C(H)F, CF$_2$, S(O), NH, O—P(O)(OH)—O, NH—C(O)—NH or NH—C(S)—NH.

In a specific embodiment, a Compound of structure (XLII) is:

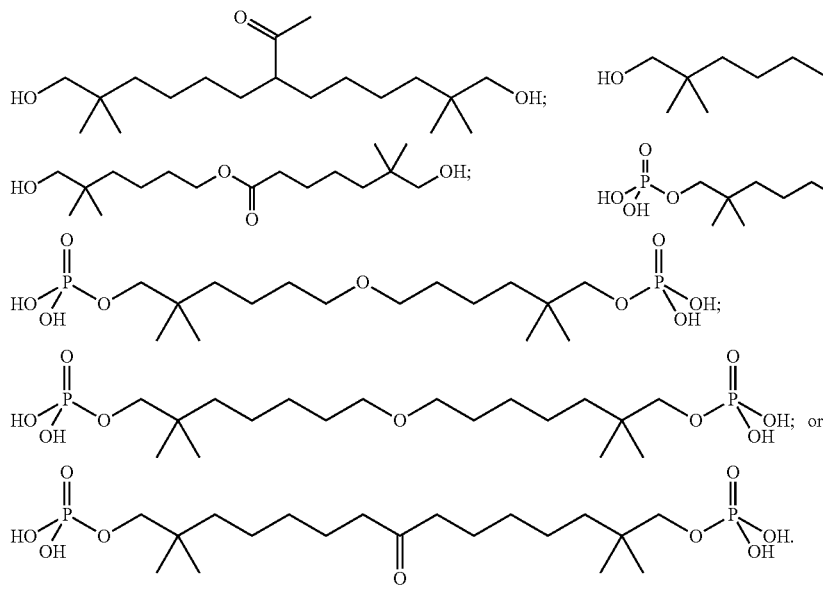

In one embodiment, a Compound has the following structure (XLIII):

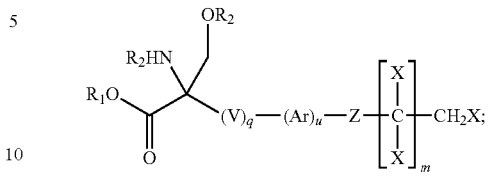

wherein:

$R_1$ is H or optionally substituted lower alkyl, aryl, aralkyl, or alkyloxyalkyl;

each $R_2$ is independently H, protecting group, or —C(=O)—CHR$_a$—NHR$_b$ where:

$R_a$ is selected from the group consisting of alkyl, aryl, acyl, keto, azido, hydroxyl, hydrazine, cyano, halo, hydrazide, alkenyl, alkynl, ether, thiol, seleno, sulfonyl, borate, boronate, phospho, phosphono, phosphine, heterocyclic, enone, imine, aldehyde, ester, thioacid, hydroxylamine, amino group, and combinations thereof; and $R_b$ is H or amino protecting group;

each V and Z is independently (CR$_c$R$_d$)$_n$, O, NR$_e$, S, Ar, CR$_c$R$_d$Ar, OAr, NR$_4$Ar, SAr, or Ar where:

each $R_c$ and $R_d$ is independently H, lower alkyl, OH, O-lower alkyl, or $R_c$ and $R_d$, taken together, is =O, =N—OH, =N—O-lower alkyl, or =N—O—CH$_2$CH$_2$—O—CH$_3$;

$R_e$ is H, lower alkyl, or —CH$_2$CH$_2$—O—CH$_3$; and n is 1 to 7;

q is 0 to 3;

Ar is an optionally substituted aryl or heteroaryl;

u is 0 or 1;

each X is independently H or halogen; and m is 4 to 12.

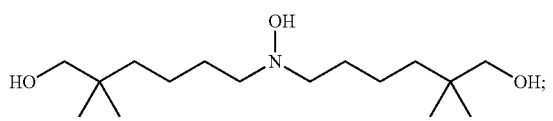

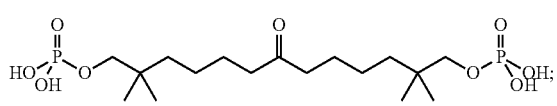

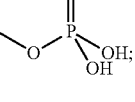

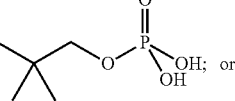

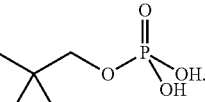

In a specific embodiment, the Compound of structure (XLIII) is:

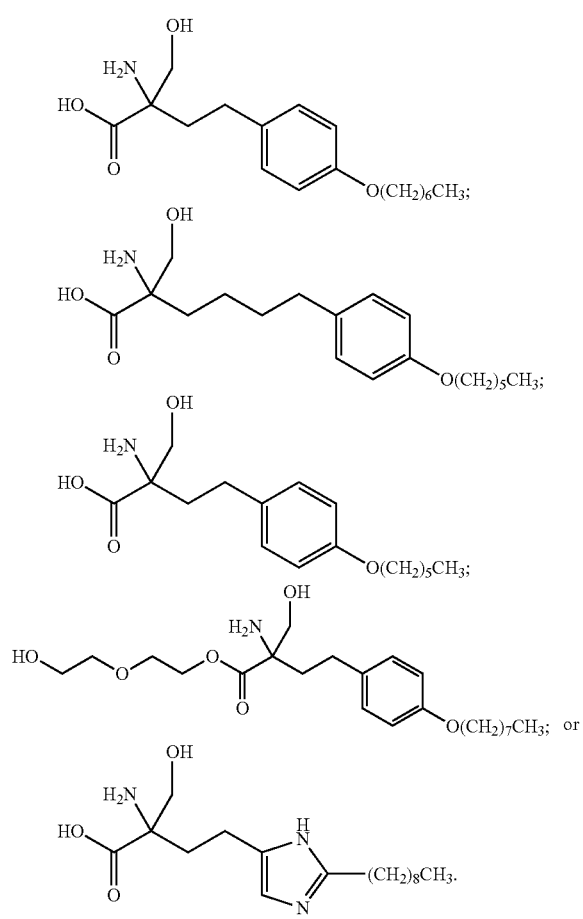

In one embodiment, a Compound has the following structure (XLIV):

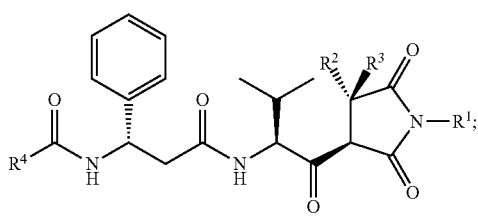

wherein:
R¹ is —H, —(C₁-C₆)alkyl, —(C₃-C₆)cycloalkyl, —(C₁-C₆)alkoxy, —O(C₁-C₆)alkyl, —N((C₁-C₆)alkyl)₂ or —NH(C₁-C₆)alkyl;
R² is —H or —(C₁-C₆)alkyl;
R³ is —H or —(C₁-C₆)alkyl; and
R⁴ is

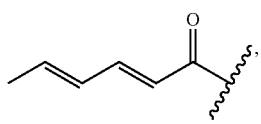

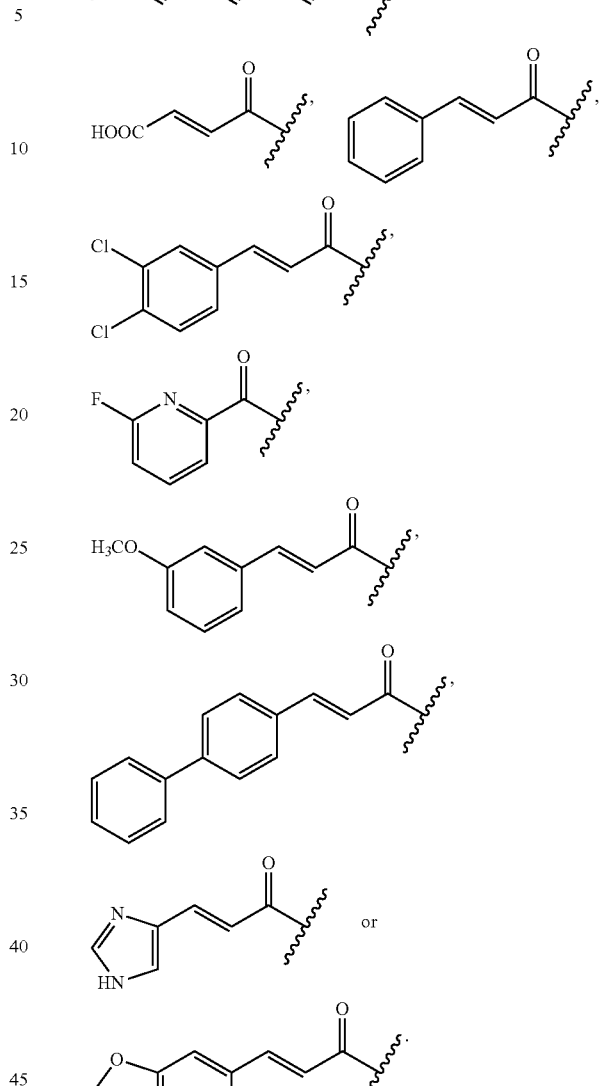

In a specific embodiment, the Compound of structure (XLIV) is:

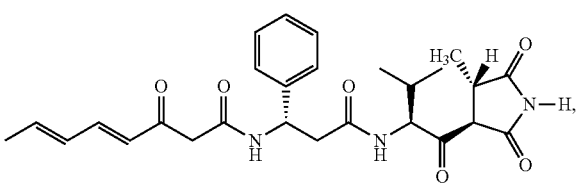

which is referred to as moiramide B.

In a specific embodiment, the Compound of structure (XLIV) is not moiramide B.

In a specific embodiment, the Compound of structure (XLIV) is:

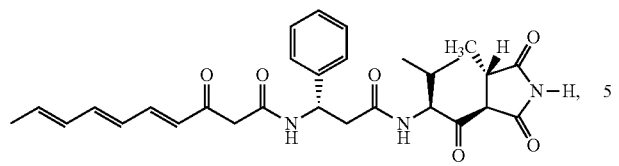
which is referred to as andrimid.
In a specific embodiment, the Compound of structure (XLIV) is not andrimid.
In a specific embodiment, the Compound of structure (XLIV) is:
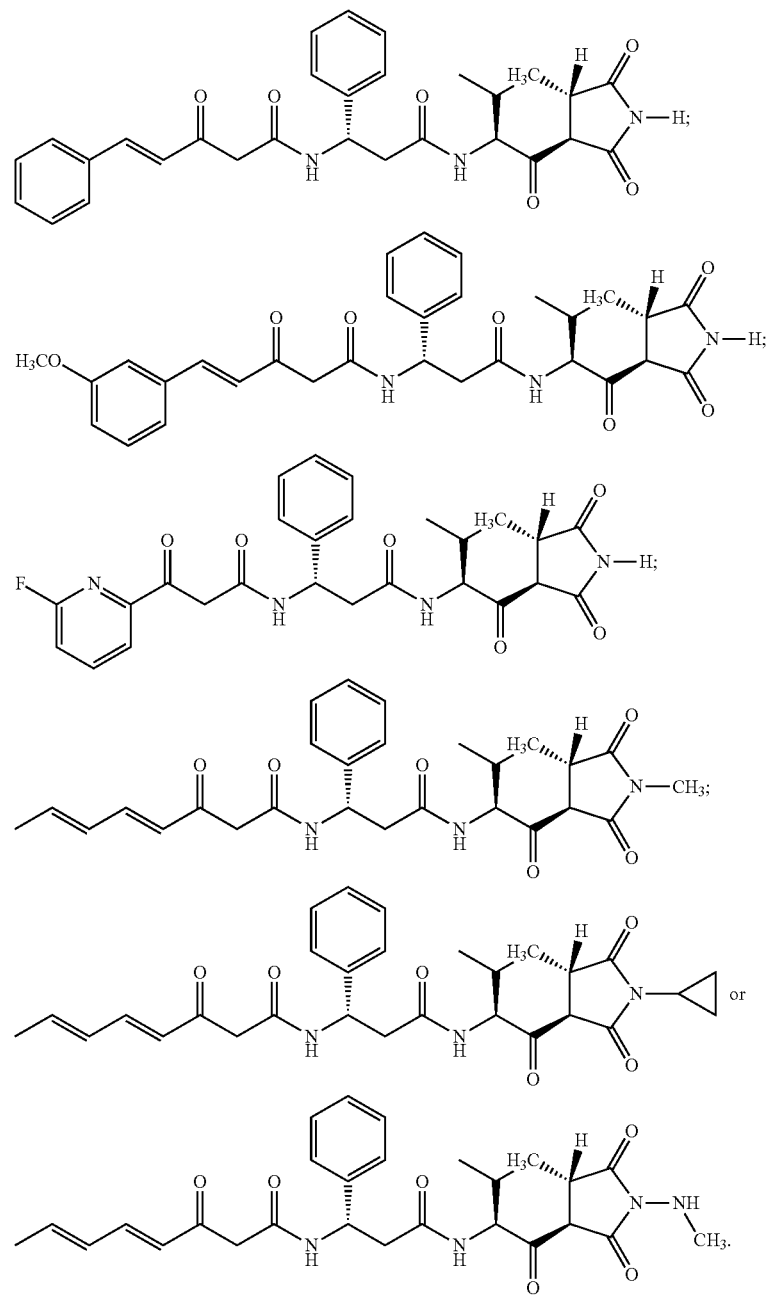

In one embodiment, a Compound is an inhibitor of class III Phosphoinositide 3-kinase (III PI3K).

In a particular embodiment, the Compound of structure (XLV) is:

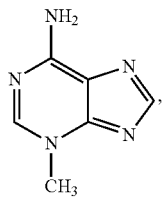

which is also known as 3-methyladenine.

In a particular embodiment, the Compound is a derivative of 3-methyladenine.

In a particular embodiment, the Compound of structure (XLVI) is:

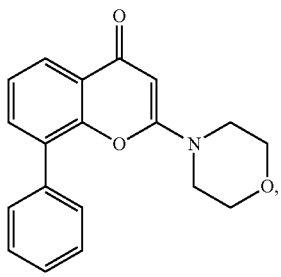 [SMILES: O=c1cc(N2CCOCC2)oc2c(-c3ccccc3)cccc12]

which is also known as LY 294002.

In a particular embodiment, the Compound is a derivative of LY 294002.

In a particular embodiment, the Compound of structure (XLVII) is:

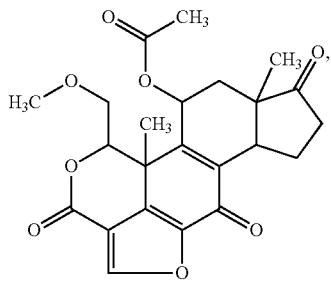 [SMILES: COCC1OC(=O)c2coc3c2C1(C)C1=C(C3=O)C2CCC(=O)C2(C)CC1OC(C)=O]

which is also known as wortmannin.

In a particular embodiment, the Compound is a derivative of wortmannin.

In particular embodiments, a Compound is an HMG-CoA reductase inhibitor. Exemplary HMG-CoA reductase inhibitors are well known in the art and include, but are not limited to, mevastatin and related molecules (e.g., see U.S. Pat. No. 3,983,140); lovastatin (mevinolin) and related molecules (e.g., see U.S. Pat. No. 4,231,938); pravastatin and related molecules (e.g., see U.S. Pat. No. 4,346,227); simvastatin and related molecules (e.g., see U.S. Pat. Nos. 4,448,784 and 4,450,171); fluvastatin (e.g., see U.S. Pat. No. 5,354,772); cerivastatin (e.g., see U.S. Pat. Nos. 5,006,530 and 5,177,080); atorvastatin (e.g., see U.S. Pat. Nos. 4,681,893, 5,273,995, 5,385,929 and 5,686,104); itavastatin (e.g., see U.S. Pat. No. 5,011,930); Shionogi-Astra/Zeneca visastatin (ZD-4522) (e.g., see U.S. Pat. No. 5,260,440), related statin compounds (e.g., see U.S. Pat. No. 5,753,675); pyrazole analogs of mevalonolactone derivatives (e.g., see U.S. Pat. No. 4,613,610); indene analogs of mevalonolactone derivatives (e.g., see International Patent Application Publication No. WO 1986/03488); 6-[2-(substituted-pyrrol-1-yl)-alkyl)pyran-2-ones and derivatives thereof (e.g., see U.S. Pat. No. 4,647,576); Searle's SC-45355 (a 3-substituted pentanedioic acid derivative) dichloroacetate, imidazole analogs of mevalonolactone (e.g., see International Patent Application No. WO 1986/07054); 3-carboxy-2-hydroxy-propane-phosphonic acid derivatives; naphthyl analogs of mevalonolactone (e.g., see U.S. Pat. No. 4,686,237); octahydronaphthalenes (e.g., see U.S. Pat. No. 4,499,289); keto analogs of mevinolin (lovastatin); phosphinic acid compounds (e.g., see GB 2205837); and quinoline and pyridine derivatives (e.g., see U.S. Pat. Nos. 5,506,219 and 5,691,322). Each of the references above is incorporated by reference herein in its entirety. The structures of such exemplary HMG-CoA reductase inhibitors are well known in the art. In some embodiments, a Compound is not an HMG-CoA reductase inhibitor Exemplary inhibitors of SCD are provided in Liu et al., J. Med. Chem. 50:3086-3100, 2007; International Patent Application Publication No. WO 2005/011655 A2; U.S. Application Publication No. 2005/0119251; and International Patent Application Publication No. WO 2007/0099236 A1, each of which is incorporated by reference herein in its entirety. Such inhibitors include, but are not limited to, pyridazine derivatives and pyridazine heterozryl-based SCD1 inhibitors.

In some embodiments, Compounds that target and inhibit ACC include, but are not limited to, pseudopeptide pyrrolidine dione antibiotics, e.g., moiramide B and synthetic analogs thereof, and andrimid and synthetic analogs thereof; and pyrrolidinedione derivatives. See Freiberg et al., J. Biol. Chem. 279:26066-26073, 2004; Freiberg et al., Antimicrob. Agents Chemother. 49:749-759, 2005; and Pohlmann et al., Bioorg. Med. Chem. Lett. 15:1189-1192, 2005, which are incorporated herein in their entirety. In other embodiments, a Compound is not a pseudopeptide pyrrolidine dione antibiotic. In certain embodiments, a Compound is not moiramide B.

In some embodiments, a Compound is a pyrrolidinedione derivative. Non-limiting examples of pyrrolidinedione derivatives are disclosed in Pohlmann et al., Bioorg. Med. Chem. Lett. 2005 15:1189-1192. In other embodiments, a Compound is not a pyrrolidinedione derivative.

Of note, ACC exists as two isozymes in humans, ACC1 and ACC2. Compounds described herein include, but are not limited to isozyme specific inhibitors of ACC. Compounds that are isozymes selective are provided in, for example, Clark et al., Bioorg. Med. Chem. Lett. 2007 17:1961-1965; and Gu et al., J. Med. Chem. 2006 49:3770-3773, each of which is incorporated by reference herein in its entirety. In some embodiments, Compounds that are phenoxy thiazolyl series of ACC inhibitors comprising a phenyl ring substitution are selective inhibitors of ACC2. In specific embodiments, a Compound is approximately at least 10 fold, 100 fold, 1,000 fold, 2,000 fold, 3,000 fold, 4,000 fold, 5,000 fold, or 10,000 fold more selective for ACC2 inhibition than ACC1 inhibition.

In certain embodiments, Compounds that target and inhibit phosphoinositide 3-kinases (PI(3)Ks) include, but are not limited to, 2-methyadenine, wortmannin, LY294002, 5-phenylthiazole derivatives (e.g., see International Patent Applications WO 2003/072557, WO 2004/078754 and WO 2005/

021519), certain 5-heteroaryl substituted thiazole derivatives (e.g., see, International Patent Application WO 2004/096797), certain 2-acylamino-5-thiazol-4-ylthiazole derivatives (e.g., see, International Patent Application WO 2005/068444), AS-605240 (see, e.g., Camp et al., Nat. Med. 2005, 11(9):936-43), and thiozolidinedione derivatives (e.g., see International Patent Application No. WO 2008/014219). 3-methyladenine inhibits class III PI(3)K (see, e.g., Petiot et al., J. Biol. Chem. 275:992-998, 2000). In particular embodiments, Compounds target and inhibit a class III PI(3)K. In specific embodiments, a Compound is 3-methyladenine. In other embodiments, a Compound is not 3-methyladenine. In some embodiments, a Compound is not an inhibitor of PI(3)K.

In certain embodiments, a Compound is a PI(3)P sequestering agent. Non-limiting examples of PI(3)P sequestering agents include peptides or chemically modified peptides containing one or more FYVE (SEQ ID NO: 55) motifs, including peptides that containing the FYVE (SEQ ID NO: 55) motif with a cell transduction domain such as the cell-membrane transduction domain of the human immunodeficiency virus type 1 (HIV-1) Tat protein (amino acid sequence: YGRKKRRQRRR (SEQ ID NO: 56) or a subset or extended version thereof). Other cell-membrane transduction domains are well known in the art and can be combined with the FYVE (SEQ ID NO: 55) sequence (including multiple repeats or variants thereof) or with other PI(3)P-sequestering sequence(s) in the design of antiviral therapeutics. In other embodiments, the FYVE (SEQ ID NO: 55) motif (with or without a cell membrane transduction domain) can be combined with other chemical moieties to increase the plasma half-life of the FYVE (SEQ ID NO: 55) motif (e.g., by protecting the FYVE motif from hydrolysis by circulating and/or cellular proteases).

In one embodiment, when a Compound is described or referred to herein, such description or reference includes pharmaceutically acceptable, salts, prodrugs, salts of prodrugs, solvates, clathrates and stereoisomers thereof.

RNAi Molecules

In certain embodiments, a Compound is an RNA interference (RNAi) molecule that can decrease the expression level of a target enzyme. RNAi molecules include, but are not limited to, small-interfering RNA (siRNA), short hairpin RNA (shRNA), microRNA (miRNA), and any molecule capable of mediating sequence-specific RNAi.

RNA interference (RNAi) is a sequence specific post-transcriptional gene silencing mechanism triggered by double-stranded RNA (dsRNA) that have homologous sequences to the target mRNA. RNAi is also called post-transcriptional gene silencing or PTGS. See, e.g., Couzin, 2002, Science 298:2296-2297; McManus et al., 2002, Nat. Rev. Genet. 3, 737-747; Hannon, G. J., 2002, Nature 418, 244-251; Paddison et al., 2002, Cancer Cell 2, 17-23. dsRNA is recognized and targeted for cleavage by an RNaseIII-type enzyme termed Dicer. The Dicer enzyme "dices" the RNA into short duplexes of about 21 to 23 nucleotides, termed siRNAs or short-interfering RNAs (siRNAs), composed of 19 nucleotides of perfectly paired ribonucleotides with about two three unpaired nucleotides on the 3' end of each strand. These short duplexes associate with a multiprotein complex termed RISC, and direct this complex to mRNA transcripts with sequence similarity to the siRNA. As a result, nucleases present in the RNA-induced silencing complex (RISC) cleave and degrade the target mRNA transcript, thereby abolishing expression of the gene product.

Numerous reports in the literature purport the specificity of siRNAs, suggesting a requirement for near-perfect identity with the siRNA sequence (Elbashir et al., 2001. EMBO J. 20:6877-6888; Tuschl et al., 1999, Genes Dev. 13:3191-3197; Hutvagner et al., Sciencexpress 297:2056-2060). One report suggests that perfect sequence complementarity is required for siRNA-targeted transcript cleavage, while partial complementarity will lead to translational repression without transcript degradation, in the manner of microRNAs (Hutvagner et al., Sciencexpress 297:2056-2060).

miRNAs are regulatory RNAs expressed from the genome, and are processed from precursor stem-loop (short hairpin) structures (approximately 80 nucleotide in length) to produce single-stranded nucleic acids (approximately 22 nucleotide in length) that bind (or hybridizes) to complementary sequences in the 3' UTR of the target mRNA (Lee et al., 1993, Cell 75:843-854; Reinhart et al., 2000, Nature 403:901-906; Lee et al., 2001, Science 294:862-864; Lau et al., 2001, Science 294:858-862; Hutvagner et al., 2001, Science 293:834-838). miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728).

Short hairpin RNA (shRNA) is a single-stranded RNA molecule comprising at least two complementary portions hybridized or capable of hybridizing to form a double-stranded (duplex) structure sufficiently long to mediate RNAi upon processing into double-stranded RNA with overhangs, e.g., siRNAs and miRNAs. shRNA also contains at least one noncomplementary portion that forms a loop structure upon hybridization of the complementary portions to form the double-stranded structure. shRNAs serve as precursors of miRNAs and siRNAs.

Usually, sequence encoding an shRNA is cloned into a vector and the vector is introduced into a cell and transcribed by the cell's transcription machinery (Chen et al., 2003, *Biochem Biophys Res Commun* 311:398-404). The shRNAs can then be transcribed, for example, by RNA polymerase III (Pol III) in response to a Pol III-type promoter in the vector (Yuan et al., 2006, *Mol Biol Rep* 33:33-41 and Scherer et al., 2004, *Mol Ther* 10:597-603). The expressed shRNAs are then exported into the cytoplasm where they are processed by proteins such as Dicer into siRNAs, which then trigger RNAi (Amarzguioui et al., 2005, *FEBS Letter* 579:5974-5981). It has been reported that purines are required at the 5' end of a newly initiated RNA for optimal RNA polymerase III transcription. More detailed discussion can be found in Zecherle et al., 1996, *Mol. Cell. Biol.* 16:5801-5810; Fruscoloni et al., 1995, *Nucleic Acids Res,* 23:2914-2918; and Mattaj et al., 1988, *Cell,* 55:435-442. The shRNAs core sequences can be expressed stably in cells, allowing long-term gene silencing in cells both in vitro and in vivo, e.g., in animals (see, McCaffrey et al., 2002, *Nature* 418:38-39; Xia et al., 2002, *Nat. Biotech.* 20:1006-1010; Lewis et al., 2002, *Nat. Genetics* 32:107-108; Rubinson et al., 2003, *Nat. Genetics* 33:401-406; and Tiscornia et al., 2003, *Proc. Natl. Acad. Sci. USA* 100:1844-1848).

Martinez et al. reported that RNA interference can be used to selectively target oncogenic mutations (Martinez et al., 2002, Proc. Natl. Acad. Sci. USA 99:14849-14854). In this report, an siRNA that targets the region of the R248W mutant of p53 containing the point mutation was shown to silence the expression of the mutant p53 but not the wild-type p53.

Wilda et al. reported that an siRNA targeting the M-BCR/ABL fusion mRNA can be used to deplete the M-BCR/ABL mRNA and the M-BCR/ABL oncoprotein in leukemic cells (Wilda et al., 2002, Oncogene 21:5716-5724).

U.S. Pat. No. 6,506,559 discloses a RNA interference process for inhibiting expression of a target gene in a cell. The process comprises introducing partially or fully double-stranded RNA having a sequence in the duplex region that is identical to a sequence in the target gene into the cell or into the extracellular environment.

U.S. Patent Application Publication No. US 2002/0086356 discloses RNA interference in a *Drosophila* in vitro system using RNA segments 21-23 nucleotides (nt) in length. The patent application publication teaches that when these 21-23 nt fragments are purified and added back to *Drosophila* extracts, they mediate sequence-specific RNA interference in the absence of long dsRNA. The patent application publication also teaches that chemically synthesized oligonucleotides of the same or similar nature can also be used to target specific mRNAs for degradation in mammalian cells.

International Patent Application Publication No. WO 2002/44321 discloses that double-stranded RNA (dsRNA) 19-23 nt in length induces sequence-specific post-transcriptional gene silencing in a *Drosophila* in vitro system. The PCT publication teaches that short interfering RNAs (siRNAs) generated by an RNase III-like processing reaction from long dsRNA or chemically synthesized siRNA duplexes with overhanging 3' ends mediate efficient target RNA cleavage in the lysate, and the cleavage site is located near the center of the region spanned by the guiding siRNA.

U.S. Patent Application Publication No. US 2002/016216 discloses a method for attenuating expression of a target gene in cultured cells by introducing double stranded RNA (dsRNA) that comprises a nucleotide sequence that hybridizes under stringent conditions to a nucleotide sequence of the target gene into the cells in an amount sufficient to attenuate expression of the target gene.

International Patent Application Publication No. WO 2003/006477 discloses engineered RNA precursors that when expressed in a cell are processed by the cell to produce targeted small interfering RNAs (siRNAs) that selectively silence targeted genes (by cleaving specific mRNAs) using the cell's own RNA interference (RNAi) pathway. The PCT publication teaches that by introducing nucleic acid molecules that encode these engineered RNA precursors into cells in vivo with appropriate regulatory sequences, expression of the engineered RNA precursors can be selectively controlled both temporally and spatially, i.e., at particular times and/or in particular tissues, organs, or cells.

International Patent Application Publication No. WO 02/44321 discloses that double-stranded RNAs (dsRNAs) of 19-23 nt in length induce sequence-specific post-transcriptional gene silencing in a *Drosophila* in vitro system. The PCT publication teaches that siRNAs duplexes can be generated by an RNase III-like processing reaction from long dsRNAs or by chemically synthesized siRNA duplexes with overhanging 3' ends mediating efficient target RNA cleavage in the lysate where the cleavage site is located near the center of the region spanned by the guiding siRNA. The PCT publication also provides evidence that the direction of dsRNA processing determines whether sense or antisense-identical target RNA can be cleaved by the produced siRNA complex. Systematic analyses of the effects of length, secondary structure, sugar backbone and sequence specificity of siRNAs on RNA interference have been disclosed to aid siRNA design. In addition, silencing efficacy has been shown to correlate with the GC content of the 5' and 3' regions of the 19 base pair target sequence. It was found that siRNAs targeting sequences with a GC rich 5' and GC poor 3' perform the best. More detailed discussion may be found in Elbashir et al., 2001, *EMBO J.* 20:6877-6888 and Aza-Blanc et al., 2003, *Mol. Cell.* 12:627-637; each of which is hereby incorporated by reference herein in its entirety.

In addition, siRNA design algorithms are disclosed in PCT publications WO 2005/018534 A2 and WO 2005/042708 A2; each of which is hereby incorporated by reference herein in its entirety. Specifically, International Patent Application Publication No. WO 2005/018534 A2 discloses methods and compositions for gene silencing using siRNA having partial sequence homology to its target gene. The application provides methods for identifying common and/or differential responses to different siRNAs targeting a gene. The application also provides methods for evaluating the relative activity of the two strands of an siRNA. The application further provides methods of using siRNAs as therapeutics for treatment of diseases. International Patent Application Publication No. WO 2005/042708 A2 provides a method for identifying siRNA target motifs in a transcript using a position-specific score matrix approach. It also provides a method for identifying off-target genes of an siRNA using a position-specific score matrix approach. The application further provides a method for designing siRNAs with improved silencing efficacy and specificity as well as a library of exemplary siRNAs.

Design softwares can be use to identify potential sequences within the target enzyme mRNA that can be targeted with siRNAs in the methods described herein. See, for example, http://www.ambion.com/techlib/misc/siRNA_finder.html ("Ambion siRNA Target Finder Software"). For example, the nucleotide sequence of ACC1, which is known in the art (GenBank Accession No. NM_198834) is entered into the Ambion siRNA Target Finder Software (http://www.ambion.com/techlib/misc/siRNA_finder.html), and the software identifies potential ACC1 target sequences and corresponding siRNA sequences that can be used in assays to inhibit human ACC1 activity by downregulation of ACC1 expression. Using this method, non-limiting examples of ACC1 target sequence (5' to 3') and corresponding sense and antisense strand siRNA sequences (5' to 3') for inhibiting ACC1 are identified and presented below:

| | ACC1 Target Sequence | Sense Strand siRNA | Antisense Strand siRNA |
|---|---|---|---|
| 1. | AATCACTTTGCCCGTGTGGCG (SEQ ID NO: 1) | UCACUUUGCCCGUGUGGCGUU (SEQ ID NO: 2) | CGCCACACGGGCAAAGUGAUU (SEQ ID NO: 3) |
| 2. | AACGTTCCCATCTCCACCCCT (SEQ ID NO: 4) | CGUUCCCAUCUCCACCCCUUU (SEQ ID NO: 5) | AGGGGUGGAGAUGGGAACGUU (SEQ ID NO: 6) |
| 3. | AAGGGAAATTGAGGCTGAGGG (SEQ ID NO: 7) | GGGAAAUUGAGGCUGAGGGUU (SEQ ID NO: 8) | CCCUCAGCCUCAAUUUCCCUU (SEQ ID NO: 9) |

-continued

| ACC1 Target Sequence | Sense Strand siRNA | Antisense Strand siRNA |
|---|---|---|
| 4. AAATTGAGGCTGAGGGAACTG (SEQ ID NO: 10) | AUUGAGGCUGAGGGAACUGUU (SEQ ID NO: 11) | CAGUUCCCUCAGCCUCAAUUU (SEQ ID NO: 12) |
| 5. AACTGGGCCCAGGGACGGCGA (SEQ ID NO: 13) | CUGGGCCCAGGGACGGCGAUU (SEQ ID NO: 14) | UCGCCGUCCCUGGGCCCAGUU (SEQ ID NO: 15) |
| 6. AAGGGCTGCTCGTGGATGAAC (SEQ ID NO: 16) | GGGCUGCUCGUGGAUGAACUU (SEQ ID NO: 17) | GUUCAUCCACGAGCAGCCCUU (SEQ ID NO: 18) |
| 7. AATCAGATGCTTCTGGAACGT (SEQ ID NO: 19) | UCAGAUGCUUCUGGAACGUUU (SEQ ID NO: 20) | ACGUUCCAGAAGCAUCUGAUU (SEQ ID NO: 21) |
| 8. AATAATGGATGAACCATCTCC (SEQ ID NO: 22) | UAAUGGAUGAACCAUCUCCUU (SEQ ID NO: 23) | GGAGAUGGUUCAUCCAUUAUU (SEQ ID NO: 24) |
| 9. AATGGATGAACCATCTCCCTT (SEQ ID NO: 25) | UGGAUGAACCAUCUCCCUUUU (SEQ ID NO: 26) | AAGGGAGAUGGUUCAUCCAUU (SEQ ID NO: 27) |

The same method can be applied to identify ACC2 target sequences (5' to 3') and the corresponding siRNA sequences (sense and antisense strands, 5' to 3'). Non-limiting examples of siRNA sequences for inhibiting ACC2 are presented below:

| ACC2 Target Sequence | Sense Strand siRNA | Antisense Strand siRNA |
|---|---|---|
| 1. AATGGTCTTGCTTCTTTGTCT (SEQ ID NO: 28) | UGGUCUUGCUUCUUUGUCUUU (SEQ ID NO: 29) | AGACAAAGAAGCAAGACCAUU (SEQ ID NO: 30) |
| 2. AAGCCGATCACCAAGAGTAAA (SEQ ID NO: 31) | GCCGAUCACCAAGAGUAAAUU (SEQ ID NO: 32) | UUUACUCUUGGUGAUCGGCUU (SEQ ID NO: 33) |
| 3. AAGAAACCCCCTTTCTTCCAG (SEQ ID NO: 34) | GAAACCCCCUUUCUUCCAGUU (SEQ ID NO: 35) | CUGGAAGAAAGGGGGUUUCUU (SEQ ID NO: 36) |
| 4. AAAGAAGACAAGAAGCAGGCA (SEQ ID NO: 37) | AGAAGACAAGAAGCAGGCAUU (SEQ ID NO: 38) | UGCCUGCUUCUUGUCUUCUUU (SEQ ID NO: 39) |
| 5. AAGGTGCTTATTGCCAACAAC (SEQ ID NO: 40) | GGUGCUUAUUGCCAACAACUU (SEQ ID NO: 41) | GUUGUUGGCAAUAAGCACCUU (SEQ ID NO: 42) |
| 6. AATCAGTGTCCCAGAAGATGT (SEQ ID NO: 43) | UCAGUGUCCCAGAAGAUGUUU (SEQ ID NO: 44) | ACAUCUUCUGGGACACUGAUU (SEQ ID NO: 45) |
| 7. AATTTCCGGAGCAGCAAGAAC (SEQ ID NO: 46) | UUUCCGGAGCAGCAAGAACUU (SEQ ID NO: 47) | GUUCUUGCUGCUCCGGAAAUU (SEQ ID NO: 48) |
| 8. AATTTGGGCACTGCTTCTCCT (SEQ ID NO: 49) | UUUGGGCACUGCUUCUCCUUU (SEQ ID NO: 50) | AGGAGAAGCAGUGCCCAAAUU (SEQ ID NO: 51) |
| 9. AATACCTCATTAACCTCCTGG (SEQ ID NO: 52) | UACCUCAUUAACCUCCUGGUU (SEQ ID NO: 53) | CCAGGAGGUUAAUGAGGUAUU (SEQ ID NO: 54) |

The same method can be applied to identify target sequences of any enzyme and the corresponding siRNA sequences (sense and antisense strands) to obtain RNAi molecules.

In certain embodiments, a Compound is an siRNA effective to inhibit expression of a target enzyme, e.g., ACC or FAS, wherein the siRNA comprises a first strand comprising a sense sequence of the target enzyme mRNA and a second strand comprising a complement of the sense sequence of the target enzyme, and wherein the first and second strands are about 21 to 23 nucleotides in length. In some embodiments, the siRNA comprises first and second strands comprise sense and complement sequences, respectively, of the target enzyme mRNA that is about 17, 18, 19, or 20 nucleotides in length.

The RNAi molecule (e.g., siRNA, shRNA, miRNA) can be both partially or completely double-stranded, and can encompass fragments of at least 18, at least 19, at least 20, at least 21, at least 22, at least 23, at least 24, at least 25, at least 30, at least 35, at least 40, at least 45, and at least 50 or more nucleotides per strand. The RNAi molecule (e.g., siRNA, shRNA, miRNA) can also comprise 3' overhangs of at least 1, at least 2, at least 3, or at least 4 nucleotides. The RNAi molecule (e.g., siRNA, shRNA, miRNA) can be of any length desired by the user as long as the ability to inhibit target gene expression is preserved.

RNAi molecules that target ACC2 have been described, e.g., in U.S. Pat. No. 7,211,423 and U.S. Patent Application Publication No. US 2008/0026363 A1, each of which is incorporated by reference herein in its entirety.

In some embodiments, methods for treatment or prevention of a virus infection in a human subject, comprising administering an effective amount of an RNAi molecule (e.g., siRNA, shRNA, miRNA) that inhibits the activity of a target enzyme (e.g., ACC, FAS, SCD) by decreasing the expression level of the target enzyme. Exemplary target enzymes that can be inhibited by RNAi molecules are provided in section 5.1.

RNAi molecules can be obtained using any of a number of techniques known to those of ordinary skill in the art. Generally, production of RNAi molecules can be carried out by chemical synthetic methods or by recombinant nucleic acid techniques. Methods of preparing a dsRNA are described, for example, in Ausubel et al., Current Protocols in Molecular Biology (Supplement 56), John Wiley & Sons, New York (2001); Sambrook et al., Molecular Cloning: A Laboratory Manual, 3.sup.rd ed., Cold Spring Harbor Press, Cold Spring Harbor (2001); and can be employed in the methods described herein. For example, RNA can be transcribed from PCR products, followed by gel purification. Standard procedures known in the art for in vitro transcription of RNA from PCR templates. For example, dsRNA can be synthesized using a PCR template and the Ambion T7 MEGASCRIPT, or other similar, kit (Austin, Tex.); the RNA can be subsequently precipitated with LiCl and resuspended in a buffer solution.

To assay for RNAi activity in cells, any of a number of techniques known to those of ordinary skill in the art can be employed. For example, the RNAi molecules are introduced into cells, and the expression level of the target enzyme can be assayed using assays known in the art, e.g., ELISA and immunoblotting. Also, the mRNA transcript level of the target enzyme can be assayed using methods known in the art, e.g., Northern blot assays and quantitative real-time PCR. Further the activity of the target enzyme can be assayed using methods known in the art and/or described herein in section 5.3. In a specific embodiment, the RNAi molecule reduces the protein expression level of the target enzyme by at least about 10%, 20%, 30%, 40%, 50%, 60%, 70%, 80%, 90%, or 95%. In one embodiment, the RNAi molecule reduces the mRNA transcript level of the target enzyme by at least about 10%, 20%, 30%, 40%, 50%, 60%, 70%, 80%, 90%, or 95%. In a particular embodiment, the RNAi molecule reduces the enzymatic activity of the target enzyme by at least about 10%, 20%, 30%, 40%, 50%, 60%, 70%, 80%, 90%, or 95%.

5.3 Screening Assays to Identify Inhibitors of Host Cell Target Enzymes

Compounds known to be inhibitors of the host cell target enzymes can be directly screened for antiviral activity using assays known in the art and/or described infra (see, e.g., Section 5.4 et seq.). While optional, derivatives or congeners of such enzyme inhibitors, or any other compound can be tested for their ability to modulate the enzyme targets using assays known to those of ordinary skill in the art and/or described below. Compounds found to modulate these targets can be further tested for antiviral activity. Compounds found to modulate these targets or to have antiviral activity (or both) can also be tested in the metabolic flux assays described in Example 1 in order to confirm the compound's effect on the metabolic flux of the cell. This is particularly useful for determining the effect of the Compound in blocking the ability of the virus to alter cellular metabolic flux, and to identify other possible metabolic pathways that may be targeted by the compound.

Alternatively, Compounds can be tested directly for antiviral activity. Those Compounds which demonstrate antiviral activity, or that are known to be antiviral but have unacceptable specificity or toxicity, can be screened against the enzyme targets of the invention. Antiviral compounds that modulate the enzyme targets can be optimized for better activity profiles.

Any host cell enzyme, known in the art and/or described in Section 5.1, is contemplated as a potential target for antiviral intervention. Further, additional host cell enzymes that have a role, directly or indirectly, in regulating the cell's metabolism are contemplated as potential targets for antiviral intervention. Compounds, such as the compounds disclosed in Section 5.2 or any other compounds, e.g., a publicly available library of compounds, can be tested for their ability to modulate (activate or inhibit) the activity of these host cell enzymes. If a compound is found to modulate the activity of a particular enzyme, then a potential antiviral compound has been identified.

In one embodiment, an enzyme that affects or is involved in fatty acid biosynthesis and/or metabolism is tested as a target for the compound, for example, ATP citrate lyase and its isoforms, HMG-CoA synthase, acetyl-CoA carboxylase and its isozymes, fatty acid synthase and its subunits, lysophosphatidic acid acetyltransferase or lysophosphatidic acid acyltransferase and its isoforms, or malonyl-CoA decarboxylase. In one embodiment, enzymes of the glycolysis pathway are tested for modulation by the compound. In one embodiment, components of the tricarboxylic acid (TCA) cycle are tested. In one embodiment, cellular components that are involved in ion homeostasis and energy transport across barriers, such as the proton ATPase, are screened for modulation (inhibition or activation) by the compounds of the invention. In some embodiments, the activity of host enzymes involved in glucose transport are tested as a target of the compound.

In preferred embodiments, a Compound is tested for its ability to modulate host metabolic enzymes by contacting a composition comprising the compound with a composition comprising the enzyme and measuring the enzyme's activity. If the enzyme's activity is altered in the presence of the compound compared to a control, then the Compound modulates the enzyme's activity. In some embodiments of the invention, the Compound increases an enzyme's activity (for example, an enzyme that is a negative regulator of fatty acid biosynthesis might have its activity increased by a potential antiviral compound). In specific embodiments, the Compound increases an enzyme's activity by at least approximately 10%, 15%, 20%, 25%, 30%, 40%, 50%, 60%, 70%, 80% or 90%. In some embodiments, the compound decreases an enzyme's activity. In particular embodiments, the Compound decreases an enzyme's activity by at least approximately 10%, 15%, 20%, 25%, 30%, 40%, 50%, 60%, 70%, 80%, 90%, 95% or 100%. In certain embodiments, the compound exclusively modulates a single enzyme. In some embodiments, the compound modulates multiple enzymes, although it might modulate one enzyme to a greater extent than another. Using the standard enzyme activity assays described herein, the activity of the compounds could be characterized. In one embodiment, a compound exhibits an irreversible inhibition or activation of a particular enzyme. In some embodiments, a compound reversibly inhibits or activates an enzyme. In some embodiments, a compound alters the kinetics of the enzyme.

In one embodiment, for example, evaluating the interaction between the test compound and host target enzyme includes one or more of (i) evaluating binding of the test compound to the enzyme; (ii) evaluating a biological activity of the enzyme; (iii) evaluating an enzymatic activity (e.g., kinase activity) of the enzyme in the presence and absence of test compound. The in vitro contacting can include forming a reaction mixture that includes the test compound, enzyme, any required cofactor (e.g., biotin) or energy source (e.g., ATP, or radiolabeled ATP), a substrate (e.g., acetyl-CoA, a sugar, a polypeptide, a nucleoside, or any other metabolite, with or without label) and evaluating conversion of the substrate into a product. Evaluating product formation can include, for example, detecting the transfer of carbons or phosphate (e.g., chemically or using a label, e.g., a radiolabel), detecting the reaction product, detecting a secondary reaction dependent on the first reaction, or detecting a physical property of the substrate, e.g., a change in molecular weight, charge, or pI.

Target enzymes for use in screening assays can be purified from a natural source, e.g., cells, tissues or organs comprising adipocytes (e.g., adipose tissue), liver, etc. Alternatively, target enzymes can be expressed in any of a number of different recombinant DNA expression systems and can be obtained in large amounts and tested for biological activity. For expression in recombinant bacterial cells, for example E. coli, cells are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as beta-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, biologically active target enzyme useful for screening compounds for the purposes of the invention. Alternatively, the target enzyme to be screened could be partially purified or tested in a cellular lysate or other solution or mixture.

Target enzyme activity assays are preferably in vitro assays using the enzymes in solution or using cell or cell lysates that express such enzymes, but the invention is not to be so limited. In certain embodiments, the enzyme is in solution. In other embodiments, the enzyme is associated with microsomes or in detergent. In other embodiments, the enzyme is immobilized to a solid or gel support. In certain embodiments, the enzyme is labeled to facilitate purification and/or detection. In other embodiments, a substrate is labeled to facilitate purification and or detection. Labels include polypeptide tags, biotin, radiolabels, fluorescent labels, or a colorimetric label. Any art-accepted assay to test the activity of metabolic enzymes can be used in the practice of this invention. Preferably, many compounds are screened against multiple targets with high throughput screening assays.

Substrate and product levels can be evaluated in an in vitro system, e.g., in a biochemical extract, e.g., of proteins. For example, the extract may include all soluble proteins or a subset of proteins (e.g., a 70% or 50% ammonium sulfate cut), the useful subset of proteins defined as the subset that includes the target enzyme. The effect of a test compound can be evaluated, for example, by measuring substrate and product levels at the beginning of a time course, and then comparing such levels after a predetermined time (e.g., 0.5, 1, or 2 hours) in a reaction that includes the test compound and in a parallel control reaction that does not include the test compound. This is one method for determining the effect of a test compound on the substrate-to-product ratio in vitro. Reaction rates can obtained by linear regression analysis of radioactivity or other label incorporated vs. reaction time for each incubation. $K_M$ and $V_{max}$ values can be determined by non-linear regression analysis of initial velocities, according to the standard Henri-Michaelis-Menten equation. $k_{cat}$ can be obtained by dividing $V_{max}$ values by reaction concentrations of enzyme, e.g., derived by colorimetric protein determinations (e.g., Bio-RAD protein assay, Bradford assay, Lowry method). In one embodiment, the Compound irreversibly inactivates the target enzyme. In another embodiment, the Compound reversibly inhibits the target enzyme. In some embodiments, the Compound reversibly inhibits the target enzyme by competitive inhibition. In some embodiments, the Compound reversibly inhibits the target enzyme by noncompetitive inhibition. In some embodiments, the Compound reversibly inhibits the target enzyme by uncompetitive inhibition. In a further embodiment, the Compound inhibits the target enzyme by mixed inhibition. The mechanism of inhibition by the Compound can be determined by standard assays known by those of ordinary skill in the art.

Methods for the quantitative measurement of enzyme activity utilizing a phase partition system are described in U.S. Pat. No. 6,994,956, which is incorporated by reference herein in its entirety. Specifically, a radiolabeled substrate and the product of the reaction are differentially partitioned into an aqueous phase and an immiscible scintillation fluid-containing organic phase, and enzyme activity is assessed either by incorporation of a radiolabeled-containing organic-soluble moiety into product molecules (gain of signal assay) or loss of a radiolabel-containing organic-soluble moiety from substrate molecules (loss of signal assay). Scintillations are only detected when the radionuclide is in the organic, scintillant-containing phase. Such methods can be employed to test the ability of a Compound to inhibit the activity of a target enzyme.

Cellular assays may be employed. An exemplary cellular assay includes contacting a test compound to a culture cell (e.g., a mammalian culture cell, e.g., a human culture cell)

and then evaluating substrate and product levels in the cell, e.g., using any method described herein, such as Reverse Phase HPLC.

Substrate and product levels can be evaluated, e.g., by NMR, HPLC (See, e.g., Bak, M. I., and Ingwall, J. S. (1994) J. Clin. Invest. 93, 40-49), mass spectrometry, thin layer chromatography, or the use of radiolabeled components (e.g., radiolabeled ATP for a kinase assay). For example, $^{31}$P NMR can be used to evaluate ATP and AMP levels. In one implementation, cells and/or tissue can be placed in a 10-mm NMR sample tube and inserted into a 1H/31P double-tuned probe situated in a 9.4-Tesla superconducting magnet with a bore of 89 cm. If desired, cells can be contacted with a substance that provides a distinctive peak in order to index the scans. Six $^{31}$P NMR spectra—each obtained by signal averaging of 104 free induction decays—can be collected using a 60° flip angle, 15-microsecond pulse, 2.14-second delay, 6,000 Hz sweep width, and 2048 data points using a GE-400 Omega NMR spectrometer (Bruker Instruments, Freemont, Calif., USA). Spectra are analyzed using 20-Hz exponential multiplication and zero- and first-order phase corrections. The resonance peak areas can be fitted by Lorentzian line shapes using NMR1 software (New Methods Research Inc., Syracuse, N.Y., USA). By comparing the peak areas of fully relaxed spectra (recycle time: 15 seconds) and partially saturated spectra (recycle time: 2.14 seconds), the correction factor for saturation can be calculated for the peaks. Peak areas can be normalized to cell and/or tissue weight or number and expressed in arbitrary area units. Another method for evaluating, e.g., ATP and AMP levels includes lysing cells in a sample to form an extract, and separating the extract by Reversed Phase HPLC, while monitoring absorbance at 260 nm.

Another type of in vitro assay evaluates the ability of a test compound to modulate interaction between a first enzyme pathway component and a second enzyme pathway component, e.g., between AMPK alpha and beta-gamma or the different enzyme activities of fatty acid synthase. This type of assay can be accomplished, for example, by coupling one of the components with a radioisotope or enzymatic label such that binding of the labeled component to the second pathway component can be determined by detecting the labeled compound in a complex. An enzyme pathway component can be labeled with $^{125}$I, $^{35}$S, $^{14}$C, or $^{3}$H, either directly or indirectly, and the radioisotope detected by direct counting of radio-emission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Soluble and/or membrane-bound forms of isolated proteins (e.g., enzyme pathway components and their receptors or biologically active portions thereof) can be used in the cell-free assays of the invention. When membrane-bound forms of the enzyme are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

In another example, the enzyme pathway component (e.g., GLUT-4 in the case of AMPK) can reside in a membrane, e.g., a liposome or other vesicle.

Cell-free assays involve preparing a reaction mixture of the target enzyme and the test compound under conditions and for a time sufficient to allow the two components to interact and bind, thus forming a complex that can be removed and/or detected.

The interaction between two molecules, e.g., target enzyme and test compound, can also be detected, e.g., using a fluorescence assay in which at least one molecule is fluorescently labeled, e.g., to evaluate an interaction between a test compound and a target enzyme. One example of such an assay includes fluorescence energy transfer (FET or FRET for fluorescence resonance energy transfer) (See, for example, Lakowicz et al., U.S. Pat. No. 5,631,169; Stavrianopoulos, et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, a proteinaceous "donor" molecule may simply utilize the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) Comb Chem HTS 2:177-190; Jameson et al. (1995) Methods Enzymol 246:283; See Anal Biochem. 255:257 (1998). Fluorescence polarization can be monitored in multi-well plates. See, e.g., Parker et al. (2000) Journal of Biomolecular Screening 5:77-88; and Shoeman, et al. (1999) 38, 16802-16809.

In another embodiment, determining the ability of the target enzyme to bind to a target molecule can be accomplished using real-time Biomolecular Interaction Analysis (BIA) (See, e.g., Sjolander, S, and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target enzyme is anchored onto a solid phase. The target enzyme/test compound complexes anchored on the solid phase can be detected at the end of the reaction, e.g., the binding reaction. For example, the target enzyme can be anchored onto a solid surface, and the test compound (which is not anchored), can be labeled, either directly or indirectly, with detectable labels discussed herein.

It may be desirable to immobilize either the target enzyme or an anti-target enzyme antibody to facilitate separation of complexed from uncomplexed forms of one or both of the proteins, as well as to accommodate automation of the assay. Binding of a test compound to target enzyme, or interaction of a target enzyme with a second component in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/target enzyme fusion proteins can be adsorbed onto glutathione sepharose beads (Sigma Chemical, St. Louis, Mo., USA) or glutathione derivatized microtiter plates, which are then combined with the test compound or the test compound and either the non-adsorbed target enzyme, and the mixture incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target enzyme binding or activity is determined using standard techniques.

Other techniques for immobilizing either a target enzyme or a test compound on matrices include using conjugation of biotin and streptavidin. Biotinylated target enzyme or test compounds can be prepared from biotin-NHS(N-hydroxysuccinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with a target enzyme but which do not interfere with binding of the target enzyme to the test compound and/or substrate. Such antibodies can be derivatized to the wells of the plate, and unbound target enzyme trapped in the wells by antibody conjugation. Methods for detecting such complexes, in addition to those described above for the GST-immobilized complexes, include immunodetection of complexes using antibodies reactive with the target enzyme, as well as enzyme-linked assays which rely on detecting an enzymatic activity associated with the target enzyme.

Alternatively, cell free assays can be conducted in a liquid phase. In such an assay, the reaction products are separated from unreacted components, by any of a number of standard techniques, including but not limited to: differential centrifugation (See, for example, Rivas, G., and Minton, A. P., (1993) Trends Biochem Sci 18:284-7); chromatography (gel filtration chromatography, ion-exchange chromatography); electrophoresis (See, e.g., Ausubel, F. et al., eds. Current Protocols in Molecular Biology 1999, J. Wiley: New York); and immunoprecipitation (See, for example, Ausubel, F. et al., eds. (1999) Current Protocols in Molecular Biology, J. Wiley: New York). Such resins and chromatographic techniques are known to one skilled in the art (See, e.g., Heegaard, N. H., (1998) J Mol Recognit 11:141-8; Hage, D. S., and Tweed, S. A. (1997) J Chromatogr B Biomed Sci Appl. 699:499-525). Further, fluorescence energy transfer may also be conveniently utilized, as described herein, to detect binding without further purification of the complex from solution.

In a preferred embodiment, the assay includes contacting the target enzyme or biologically active portion thereof with a known compound which binds the target enzyme to form an assay mixture, contacting the assay mixture with a test compound, and determining the ability of the test compound to interact with the target enzyme, wherein determining the ability of the test compound to interact with the target enzyme includes determining the ability of the test compound to preferentially bind to the target enzyme, or to modulate the activity of the target enzyme, as compared to the known compound (e.g., a competition assay). In another embodiment, the ability of a test compound to bind to and modulate the activity of the target enzyme is compared to that of a known activator or inhibitor of such target enzyme.

The target enzymes of the invention can, in vivo, interact with one or more cellular or extracellular macromolecules, such as proteins, which are either heterologous to the host cell or endogenous to the host cell, and which may or may not be recombinantly expressed. For the purposes of this discussion, such cellular and extracellular macromolecules are referred to herein as "binding partners." Compounds that disrupt such interactions can be useful in regulating the activity of the target enzyme. Such compounds can include, but are not limited to molecules such as antibodies, peptides, and small molecules. In an alternative embodiment, the invention provides methods for determining the ability of the test compound to modulate the activity of a target enzyme through modulation of the activity of a downstream effector of such target enzyme. For example, the activity of the effector molecule on an appropriate target can be determined, or the binding of the effector to an appropriate target can be determined, as previously described.

To identify compounds that interfere with the interaction between the target enzyme and its cellular or extracellular binding partner(s), a reaction mixture containing the target enzyme and the binding partner is prepared, under conditions and for a time sufficient, to allow the two products to form a complex. In order to test an inhibitory compound, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target enzyme can also be compared to complex formation within reaction mixtures containing the test compound and mutant target enzyme. This comparison can be important in those cases wherein it is desirable to identify compounds that disrupt interactions of mutant but not normal target enzymes.

The assays described herein can be conducted in a heterogeneous or homogeneous format. Heterogeneous assays involve anchoring either the target enzyme or the binding partner, substrate, or tests compound onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target enzyme and a binding partners or substrate, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target enzyme or the interactive cellular or extracellular binding partner or substrate, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target enzyme and the interactive cellular or extracellular binding partner product or substrate is prepared in that either the target enzyme or their binding partners or substrates are labeled, but the signal generated by the label is quenched due to complex formation (See, e.g., U.S. Pat. No. 4,109,496 that utilizes this approach for immunoassays). The addition of a test substance that competes with and displaces one of the species from the preformed complex will result in the generation of a signal above background. In this way, test compounds that disrupt target enzyme-binding partner or substrate contact can be identified.

In yet another aspect, the target enzyme can be used as "bait protein" in a two-hybrid assay or three-hybrid assay (See, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent, International patent application Publication No. WO94/10300), to identify other proteins that bind to or interact with target enzyme ("target enzyme binding protein" or "target enzyme–bp") and are involved in target enzyme pathway activity. Such target enzyme-bps can be activators or inhibitors of the target enzyme or target enzyme targets as, for example, downstream elements of the target enzyme pathway.

In another embodiment, modulators of a target enzyme's gene expression are identified. For example, a cell or cell free mixture is contacted with a candidate compound and the expression of the target enzyme mRNA or protein evaluated relative to the level of expression of target enzyme mRNA or protein in the absence of the candidate compound. When expression of the target enzyme component mRNA or protein is greater in the presence of the candidate compound than in its absence, the candidate compound is identified as a stimulator of target enzyme mRNA or protein expression. Alternatively, when expression of the target enzyme mRNA or protein is less (statistically significantly less) in the presence of the candidate compound than in its absence, the candidate compound is identified as an inhibitor of the target enzyme mRNA or protein expression. The level of the target enzyme mRNA or protein expression can be determined by methods for detecting target enzyme mRNA or protein, e.g., Westerns, Northerns, PCR, mass spectroscopy, 2-D gel electrophoresis, and so forth, all which are known to those of ordinary skill in the art.

Assays for producing enzyme targets, testing their activity, and conducting screens for their inhibition or activation are described below using examples of enzymes related to fatty acid biosynthesis. These assays can be adapted by one of ordinary skill in the art, or other assays known in the art can be used, to test the activity of other targets of the invention.

AMP-Activated Protein Kinase (AMPK)

In one embodiment of the present invention, a virus that upregulates fatty acid biosynthesis would be inhibited by a compound that activates AMP-activated protein kinase (AMPK), as AMPK is an inhibitor of acetyl CoA carboxylase. In a preferred embodiment, AMPK inhibition is a preferred result, as viruses that depend on the upregulation of glycolysis and depend on AMPK activity would be inhibited by an AMPK inhibitor.

AMPK can exemplarily be purified from porcine liver. Liver (1 kg) is homogenized in 4,000 ml of buffer. A 2.5-7.0% (w/v) PEG 6000 fraction is prepared and the resultant fraction batched onto 1,500 ml of DEAE cellulose (Whatman, Clifton, N.J.) and eluted with buffer containing 0.25 M NaCl. The eluate is chromatographed on, e.g., Blue Sepharose (Pharmacia, Uppsala, Sweden) and the AMPK eluted with buffer containing 1 M NaCl. The enzyme fraction is concentrated and desalted by 10% (w/v) PEG-6000 precipitation prior to chromatography by peptide substrate affinity chromatography. The peptide substrate affinity column is washed with the same buffer containing 0.1% (v/v) Triton X-100 and 0.5 M NaCl and the AMPK eluted with this buffer containing 2 M NaCl and 30% (v/v) ethylene glycol.

In addition to the general assays for enzyme activity and compound screening described above, assays for measuring the activity of AMPK, which can be used to test the effect of a potential antiviral compound, are taught in US Patent Publication No. 20060147947; U.S. Pat. No. 7,220,729; U.S. Pat. No. 6,124,125; and Feng et al. 2004. Antiviral Res. 62, A43, which are incorporated by reference herein in their entirety. An in vitro assay for AMPK activity can include forming a reaction mixture that includes the test compound, AMPK, AMP, a substrate (e.g., a protein), and ATP (e.g., radiolabeled ATP) and evaluating transfer of a phosphate from the ATP to the substrate. Evaluating transfer of the phosphate can include, for example, detecting the phosphate (e.g., chemically or using a label, e.g., a radiolabel) or detecting a physical property of the substrate, e.g., a change in molecular weight, charge, or pI.

AMPK activity can be assayed in vitro. See, e.g., Hardie et al. (1997) Eur. J. Biochem. 246: 259; Hardie et al., (1998) Annu Rev. Biochem. 67:851; Vavvas et al. (1997) J. Biol. Chem. 272:13256; and Winder et al. (1996) Am. J. Physiol. Endocrinol. Metab. 270:E299. The reaction mixture can include radiolabeled ATP, e.g., [$^{32}$P]ATP and an artificial peptide substrate, e.g., a 15-amino acid peptide called "SAMS" which is an amino acid sequence from the acetyl-CoA carboxylase (ACC) enzyme. The SAMS peptide can include the sequence: HMRSAMSGLHLVKRR. See, e.g., Davies et al. (1989) Eur. J. Biochem, 186:123. A peptide from glycogen synthase can also be used, e.g., a peptide that includes the sequence PLSRTLSVAAKK.

An increase in AMPK activity will cause an increase in phosphorylation of the peptide. In some implementations, the reaction mixture can include AMP or creatine phosphate. Phosphorylation can be detected, e.g., using a scintillation counter after separation of free ATP from the peptide.

Acetyl-CoA Carboxylase (ACC)

Acetyl-CoA carboxylase (ACC) catalyzes the first committed step of fatty acid biosynthesis and is one of the rate-limiting steps of fatty acid biosynthesis, which converts ATP, bicarbonate and acetyl-CoA to malonyl-CoA, ADP and inorganic phosphate. ACC enzymatic assays can be carried out using recombinant, purified ACC1 and/or ACC2. The nucleotide and amino acid sequences of human and rat ACC2 have been described, e.g., see U.S. Pat. No. 7,211,423, which is incorporated herein in its entirety. It is thus noted that in some embodiments of this invention, it is generally desirable to determine the specificity of a particular compound for a particular isozyme or enzyme isoform. Recombinant ACC1 or ACC2 can be labeled with a tag, e.g., Myc, Glutathione S-transferase (GST), polyHis, HA, Flag, or Mannose binding protein (MBP), expressed in any suitable host cell, e.g., bacteria, insect cells, yeast cells, or mammalian cells, and purified by affinity chromatography. In an exemplary assay, steady-state kinetic parameters are determined by monitoring the ACC- and ATP-dependent incorporation of radioactivity from acid-labile H[$^{14}$C]O$_3$ into acetyl-CoA to form acid-stable malonyl-CoA product. Reactions are conducted at 37° C., and can be carried out on a large scale, e.g., in 96-well microplates. Reactions are quenched and unincorporated label is removed. The amount of $^{14}$C present in the plates can be measured by scintillation counting, and reaction rates obtained by linear regression analysis of radioactivity incorporated vs. reaction time for each incubation. $K_M$ and $V_{max}$ values can be determined by non-linear regression analysis of initial velocities, according to the standard Henri-Michaelis-Menten equation. $k_{cat}$ can be obtained by dividing $V_{max}$ values by reaction concentrations of enzyme, derived by colorimetric protein determinations. Variation in these values upon titration of a particular compound indicates that the compound modulates ACC activity (See Cheng et al. 2007. Protein Exp and Purif. 51:11-21, which is incorporated herein in its entirety). Other assays for ACC activity are taught in U.S. Pat. No. 6,069,298; International Patent Application Publication WO 2003/072602; European Patent Application EP1607477; Oizumi et al. 1990. J Chromatogr 529: 55-63; Bijleveld et al. 1987. Biochim Biophys Acta 918:274-283; and Haas A. 1994. Methods 126: 87-97, each of which is incorporated by reference herein in its entirety.

Assays to measure enzymatic activity of ACC described in the art, e.g., as disclosed in U.S. Pat. No. 6,994,956 (which is incorporated by reference herein in its entirety), can be used to test the ability of Compounds to inhibit ACC enzymatic activity. Such assays may also be used in high throughput screening assays. The methods described in U.S. Pat. No. 6,994,956 allow for radiometric detection of ACC activity via a gain of signal assay using the [2-$^{14}$C]malonyl-CoA product of the reaction between NaHCO$_3$ and [1-$^{14}$C]acetyl-CoA catalyzed by ACC, as a substrate for FAS. The radiometric detection of ACC activity is mediated by partitioning the radioactive products of the ACC-FAS coupled assay ($^{14}$C-radiolabled oleic acid and palmitic acid) into the PPSF (Microscint™-E) following acidification of the reaction mixture. For example, a 96-well density reaction is partitioned in the following manner: 100 µL enzyme assay inhibitor test mix containing enzyme (ACC and FAS), substrates, test compounds, and buffer components is incubated at room temperature to generate the fatty acid products. The enzymatic reaction is stopped by the addition of 20 µL of 2N HCl, followed by addition of 150 µL Microscint™-E. Partitioning does not require a specific mixing step, but does require several hours for establishment and is stable for 24 hours. Neither the radioactive substrate [1-$^{14}$C]acetyl-CoA nor the product of the ACC reaction [2-$^{14}$C]malonyl-CoA partitions into the organic phase.

Enzyme activity is proportional to the radioactivity in the organic phase as determined by liquid scintillation counting. The amount of radioactivity detected in the PPSF (phase-partition scintillation fluid) is dependent upon the amount of FAS in the well and the amount of time the enzymatic reaction is allowed to proceed, that is, CPMs are dose-dependent with respect to reaction time and concentration of ACC. The effectiveness of acidification and the PPSF in partitioning long chain fatty acids into the PPSF may be assessed using a known amount of authentic radiolabeled palmitic acid. The theoretical signal to background of the assay may be established by comparing CPMs in the PPSF using equimolar amounts and equal amounts of radioactivity of radiolabeled substrate and product.

A sample reaction as described below may be carried out in the presence or absence of a Compound: ACC and FAS at varying concentrations are incubated for 75 minutes at room temperature with 4 mM ATP, 400 µM NADPH, and 16 µM acetyl-CoA (0.015 µCi; [acetyl-1-$^{14}$C]-CoA) in a buffer containing 50 mM HEPES (pH 7.5), 20 mM NaHCO$_3$, 10 mM citric acid, 5 mM DTT, 10 mM MgCl$_2$, 1 mM EDTA, and 0.03% BSA in a total volume of 100 µL. The reaction is terminated by the addition 10 µL of 10 N acetic acid, followed by 150 μL Microscint™-CAT. The mix is allowed to incubate overnight prior to data acquisition.

Other non-limiting example of assays to measure the enzymatic activity of ACC are presented below. Spectrophotometric assays can be used to measure the partial reaction of ATP-dependent biotin, where the rate of ATP hydrolysis by biotin carboxylase is measured spectrophotometrically at 340 nm by coupling the production of ADP to pyruvate kinase and lactate dehydrogenase (see Levert et al., Biochemistry 39:4122-3128, 2000). Also, spectrophotometric assays can be used to monitor the ACC-catalyzed decarboxylation of malonyl-CoA, where the acetyl-CoA produced in the ACC reaction is condensed with oxaloacetic acid produced by the action of malate dehydrogenase on malate and NAD to produce citrate in a citrate synthase catalyzed reaction, and NADH production is measured as increase in absorbance at 340 nm (see Winder et al., J. Appl. Physiol. 882219-2226, 2000). Radiolabeled assays can be used to measure the production of [3-$^{14}$C]malonyl-CoA from NaH$_{14}$CO$_3$ and acetyl-CoA (see Herbert et al., Biochem. J. 318:997-1006, 1996).

Lysonhosphatidic Acid Acyltransferase (Including Lysophosphatidic Acid Acetyltransferase) (LPAAT) Assays LPAAT polypeptides can be expressed in any of a number of different recombinant DNA expression systems, e.g., recombinant LPAAT can be expressed in and purified from *E. coli*, to enable large scale production of pure, biologically active hLPAAT-alpha, hLPAAT-beta, hLPAAT-gamma-1, hLPAAT-gamma-2, and hLPAAT-delta useful for screening compounds for the purposes of the invention.

Screening compounds for inhibition of LPAAT enzymes comprises, for example, contacting hLPAAT-alpha, hLPAAT-beta, hLPAAT-gamma1, hLPAAT-gamma2, and/or hLPAAT-delta in the presence of compound and substrate for LPAAT, namely LPA and fatty acyl-CoA. These hLPAAT proteins can either be purified prior to incubation or can be contained in extracts from a cell line or cell lines (for example, SD, ECV304, A549) transfected with cDNA encoding these polypeptides (West et al., DNA Cell Biol. 16:691, 1997). Alternatively, hLPAAT protein can be purified from transfected cells, and the protein, being a transmembrane protein, can then be reconstituted in a lipid bilayer to form liposomes for delivery into cells (Weiner, Immunomethods 4:201, 1994).

The effect of a compound or composition on hLPAAT-alpha, hLPAAT-beta, hLPAAT-gamma1, hLPAAT-gamma2, or hLPAAT-delta activity can be determined, for example, by measuring the generation of PA and CoA. PA can be measured by, for example, TLC methods described in Examples 3 and 7, found below. Alternatively, LPAAT activity can be assayed by detecting the formation of free CoA in reaction. CoA, which contains a free sulfhydryl-group, can be measured either by, for example, colorimetric or fluorescenic methods with sulfhydryl-specific reagents, such as, 5,5'-dithiobis-(2-nitrobenzoic acid) (DTNB) or ThioGlo (Covalent Associates, Woburn, Mass.). The observed effect on hLPAAT-alpha, hLPAAT-beta, hLPAAT-gamma1, hLPAAT-gamma2, or hLPAAT-delta may be either inhibitory or stimulatory.

Exemplary assays for the activity of Lysophosphatidic acid acetyltransferase are found in US Patent Publication 20040043465; Bonham et al. 2003. Expert Opin. Ther. Targets 7/5:643-661; and U.S. Pat. No. 6,136,964, each of which is incorporated by reference herein in its entirety.

HMG CoA Synthase

HMG-CoA synthase can be purified from liver. In an exemplary protocol, livers from male Charles River CD rats (225-350 g) are homogenized in 0.25M sucrose which is adjusted with phenylmethylsulfonylfluoride (PMSF) and N-p-tosyl-1-lysine chloromethyl ketone (TLCK) so that the final concentration of each is 50 and 25 μg/ml, respectively. The homogenate is first centrifuged at 700×g for 10 minutes, the supernatant decanted and re-centrifuged at 7,700×g for 20 minutes. This supernatant is filtered through a fine nylon screen to remove most of the fat layer and re-centrifuged at 100,000×g for 1 hour. This supernatant is removed and 1M potassium phosphate, dithiothreitol (DTT) and ethylene glycolbis(beta-aminoethyl ether)-N,N,N',N'-tetraacetic acid (EGTA) added to give a final concentration of 0.1M (pH 7.2), 0.5 mM and 0.1 mM, respectively. Solid ammonium sulfate is added to 50% saturation to the protein solution, it is centrifuged at 15,000×g and the supernatant discarded. This precipitated protein could be stored at −70° C. for at least one month with very little loss of activity. The ammonium sulfate precipitate is dissolved in a minimal amount of 0.06M potassium phosphate buffer (pH 7.2) containing 0.5 mM dithiothreitol and 0.1 mM EGTA (referred to as 0.06M phosphate buffer) and dialyzed overnight against 2 liters of the same buffer to remove the ammonium sulfate and to inactivate HMG-CoA lyase (Clinkenbeard, et al., J. Biol. Chem. 250, 3108-3116 (1975)).

The dialyzed extract is added to a column of DEAE-52 (Whatman) which has been equilibrated with 0.06M phosphate buffer (10 mg of protein to 1 ml bed volume of the resin). The DEAE-cellulose is eluted with 0.06M phosphate buffer until the optical density at 280 nm is essentially zero. This fraction contains the beta-ketoacetyl-CoA thiolase activity. The HMG-CoA synthase is eluted from the column with 0.1M KCl in 0.06M phosphate buffer (pH 7.2) containing 0.5 mM DTT and 0.1 mM EGTA, and was virtually free of all thiolase activity. The protein is precipitated by the addition of ammonium sulfate to give 50% saturation. This solution was stirred for 10 minutes at 4° C. and the precipitate collected by centrifugation at 15,000 rpm for 10 minutes. The supernatant is discarded and the precipitate dissolved in a minimum of 0.06M phosphate buffer, pH 7.2 (about 10 ml) and the enzyme stored at −80° C.

Intrinsic activity of HMG-CoA synthase is measured in the following in vitro assay. Enzyme protein (ca. 12.2 μg) is added to a solution containing 117 mM Tris-HCl (pH 8.0), 11.7 mM MgCl$_2$, 1.17 mM Ethylenediaminetetraacetic acid (EDTA), 0.58 mM dithiothreitol, in the presence or absence of the test compound (added as, e.g., a 2 μg/ml solution in dimethylsulfoxide). The incubation is in a volume of 0.085 ml at 30° C. in a shaking water bath. After 5 minutes, 15 μl of a solution containing acetoacetyl-CoA and 0.1 μCi of 1[$^{14}$C]-acetyl-CoA is added to give final concentrations of 0.1 and 0.4 mM, respectively. The incubation is continued for 2 more minutes and the reaction stopped by the addition of 50 μl of the assay mixture to 0.2 ml of 6N HCl in a glass scintillation vial. The vial is heated for 1 hour at 110° C. after which time 0.2 ml more of 6N HCl is again added to each vial and the heating continued for another hour. Following this, 1.0 ml of 0.9% saline is added to each vial and finally 10 ml of scintillation liquid. Radioactivity is determined in a Packard Tri-Carb liquid scintillation counter. Percent inhibition is calculated a standard formula. IC$_{50}$ values are determined by plotting the log of the concentration of the test compound verses the percentage inhibition and fitting a straight line to the resulting data by using the least squares method.

Exemplary assays for measuring the activity of HMG-CoA synthase are provided in U.S. Pat. No. 5,064,856, European Patent Application EP99107413, and Omura S. 1992. J Industrial Microbiol 10:135-156, each of which is incorporated by reference herein in its entirety.

ATP Citrate Lyase

Rat or human ATP citrate lyase can be purified and used in accordance with the methods of this invention. Male Wistar rats are fasted for 24 h, then fed on a high carbohydrate diet for 72 h prior to removal of the livers. ATP Citrate lyase is prepared according to the method of Wraight et al. (Anal. Biochem., 1985, 144, 604-609) with modifications for large scale purification according to Wells (Eur. J. Biochem., 1991, 199, 163-168). Purity of protein can be determined by SDS-PAGE. Human ATP citrate lyase is prepared as described in European Journal of Biochemistry, 1992, 204, 491-99, with modifications for large scale purification according to Wells as referred to above. Purity of protein obtained by this method is judged by SDS-PAGE.

ATP citrate lyase activity is assayed at 25° C. by reducing the oxaloacetate produced with malate dehydrogenase and NADH while monitoring at 340 nm using a Beckman DU50 spectrophotometer (according to the method of Linn et al (J. Biol. Chem., 1979, 254, 1691-1698). Briefly, ATP citrate lyase (human or rat) is added to a 1 ml cuvette containing 50 mM Tris/HCl, pH=8.0, 0.2 mM NADH, 10 mM $MgCl_2$, 10 mM KCl, 5 mM ATP, 200 µM coenzyme A, 10 mM dithiothreitol and malate dehydrogenase. An aqueous solution of inhibitor is added (for inhibitors that are insoluble in water, a stock solution is prepared in DMSO. However the final DMSO concentration in the cuvette is not allowed to exceed 1%.). Finally, tripotassium citrate is added to 100 µM final. This is $K_M$ for citrate (Wells et al (Eur. J. Biochem., 1992, 204, 249-255) and Houston et al (Biochim. Biophys. Acta, 1985, 844, 233-239)). Data analysis is performed using the curve fitting package Enzfitter (Elsevier Biosoft).

Assays, incorporated by reference herein by reference in their entirety, for the activity of ATP citrate lyase may be found in U.S. Pat. No. 5,447,954; International Patent Application Publication No. WO 2004/100885; and an assay in yeast found in Holdsworth et al. 1998. J Gen Microbiol 134: 2907-2915.

Fatty Acid Synthase

Exemplarily, subcutaneous adipose tissue is disrupted, cells are lysed, and the soluble lysate is used for enzyme assays. Assays are started by the addition of malonyl CoA and the rate of oxidation of NADPH is measured. Methods for isolating and testing the activity of fatty acid synthase are provided in Wiesner et al. 1988 European J Biochemistry 177:69-79 and in A K Joshi and S Smith. 1993. Biochem J. 296: 143-149.

The activity of fatty acid synthase can be measured by a modification of the spectrophotometric method (Lowry et al. 1951. "Protein measurement with the Folin phenol reagent," J Biol. Chem. 193(1):265-75). Detailed assays for fatty acid synthase activity may be found in U.S. Pat. No. 4,735,895; International Patent Application Publication No. WO 2003/051307; and US Patent Application Publication No. US20070099230 and US20020151463, each of which is incorporated by reference herein in its entirety 5.3.1 High Throuput Screening of Compounds and Target Enzymes In one embodiment, high throughput screening using, e.g., mass spectrometry can be used to screen a number of compounds and a number of potential target enzymes simultaneously. Mass spectrometry can be utilized for determination of metabolite levels and enzymatic activity.

The levels of specific metabolites (e.g. AMP, ATP) can be quantified by liquid chromatography-mass spectrometry (LC-MS/MS). A metabolite of interest will have a specific chromatographic retention time at which point the mass spectrometer performs a selected reaction monitoring scan event (SRM) that consists of three identifiers:
  1) The metabolite's mass (the parent ion);
  2) The energy required to fragment the parent ion in a collision with argon to yield a fragment with a specific mass; and
  3) The mass of the specific fragment ion.

Utilizing the above identifiers, the accumulation of a metabolite can be measured whose production depends on the activity of a metabolic enzyme of interest. By adding an excess of enzyme substrate to a cellular lysate, so as to make the activity of the enzyme rate limiting, the accumulation of enzymatic product over time is then measured by LC-MS/MS as outlined above, and serves as a function of the metabolic enzyme's activity. An example of such an assay is reported in Munger et al, 2006 PLoS Pathogens, 2: 1-11, incorporated herein by reference in its entirety, in which the activity of phosphofructokinase present in infected lysates was measured by adding an excess of the phosphofructokinase substrates ATP and fructose phosphate and measuring fructose bisphosphate accumulation by LC-MS/MS. This approach can be adopted to measure the activities of numerous host target enzymes.

5.3.2 Kinetic Flux Profiling (KFP) to Assess Potential Antiviral Compounds

In a further embodiment of the invention, cellular metabolic fluxes are profiled in the presence or absence of a virus using kinetic flux profiling (KFP) (See Section 6; Munger et al. 2006 PLoS Pathogens, 2: 1-11) in the presence or absence of a compound found to inhibit a target enzyme in one of the aforementioned assays. Such metabolic flux profiling provides additional (i) guidance about which components of a host's metabolism can be targeted for antiviral intervention; (ii) guidance about the metabolic pathways targeted by different viruses; and (iii) validation of compounds as potential antiviral agents based on their ability to offset the metabolic flux caused by a virus or trigger cell-lethal metabolic derangements specifically in virally infected cells. In one embodiment, the kinetic flux profiling methods of the invention can be used for screening to determine (i) the specific alterations in metabolism caused by different viruses and (ii) the ability of a compound to offset (or specifically augment) alterations in metabolic flux caused by different viruses.

Thus, in one embodiment of the invention, cells are infected with a virus and metabolic flux is assayed at different time points after virus infection, such time points known to one of skill in the art. For example, flux can be measured 24, 48, or 72 hours post-infection. If the metabolic flux is altered in the presence of the virus, then the virus alters cellular metabolism during infection. The type of metabolic flux alteration observed (See above and examples herein) will provide guidance as to the cellular pathways that the virus acts on. Assays well known to those of skill in the art and described herein below can then be employed to confirm the target of the virus. For example, if it appears that the virus modulates the activity of fatty acid synthase, cerulenin can be tested for its ability to interfere with the virus in the assays for antiviral activity described in Section 5.4 below. If it appears that the virus modulates ATP citrate lyase, radicicol and its derivatives can be tested for their antiviral effect. If these well-characterized compounds are effective antivirals, a specific virus metabolic target has been identified and other compounds that modulate these targets can similarly be assessed as potential antivirals. See Table 2 for examples of test compounds that can be used in the invention, compounds that may be used as antivirals, and compounds useful as test compounds for identifying metabolic targets of novel drugs or other viruses for antiviral intervention.

TABLE 2

Compounds and target enzymes related to host cell metabolism

| inhibitor (test compounds for validation of relevance of the enzyme target and/or potential antiviral compounds) | enzyme target |
|---|---|
| 4S-hydroxycitrate; compounds of structure (X) | ATP citrate lyase - renal in rats |
| Radicicol (monorden) and derivatives; compounds of structure (II) | ATP citrate lyase I in vitro rat liver |
| SB-204990 (compounds of structure (III)) + SB-201076 (compounds of structure (IV)) | ATP citrate lyase I in vitro rat liver enzyme |
| SB-204990; compounds of structure (III) | ATP citrate lyase I in vitro rat liver enzyme |
| 2,2-difluorocitrate; compounds of structure (X) | ATP citrate lyase |
| 2-chloro-1,3,8-trihydroxy-6-methyl-9-anthrone; compounds of structure (V) | ATP citrate lyase - Rat Liver |
| thiol-citrates; compounds of structure (X) | ATP citrate lyase - Rat Liver |
| Purpurone; compounds of structure (VII) | ATP citrate lyase |
| 3-oxobutylsulfoxyl-CoA; compounds of structure (XI) | HMG-CoA synthase |
| CP-610431, CP-640186; compounds of structure (VI) | Acetyl-CoA Carboxylase (ACC) |
| Soraphen-A; compounds of structure (VIII) | Acetyl-CoA Carboxylase (ACC) |
| Haloxyfop; compounds of structure (IX) | Acetyl-CoA Carboxylase (ACC) |
| Sethoxydim; compounds of structure (XII) | Acetyl-CoA Carboxylase (ACC) |
| Cerulenin; compounds of structure (XIII) and compounds of structure (XIV) | Fatty Acid Synthase - keto-acyl synthase domain |
| C75; compounds of structure (XV) | Fatty Acid Synthase - keto-acyl synthase domain |
| Orlistat; compounds of structure (I) | Fatty Acid Synthase; Fatty Acid Synthase - thioesterase domain |
| Triclosan; compounds of structure (XXI) | Fatty Acid Synthase |
| epigallocatechin-3-gallate; compounds of structure (XXII) | Fatty Acid Synthase |
| naturally occurring flavonoids (e.g., luteolin, quercetin, and kaempferol) | Fatty Acid Synthase |
| CT32228; compounds of structure (XVI) | Lysophosphatidic Acid Acyltransferase-beta |
| oxfenicine; compounds of structure (XIX) | Carnitine Palmitoyl transferase (CPTI) |
| Etomoxir; compounds of structure (XVII) | Carnitine Palmitoyl Transferase 1 (CPTI) |
| CBM-301106 | Malonyl-CoA decarboxylase (downstream effect on CPT I) |
| 3-Carboxypropyl-CoA | methylmalonyl-CoA mutase |
| Chloroquine; compounds of structure (XX) | Glutamate Dehydrogenase |
| Compound C (6-[4-(2-Piperidin-1-yl-ethoxy)-phenyl)]-3-pyridin-4-yl-pyrrazolo[1,5-a]-pyrimidine); compounds of structure (XVIII) | AMP-activated protein Kinase (AMPK) |
| TOFA (5-(tetradecyloxy)-2-furoic acid); compounds of structure (XXIII) | Acetyl-CoA carboxylase (ACC) |

In one embodiment of the invention, a virus infected cell is contacted with a compound and metabolic flux is measured. If the metabolic flux in the presence of the compound is different from the metabolic flux in the absence of the compound, in a manner wherein the metabolic effects of the virus have been inhibited or augmented, then a compound that modulates the virus' ability to alter the metabolic flux has been identified. The type of metabolic flux alteration observed will provide guidance as to the cellular pathway that the compound is acting on. Assays well known to those of skill in the art and described herein can then be employed to confirm the target of the antiviral compound.

In one embodiment, high throughput metabolome quantitation mass spectrometry can be used to screen for changes in metabolism caused by infection of a virus and whether or not a compound or library of compounds offsets these changes. See Munger et al. 2006. PLoS Pathogens, 2: 1-11.

5.3.3 Compounds

Using metabolome and fluxome-based analysis of virus infected cells, the inventors discovered that the host cell target enzymes listed in Table 1 (Section 5.1) are affected by virus infection. Based on these findings, compounds that are structurally related to known inhibitors of these enzymes are identified and screened for their specific modulation of the activity of these enzymes. See Table 2 (Section 5.3.2 above). Further, any compound of interest can be tested for its ability to modulate the activity of these enzymes. Alternatively, compounds can be tested for their ability to inhibit any other host cell enzyme related to metabolism. Once such compounds are identified as having metabolic enzyme—modulating activity, they can be further tested for their antiviral activity as described in Section 5.4. Alternatively, Compounds can be screened for antiviral activity and optionally characterized using the metabolic screening assays described herein.

In one embodiment, high throughput screening methods are used to provide a combinatorial chemical or peptide library (e.g., a publicly available library) containing a large number of potential therapeutic compounds (potential modulators or ligand compounds). Such "combinatorial chemical libraries" or "ligand libraries" are then screened in one or more assays, as described in Section 5.3 herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (See, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (See Ausubel, Berger and Sambrook, all supra), peptide nucleic acid libraries (See, e.g., U.S. Pat. No. 5,539,083), antibody libraries (See, e.g., Vaughn et al., Nature Biotechnology, 14(3):309-314 (1996) and PCT/US96/10287), carbohydrate libraries (See, e.g., Liang et al., Science, 274:1520-1522 (1996) and International Patent Application Publication NO. WO 1997/000271), small organic molecule libraries (See, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework). Examples of lead compounds which can be used as starting molecules for library generation include, e.g., in the case of AMPK, biguanides such as metformin; thiazolidinediones, e.g., rosiglitazone and pioglitazone; an AMP analog such as AICAR=5'-aminoimidazole-4-carboxyamide-ribosid; leptin and leptin-related molecules; adiponectin and Adiponectin-related molecules.

Devices for the preparation of combinatorial libraries are commercially available (See, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (See, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.). The test compounds can also be obtained from: biological libraries; peptoid libraries (libraries of molecules having the functionalities of peptides, but with a novel, non-peptide backbone which are resistant to enzymatic degradation but which nevertheless remain bioactive; See, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library). Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223, 409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991)

J. Mol. Biol. 222:301-310; Ladner supra.). Enzymes can be screened for identifying compounds which can be selected from a combinatorial chemical library or any other suitable source (Hogan, Jr., Nat. Biotechnology 15:328, 1997).

Any assay herein, e.g., an in vitro assay or an in vivo assay, can be performed individually, e.g., just with the test compound, or with appropriate controls. For example, a parallel assay without the test compound, or other parallel assays without other reaction components, e.g., without a target or without a substrate. Alternatively, it is possible to compare assay results to a reference, e.g., a reference value, e.g., obtained from the literature, a prior assay, and so forth. Appropriate correlations and art known statistical methods can be used to evaluate an assay result. See Section 5.3.1 above.

Once a compound is identified as having a desired effect, production quantities of the compound can be synthesized, e.g., producing at least 50 mg, 500 mg, 5 g, or 500 g of the compound. Although a compound that is able to penetrate a host cell is preferable in the practice of the invention, a compound may be combined with solubilizing agents or administered in combination with another compound or compounds to maintain its solubility, or help it enter a host cell, e.g., by mixture with lipids. The compound can be formulated, e.g., for administration to a subject, and may also be administered to the subject.

5.4 Characterization of Antiviral Activity of Compounds

5.4.1 Viruses

The present invention provides Compounds for use in the prevention, management and/or treatment of viral infection. The antiviral activity of Compounds against any virus can be tested using techniques described in Section 5.4.2 herein below. The virus may be enveloped or naked, have a DNA or RNA genome, or have a double-stranded or single-stranded genome. See, e.g., FIG. 1 modified from Flint et al., Principles of Virology: Molecular Biology, Pathogenesis and Control of Animal Viruses. 2nd edition, ASM Press, 2003, for a subset of virus families and their classification, as well as a subset of viruses against which Compounds can be assessed for antiviral activity. In specific embodiments, the virus infects human. In other embodiments, the virus infects non-human animals. In a specific embodiment, the virus infects pigs, fowl, other livestock, or pets.

In certain embodiments, the virus is an enveloped virus. Enveloped viruses include, but are not limited to viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Non-limiting examples of viruses that belong to these families are included in Table 3.

TABLE 3

Families of Enveloped Viruses

| Virus Family | Members |
|---|---|
| Hepadnavirus (Hepadnaviridae) | hepatitis B virus (HBV), woodchuck hepatitis virus, ground squirrel hepatitis virus, duck hepatitis B virus, heron hepatitis B virus |
| Herpesvirus (Herpesviridae) | herpes simplex virus (HSV) types 1 and 2, varicella-zoster virus, cytomegalovirus (CMV), human cytomegalovirus (HCMV), Epstein-Barr virus (EBV), human herpesvirus 6 (variants A and B), human herpesvirus 7, human herpesvirus 8, Kaposi's sarcoma - associated herpes virus (KSHV), B virus |
| Poxvirus (Poxviridae) | vaccinia virus, variola virus, smallpox virus, monkeypox virus, cowpox virus, camelpox virus, mousepox virus, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus |
| Flavivirus (Flaviviridae) | dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus |
| Togavirus (Togaviridae) | Venezuelan equine encephalitis virus, chikungunya virus, Ross River virus, Mayaro virus, Sindbis virus, rubella virus |
| Retrovirus (Retroviridae) | human immunodeficiency virus (HIV) types 1 and 2, human T cell leukemia virus (HTLV) types 1, 2, and 5, mouse mammary tumor virus (MMTV), Rous sarcoma virus (RSV), lentiviruses |
| Coronavirus (Coronaviridae) | severe acute respiratory syndrome (SARS) virus |
| Filovirus (Filoviridae) | Ebola virus, Marburg virus |
| Rhabdovirus (Rhabdoviridae) | rabies virus, vesicular stomatitis virus |
| Bunyavirus (Bunyaviridae) | Crimean-Congo hemorrhagic fever virus, Rift Valley fever virus, La Crosse virus, Hantaan virus |
| Orthomyxovirus (Orthomyxoviridae) | influenza virus (types A, B, and C) |
| Paramyxovirus (Paramyxoviridae) | parainfluenza virus, respiratory syncytial virus (types A and B), measles virus, mumps virus |
| Arenavirus (Arenaviridae) | lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, Tamiami virus |

In some embodiments, the virus is a non-enveloped virus, i.e., the virus does not have an envelope and is naked. Non-limiting examples of such viruses include viruses that are members of the parvovirus family, circovirus family, polyoma virus family, papillomavirus family, adenovirus family, iridovirus family, reovirus family, birnavirus family, calicivirus family, and picornavirus family. Examples of viruses that belong to these families include, but are not limited to, those set forth in Table 4.

TABLE 4

Families of Non-Enveloped (Naked) Viruses

| Virus Family | Members |
|---|---|
| Parvovirus (Parvoviridae) | canine parvovirus, parvovirus B19 |
| Circovirus (Circoviridae) | porcine circovirus type 1 and 2, BFDV (Beak and Feather Disease Virus), chicken anaemia virus |
| Polyomavirus (Polyomaviridae) | simian virus 40 (SV40), JC virus, BK virus, Budgerigar fledgling disease virus |
| Papillomavirus (Papillomaviridae) | human papillomavirus, bovine papillomavirus (BPV) type 1 |
| Adenovirus (Adenoviridae) | human adenovirus (HAdV-A, HAdV-B, HAdV-C, HAdV-D, HAdV-E, and HAdV-F), fowl adenovirus A, ovine adenovirus D, frog adenovirus |
| Reovirus (Reoviridae) | human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1 |
| Birnavirus (Birnaviridae) | bursal disease virus, pancreatic necrosis virus |
| Calicivirus (Caliciviridae) | swine vesicular exanthema virus, rabbit hemorrhagic disease virus, Norwalk virus, Sapporo virus |
| Picornavirus (Picornaviridae) | human polioviruses (1-3), human coxsackieviruses A1-22, 24 (CA1-22 and CA24, CA23 = echovirus 9), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardioviruses, aphthoviruses, echoviruses |

In certain embodiments, the virus is a DNA virus. In other embodiments, the virus is a RNA virus. In one embodiment, the virus is a DNA or a RNA virus with a single-stranded genome. In another embodiment, the virus is a DNA or a RNA virus with a double-stranded genome.

In some embodiments, the virus has a linear genome. In other embodiments, the virus has a circular genome. In some embodiments, the virus has a segmented genome. In other embodiments, the virus has a non-segmented genome.

In some embodiments, the virus is a positive-stranded RNA virus. In other embodiments, the virus is a negative-stranded RNA virus. In one embodiment, the virus is a segmented, negative-stranded RNA virus. In another embodiment, the virus is a non-segmented negative-stranded RNA virus.

In some embodiments, the virus is an icosahedral virus. In other embodiments, the virus is a helical virus. In yet other embodiments, the virus is a complex virus.

In certain embodiments, the virus is a herpes virus, e.g., HSV-1, HSV-2, and CMV. In other embodiments, the virus is not a herpes virus (e.g., HSV-1, HSV-2, and CMV). In a specific embodiment, the virus is HSV. In an alternative embodiment, the virus is not HSV. In another embodiment, the virus is HCMV. In a further alternative embodiment, the virus is not HCMV. In another embodiment, the virus is a liver trophic virus. In an alternative embodiment, the virus is not a liver trophic virus. In another embodiment, the virus is a hepatitis virus. In an alternate embodiment, the virus is not a hepatitis virus. In another embodiment, the virus is a hepatitis C virus. In a further alternative embodiment, the virus is not a hepatitis C virus. In another specific embodiment, the virus is an influenza virus. In an alternative embodiment, the virus is not an influenza virus. In some embodiments, the virus is HIV. In other embodiments, the virus is not HIV. In certain embodiments, the virus is a hepatitis B virus. In another alternative embodiment, the virus is not a hepatitis B virus. In a specific embodiment, the virus is EBV. In a specific alternative embodiment, the virus is not EBV. In some embodiments, the virus is Kaposi's sarcoma-associated herpes virus (KSHV). In some alternative embodiments, the virus is not KSHV. In certain embodiments the virus is a variola virus. In certain alternative embodiments, the virus is not variola virus. In one embodiment, the virus is a Dengue virus. In one alternative embodiment, the virus is not a Dengue virus. In other embodiments, the virus is a SARS virus. In other alternative embodiments, the virus is not a SARS virus. In a specific embodiment, the virus is an Ebola virus. In an alternative embodiment, the virus is not an Ebola virus. In some embodiments the virus is a Marburg virus. In an alternative embodiment, the virus is not a Margurg virus. In certain embodiments, the virus is a measles virus. In some alternative embodiments, the virus is not a measles virus. In particular embodiments, the virus is a vaccinia virus. In alternative embodiments, the virus is not a vaccinia virus. In some embodiments, the virus is varicella-zoster virus (VZV). In an alternative embodiment the virus is not VZV. In some embodiments, the virus is a picornavirus. In alternative embodiments, the virus is not a picornavirus. In certain embodiments the virus is not a rhinovirus. In certain embodiments, the virus is a poliovirus. In alternative embodiments, the virus is not a poliovirus. In some embodiments, the virus is an adenovirus. In alternative embodiments, the virus is not adenovirus. In particular embodiments, the virus is a coxsackievirus (e.g., coxsackievirus B3). In other embodiments, the virus is not a coxsackievirus (e.g., coxsackievirus B3). In some embodiments, the virus is a rhinovirus. In other embodiments, the virus is not a rhinovirus. In certain embodiments, the virus is a human papillomavirus (HPV). In other embodiments, the virus is not a human papillomavirus. In certain embodiments, the virus is a virus selected from the group consisting of the viruses listed in Tables 3 and 4. In other embodiments, the virus is not a virus selected from the group consisting of the viruses listed in Tables 3 and 4. In one embodiment, the virus is not one or more viruses selected from the group consisting of the viruses listed in Tables 3 and 4.

The antiviral activities of Compounds against any type, subtype or strain of virus can be assessed. For example, the antiviral activity of Compounds against naturally occurring strains, variants or mutants, mutagenized viruses, reassortants and/or genetically engineered viruses can be assessed.

The lethality of certain viruses, the safety issues concerning working with certain viruses and/or the difficulty in working with certain viruses may preclude (at least initially) the characterization of the antiviral activity of Compounds on such viruses. Under such circumstances, other animal viruses that are representative of such viruses may be utilized. For example, SIV may be used initially to characterize the antiviral activity of Compounds against HIV. Further, Pichinde virus may be used initially to characterize the antiviral activity of Compounds against Lassa fever virus.

In some embodiments, the virus achieves peak titer in cell culture or a subject in 4 hours or less, 6 hours or less, 8 hours or less, 12 hours or less, 16 hours or less, or 24 hours or less. In other embodiments, the virus achieves peak titers in cell culture or a subject in 48 hours or less, 72 hours or less, or 1 week or less. In other embodiments, the virus achieves peak titers after about more than 1 week. In accordance with these embodiments, the viral titer may be measured in the infected tissue or serum.

In some embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more. In certain embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more within 4 hours, 6 hours, 8 hours, 12 hours, 16 hours, or 24 hours or less. In other embodiments, the virus achieves in cell culture a viral titer of $10^4$ pfu/ml or more, $5\times10^4$ pfu/ml or more, $10^5$ pfu/ml or more, $5\times10^5$ pfu/ml or more, $10^6$ pfu/ml or more, $5\times10^6$ pfu/ml or more, $10^7$ pfu/ml or more, $5\times10^7$ pfu/ml or more, $10^8$ pfu/ml or more, $5\times10^8$ pfu/ml or more, $10^9$ pfu/ml or more, $5\times10^9$ pfu/ml or more, or $10^{10}$ pfu/ml or more within 48 hours, 72 hours, or 1 week.

In some embodiments, the virus achieves a viral yield of 1 pfu/ml or more, 10 pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject. In certain embodiments, the virus achieves a viral yield of 1 pfu/ml or more, 10 pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject within 4 hours, 6 hours, 8 hours, 12 hours, 16 hours, 24 hours, or 48 hours. In certain embodiments, the virus achieves a viral yield of 1 pfu/ml or more, 10 pfu/ml or more, $10^1$ pfu/ml or more, $5\times10^1$ pfu/ml or more, $10^2$ pfu/ml or more, $5\times10^2$ pfu/ml or more, $10^3$ pfu/ml or more, $2.5\times10^3$ pfu/ml or more, $5\times10^3$ pfu/ml or more, $10^3$ pfu/ml or more, $2.5\times10^3$ pfu/ml or more, $5\times10^3$ pfu/ml or more, $10^4$ pfu/ml or more, $2.5\times10^4$ pfu/ml or more, $5\times10^4$ pfu/ml or more, or $10^5$ pfu/ml or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 pfu or more, 10 pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject. In certain embodiments, the virus achieves a viral yield of 1 pfu or more, 10 pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject within 4 hours, 6 hours, 8 hours, 12 hours, 16 hours, 24 hours, or 48 hours. In certain embodiments, the virus achieves a viral yield of 1 pfu or more, 10 pfu or more, $10^1$ pfu or more, $5\times10^1$ pfu or more, $10^2$ pfu or more, $5\times10^2$ pfu or more, $10^3$ pfu or more, $2.5\times10^3$ pfu or more, $5\times10^3$ pfu or more, $10^4$ pfu or more, $2.5\times10^4$ pfu or more, $5\times10^4$ pfu or more, or $10^5$ pfu or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed.

In some embodiments, the virus achieves a viral yield of 1 infectious unit or more, 10 infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject. In certain embodiments, the virus achieves a viral yield of 1 infectious unit or more, 10 infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject within 4 hours, 6 hours, 8 hours, 12 hours, 16 hours, 24 hours, or 48 hours. In certain embodiments, the virus achieves a viral yield of 1 infectious unit or more, 10 infectious units or more, $10^1$ infectious units or more, $5\times10^1$ infectious units or more, $10^2$ infectious units or more, $5\times10^2$ infectious units or more, $10^3$ infectious units or more, $2.5\times10^3$ infectious units or more, $5\times10^3$ infectious units or more, $10^4$ infectious units or more, $2.5\times10^4$ infectious units or more, $5\times10^4$ infectious units or more, or $10^5$ infectious units or more in a subject within 48 hours, 72 hours, or 1 week. In accordance with these embodiments, the viral yield may be measured in the infected tissue or serum. In a specific embodiment, the subject is immunocompetent. In another embodiment, the subject is immunocompromised or immunosuppressed. In a specific embodiment, the virus achieves a yield of less than $10^4$ infectious units. In other embodiments the virus achieves a yield of $10^5$ or more infectious units.

In some embodiments, the virus achieves a viral titer of 1 infectious unit per ml or more, 10 infectious units per ml or more, $5\times10^1$ infectious units per ml or more, $10^2$ infectious units per ml or more, $5\times10^2$ infectious units per ml or more, $10^3$ infectious units per ml or more, $2.5\times10^3$ infectious units per ml or more, $5\times10^3$ infectious units per ml or more, $10^4$ infectious units per ml or more, $2.5\times10^4$ infectious units per ml or more, $5\times10^4$ infectious units per ml or more, or $10^5$ infectious units per ml or more in a subject. In certain embodiments, the virus achieves a viral titer of 10 infectious units per ml or more, $5 \times 10^1$ infectious units per ml or more, $10^2$ infectious units per ml or more, $5 \times 10^2$ infectious units per ml or more, $10^3$ infectious units per ml or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 4 hours, 6 hours, 8 hours, 12 hours, 16 hours, 24 hours, or 48 hours. In certain embodiments, the virus achieves a viral titer of 1 infectious unit per mL or more, 10 infectious units per ml or more, $5 \times 10^1$ infectious units per ml or more, $10^2$ infectious units per ml or more, $5 \times 10^2$ infectious units per ml or more, $10^3$ infectious units per mL or more, $2.5 \times 10^3$ infectious units per ml or more, $5 \times 10^3$ infectious units per ml or more, $10^4$ infectious units per ml or more, $2.5 \times 10^4$ infectious units per ml or more, $5 \times 10^4$ infectious units per ml or more, or $10^5$ infectious units per ml or more in a subject within 48 hours, 72 hours, or 1 week. In accordance with these embodiments, the viral titer may be measured in the infected tissue or serum. In a specific embodiment, the subject is immunocompetent. In another embodiment, the subject is immunocompromised or immunosuppressed. In a specific embodiment, the virus achieves a titer of less than $10^4$ infectious units per ml. In some embodiments, the virus achieves $10^5$ or more infectious units per ml.

In some embodiments, the virus infects a cell and produces, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell. In certain embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 4 hours, 6 hours, 8 hours, 12 hours, 16 hours, or 24 hours. In other embodiments, the virus infects a cell and produces 10 or more, $10^1$ or more, $2.5 \times 10^1$ or more, $5 \times 10^1$ or more, $7.5 \times 10^1$ or more, $10^2$ or more, $2.5 \times 10^2$ or more, $5 \times 10^2$ or more, $7.5 \times 10^2$ or more, $10^3$ or more, $2.5 \times 10^3$ or more, $5 \times 10^3$ or more, $7.5 \times 10^3$ or more, $10^4$ or more, $2.5 \times 10^4$ or more, $5 \times 10^4$ or more, $7.5 \times 10^4$ or more, or $10^5$ or more viral particles per cell within 48 hours, 72 hours, or 1 week.

In other embodiments, the virus is latent for a period of about at least 1 day, 2 days, 3 days, 4 days, 5 days, 6 days, 7 days, 8 days, 9 days, 10 days, 11 days, 12 days, 13 days, 14 days, or 15 days. In another embodiment, the virus is latent for a period of about at least 1 week, or 2 weeks, 3 weeks, 4 weeks, 5 weeks, 6 weeks, 7 weeks, 8 weeks, 9 weeks, or 10 weeks. In a further embodiment, the virus is latent for a period of about at least 1 month, 2 months, 3 months, 4 months, 5 months, 6 months, 7 months, 8 months, 9 months, 10 months, or 11 months. In yet another embodiment, the virus is latent for a period of about at least 1 year, 2 years, 3 years, 4 years, 5 years, 6 years, 7 years, 8 years, 9 years, 10 years, 11 years, 12 years, 13 years, 14 years, or 15 years. In some embodiments, the virus is latent for a period of greater than 15 years.

5.4.2 In Vitro Assays to Detect Antiviral Activity

The antiviral activity of Compounds may be assessed in various in vitro assays described herein or others known to one of skill in the art. Non-limiting examples of the viruses that can be tested for Compounds with antiviral activities against such viruses are provided in Section 5.4.1, supra. In specific embodiments, Compounds exhibit an activity profile that is consistent with their ability to inhibit viral replication while maintaining low toxicity with respect to eukaryotic cells, preferably mammalian cells. For example, the effect of a Compound on the replication of a virus may be determined by infecting cells with different dilutions of a virus in the presence or absence of various dilutions of a Compound, and assessing the effect of the Compound on, e.g., viral replication, viral genome replication, and/or the synthesis of viral proteins. Alternatively, the effect of a Compound on the replication of a virus may be determined by contacting cells with various dilutions of a Compound or a placebo, infecting the cells with different dilutions of a virus, and assessing the effect of the Compound on, e.g., viral replication, viral genome replication, and/or the synthesis of viral proteins. Altered viral replication can be assessed by, e.g., plaque formation. The production of viral proteins can be assessed by, e.g., ELISA, Western blot, or flow cytometry analysis. The production of viral nucleic acids can be assessed by, e.g., RT-PCR, PCR, Northern blot analysis, or Southern blot.

In certain embodiments, Compounds reduce the replication of a virus by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, Compounds reduce the replication of a virus by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, Compounds reduce the replication of a virus by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, Compounds reduce the replication of a virus by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such Compounds may be further assessed for their safety and efficacy in assays such as those described in Section 5.4, infra.

In certain embodiments, Compounds reduce the replication of a viral genome by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, Compounds reduce the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, Compounds reduce the replication of a viral genome by about at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, Compounds reduce the replication of a viral genome by about 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such Compounds may be further assessed for their safety and efficacy in assays such as those described in Section 5.4, infra.

In certain embodiments, Compounds reduce the synthesis of viral proteins by approximately 10%, preferably 15%, 25%, 30%, 45%, 50%, 60%, 75%, 95% or more relative to a negative control (e.g., PBS, DMSO) in an assay described herein or others known to one of skill in the art. In some embodiments, Compounds reduce the synthesis of viral proteins by approximately at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to a negative control (e.g., PBS, DMSO) in an assay described herein or others known to one of skill in the art. In other embodiments, Compounds reduce the synthesis of viral proteins by approximately at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to a negative control (e.g., PBS, DMSO) in an assay described herein or others known to one of skill in the art. In other embodiments, Compounds reduce the synthesis of viral proteins by approximately 1 log, 1.5 logs, 2 logs, 2.5 logs, 3 logs, 3.5 logs, 4 logs, 4.5 logs, 5 logs or more relative to a negative control (e.g., PBS, DMSO) in an assay described herein or others known to one of skill in the art. In accordance with these embodiments, such Compounds may be further assessed for their safety and efficacy in assays such as those described in Section 5.5, infra.

In some embodiments, Compounds result in about a 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more inhibition/reduction of viral yield per round of viral replication. In certain embodiments, Compounds result in about a 2 fold or more reduction inhibition/reduction of viral yield per round of viral replication. In specific embodiments, Compounds result in about a 10 fold or more inhibition/reduction of viral yield per round of viral replication.

The in vitro antiviral assays can be conducted using any eukaryotic cell, including primary cells and established cell lines. The cell or cell lines selected should be susceptible to infection by a virus of interest. Non-limiting examples of mammalian cell lines that can be used in standard in vitro antiviral assays (e.g., viral cytopathic effect assays, neutral red update assays, viral yield assay, plaque reduction assays) for the respective viruses are set out in Table 5.

TABLE 5

Examples of Mammalian Cell Lines in Antiviral Assays

| Virus | cell line |
|---|---|
| herpes simplex virus (HSV) | primary fibroblasts (MRC-5 cells) |
|  | Vero cells |
| human cytomegalovirus (HCMV) | primary fibroblasts (MRC-5 cells) |
| Influenza | Madin Darby canine kidney (MDCK) |
|  | primary chick embryo |
|  | chick kidney |
|  | calf kidney |
|  | African green monkey kidney (Vero) cells |
|  | mink lung |
|  | human respiratory epithelia cells |
| hepatitis C virus | Huh7 (or Huh7.7) |
|  | primary human hepatocytes (PHH) |
|  | immortalized human hepatocytes (IHH) |
| HIV-1 | MT-2 cells (T cells) |
| Dengue virus | Vero cells |
| Measles virus | African green monkey kidney (CV-1) cells |
| SARS virus | Vero 76 cells |
| Respiratory syncytial virus | African green monkey kidney (MA-104) cells |
| Venezuelan equine encephalitis virus | Vero cells |
| West Nile virus | Vero cells |
| yellow fever virus | Vero cells |
| HHV-6 | Cord Blood Lymphocytes (CBL) |
|  | Human T cell lymphoblastoid cell lines (HSB-2 and SupT-1) |
| HHV-8 | B-cell lymphoma cell line (BCBL-1) |
| EBV | umbilical cord blood lymphocytes |

Sections 5.4.2.1 to 5.4.2.7 below provide non-limiting examples of antiviral assays that can be used to characterize the antiviral activity of Compounds against the respective virus. One of skill in the art will know how to adapt the methods described in Sections 5.4.2.1 to 5.4.2.7 to other viruses by, e.g., changing the cell system and viral pathogen, such as described in Table 5.

5.4.2.1 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei). For adenovirus infection, crystalline arrays of adenovirus capsids accumulate in the nucleus to form an inclusion body.

The CPE assay can provide a measure of the antiviral effect of a Compound. In a non-limiting example of such an assay, Compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). CPE is read microscopically after a known positive control drug is evaluated in parallel with Compounds in each test. Non-limiting examples of positives controls are ribavirin for dengue, influenza, measles, respiratory syncytial, parainfluenza, Pichinde, Punta Toro and Venezuelan equine encephalitis viruses; cidofovir for adenovirus; pirodovir for rhinovirus; 6-azauridine for West Nile and yellow fever viruses; and alferon (interferon α-n3) for SARS virus. The data are expressed as 50% effective concentrations or approximated virus-inhibitory concentration, 50% endpoint (EC50) and cell-inhibitory concentration, 50% endpoint (IC50). General selectivity index ("SI") is calculated as the IC50 divided by the EC50. These values can be calculated using any method known in the art, e.g., the computer software program MacSynergy II by M. N. Prichard, K. R. Asaltine, and C. Shipman, Jr., University of Michigan, Ann Arbor, Mich.

In one embodiment, a Compound has an SI of greater than 3, or 4, or 5, or 6, or 7, or 8, or 9, or 10, or 11, or 12, or 13, or 14, or 15, or 20, or 21, or 22, or 23, or 24, or 25, or 30, or 35, or 40, or 45, or 50, or 60, or 70, or 80, or 90, or 100, or 200, or 300, or 400, or 500, 1,000, or 10,000. In some embodiments, a Compound has an SI of greater than 10. In a specific embodiment, Compounds with an SI of greater than 10 are further assessed in other in vitro and in vivo assays described herein or others known in the art to characterize safety and efficacy.

5.4.2.2 Neutral Red (NR) Dye Uptake Assay

The NR Dye Uptake assay can be used to validate the CPE inhibition assay (See Section 5.4.2.1). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An EC50 is determined for samples with infected cells and contacted with Compounds, and an IC50 is determined for samples with uninfected cells contacted with Compounds.

5.4.2.3 Virus Yield Assay

Lysed cells and supernatants from infected cultures such as those in the CPE inhibition assay (See section 5.3.2.1) can be used to assay for virus yield (production of viral particles after the primary infection). In a non-limiting example, these supernatants are serial diluted and added onto monolayers of susceptible cells (e.g., Vero cells). Development of CPE in these cells is an indication of the presence of infectious viruses in the supernatant. The 90% effective concentration (EC90), the test compound concentration that inhibits virus yield by 1 $\log_{10}$, is determined from these data using known calculation methods in the art. In one embodiment, the EC90 of Compound is at least 1.5 fold, 2 fold, 3 fold, 4 fold, 5 fold, 6 fold, 7 fold, 8 fold, 9 fold, 10 fold, 20 fold, 30 fold, 40 fold, or 50 fold less than the EC90 of the negative control sample.

5.4.2.4 Plaque Reduction Assay

In a non-limiting example of such an assay, the virus is diluted into various concentrations and added to each well containing a monolayer of the target mammalian cells in triplicate. The plates are then incubated for a period of time to achieve effective infection of the control sample (e.g., 1 hour with shaking every fifteen minutes). After the incubation period, an equal amount of 1% agarose is added to an equal volume of each Compound dilution prepared in 2× concentration. In certain embodiments, final Compound concentrations between 0.03 μg/ml to 100 μg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

5.4.2.5 Virus Titer Assay

In this non-limiting example, a monolayer of the target mammalian cell line is infected with different amounts (e.g., multiplicity of 3 plaque forming units (pfu) or 5 pfu) of virus (e.g., HCMV or HSV) and subsequently cultured in the presence or absence of various dilutions of Compounds (e.g., 0.1 μg/ml, 1 μg/ml, 5 μg/ml, or 10 μg/ml). Infected cultures are harvested 48 hours or 72 hours post infection and titered by standard plaque assays known in the art on the appropriate target cell line (e.g., Vero cells, MRC5 cells). In certain embodiments, culturing the infected cells in the presence of Compounds reduces the yield of infectious virus by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to culturing the infected cells in the absence of Compounds. In a specific embodiment, culturing the infected cells in the presence of Compounds reduces the PFU/ml by at least 10 fold relative to culturing the infected cells in the absence of Compounds.

In certain embodiments, culturing the infected cells in the presence of Compounds reduces the yield of infectious virus by at least 0.5 log 10, 1 log 10, 1.5 log 10, 2 log 10, 2.5 log 10, 3 log 10, 3.5 log 10, 4 log 10, 4.5 log 10, 5 log 10, 5.5 log 10, 6 log 10, 6.5 log 10, 7 log 10, 7.5 log 10, 8 log 10, 8.5 log 10, or 9 log 10 relative to culturing the infected cells in the absence of Compounds. In a specific embodiment, culturing the infected cells in the presence of Compounds reduces the yield of infectious virus by at least 1 log 10 or 2 log 10 relative to culturing the infected cells in the absence of Compounds. In another specific embodiment, culturing the infected cells in the presence of Compounds reduces the yield of infectious virus by at least 2 log 10 relative to culturing the infected cells in the absence of Compounds.

5.4.2.6 Flow Cytometry Assay

Flow cytometry can be utilized to detect expression of virus antigens in infected target cells cultured in the presence or absence of Compounds (See, e.g., McSharry et al., Clinical Microbiology Rev., 1994, 7:576-604). Non-limiting examples of viral antigens that can be detected on cell surfaces by flow cytometry include, but are not limited to gB, gC, gC, and gE of HSV; E protein of Japanese encephalitis; virus gp52 of mouse mammary tumor virus; gpI of varicella-zoster virus; gB of HCMV; gp160/120 of HIV; HA of influenza; gp110/60 of HHV-6; and H and F of measles virus. In other embodiments, intracellular viral antigens or viral nucleic acid can be detected by flow cytometry with techniques known in the art.

5.4.2.7 Genetically Engineered Cell Lines for Antiviral Assays

Various cell lines for use in antiviral assays can be genetically engineered to render them more suitable hosts for viral infection or viral replication and more convenient substrates for rapidly detecting virus-infected cells (See, e.g., Olivo, P. D., Clin. Microbiol. Rev., 1996, 9:321-334). In some aspects, these cell lines are available for testing the antiviral activity of Compound on blocking any step of viral replication, such as, transcription, translation, pregenome encapsidation, reverse transcription, particle assembly and release. Nonlimiting examples of genetically engineered cells lines for use in antiviral assays with the respective virus are discussed below.

HepG2-2.2.15 is a stable cell line containing the hepatitis B virus (HBV) ayw strain genome that is useful in identifying and characterizing Compounds blocking any step of viral replication, such as, transcription, translation, pregenome encapsidation, reverse transcription, particle assembly and release. In one aspect, Compounds can be added to HepG2-2.2.15 culture to test whether Compound will reduce the production of secreted HBV from cells utilizing real time quantitative PCR (TaqMan) assay to measure HBV DNA copies. Specifically, confluent cultures of HepG2-2.2.15 cells cultured on 96-well flat-bottomed tissue culture plates and are treated with various concentration of daily doses of Compounds. HBV virion DNA in the culture medium can be assessed 24 hours after the last treatment by quantitative blot hybridization or real time quantitative PCR (TaqMan) assay. Uptake of neutral red dye (absorbance of internalized dye at 510 nM [A510]) can be used to determine the relative level of toxicity 24 hours following the last treatment. Values are presented as a percentage of the average A510 values for separate cultures of untreated cells maintained on the same plate. Intracellular HBV DNA replication intermediates can be assessed by quantitative Southern blot hybridization. Intracellular HBV particles can be isolated from the treated HepG2-2.2.15 cells and the pregenomic RNA examined by Southern blot analysis. ELISAs can be used to quantify the amounts of the HBV envelope protein, surface antigen (HBsAg), and secreted e-antigen (HBeAg) released from cultures. Lamivudine (3TC) can be used as a positive assay control. (See Korba & Gerin, Antivir. Res. 19:55-70, 1992).

In one aspect, the cell line Huh7 ET (luc-ubi-neo/ET), which contains a new HCV RNA replicon with a stable luciferase (LUC) reporter, can be used to assay Compounds antiviral activity against hepatitis C viral replication (See Krieger, N., V. Lohmann, and R. Bartenschlager J. Virol., 2001, 75:4614-4624). The activity of the LUC reporter is directly proportional to HCV RNA levels and positive control antiviral compounds behave comparably using either LUC or RNA endpoints. Subconfluent cultures of Huh7 ET cells are plated onto 96-well plates, Compounds are added to the appropriate wells the next day, and the samples as well as the positive (e.g., human interferon-alpha 2b) and negative control samples are processed 72 hr later when the cells are still subconfluent. The HCV RNA levels can also be assessed using quantitative PCR (TaqMan). In some embodiments, Compounds reduce the LUC signal (or HCV RNA levels) by 20%, 35%, 30%, 35%, 40%, 45%, 50%, 55%, 60%, 65%, 70%, 75%, 80%, 90%, or 95% or more relative to the untreated sample controls. In a preferred embodiment, Compounds reduce the LUC signal (or HCV RNA levels) by 50% or more relative to the untreated cell controls. Other relevant cell culture models to study HCV have been described, e.g., See Durantel et al., J. Hepatology, 2007, 46:1-5.

The antiviral effect of Compound can be assayed against EBV by measuring the level of viral capsid antigen (VCA) production in Daudi cells using an ELISA assay. Various concentrations of Compounds are tested (e.g., 50 mg/ml to 0.03 mg/ml), and the results obtained from untreated and Compound treated cells are used to calculate an EC50 value. Selected compounds that have good activity against EBV VCA production without toxicity will be tested for their ability to inhibit EBV DNA synthesis.

For assays with HSV, the BHKICP6LacZ cell line, which was stably transformed with the *E. coli* lacZ gene under the transcriptional control of the HSV-1 UL39 promoter, can be used (See Stabell et al., 1992, Methods 38:195-204). Infected cells are detected using β-galactosidase assays known in the art, e.g., colorimetric assay.

Standard antiviral assays for influenza virus has been described, See, e.g., Sidwell et al., Antiviral Research, 2000, 48:1-16. These assays can also be adapted for use with other viruses.

5.5 Characterization of Safety and Efficacy of Compounds

The safety and efficacy of Compounds can be assessed using technologies known to one of skill in the art. Sections 5.5.1 and 5.5.2 below provide non-limiting examples of cytotoxicity assays and animal model assays, respectively, to characterize the safety and efficacy of Compounds. In certain embodiments, the cytotoxicity assays described in Section 5.5.1 are conducted following the in vitro antiviral assays described in Section 5.4, supra. In other embodiments, the cytotoxicity assays described in Section 5.5.1 are conducted before or concurrently with the in vitro antiviral assays described in Section 5.4, supra.

In some embodiments, Compounds differentially affect the viability of uninfected cells and cells infected with virus. The differential effect of a Compound on the viability of virally infected and uninfected cells may be assessed using techniques such as those described in Section 5.5.1, infra, or other techniques known to one of skill in the art. In certain embodiments, Compounds are more toxic to cells infected with a virus than uninfected cells. In specific embodiments, Compounds preferentially affect the viability of cells infected with a virus. Without being bound by any particular concept, the differential effect of a Compound on the viability of uninfected and virally infected cells may be the result of the Compound targeting a particular enzyme or protein that is differentially expressed or regulated or that has differential activities in uninfected and virally infected cells. For example, viral infection and/or viral replication in an infected host cells may alter the expression, regulation, and/or activities of enzymes and/or proteins. Accordingly, in some embodiments, other Compounds that target the same enzyme, protein or metabolic pathway are examined for antiviral activity. In other embodiments, congeners of Compounds that differentially affect the viability of cells infected with virus are designed and examined for antiviral activity. Non-limiting examples of antiviral assays that can be used to assess the antiviral activity of Compound are provided in Section 5.4, supra.

5.5.1 Cytotoxicity Studies

In a preferred embodiment, the cells are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. Other non-limiting examples of cell lines that can be used to test the cytotoxicity of Compounds are provided in Table 5.

Many assays well-known in the art can be used to assess viability of cells (infected or uninfected) or cell lines following exposure to a Compound and, thus, determine the cytotoxicity of the Compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic-40%), Ps (partially toxic—slight—20%), or 0 (no toxicity—0%), conforming to the degree of cytotoxicity seen. A 50% cell inhibitory (cytotoxic) concentration (IC50) is determined by regression analysis of these data.

Compounds can be tested for in vivo toxicity in animal models. For example, animal models, described herein and/or others known in the art, used to test the antiviral activities of Compounds can also be used to determine the in vivo toxicity of these Compounds. For example, animals are administered a range of concentrations of Compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a Compound in accordance with the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. A Compound identified in accordance with the invention that exhibits large therapeutic indices is preferred. While a Compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a Compound identified in accordance with the invention for use in humans. The dosage of such agents lies preferably within a range of circulating concentrations that include the ED50 with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 5.7.4, infra.

5.5.2 Animal Models

Compounds and compositions are preferably assayed in vivo for the desired therapeutic or prophylactic activity prior to use in humans. For example, in vivo assays can be used to determine whether it is preferable to administer a Compound and/or another therapeutic agent. For example, to assess the use of a Compound to prevent a viral infection, the Compound can be administered before the animal is infected with the virus. In another embodiment, a Compound can be administered to the animal at the same time that the animal is infected with the virus. To assess the use of a Compound to treat or manage a viral infection, in one embodiment, the Compound is administered after a viral infection in the animal. In another embodiment, a Compound is administered to the animal at the same time that the animal is infected with the virus to treat and/or manage the viral infection. In a specific embodiment, the Compound is administered to the animal more than one time.

Compounds can be tested for antiviral activity against virus in animal models systems including, but are not limited to, rats, mice, chicken, cows, monkeys, pigs, goats, sheep, dogs, rabbits, guinea pigs, etc. In a specific embodiment of the invention, Compounds are tested in a mouse model system. Such model systems are widely used and well-known to the skilled artisan.

Animals are infected with virus and concurrently or subsequently treated with a Compound or placebo. Samples obtained from these animals (e.g., serum, urine, sputum, semen, saliva, plasma, or tissue sample) can be tested for viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below (Sections 5.5.2.1-5.5.2.5) can be adapted for other viral systems.

The effect of a Compound on the virulence of a virus can also be determined using in vivo assays in which the titer of the virus in an infected subject administered a Compound, the length of survival of an infected subject administered a Compound, the immune response in an infected subject administered a Compound, the number, duration and/or severity of the symptoms in an infected subject administered a Compound, and/or the time period before onset of one or more symptoms in an infected subject administered a Compound is assessed. Techniques known to one of skill in the art can be used to measure such effects.

5.5.2.1 Herpes Simplex Virus (HSV)

Mouse models of herpes simplex virus type 1 or type 2 (HSV-1 or HSV-2) can be employed to assess the antiviral activity of Compounds in vivo. BALB/c mice are commonly used, but other suitable mouse strains that are susceptible can also be used. Mice are inoculated by various routes with an appropriate multiplicity of infection of HSV (e.g., $10^5$ pfu of HSV-1 strain E-377 or $4 \times 10^4$ pfu of HSV-2 strain MS) followed by administration of Compounds and placebo. For i.p. inoculation, HSV-1 replicates in the gut, liver, and spleen and spreads to the CNS. For i.n. inoculation, HSV-1 replicates in the nasaopharynx and spreads to the CNS. Any appropriate route of administration (e.g., oral, topical, systemic, nasal), frequency and dose of administration can be tested to determine the optimal dosages and treatment regimens using Compounds, optionally in combination with other therapies.

In a mouse model of HSV-2 genital disease, intravaginal inoculation of female Swiss Webster mice with HSV-1 or HSV-2 is carried out, and vaginal swabs are obtained to evaluate the effect of therapy on viral replication (See, e.g., Crute et al., Nature Medicine, 2002, 8:386-391). For example, viral titers by plaque assays are determined from the vaginal swabs. A mouse model of HSV-1 using SKI-1-1 mice, a strain of immunocompetent hairless mice, to study cutaneous lesions is also described in the art (See, e.g., Crute et al., Nature Medicine, 2002, 8:386-391 and Bolger et al., Antiviral Res., 1997, 35:157-165). Guinea pig models of HSV have also been described, See, e.g., Chen et al., Virol. J, 2004 Nov. 23, 1:11. Statistical analysis is carried out to calculate significance (e.g., a P value of 0.05 or less).

5.5.2.2 HCMV

Since HCMV does not generally infect laboratory animals, mouse models of infection with murine CMV (MCMV) can be used to assay antiviral activity Compounds in vivo. For example, a MCMV mouse model with BALB/c mice can be used to assay the antiviral activities of Compounds in vivo when administered to infected mice (See, e.g., Kern et al., Antimicrob. Agents Chemother., 2004, 48:4745-4753). Tissue homogenates isolated from infected mice treated or untreated with Compounds are tested using standard plaque assays with mouse embryonic fibroblasts (MEFs). Statistical analysis is then carried out to calculate significance (e.g., a P value of 0.05 or less).

Alternatively, human tissue (i.e., retinal tissue or fetal thymus and liver tissue) is implanted into SCID mice, and the mice are subsequently infected with HCMV, preferably at the site of the tissue graft (See, e.g., Kern et al., Antimicrob. Agents Chemother., 2004, 48:4745-4753). The pfu of HCMV used for inoculation can vary depending on the experiment and virus strain. Any appropriate routes of administration (e.g., oral, topical, systemic, nasal), frequency and dose of administration can be tested to determine the optimal dosages and treatment regimens using Compounds, optionally in combination with other therapies. Implant tissue homogenates isolated from infected mice treated or untreated with Compounds at various time points are tested using standard plaque assays with human foreskin fibroblasts (HFFs). Statistical analysis is then carried out to calculate significance (i.e., a P value of 0.05 or less).

Guinea pig models of CMV to study antiviral agents have also been described, See, e.g., Bourne et al., Antiviral Res., 2000, 47:103-109; Bravo et al., Antiviral Res., 2003, 60:41-49; and Bravo et al, J. Infectious Diseases, 2006, 193:591-597.

5.5.2.3 Influenza

Animal models, such as ferret, mouse and chicken, developed for use to test antiviral agents against influenza virus have been described, See, e.g., Sidwell et al., Antiviral Res., 2000, 48:1-16; and McCauley et al., Antiviral Res., 1995, 27:179-186. For mouse models of influenza, non-limiting examples of parameters that can be used to assay antiviral activity of Compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+(epithelial layer columnar and even in outline with only slightly increased proliferation; cilia still visible on many cells); 2+(prominent changes in the epithelial layer ranging from attenuation to marked proliferation; cells disorganized and layer outline irregular at the luminal border); 3+(epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+(focal squamous metaplasia of the epithelial layer); 2+(diffuse squamous metaplasia of much of the epithelial layer, cilia may be evident focally); 2.5+(diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+(few infected cells); 1+(few infected cells, as widely separated individual cells); 1.5+(few infected cells, as widely separated singles and in small clusters); 2+(moderate numbers of infected cells, usually affecting clusters of adjacent cells in portions of the epithelial layer lining bronchioles, or in small sublobular foci in alveoli); 3+(numerous infected cells, affecting most of the epithelial layer in bronchioles, or widespread in large sublobular foci in alveoli).

5.5.2.4 Hepatitis

A HBV transgenic mouse model, lineage 1.3.46 (official designation, Tg[HBV 1.3 genome] Chi46) has been described previously and can be used to test the in vivo antiviral activities of Compounds as well as the dosing and administration regimen (See, e.g., Cavanaugh et al., J. Virol., 1997, 71:3236-3243; and Guidotti et al., J. Virol., 1995, 69:6158-6169). In these HBV transgenic mice, a high level of viral replication occurs in liver parenchymal cells and in the proximal convoluted tubules in the kidneys of these transgenic mice at levels comparable to those observed in the infected liver of patients with chronic HBV hepatitis. HBV transgenic mice that have been matched for age (i.e., 6-10 weeks), sex (i.e., male), and levels of hepatitis B surface antigen (HBsAg) in serum can be treated with Compounds or placebo followed by antiviral activity analysis to assess the antiviral activity of Compounds. Non-limiting examples of assays that can be performed on these mice treated and untreated with Compounds include Southern analysis to measure HBV DNA in the liver, quantitative reverse transcriptase PCR (qRT-PCR) to measure HBV RNA in liver, immunoassays to measure hepatitis e antigen (HBeAg) and HBV surface antigen (HBsAg) in the serum, immunohistochemistry to measure HBV antigens in the liver, and quantitative PCR (qPCR) to measure serum HBV DNA. Gross and microscopic pathological examinations can be performed as needed.

Various hepatitis C virus (HCV) mouse models described in the art can be used in assessing the antiviral activities of Compounds against HCV infection (See Zhu et al., Antimicrobial Agents and Chemother., 2006, 50:3260-3268; Bright et al., Nature, 2005, 436:973-978; Hsu et al., Nat. Biotechnol., 2003, 21:519-525; Ilan et al., J. Infect. Dis. 2002, 185: 153-161; Kneteman et al., Hepatology, 2006, 43:1346-1353; Mercer et al., Nat. Med., 2001, 7:927-933; and Wu et al., Gastroenterology, 2005, 128:1416-1423). For example, mice with chimeric human livers are generated by transplanting normal human hepatocytes into SCID mice carrying a plasminogen activator transgene (Alb-uPA) (See Mercer et al., Nat. Med., 2001, 7:927-933). These mice can develop prolonged HCV infections with high viral titers after inoculation with HCV (e.g., from infected human serum). Thus, these mice can be administered a Compound or placebo prior to, concurrently with, or subsequent to HCV infection, and replication of the virus can be confirmed by detection of negative-strand viral RNA in transplanted livers or expression of HCV viral proteins in the transplanted hepatocyte nodules. The statistical significance of the reductions in the viral replication levels are determined.

Another example of a mouse model of HCV involves implantation of the HuH7 cell line expressing a luciferase reporter linked to the HCV subgenome into SCID mice, subcutaneously or directly into the liver (See Zhu et al., Antimicrobial Agents and Chemother., 2006, 50:3260-3268). The mice are treated with a Compound or placebo, and whole-body imaging is used to detect and quantify bioluminescence signal intensity. Mice treated with a Compound that is effective against HCV have less bioluminescence signal intensity relative to mice treated with placebo or a negative control.

5.5.2.5 HIV

The safety and efficacy of Compounds against HIV can be assessed in vivo with established animal models well known in the art. For example, a Trimera mouse model of HIV-1 infection has been developed by reconstituting irradiated normal BALB/c mice with murine SCID bone marrow and engrafted human peripheral blood mononuclear cells (See Ayash-Rashkovsky et al., FASEB J., 2005, 19:1149-1151). These mice are injected intraperitoneally with T- and M-tropic HIV-1 laboratory strains. After HIV infection, rapid loss of human $CD4^+$ T cells, decrease in CD4/CD8 ratio, and increased T cell activation can be observed. A Compound can be administered to these mice and standard assays known in the art can be used to determine the viral replication capacity in animals treated or untreated with a Compound. Non-limiting examples of such assays include the COBAS AMPLICOR® RT-PCR assay (Roche Diagnostics, Branchberg, N.J.) to determine plasma viral load (HIV-1 RNA copies/ml); active HIV-1 virus replication assay where human lymphocytes recovered from infected Trimera mice were cocultured with target T cells (MT-2 cells) and HIV-dependent syncytia formation was examined; and human lymphocytes recovered from infected Trimera mice were cocultured with cMAGI indicator cells, where HIV-1 LTR driven trans-activation of β-galactosidase was measured. Levels of anti-HIV-1 antibodies produced in these mice can also be measured by ELISA. Other established mouse models described in the art can also be used to test the antiviral activity of Compounds in vivo (See, Mosier et al., Semin. Immunol., 1996, 8:255-262; Mosier et al., Hosp. Pract. (Off Ed)., 1996, 31:41-48, 53-55, 59-60; Bonyhadi et al., Mol. Med. Today, 1997, 3:246-253; Jolicoeur et al., Leukemia, 1999, 13:S78-S80; Browning et al., Proc. Natl. Acad. Sci. USA, 1997, 94:14637-14641; and Sawada et al., J. Exp. Med., 1998, 187:1439-1449). A simian immunodeficiency virus (SIV) nonhuman primate model has also been described (See Schito et al., Curr. HIV Res., 2006, 4:379-386).

5.6 Pharmaceutical Compositions

Any Compound described or incorporated by referenced herein may optionally be in the form of a composition comprising the Compound.

In certain embodiments provided herein, compositions (including pharmaceutical compositions) comprise a Compound and a pharmaceutically acceptable carrier, excipient, or diluent.

In other embodiments, provided herein are pharmaceutical compositions comprising an effective amount of a Compound and a pharmaceutically acceptable carrier, excipient, or diluent. The pharmaceutical compositions are suitable for veterinary and/or human administration.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP)SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise a Compound, microcrystalline cellulose, pre gelatinized starch, and magnesium stearate.

Further provided herein are anhydrous pharmaceutical compositions and dosage forms comprising one or more Compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one Compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a Compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a Compound preferably in purified form, together with a suitable amount of carrier so as to provide the form for proper administration to the patient. The formulation should suit the mode of administration. In a preferred embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration. In a specific embodiment, the composition is formulated in accordance with routine procedures as a composition adapted for intravenous, subcutaneous, intramuscular, oral, intranasal or topical administration to human beings. In a preferred embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a Compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A Compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Agents that increase the solubility of one or more of the Compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a Compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more Compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more Compounds so as to improve delivery. In this regard, stearates can serve as a lipid vehicle for the formulation, as an emulsifying agent or surfactant, and as a delivery enhancing or penetration enhancing agent. Different salts, hydrates or solvates of the Compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

5.7 Prophylactic and Therapeutic Methods

The present invention provides methods of preventing, treating and/or managing a viral infection, said methods comprising administering to a subject in need thereof one or more Compounds. In a specific embodiment, the invention provides a method of preventing, treating and/or managing a viral infection, said method comprising administering to a subject in need thereof a dose of a prophylactically or therapeutically effective amount of one or more Compounds or a composition comprising a Compound. A Compound or a composition comprising a Compound may be used as any line of therapy (e.g., a first, second, third, fourth or fifth line therapy) for a viral infection.

In another embodiment, the invention relates to a method for reversing or redirecting metabolic flux altered by viral infection in a human subject by administering to a human subject in need thereof, an effective amount of one or more Compounds or a composition comprising one or more Compounds. For example, viral infection can be treated using combinations of the enzyme inhibition Compounds that produce beneficial results, e.g., synergistic effect; reduction of side effects; a higher therapeutic index. In one such embodiment, a citrate lyase inhibitor can be used in combination with an Acetyl-CoA Carboxylase (ACC).

In specific embodiments, a Compound is the only active ingredient administered to prevent, treat, manage or ameliorate said viral infection. In a certain embodiment, a composition comprising a Compound is the only active ingredient.

The choice of Compounds to be used depends on a number of factors, including but not limited to the type of viral infection, health and age of the patient, and toxicity or side effects. For example, treatments that inhibit enzymes required for core ATP production, such as proton ATPase are not preferred unless given in a regimen that compensates for the toxicity; e.g., using a localized delivery system that limits systemic distribution of the drug.

The present invention encompasses methods for preventing, treating, and/or managing a viral infection for which no antiviral therapy is available. The present invention also encompasses methods for preventing, treating, and/or managing a viral infection as an alternative to other conventional therapies.

The present invention also provides methods of preventing, treating and/or managing a viral infection, said methods comprising administering to a subject in need thereof one or more of the Compounds and one or more other therapies (e.g., prophylactic or therapeutic agents). In a specific embodiment, the other therapies are currently being used, have been used or are known to be useful in the prevention, treatment and/or management of a viral infection. Non-limiting examples of such therapies are provided in Section 5.6.3, infra. In a specific embodiment, one or more Compounds are administered to a subject in combination with one or more of the therapies described in Section 5.6.3, infra. In another embodiment, one or more Compounds are administered to a subject in combination with a supportive therapy, a pain relief therapy, or other therapy that does not have antiviral activity.

The combination therapies of the invention can be administered sequentially or concurrently. In one embodiment, the combination therapies of the invention comprise a Compound and at least one other therapy which has the same mechanism of action. In another embodiment, the combination therapies of the invention comprise a Compound and at least one other therapy which has a different mechanism of action than the Compound.

In a specific embodiment, the combination therapies of the present invention improve the prophylactic and/or therapeutic effect of a Compound by functioning together with the Compound to have an additive or synergistic effect. In another embodiment, the combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

5.7.1 Patient Population

In some embodiments, Compounds, compositions comprising a Compound, or a combination therapy is administered to a subject suffering from a viral infection. In other embodiments, Compounds, compositions comprising a Compound, or a combination therapy is administered to a subject predisposed or susceptible to a viral infection. In some embodiments, Compounds, compositions comprising a Compound, or a combination therapy is administered to a subject that lives in a region where there has been or might be an outbreak with a viral infection. In some embodiments, the viral infection is a latent viral infection. In one embodiment, a Compound or a combination therapy is administered to a human infant. In one embodiment, a Compound or a combination therapy is administered to a premature human infant. In other embodiments, the viral infection is an active infection. In yet other embodiments, the viral infection is a chronic viral infection. Non-limiting examples of types of virus infections include infections caused by those provided in Section 5.4.1, supra. In a specific embodiment, the viral infection is an enveloped virus infection. In some embodiments, the enveloped virus is a DNA virus. In other embodiments, the enveloped virus is a RNA virus. In some embodiments, the enveloped virus has a double stranded DNA or RNA genome. In other embodiments, the enveloped virus has a single-stranded DNA or RNA genome. In a specific embodiment, the virus infects humans.

In certain embodiments, a Compound, a composition comprising a Compound, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, a Compound, a composition comprising a Compound, or a combination therapy is administered to a human at risk for a virus infection. In certain embodiments, a Compound, a composition comprising a Compound, or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a Compound, a composition comprising a Compound, or a combination therapy is administered to a human infant. In other embodiments, a Compound, or a combination therapy is administered to a human child. In other embodiments, a Compound, a composition comprising a Compound, or a combination therapy is administered to a human adult. In yet other embodiments, a Compound, a composition comprising a Compound, or a combination therapy is administered to an elderly human.

In certain embodiments, a Compound, a composition comprising a Compound, or a combination therapy is administered to a pet, e.g., a dog or cat. In certain embodiments, a Compound, a composition comprising a Compound, or a combination therapy is administered to a farm animal or livestock, e.g., pig, cows, horses, chickens, etc. In certain embodiments, a Compound, a composition comprising a Compound, or a combination therapy is administered to a bird, e.g., ducks or chicken.

In certain embodiments, a Compound, a composition comprising a Compound, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, a Compound, a composition comprising a Compound, or a combination therapy is administered to a subject receiving or recovering from immunosuppressive therapy. In certain embodiments, a Compound, a composition comprising a Compound, or a combination therapy is administered to a subject that has or is at risk of getting cancer, AIDS, another viral infection, or a bacterial infection. In certain embodiments, a subject that is, will or has undergone surgery, chemotherapy and/or radiation therapy. In certain embodiments, a Compound, a composition comprising a Compound, or a combination therapy is administered to a subject that has cystic fibrosis, pulmonary fibrosis, or another disease which makes the subject susceptible to a viral infection. In certain embodiments, a Compound, a composition comprising a Compound, or a combination therapy is administered to a subject that has, will have or had a tissue transplant. In some embodiments, a Compound, a composition comprising a Compound, or a combination therapy is administered to a subject that lives in a nursing home, a group home (i.e., a home for 10 or more subjects), or a prison. In some embodiments, a Compound, a composition comprising a Compound, or a combination therapy is administered to a subject that attends school (e.g., elementary school, middle school, junior high school, high school or university) or daycare. In some embodiments, a Compound, a composition comprising a Compound, or a combination therapy is administered to a subject that works in the healthcare area, such as a doctor or a nurse, or in a hospital. In certain embodiments, a Compound, a composition comprising a Compound, or a combination therapy is administered to a subject that is pregnant or will become pregnant.

In some embodiments, a patient is administered a Compound or a composition comprising a Compound, or a combination therapy before any adverse effects or intolerance to therapies other than Compounds develops. In some embodiments, Compounds or compositions comprising one or more Compounds, or combination therapies are administered to refractory patients. In a certain embodiment, refractory patient is a patient refractory to a standard antiviral therapy. In certain embodiments, a patient with a viral infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, Compounds or compositions comprising one or more Compounds, or combination therapies are administered to a patient to prevent the onset or reoccurrence of viral infections in a patient at risk of developing such infections. In some embodiments, Compounds or compositions comprising one or more Compounds, or combination therapies are administered to a patient who are susceptible to adverse reactions to conventional therapies.

In some embodiments, one or more Compounds or compositions comprising one or more Compounds, or combination therapies are administered to a patient who has proven refractory to therapies other than Compounds, but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more Compounds or compositions comprising one or more Compounds, or combination therapies has not received a therapy prior to the administration of the Compounds or compositions or combination therapies. In other embodiments, one or more Compounds or compositions comprising one or more Compounds, or combination therapies are administered to a subject who has received a therapy prior to administration of one or more Compounds or compositions comprising one or more Compounds, or combination therapies. In some embodiments, the subject administered a Compound or a composition comprising a Compound was refractory to a prior therapy or experienced adverse side effects to the prior therapy or the prior therapy was discontinued due to unacceptable levels of toxicity to the subject.

5.7.2 Mode of Administration

When administered to a patient, a Compound is preferably administered as a component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of a Compound into the bloodstream.

In specific embodiments, it may be desirable to administer a Compound locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a Compound into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Compound is formulated as a suppository, with traditional binders and vehicles such as triglycerides.

For viral infections with cutaneous manifestations, the Compound can be administered topically. Similarly, for viral infections with ocular manifestation, the Compounds can be administered ocularly.

In another embodiment, a Compound is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, a Compound is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising a Compound is placed in close proximity to the tissue infected with a virus to be prevented, treated and/or managed. In accordance with this embodiment, the close proximity of the controlled-release system to the infection may result in only a fraction of the dose of the compound required if it is systemically administered.

In certain embodiments, it may be preferable to administer a Compound via the natural route of infection of the virus against which a Compound has antiviral activity. For example, it may be desirable to administer a Compound of the invention into the lungs by any suitable route to treat or prevent an infection of the respiratory tract by viruses (e.g., influenza virus). Pulmonary administration can also be employed, e.g., by use of an inhaler or nebulizer, and formulation with an aerosolizing agent for use as a spray.

5.7.3 Agents for Use in Combination with Compounds

Therapeutic or prophylactic agents that can be used in combination with Compounds for the prevention, treatment and/or management of a viral infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a viral infection or can be used in combination with Compounds in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference (61$^{st}$ ed. 1007) for information regarding therapies (e.g., prophylactic or therapeutic agents) which have been or are currently being used for preventing, treating and/or managing viral infections.

5.7.3.1 Antiviral Agents

Antiviral agents that can be used in combination with Compounds include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination Compounds include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.7.3.2 Antibacterial Agents

Antibacterial agents, including antibiotics, that can be used in combination with Compounds include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracyclins, and analogs thereof. In some embodiments, antibiotics are administered in combination with a Compound to prevent and/or treat a bacterial infection.

In a specific embodiment, Compounds are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with Compounds include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.7.4 Dosages & Frequency of Administration

The amount of a Compound, or the amount of a composition comprising a Compound, that will be effective in the prevention, treatment and/or management of a viral infection can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

In some embodiments, the dosage of a Compound is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, a Compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die (LD10). In general the starting dose of a Phase I clinical trial is based on preclinical testing. A standard measure of toxicity of a drug in preclinical testing is the percentage of animals that die because of treatment. It is well within the skill of the art to correlate the LD10 in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about $\frac{1}{10}$ the murine LD10, although it may be even lower if other species (i.e., dogs) were more sensitive to the Compound. In other embodiments, the standard conservative starting dose is about $\frac{1}{100}$, $\frac{1}{95}$, $\frac{1}{90}$, $\frac{1}{85}$, $\frac{1}{80}$, $\frac{1}{75}$, $\frac{1}{70}$, $\frac{1}{65}$, $\frac{1}{60}$, $\frac{1}{55}$, $\frac{1}{50}$, $\frac{1}{45}$, $\frac{1}{40}$, $\frac{1}{35}$, $\frac{1}{30}$, $\frac{1}{25}$, $\frac{1}{20}$, $\frac{1}{15}$, $\frac{2}{10}$, $\frac{3}{10}$, $\frac{4}{10}$, or $\frac{5}{10}$ of the murine LD10. In other embodiments, an starting dose amount of a Compound in a human is lower than the dose extrapolated from animal model studies. In another embodiment, an starting dose amount of a Compound in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of Compounds or compositions include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 M. In another embodiment, the dosage is a concentration of at least 5 at least 10 µM, at least 50 µM, at least 100 µM, at least 500 µM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 M. In another embodiment, the dosage is a concentration of at least 5 µM, at least 10 µM, at least 50 µM, at least 100 µM, at least 500 µM, at least 1 mM, at least 5 mM, at least 10 mM, at least 50 mM, at least 100 mM, or at least 500 mM. In a specific embodiment, the dosage is 0.25 µg/kg or more, preferably 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 µg, about 150 mg to about 300 mg, about 150 mg to about 400 mg, 250 µg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a Compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one Compound is administered, then, in some embodiments, the dosages correspond to the total amount administered. In a specific embodiment, oral compositions contain about 10% to about 95% a compound of the invention by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of a Compound or a composition, wherein the prophylactically or therapeutically effective amount is not the same for each dose. In another embodiment, a subject is administered one or more doses of a prophylactically or therapeutically effective amount of a Compound or a composition, wherein the dose of a prophylactically or therapeutically effective amount administered to said subject is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of a prophylactically or therapeutically effective amount of a Compound or composition, wherein the dose is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

In certain embodiments, a subject is administered a Compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a Compound or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered a Compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a Compound or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a Compound or a composition in an amount effective to inhibit or reduce viral infection by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a Compound or a composition in an amount effective to inhibit or reduce viral infection by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered a Compound or a composition in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered a Compound or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered a Compound or a composition in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered a Compound or a composition in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a subject is administered a Compound or a composition in an amount effective to inhibit or reduce viral induced lipid synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered a Compound or a composition in an amount effective to inhibit or reduce viral induced lipid synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a Compound or a composition in an amount effective to inhibit or reduce viral induced lipid synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a dose of a Compound or a composition is administered to a subject every day, every other day, every couple of days, every third day, once a week, twice a week, three times a week, or once every two weeks. In other embodiments, two, three or four doses of a Compound or a composition is administered to a subject every day, every couple of days, every third day, once a week or once every two weeks. In some embodiments, a dose(s) of a Compound or a composition is administered for 2 days, 3 days, 5 days, 7 days, 14 days, or 21 days. In certain embodiments, a dose of a Compound or a composition is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a viral infection can be determined using references available to a clinician such as, e.g., the Physicians' Desk Reference ($61^{st}$ ed. 2007). Preferably, dosages lower than those which have been or are currently being used to prevent, treat and/or manage the infection are utilized in combination with one or more Compounds or compositions.

For Compounds which have been approved for uses other than prevention, treatment or management of viral infections, safe ranges of doses can be readily determined using references available to clinicians, such as e.g., the Physician's Desk Reference ($61^{St}$ ed. 2007).

The above-described administration schedules are provided for illustrative purposes only and should not be considered limiting. A person of ordinary skill in the art will readily understand that all doses are within the scope of the invention.

In one embodiment, Orlistat (also sold by the trade name Xenical®) is administered as a 120 mg capsule three times daily with a fat containing meal. Without being limited by theory, while dosages of Orlistat above 120 mg do not show any additional benefits for this indication, dosages as high as 800 mg once daily and 400 mg three times daily have not shown adverse side effects.

In certain embodiments, a Compound of structure (I) is administered as a solid dosage form, for example, as a capsule.

In other embodiments, a Compound of structure (I) is administered at a dose of from about 100 mg to about 800 mg. In a particular embodiment, a compound of structure (I) is administered at a dose of 120 mg, 400 mg or 800 mg.

In other embodiments, a Compound of structure (I) is administered once, twice or three times per day.

In a particular embodiment, a Compound of structure (I) is administered three times per day as a 120 mg capsule. A Compound of structure (I) can be administered with a meal, for example, a fat containing meal.

In one embodiment a Compound of structure (II) is administered doses in the range of 0.001 mg/kg, to about 50 mg/kg of body weight per day.

In another embodiment a Compound of structure (II) is administered at doses in the range of 0.01 mg/kg to about 25 mg/kg of body weight per day.

In another embodiment a Compound of structure (II) is administered at doses in the range 0.1 mg/kg to about 10 mg/kg of body weight per day.

In another embodiment a Compound of structure (II) is administered at doses in the range of about 50 mg/kg to about 100 mg/kg per day.

In another embodiment a Compound of structure (II) is administered at doses below 0.001 mg/kg per day.

In one embodiment a Compound of structure (III) is administered doses in the range of 0.001 mg/kg, to about 100 mg/kg of body weight per day.

In another embodiment a Compound of structure (III) is administered at doses in the range of 0.01 mg/kg to about 50 mg/kg of body weight per day.

In another embodiment a Compound of structure (III) is administered at doses in the range 10 mg/kg to about 30 mg/kg of body weight per day.

In another embodiment a Compound of structure (III) is administered at doses in the range of about 50 mg/kg to about 100 mg/kg per day.

In another embodiment a Compound of structure (III) is administered at doses below 0.001 mg/kg per day.

In one embodiment a Compound of structure (IV) is administered doses in the range of 0.001 mg/kg, to about 100 mg/kg of body weight per day.

In another embodiment a Compound of structure (IV) is administered at doses in the range of 0.01 mg/kg to about 50 mg/kg of body weight per day.

In another embodiment a Compound of structure (IV) is administered at doses in the range 10 mg/kg to about 30 mg/kg of body weight per day.

In another embodiment a Compound of structure (IV) is administered at doses in the range of about 50 mg/kg to about 100 mg/kg per day.

In another embodiment a Compound of structure (IV) is administered at doses below 0.001 mg/kg per day.

In one embodiment a Compound of structure (VI) is administered doses in the range of 0.001 mg/kg, to about 50 mg/kg of body weight per day.

In another embodiment a Compound of structure (VI) is administered at doses in the range of 0.01 mg/kg to about 25 mg/kg of body weight per day.

In another embodiment a Compound of structure (VI) is administered at doses in the range 0.1 mg/kg to about 10 mg/kg of body weight per day.

In another embodiment a Compound of structure (VI) is administered at doses in the range of about 50 mg/kg to about 100 mg/kg per day.

In another embodiment a Compound of structure (VI) is administered at doses below 0.001 mg/kg per day.

In another embodiment a Compound of structure (VI) is administered orally as a capsule at doses in the range of 0.25 mg to about 500 mg.

In another embodiment a Compound of structure (VI) is administered orally as a tablet at doses in the range of 0.25 mg to about 500 mg.

In another embodiment a Compound of structure (VI) is administered orally as a suspension at doses in the range of 0.25 mg to about 500 mg.

In another embodiment a Compound of structure (VI) is administered as an inhalation aerosol at doses in the range of 0.10 mg to about 100 mg.

In another embodiment a Compound of structure (VI) is administered as a suppository at doses in the range of 10 mg to about 500 mg.

In another embodiment a Compound of structure (VI) is administered intravenously at doses in the range of 0.1 mg/ml to about 100 mg/ml.

In one embodiment a Compound of structure (VIII) is administered in doses in the range of 1 mg to about 100 mg per day.

In another embodiment a Compound of structure (VIII) is administered in doses in the range of 1 mg to about 10 mg per day.

In another embodiment a Compound of structure (VIII) is administered orally as a tablet in doses in the range of 1 mg to about 100 mg.

In another embodiment a Compound of structure (VIII) is administered orally as a capsule in doses in the range of 1 mg to about 100 mg.

In another embodiment a Compound of structure (VIII) is administered orally as a sachet in doses in the range of 1 mg to about 100 mg.

In another embodiment a Compound of structure (VIII) is administered as an injection in doses in the range of 1 mg to about 100 mg.

In one embodiment, a Compound of structure (XIII) is administered at a dose of about 10 µg/kg/day to about 100 mg/kg/day.

In another embodiment, a Compound of structure (XIII) is administered as an oral (e.g., tablet) or parenteral dosage form.

In another embodiment, a Compound of structure (XIII) is administered as a solid dosage form containing from about 2 µg to about 1000 mg of a Compound of structure (XIII). In a particular embodiment, a Compound of structure (XIII) is administered as a solid dosage form containing 500 mg of a Compound of structure (XIII).

In one embodiment, a Compound of structure (XIV) is administered at a dose of about 0.5 mg/kg to about 100 mg/kg.

In another embodiment, a Compound of structure (XIV) is administered orally or systemically.

In one embodiment, a Compound of structure (XV) is administered at a dose of about 1 mg/kg to about 100 mg/kg. In a particular embodiment, a Compound of structure (XV) is administered at a dose of 10 mg/kg.

In another embodiment, a Compound of structure (XV) is administered intraperitoneally as a liquid dosage form. In a particular embodiment, a Compound of structure (XV) is administered intraperitoneally as a liquid dosage form at a concentration of 10 mg/kg.

In one embodiment, a Compound of structure (XVI) is administered at a daily dosage of about 5 to about 200 mg/kg of body weight. In another embodiment, a Compound of structure (XVI) is administered at a daily dosage of about 10 to about 100 mg/kg of body weight, in one or more dosages per day.

In a specific embodiment, a Compound that is TOFA is administered to a human at a dose of about 500 mg/day to about 1,000 mg/day.

In another embodiment, a Compound that is an ACC inhibitor, e.g., TOFA, is administered at a rodent dose of 150 mg/kg/day to yield plasma levels of approximately 75 µM (or approximately 30 µg/mL). In a certain embodiment, a Compound that is an ACC inhibitor, e.g., TOFA, is administered to a human at a dose of approximately 1,500 mg/day (on BSA basis). In a particular embodiment, a Compound that is an ACC inhibitor, e.g., TOFA, is administered to a human at a dose of about 1,000 mg/day to about 1,500 mg/day (on BSA basis). In another embodiment, a Compound that is an ACC inhibitor, e.g., TOFA, is administered to a human at a dose of about 1,500 mg/day to about 2,000 mg/day (on BSA basis). In specific embodiments, a Compound that is an ACC inhibitor, e.g., TOFA, is administered to a human, wherein the concentration of the Compound in tissue, e.g., lung tissue or liver tissue, is higher than the concentration of the Compound in plasma. In some embodiments, a Compound that is an ACC inhibitor, e.g., TOFA, is administered to a human, wherein the concentration of the Compound in lung tissue is about 1.5 times, or about 2 times, or about 3 times, or about 4 times, or about 5 times higher than the concentration of the Compound in plasma. In specific embodiments, a Compound that is an ACC inhibitor, e.g., TOFA, is administered to a human, wherein the concentration of the Compound in lung tissue is about 3 times higher than the concentration of the Compound in plasma. In certain embodiments, a Compound that is an ACC inhibitor, e.g., TOFA, is administered to a human, wherein the concentration of the Compound in liver tissue is about 5 times, or about 10 times, or about 15 times, or about 20 times, or about 25 times, or about 30 times, or about 35 times, or about 40 times, or about 50 times higher than the concentration of the Compound in plasma. In particular embodiments, a Compound that is an ACC inhibitor, e.g., TOFA, is administered to a human, wherein the concentration of the Compound in liver tissue is about 30 times higher than the concentration of the Compound in plasma.

5.7.5 Cell Culture Uses

The present invention provides for the use of Compounds as ingredients in cell culture-related products in which it is desirable to have antiviral activity. In one embodiment, one or more Compounds is added to cell culture media. In certain embodiments, Compounds that prove too toxic or are not used in subjects are added to cell culture-related products, such as media.

6. EXAMPLES

Biological Reagents and Cell Culture

MRC-5 fibroblasts (ATCC) were cultured in Dulbecco's modified Eagle medium (DMEM) containing 7.5% fetal calf serum and 4.5 g/L glucose. All infections with human cytomegalovirus were carried out with BADwt, which is derived from a bacterial artificial chromosome (BAC) clone of the AD169 strain of HCMV (see Giaever et al., Nature 418, 387 (Jul. 25, 2002)). The BAC was inserted into the genome of HCMV without deletion of any viral sequence and was excised by a co-transfected CRE recombinase that mediates recombination at the loxP sites, which flank the BAC, leaving just the loxP site in the viral clone. This clone has been tested in a diversity of assays and has always displayed a wild-type AD169 phenotype.

For all metabolic experiments, fibroblasts were grown to confluence in 10-cm dishes, resulting in ~1.5×10$^6$ cells per dish. After incubation for 3-5 d at confluence, serum-containing medium was removed, serum-free medium added and cells were maintained in serum-free DMEM for 24 h, which has been previously demonstrated to synchronize cells in the G0 stage of the cell cycle (Munger et al., PLoS Pathog 2, e132 (Dec. 15, 2006)). Cells were mock infected or infected with HCMV at a multiplicity of 3.0 pfu/cell. After a 2-h adsorption period, the inoculums were aspirated and fresh serum-free DMEM was added. For determination of HCMV growth in the presence of metabolic inhibitors, viral titers were determined by standard plaque assay on MRC-5 cells.

Madin-darby canine kidney epithelial Cells (MDCK cells) were obtained from the ATCC and were cultured in DMEM containing 7.5% fetal calf serum and 4.5 g/L glucose. MDCK cells were infected with the A/WSN/33 Influenza strain (ATCC) in DMEM containing 0.2% BSA, 0.01% $CaCl_2$, 0.01% $MgCl_2$, 1 μg/ml trypsin (Worthington) and 0.1% FBS. For determination of Influenza A growth in the presence of metabolic inhibitors, viral titers were determined by standard plaque assay on MDCK cells.

Metabolic Flux Experiments and Metabolite Extraction.

So as to limit experimental artifacts during metabolic flux experiments it is important to introduce labeled nutrient to cells with as little metabolic perturbation as possible. Since we have found that the levels of certain metabolites in media and cells change over time (Munger et al., PLoS Pathog. 2, e132 (Dec. 15, 2006)), the media of mock and HCMV-infected cultures were aspirated and replaced with fresh DMEM (containing 10 mM HEPES) 24 h post-infection and again at 47 h post-infection so as to prevent metabolic changes induced by the fresh media change at the time of label introduction. Forty-eight hours post-infection the media of mock and HCMV-infected cultures were aspirated and replaced with DMEM (with 10 mM HEPES) containing 4.5 g/L $^{12}C$ glucose for the t=0 time points or with DMEM (with 10 mM HEPES) containing 4.5 g/L universally labeled $^{13}C$ glucose (Cambridge isotopes, http://www.isotope.com/) for the other time points. Metabolites were extracted by adding methanol:water 80:20 (80% methanol) at −75° C. was added either immediately, for the t=0 time points, or after 0.5, 1, 2, 5, 15, 30, 60, or 120 min of incubation. After metabolism quenching, cells were scraped from the plastic tissue culture dish while on dry ice. The resulting cell suspension was vortexed, centrifuged at 6000×g for 5 min, and re-extracted twice more with 80% methanol at −75° C. After pooling the three extractions, the samples were completely dried under nitrogen gas, dissolved in 220 μl 50% methanol, spun at 13,000×g for 5 min to remove debris and analyzed by LC-MS/MS as described below with the virally infected and mock-infected samples alternated (to avoid artifacts in the measurement of unstable compounds due to differential processing times) When sampling media for metabolite extraction, medium was taken and mixed with a volume of −75° C. 100% methanol to create an 80:20 methanol:media mixture. Media samples were then centrifuged, dried and resuspended as above.

Determination of Metabolite Concentrations.

Absolute quantitation of metabolites by mass spectrometry requires addition of internal standards. Heavy-isotope standards are expensive and are not available for numerous metabolites of interest. To overcome this obstacle we sought to reconstitute the fibroblast metabolic network with $^{13}$-Carbon and use $^{12}C$-metabolites as internal standards. Towards this end, we grew primary fibroblasts for ~3 passage doublings in DMEM deficient in $^{12}C$-glucose and $^{12}C$-glutamine but supplemented to the original level with $^{13}C$-glucose and $^{13}C$-glutamine. The efficiency of the carbon replacement is shown in table S1. Cells were incubated at confluence for 3 days, serum starved and infected as indicated above with the exception that all media was DMEM containing $^{13}C$-glucose and $^{13}C$-glutamine. Cells were harvested by the addition of −75° C. 80% methanol containing $^{12}C$-metabolite internal standards at the concentrations indicated in Table S4. To quantify metabolite levels, SRM peak heights for both $^{12}C$-internal standard and $^{13}C$-metabolite pools were measured. Metabolite pool concentrations were calculated based on the specific internal standard peak height, the initial internal standard concentration and the efficiency of the original $^{13}C$ replacement. Results are the average of three independent infections.

To measure the uptake and excretion of various metabolites, samples from uncultured media or media from mock or HCMV-infected cultures starting at 44 hrs post infection and then taken 0.5, 1, 2, 4, 6, 8 hours later. Results are the average of 6 independent infections. To obtain glucose uptake, a standard glucometer was utilized to measure the change of glucose concentration in cell culture media. Lactate, which fragments poorly, was measured in single ion mode (SIM), while glutamine, aspartate and glutamate levels were measured by SRM peak height as outlined below. $^{13}C$ internal standards of known concentrations for lactate, glutamine, aspartate and glutamate were added to the 80% methanol extraction solvent (Cambridge isotopes, http://www.isotope.com).

Glycolysis Versus Pentose Phosphate Pathway Estimation.

Estimation of the relative carbon flux between glycolysis and the pentose phosphate pathway was performed largely as described in Lee et al., *Am J Physiol* 274, E843 (May, 1998). Specifically, forty-eight hours after mock or viral infection of MRC5 cells, the tissue culture media was aspirated and DMEM containing 30% 1,2-$C^{13}$-glucose and 70% $C^{12}$ glucose (4.5 g/l glucose total) was added. After four hours of incubation cells were extracted as above and analyzed by mass spectrometry for the relative levels of 1-$C^{13}$-lactate versus 1,2-$C^{13}$-lactate. The relative ratio of lactate production through oxidative pentose phosphate pathway is equal to the fraction of 1-$C^{13}$-lactate labeled lactate divided by the sum of 1-$C^{13}$-lactate and 1,2-$C^{13}$-lactate. The amount of 1-$C^{13}$-lactate was corrected for the naturally occurring isotope abundance of carbon-13, which is 1.1%.

Estimation of Pyruvate Contribution to TCA Cycle Resulting from Oxidation Versus Carboxylation.

Upon oxidation of pyruvate to acetyl-CoA, the third carbon of pyruvate is released as $CO_2$ which does not occur during pyruvate carboxylation. Forty-eight hours after mock or viral infection of MRC5 cells, the tissue culture media was aspirated and DMEM containing 100% 3-$C^{13}$-glucose was added. After 6 hours of incubation in DMEM containing 3-$C^{13}$-glucose, cellular metabolites were extracted and processed as above. The relative amounts of 3-$C^{13}$ labeling of TCA components were corrected for both natural isotope abundance and for the incomplete labeling of 3-carbon glycolytic compounds (if cells oxidize only 3-$C^{13}$-glucose, only 50% of the three carbon glycolytic components will receive the 3-Carbon from glucose).

LC-MS/MS Instrumentation.

Positive mode LC-MS/MS was performed using an LC-10A HPLC system (Shimadzu, http://www.shimadzu.com) a luna aminopropyl column (either a 100 mm×1 mm with a 3-1 µm particle size or a 250 mm×2 with a 5-µm from Phenomenex, http://www.phenomenex.com) coupled to the mass spectrometer. The LC parameters were as follows: autosampler temperature, 4° C.; injection volume, 20 µL; column temperature, 15° C.; and flow rate, 50 µL/min for the 100 mm column and 150 µL/min for the 250 mm column. The LC solvents for both columns were Solvent A: 20 mM ammonium acetate+20 mM ammonium hydroxide in 95:5 water:acetonitrile (pH 9.45); and Solvent B: acetonitrile. The gradients were as follows for the 100 mm column: t=0, 85% B; t=12, 0% B; t=24, 0% B, t=26, 85% B; t=40, 85% B and for the 250 mm column: t=0, 85% B; t=15 min, 0% B; t=28 mM, 0% B; t=30 min, 85% B; t=40 min, 85% B; and negative mode-t=0, 85% B; t=15 min, 0% B; t=38 min, 0% B; t=40 min, 85% B; t=50 min, 85% B.

Negative mode LC-MS/MS was performed as described in (Luo et al., *J. Chromatogr. A* 1147, 153 (Apr. 20, 2007)) with slight modifications. Samples were analyzed using an LC-20 AD HPLC system (Shimadzu, http://www.shimadzu.com) with a luna C18 column (150×2 mm with a 4 µM particle size from Phenomenex, http://www.phenomenex.com) coupled to the mass spectrometer. The LC parameters were as follows: autosampler temperature, 4° C.; injection volume, 20 µL; column temperature, 25° C.; and flow rate, 200 µL/min. The LC solvents were Solvent A: 15 mM Acetic Acid, 10 mM Tributylamine in 97:3 water:Acetic Acid (pH 4.95) and Solvent B: Methanol. The gradient was as follows: t=0, 0% B; t=5, 0% B; t=10, 20% B; t=20, 20% B; t=35, 65% B; t=38, 95% B; t=42, 95% B, t=43, 0% B; t=50, 0% B.

Mass spectrometric analyses were performed on a Finnigan TSQ Quantum Ultra (for positive mode) or a Finnigan TSQ Discovery Max (for negative mode) triple-quadrupole mass spectrometer (Thermo Electron Corporation, http://www.thermo.com), equipped with an electrospray ionization (ESI) source. For both modes, the ESI spray voltage was 3,200 V and nitrogen was used as sheath and auxiliary gas at 20 psi and at 10 psi respectively. Argon was used as the collision gas at 1.5 mTorr, with the capillary temperature set at 325° C. Scan time for each SRM transition was 0.1 s with a scan width of 1 m/z. The LC runs were divided into time segments, with the SRM scans within each time segment limited to those compounds eluting during that time interval. For compounds eluting at the boundaries between time segments, the SRM scan corresponding to the compound is conducted in both time segments. The instrument control, data acquisition, and data analysis were performed by the Xcalibar software (Thermo Electron Corporation, version 1.4 SR1), which also controlled the chromatography system.

Measurement of Lipid Synthesis.

To quantify the amount of glucose being utilized for phospholipid synthesis primary fibroblasts were grown in 12-well plates and maintained for 3-5 d, at which time serum-containing medium was removed, and serum-free medium added. After maintenance in serum-free DMEM for 24 h, cells were either mock-infected or infected with BADwt (MOI=3.0). Forty-eight hours after infection, 8 µC/ml of D[6-$^{14}C$]Glucose was added to mock or virally infected cells in DMEM containing 1 g/L glucose. After incubation for 4 h at 37° C., the cellular culture medium was aspirated, the cells were washed with PBS and phospholipids were extracted with the addition of 500 µL of hexane:isopropanol (3:2). Wells were washed with an additional 400 µL of hexane:isopropanol (3:2). Phospholipid extractions were then dried under $N_2$ gas, resuspended in 500 µl, 1N KOH in 90% methanol:water, incubated at 70° C. for 60 min, after which time 100 µL 2.5 m $H_2SO_4$ was added. Seven-hundred µL of hexane was then added to extract the fatty acids. The organic and aqueous phases were separated by centrifugation and scintillation counted. Results of three separate infections are reported with the standard error of the mean.

6.1 Example 1

Approach To Identifying Metabolic Fluxes Upregulated By Viral Infection

Viral replication requires energy and macromolecular precursors derived from the metabolic network of the host cell. Until recently however, adequate technology for evaluating the effect of viral infection on host metabolism was not available.

Viruses can alter cellular metabolic activity through a variety of routes. These include affecting transcription, translation, and/or degradation of mRNAs and/or proteins, relocalization of mRNAs and/or proteins, covalent modification of proteins, and allosteric regulation of enzymes or other proteins; and alterations to the composition of protein-containing complexes that modify their activity. The net result of all of these changes is modulation of metabolic fluxes to meet the needs of the virus. Thus, metabolic flux changes represent the ultimate endpoint of the virus' efforts to modulate host cell metabolism. Accordingly, fluxes that are increased by the virus are especially likely to be critical to viral survival and replication and to represent valuable drug targets.

A novel approach has been developed to profile metabolic fluxes. It builds upon an approach to measuring nitrogen metabolic fluxes in *E. coli* developed by Rabinowitz and colleagues (Yuan et al., 2006, Nat. Chem. Biol. 2:529-530), which is incorporated herein by reference. The essence of this kinetic flux profiling (KFP) approach is as follows:

(1) Cells (either uninfected or infected with virus) are rapidly switched from unlabeled to isotope-labeled nutrient (or vice versa); for the present purposes, preferred nutrients include uniformly or partially $^{13}$C-labeled or $^{15}$N-labeled glucose, glutamine, glutamate, or related compounds including without limitation pyruvate, lactate, glycerol, acetate, aspartate, arginine, and urea. Labels can include all known isotopes of H, C, N, O, P, or S, including both stable and radioactive labels. Results are dependent on the interplay between the host cell type and the viral pathogen, including the viral load and time post infection.

(2) Metabolism is quenched at various time points following the isotope-switch (e.g., 0.2, 0.5, 1, 2, 5, 10, 20, 30 min and 1, 2, 4, 8, 12, 16, 24, 36, 48 h or a subset or variant thereof). One convenient means of metabolism quenching is addition of cold (e.g., dry-ice temperature) methanol, although other solvents and temperatures, including also boiling solvents, are possible.

(3) The metabolome, including its extent of isotope labeling, is quantified for each collected sample. One convenient means of such quantitation is extraction of metabolites from the cells followed by liquid chromatography-tandem mass spectrometry (LC-MS/MS) analysis of the extract. Appropriate extraction protocols and LC-MS/MS methods are known in the art. See the following citations, which are herein incorporated by reference (Bajad et al., 2006, J Chromatogr. A 1125:76-88; Bolling and Fiehn, 2005, Plant Physiol. 139:1995-2005; Coulier et al., 2006, Anal Chem. 78:6573-6582; Kimball and Rabinowitz, 2006, Anal Biochem. 358:273-280; Lu et al., 2006, J. Am. Soc. Mass Spectrom. 17:37-50; Lu et al., 2007, J Am Soc Mass Spectrom. 18:898-909; Luo et al., 2007, J. Chromatogr. A 1147: 153-164; Maharjan and Ferenci, 2003, Anal Biochem 313: 145-154; Milne et al., 2006, Methods 39:92-103; Munger et al., 2006, PLoS Pathog. 2:e132; Olsson et al., 2004, Anal Chem. 76:2453-2461; Rabinowitz and Kimball, 2007, Anal Chem. 79:6167-73; Schaub et al., 2006, Biotechnol. Prog. 22:1434-1442; van Winden et al., 2005, FEMS Yeast Research 5:559-568; Villas-Boas et al., 2005, Yeast 22:1155-1169; Wittmann et al., 2004, Anal Biochem. 327: 135-139; Wu et al., 2005, Anal Biochem. 336:164-171; Yuan et al., 2006, Nat. Chem. Biol. 2:529-530).

(4) The resulting data is analyzed to determine the cellular metabolic fluxes.

The KFP data is analyzed based on the following principles, through whose application those skilled in the art of cellular metabolism can identify flux changes associated with viral infection by comparing results for infected versus uninfected samples:

(1) Metabolites closer to the added nutrient in the metabolic network will become labeled before their downstream products. Thus, the pattern of labeling provides insight into the route taken to forming a particular metabolite. For example, more rapid labeling of oxaloacetate than citrate upon switching cells from unlabeled to uniformly $^{13}$C-labeled glucose would imply formation of oxaloacetate via phosphoenolpyruvate carboxylase or phosphoenolpyruvate carboxykinase rather than via clockwise turning of the tricarboxylic acid cycle.

(2) The speed of labeling provides insight into the quantitative flux through different metabolic pathways, with fast labeling of a metabolite pool resulting from large flux through that pool and/or low absolute pool size of it. For the ideal case of a well-mixed system in which a nutrient is being directly converted into an intracellular metabolite, instantaneous switching of the nutrient input into isotope-labeled form, without other modulation of the system, results over time in disappearance of the unlabeled metabolite:

$$dX^U/dt = -f_X X^U/X^T \qquad \text{Eq. (A)}$$

where $X^T$ is the total pool of metabolite X; $X^U$ the unlabeled form; and $f_X$ is the sum of all fluxes consuming the metabolite. For $f_X$ and $X^T$ constant (i.e., the system at pseudo-steady-state prior to the isotope switch), $$X^U/X^T = \exp(-f_X t/X^T) \qquad \text{Eq. (B)}$$

and $$f_X = X^T k_X \qquad \text{Eq. (C)}$$

where $k_X$ is the apparent first-order rate constant for disappearance of the unlabeled metabolite. According to Eq. (C), the total flux through metabolite X can be determined based on two parameters that can be measured directly experimentally: the intracellular pool size of the metabolite and the rate of disappearance of the unlabeled form. While in practice isotope switching is not instantaneous and slightly more complex equations are required, the full differential equations can still often be solved analytically and typically involve only two free parameters, with one of these, $k_X$, directly yielding total metabolic flux as shown above (Yuan et al., 2006, Nat. Chem. Biol. 2:529-530).

In certain cases involving branched and cyclic pathways, however, the mathematics become more complex and use of more sophisticated computational algorithms to facilitate data analysis may be beneficial. The cellular metabolic network can be described by a system of differential equations describing changes in metabolite levels over time (including changes in isotopic labeling patterns). See the following citations, which are hereby incorporated by reference (Reed et al., 2003, Genome Biol. 4:R54; Sauer, 2006, Mol. Syst. Biol. 2:62; Stephanopoulos, 1999, Metab. Eng. 1:1-11; Szyperski et al., 1999, Metab. Eng. 1:189-197; Zupke et al., 1995). Such descriptions, wherein the form of the equations is parallel to Eq. (A) above, can be solved for fluxes $f_{x1}$, $f_{x2}$, etc. based on experimentally observed data describing metabolite concentrations and labeling kinetics ($X^T$ at pseudo-steady-state and $X^U/X^T$ as a function of time). One appropriate class of algorithm for obtaining such solutions is described in the following citations, which are hereby incorporated by reference (Feng and Rabitz, 2004, Biophys. J. 86:1270-1281; Feng et al., 2006, J. Phys. Chem. A. Mol. Spectrosc. Kinet. Environ. Gen. Theory 110:7755-7762).

In general, changes in fluxes induced by viral infections occur slowly relative to the turnover of metabolites. Accordingly, the steady-state assumption generally applies to virally perturbed metabolic networks over short to moderate timescales (e.g., for CMV, up to ~2 h; the exact length of time depends on the nature of the viral pathogen, with more aggressive pathogens generally associated with shorter time scales).

At steady-state, the flux through all steps of a linear metabolic pathway must be equal. Accordingly, if flux through one step of a pathway is markedly increased by viral infection, the flux through the other steps is likely also increased. A complication arises due to branching, however. While the effect of branching is small in the case that the side branches are associated with low relative flux, the possibility of branching (as well as non-steady-state conditions) points to the need for more experimental data than just one measured pathway flux to implicate other pathway steps as viable drug targets. If increased flux is experimentally demonstrated at both steps upstream and downstream of an unmeasured step of the pathway, however, then one can have greatly increased confidence that the flux at the (unmeasured) intermediate step is also increased. Accordingly, herein we consider demonstration of increased flux at both the upstream and downstream steps (but, in selected embodiments, neither individually) to be adequate to validate the intermediate flux (and associated catalyzing enzyme) as a valid antiviral drug target.

6.2 Example 2

Upregulation of Glycerol-3-Phosphate Dehydrogenase, Citrate Transport Protein, and Citrate Lyase Flux by Human Cytomegalovirus The kinetic flux profiling (KFP) approach described herein was used to examine changes in carbon metabolic fluxes induced by human cytomegalovirus (CMV) infection of primary human foreskin fibroblasts. Uniformly $^{13}$C-labeled glucose was used as the isotopic tracer. For the following glycolytic and glycolysis-associated metabolites, concentrations were substantially increased at 48 hours post infection (hpi), (compared to uninfected, quiescent fibroblasts) and rates of isotope labeling were either unchanged or increased: hexose phosphate (a combined signal from metabolites including glucose-6-phosphate, glucose-1-phosphate, and fructose-6-phosphate), fructose bisphosphate, glyeraldehyde-3-phosphate, phosphoenolpyruvate, and acetyl-coenzyme A. The combination of increased concentrations and unchanged or increased turnover rates implied increased metabolic flux (See Eq. C).

The labeling of glycerol-3-phosphate, a byproduct of glycolysis required for the formation of phospholipids, diacylglyercols, and triglycerides, was also found to be increased by CMV infection. This indicated that glycerol-3-phosphate dehydrogenase flux was induced by CMV infection.

The labeling of components of the citric acid cycle was also examined. Results are summarized in FIG. 2A, with full data for two especially important metabolites, citrate and malate, shown in FIG. 2B.

The observation that CMV infection markedly increases citrate labeling without a parallel increase in malate labeling was diagnostic for dramatic upregulation of citrate transport protein and citrate lyase flux induced by virus: as the total citrate concentration did not change substantially (i.e., the unlabeled citrate concentration fell in parallel with the rise in the labeled citrate), there must be outflow from citrate which was up-regulated by the virus. This outflow must not generate labeled ketoglutarate, succinate, or malate (as fast labeling of these species was not observed). Accordingly, the outflow cannot be via isocitrate to ketoglutarate (TCA cycle; would form labeled ketoglutarate, succinate, and malate) or via isocitrate to succinate (glyoxylate cycle; would form labeled succinate and malate). The only remaining possibility was enhanced outflow to cytosolic acetyl-CoA+malate via the steps stated below.

(1) Mitochondrial citrate transport protein catalyzes the exchange of citrate plus a proton for malate across the inner mitochondrial membrane
(2) Citrate lyase in the cytosol catalyzes the reaction citrate+ATP+CoA+water→acetyl-CoA+ADP+Pi+oxaloacetate
(3) The resulting oxaloacetate is reduced to malate by NADH by cytosolic malate dehydrogenase Note that, in contrast to the glyoxylate cycle or TCA cycle, these steps form unlabeled malate from 2C-labeled citrate (with the labeling of citrate resulting from to condensation of AcCoA [acetyl moiety labeled] with unlabeled oxaloacetate in mitochondria; the citrate labeling pattern induced by CMV infection was confirmed by MS/MS analysis to match that expected for citrate made by citrate-synthase-catalyzed condensation of acetyl-CoA [acetyl group labeled] with oxaloacetate [unlabeled]).

The resulting cytosolic malate can then potentially be converted to pyruvate+NADPH by NADP$^+$-linked malate enzyme (also known as malic enzyme).

As steps (1) and (2) of this process are essential to it, the data observed in FIG. 2 proved that increased citrate transport protein and citrate lyase flux are induced by CMV.

6.3 Example 3

Upregulation of Glutaminase and Glutamate Dehydrogenase Flux by Human Cytomegalovirus In this example, uniformly $^{13}$C-labeled glutamine was used as the isotopic tracer. Labeling kinetics of the amino acid glutamate, as well as TCA cycle components ketoglutarate, succinate, fumarate, and malate were observed in fibroblasts at 48 hours post CMV infection versus uninfected, quiescent fibroblasts. Concentrations of the metabolites were increased and the rates of isotope labeling also increased in the CMV-infected samples. The formation of labeled glutamate (and downstream TCA cycle compounds such as ketoglutarate, succinate, fumarate, and malate) from labeled glutamine involves flux through the enzyme glutaminase. Accordingly, the KFP data demonstrated increased glutaminase flux. The glutamate must then be converted to ketoglutarate by glutamate dehydrogenase. Accordingly, the KFP data demonstrated increased glutamate dehydrogenase flux. There are two forms of glutamate dehydrogenase in the human genome: glutamate dehydrogenase I and glutamate dehydrogenase II, which produce NADH and NADPH respectively upon deamination of glutamate to form ketoglutarate+ammonia. Based on these data, glutaminase and both forms of glutamate dehydrogenease constitute new antiviral drug targets, and delivery to an infected individual of inhibitors thereof constitutes a method of treating viral infection. Increased flux through glutamate dehydrogenase is particularly interesting, because the NADPH formed thereby enables the reductive steps of fatty acid biosynthesis. Accordingly, inhibition of glutamate dehydrogenase II constitutes a method of blocking fatty acid biosynthesis and thereby treating viral infection.

6.4 Example 4

Upregulation of Biosynthesis of Free Fatty Acids and Lipids by Human Cytomegalovirus In this example, $^{14}$C-labeled glucose was used as the isotopic tracer, and labeling of downstream metabolites was measured based on radioactivity (as measured by scintillation counting) rather than by mass spectrometry. The targeted metabolites were the total pool of free (i.e., not covalently protein-bound) lipids and fatty acids, which were separated from other cellular material (importantly including lipids covalently linked to proteins) by extraction using a hydrophobic solvent such as chloroform-ethyl acetate mixtures. CMV infection resulted in increased flux from the labeled glucose into the free lipids and fatty acids as shown in FIG. 3. Accordingly, inhibition of fatty acid biosynthesis (including without limitation inhibition of free fatty acid and lipid biosynthesis, as distinguished from inhibition of covalent modification of proteins by lipids, e.g., protein palmitoylation) constitutes a method of treating viral infection. As fatty acid biosynthesis is reliant on the enzyme fatty acid synthase (including its acyl carrier protein), these data demonstrate that fatty acid synthase is an antiviral drug target.

6.5 Example 5

Validation of Fatty Acid Synthase as an Antiviral Drug Target

The ability of CMV and herpes simplex virus 1 (HSV-1) to replicate was determined in the presence versus absence of the fatty acid synthase inhibitor C75. Note that C75, unlike, cerulenin, does not directly inhibit protein palmitoylation. Treatment with 5-10 µM C75 resulted in a greater than 100-fold decrease in titers of both CMV and HSV-1. These results validated fatty acid synthase, as distinct from protein palmitoylation, as an antiviral drug target.

6.6 Example 6

Identification of Acetyl CoA Carboxylase as an Antiviral Drug Target

The observation that both citrate lyase flux and fatty acid synthase flux were increased by CMV infection of human fibroblasts implied, based on flux balance constraints, that the intermediate flux of acetyl CoA carboxylase, must also be increased. This discovery of increased acetyl CoA carboxylase flux implied that acetyl CoA carboxylase constitutes an antiviral drug target.

6.7 Example 7

Determination of Enzyme Transcriptional Changes Induced by CMV Infection

At 4, 24, 48 or 72 h post mock or CMV infection, RNA was prepared using Trizol as recommended by the manufacturer (Invitrogen, Carlsbad, Calif.) and subsequently purified through an RNAeasy column (Quiagen, Valencia, Calif.). Fluorescent cRNA (Cy3 and Cy5) was prepared from all samples as well as a control RNA set (Human universal reference total RNA from Clontech) using the Low RNA Linear Amplification Kit (Agilent, Palo Alto, Calif.) as per manufacturer's instructions. Independent duplicate samples were dye reversed and sample cRNA was mixed with alternatively labeled (Cy3 vs Cy5) control cRNA and hybridized to Human Whole Genome Oligo Microarray as per the manufacturer's instructions (Agilent, Palo Alto, Calif.). Slides were scanned with an Agilent Scanner (Model #G2505B) and data was extracted with Feature Extractor 7.5 software. The resulting data files were imported into Genespring GX 7.3. The recorded fluorescent values were then subjected to the default per-chip and per-gene Lowness normalization with the cross-gene error model active. Only probe sets whose fluorescent signal was flagged as present or unknown were examined. Probe sets were further filtered by control channel expression; all probes with a cRNA control signal of less than 33 fluorescent units were not analyzed further. Analysis of variance (ANOVA) was then performed on the remaining probes using mock versus CMV-infection as the parameter and grouping the mock 24, 48, and 72 h time points together and the CMV-infected 24, 48, and 72 h time points together. The 4 h time points were left out as there was little change between mock and CMV-infected metabolic genes at this time point. The Welsh ANOVA analysis was performed using error model variances and Benjamini/Hochberg multiple testing correction with a value cutoff of 0.05. Known or suspected enzymes meeting this P value cutoff are listed in Table 6.

No significant effect was found for citrate lyase, acetyl CoA carboxylase, fatty acid synthase, glutaminase, glutamate dehydrogenase I or II, or glycerol-3-phosphate dehydrogenase. The failure to identify these enzymes based on transcriptional data (despite the increased flux through their reactions as proven by KFP) demonstrates the inadequacy of previous methods such as transcriptional profiling for identifying antiviral drug targets within metabolism. It thereby points to the novelty and unanticipated nature of the targets selected through the KFP approach described herein. Nevertheless, enzymes transcriptionally upregulated by the virus also constitute antiviral drug targets in their own right. Note that malic enzyme 1, an enzyme associated with generation of NADPH to drive lipid biosynthesis, was transcriptionally upregulated by the virus.

TABLE 6

CMV Infection Induces Transcriptional Changes in Host Metabolic Enzymes

| Metabolic Pathway | Enzyme | Change after infection |
|---|---|---|
| Fatty Acid Metabolism | methylmalonyl Coenzyme A mutase | − |
| | acetyl-Coenzyme A carboxylase beta | − |
| | acyl-Coenzyme A oxidase 2, branched chain | − |
| | putative acyl-CoA dehydrogenase | − |
| | acyl-Coenzyme A dehydrogenase, short/branched chain | + |
| | putative acyl-CoA dehydrogenase | − |
| | xenobiotic/medium-chain fatty acid:CoA ligase | + |
| | enoyl Coenzyme A hydratase domain containing 3 | + |
| | phospholipid scramblase 1 | + |
| | phospholipid scramblase 2 | − |
| | phospholipid scramblase 4 | − |
| | fatty acid desaturase 1 | − |
| | CPT-Carnitine Palmatoyl transferase | + |
| | fatty acid binding protein 5 (psoriasis-associated) | + |
| | fatty acid binding protein 5 (psoriasis-associated) | + |
| | fatty acid binding protein 5 (psoriasis-associated) | + |
| | fatty acid binding protein 5 (psoriasis-associated) | + |
| | fatty acid binding protein 3, muscle and heart (mammary-derived growth inhibitor) | − |

TABLE 6-continued

CMV Infection Induces Transcriptional Changes in Host Metabolic Enzymes

| Metabolic Pathway | Enzyme | Change after infection |
|---|---|---|
| Glucose Transport | GLUT4 | + |
| Glycolysis | glucose phosphate isomerase | + |
| | triosephosphate isomerase 1 | + |
| | phosphoglycerate kinase 1 | + |
| | enolase 1, (alpha) | + |
| | pyruvate kinase, muscle | − |
| TCA | aconitase 2, mitochondrial | + |
| | isocitrate dehydrogenase 3 (NAD+) alpha | + |
| | succinate-CoA ligase, alpha subunit | + |
| | succinate dehydrogenase, subunit A | + |
| | malate dehydrogenase 2, NAD (mitochondrial) | + |
| | malic enzyme 1, NADP(+)- dependent, cytosolic | + |
| Proton ATPase | F0 complex, subunit b, isoform 1 | + |
| | F0 complex, subunit c (subunit 9) isoform 3 | + |
| | F0 complex, subunit c (subunit 9), isoforms 1 | + |
| | F0 complex, subunit e | + |
| | F0 complex, subunit F6 | + |
| | F0 complex, subunit g | + |
| | F1 complex, alpha subunit, isoform 1 | + |
| | F1 complex, beta polypeptide | + |
| | F1 complex, epsilon subunit | + |
| | F1 complex, O subunit | + |
| Misc | lactate dehydrogenase B | + |
| | dicarbonyl/L-xylulose reductase | + |
| | hydroxyprostaglandin dehydrogenase 15-(NAD) | − |
| | ribulose-5-phosphate-3-epimerase | + |

6.8 Example 8

Compounds Inhibit Viral Replication of HSV And HCMV

These examples demonstrate the effectiveness of a fatty acid synthase inhibitor, i.e., C75, trans-4-carboxy-5-octyl-3-methylene-butyrolactone, and a carnitine palmitoyl transferase 1 (CPT-1) inhibitor, i.e., Etomoxir, in reducing viral replication of HSV and/or HCMV.

6.8.1 C75 Inhibits Herpes Simplex Virus (HSV) Viral Replication

Primary fibroblasts (MRC-5 cells) were grown in DMEM (high glucose) containing 7.5% FBS. Twenty-four hours prior to infection, cells were serum starved by incubation in DMEM (without serum). Subsequently, the cells were infected at a multiplicity of 5.0 plaque forming units (PFU) per cell in the presence of C75 (5 µg/ml) or an equivalent amount of carrier (DMSO). After 2 hours of viral adsorption at 37° C., the viral inoculums were aspirated and the cells were washed once with low pH sodium citrate buffer (40 mM sodium citrate, 10 mM KCl, 135 mM NaCl, pH 3.0) to inactivate unbound virus and then once with PBS buffer before adding growth medium containing C75 (5 µg/ml) or an equivalent amount of carrier. Infected fibroblast cultures were harvested 48 hours post infection and viral titer was determined by standard plaque assay on Vero cells. As shown in FIG. 4, C75 reduced viral replication by more than 2 logs.

6.8.2 C75 Inhibits Human Cytomegalovirus (HCMV) Viral Replication

Primary fibroblasts (MRC-5 cells) were grown in DMEM (high glucose) containing 7.5% FBS and infected at a multiplicity of 3.0 plaque forming units per cell in the presence of C75 (10 µg/ml) or an equivalent amount of carrier (DMSO). After 2 hours of viral adsorption at 37° C., the viral inoculums were aspirated and the cells were washed once with low pH sodium citrate buffer (40 mM sodium citrate, 10 mM KCl, 135 mM NaCl, pH 3.0) to inactivate unbound virus and then once with PBS buffer before adding growth medium containing C75 (10 µg/ml) or an equivalent amount of carrier. Infected fibroblast cultures were harvested 72 hours post infection and viral titer was determined by standard plaque assay on MRC-5 cells. As shown in FIG. 5, C75 reduced viral replication by more than 3 logs.

6.8.3 Etomoxir Inhibits HCMV Viral Replication

Etomoxir, an inhibitor of carnitine palmitoyl transferase 1 (CPT-1), has antiviral activity against HCMV in an in vitro viral replication assay. Primary fibroblasts were serum starved for 24 hours prior to infection with HCMV (AD 169, multiplicity of infection of 1.0) in the presence of Etomoxir (5 µM) or an equivalent amount of carrier (DMSO). Infected fibroblast cultures were harvested 96 hours post infection and viral titer was determined by standard plaque assay. As shown in FIG. 6, Etomoxir reduced viral replication by more than 1 log.

6.9 Example 9

Figure 7:
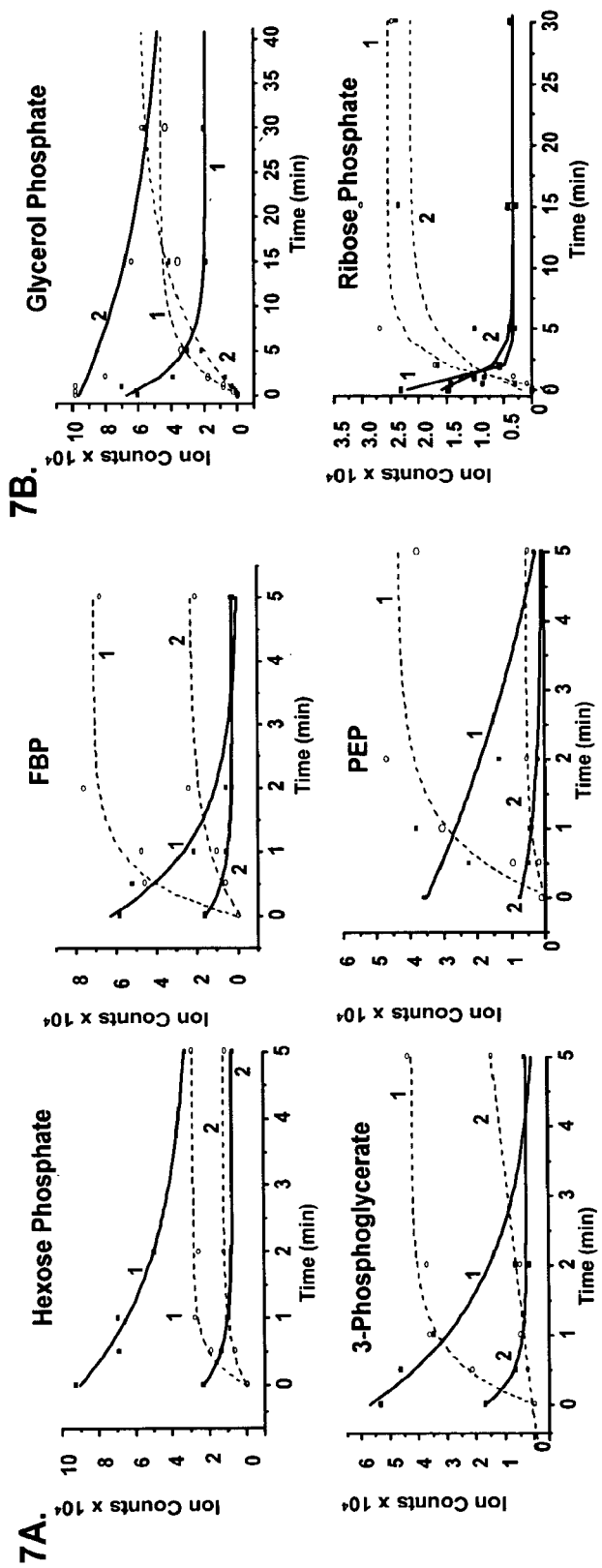

Modulation of Metabolic Flux by CMV 6.9.1 CMV Infection Directs Metabolic Flux of Glycolytic and Related Compounds FIG. 7 shows the labeling kinetics of (A) glycolytic (in order of pathway occurrence) and (B) related compounds in mock-infected versus CMV-infected human fibroblasts. Labeling was conducted using uniformly $^{13}$C-glucose, with the switch from unlabeled to uniformly labeled glucose occurring at t=0 min. Results for the virally-infected cells are labeled with "1" and for the mock-infected cells labeled with "2". The solid squares indicate the levels of unlabeled compounds (uniformly $^{12}$C), which fall after the isotope-switch. The open circles indicate the levels of partially or fully $^{13}$C-labeled compounds, which rise after the isotope switch. For each of the compounds shown in this figure, the primary form of the labeled compound involved complete labeling (uniformly $^{13}$C). The more rapid drop in the unlabeled forms and rise of the labeled forms (for the compounds with the exception of ribose phosphate) indicates faster glycolytic flux and glycerol phosphate flux in the infected cells.

6.9.2 CMV Infection Directs Metabolic Flux of Nucleotide Triphosphates and their Precursor PRPP FIG. 8 shows the labeling kinetics of nucleotide triphosphates and their precursor PRPP in mock-infected versus CMV-infected human fibroblasts. Labeling was conducted using uniformly $^{13}$C-glucose, with the switch from unlabeled to uniformly labeled glucose occurring at t=0 min. Results for the virally-infected cells are labeled with "1", and for the mock-infected cells labeled with "2". The solid squares indicate the levels of unlabeled compounds (uniformly $^{12}$C), which fall after the isotope-switch. The open circles indicate the levels of partially or fully $^{13}$C-labeled compounds, which rise after the isotope switch. For PRPP, the primary form of the labeled compound involved complete labeling (uniformly $^{13}$C). For ATP and UTP, the ribose moiety was generally completely labeled, whereas the base moiety was often not. The more rapid drop in the unlabeled forms and rise of the labeled forms indicates faster nucleotide biosynthetic flux in the infected cells.

Figure 9:
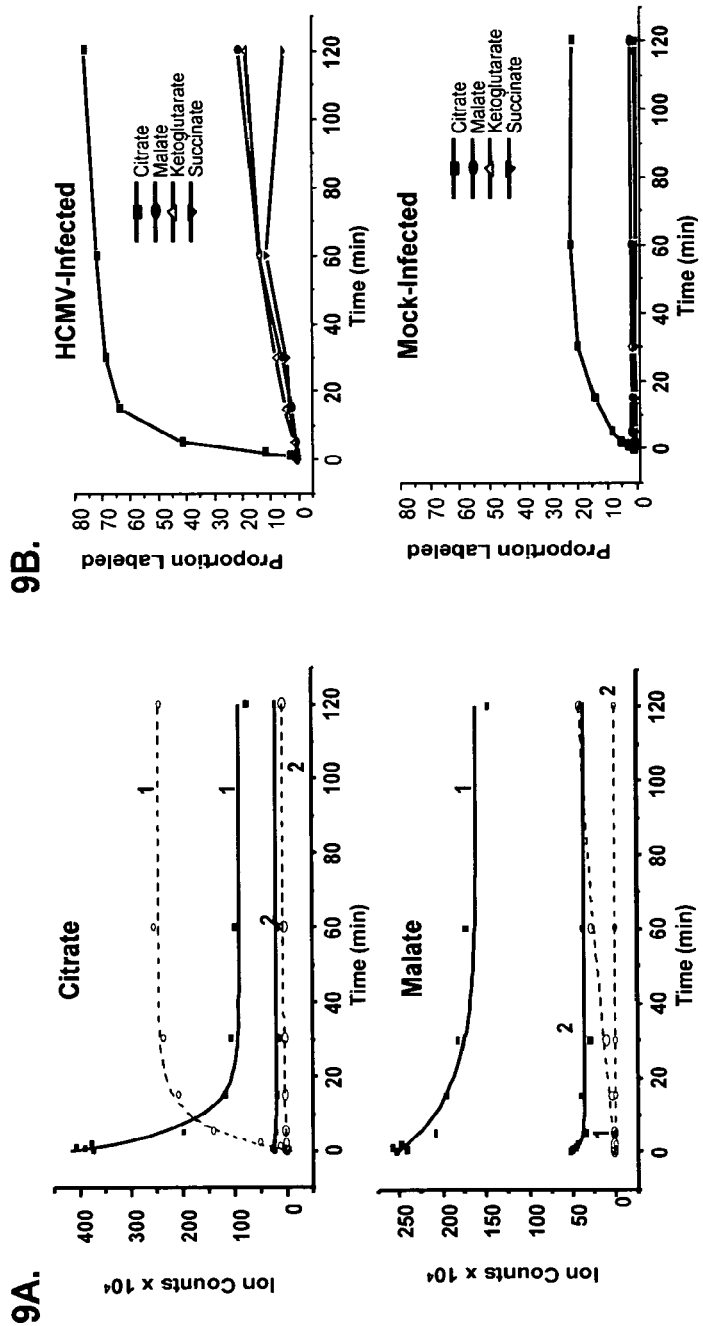

6.9.3 Cmv Infection Directs Metabolic Flux of TCA Cycle Compounds: Glucose Labeling FIG. 9 shows (A) the labeling kinetics of TCA cycle compounds and (B) the fractional labeling of these compounds (proportional labeled=[amount labeled]/[amount labeled+amount fully unlabeled]). Results are for mock-infected versus CMV-infected human fibroblasts. Labeling was conducted using uniformly $^{13}$C-glucose, with the switch from unlabeled to uniformly labeled glucose occurring at t=0 min. In part (A), results for the virally-infected cells are labeled with "1", and for the mock-infected cells labeled with "2". Again in part (A), the solid squares indicate the levels of unlabeled compounds (uniformly $^{12}$C), which fall after the isotope-switch and the open circles indicate the levels of malate and citrate containing $2\times^{13}$C atoms (the dominate labeled forms), which rise after the isotope switch. The more rapid drop in the unlabeled forms and rise of the labeled forms indicates faster TCA cycle flux in the infected cells. The most striking finding, however, is that citrate labeling greatly exceeds malate labeling, pointing to citrate being used substantially for de novo fatty acid biosynthesis (via citrate lyase and AcCoA carboxylase).

Figure 10:
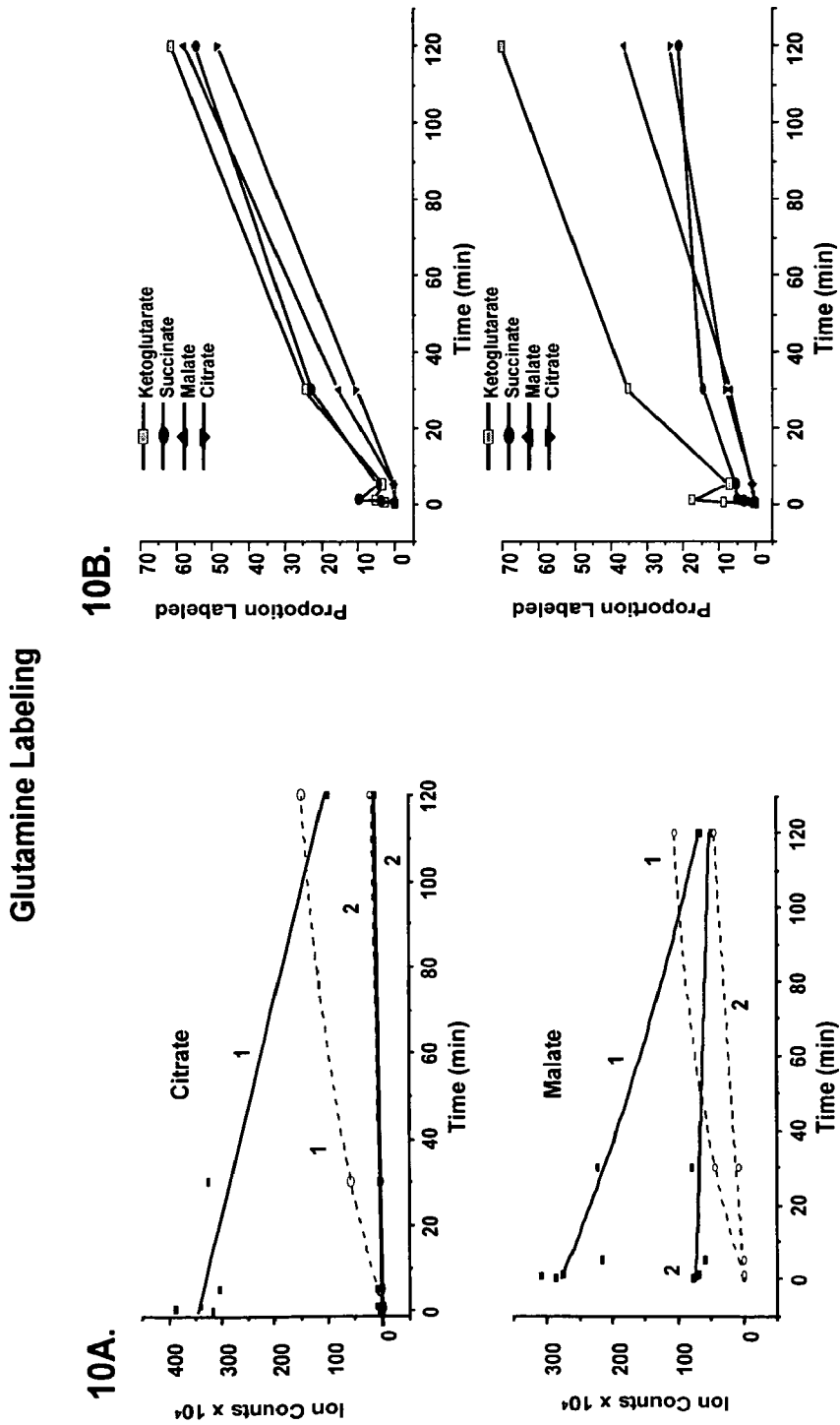

6.9.4 CMV Infection Directs Metabolic Flux of TCA Cycle Compounds: Glutamine Labeling FIG. 10 shows (A) the labeling kinetics of TCA cycle compounds and (B) the fractional labeling of these compounds (proportional labeled=[amount labeled]/[amount labeled+amount fully unlabeled]). Results are for mock-infected versus CMV-infected human fibroblasts. Labeling was conducted using uniformly $^{13}$C-glutamine, with the switch from unlabeled to uniformly labeled glutamine occurring at t=0 min. In part (A), results for the virally-infected cells are labeled with "1", and for the mock-infected cells labeled with "2". Again in part (A), the solid squares indicate the levels of unlabeled compounds (uniformly $^{12}$C), which fall after the isotope-switch and the open circles indicate the levels of partially or fully labeled compounds, which rise after the isotope switch. The more rapid drop in the unlabeled forms and rise of the labeled forms indicates faster TCA cycle flux in the infected cells. The labeling kinetics of citrate and malate (with malate labeling occurring slightly more rapidly than citrate labeling), in combination with the results on the preceding page (regarding glucose labeling of these compounds) indicate that glutamine, not glucose, is the primary fuel driving the TCA cycle clockwise from ketoglutarate to oxaloacetate.

6.9.5 Schematic of Central Carbon Metabolic Flows in CMV Infected Cells

FIG. 11 shows a schematic of central carbon metabolic flows in virally infected cells (data from CMV was used to create the diagram, but the diagram should apply to all fast-growing enveloped viruses), with glucose and metabolites formed from it shown in shading, and glutamine and metabolites formed from it shown without shading. Citrate receives carbon from both glutamine and glucose, but it is the glucose carbons which drive lipid biosynthesis.

6.10 Example 10

Integrated Metabolomic and Fluxomic Analysis of Cellular Response to Viral Infection FIG. 12 provides an overview of the integrated metabolomic and fluxomic analysis of cellular response to viral infection, including, e.g., goals, methods to measure metabolites and flux, analysis of whether viral infection disrupt metabolic homeostasis, determination of whether transcription is involved, analysis of how viral infection affect glycolysis (with respect to flux and concentration of relevant metabolites). The data presented herein indicate that viral infection may up-regulate glycolysis to drive lipid biosynthesis. Thus, blocking lipid biosynthesis induced by viral infection may inhibit viral replication.

6.11 Example 11

Dose Response of C75 and TOFA in Inhibition of HCMV Replication

Primary fibroblasts (MRC-5 cells) were grown in DMEM (high glucose) containing 10% FBS and infected at a multiplicity of 3.0 plaque forming units per cell. The HCMV used was wild-type virus with the exception that it carried a green fluorescent protein reporter to facilitate determination of viral titers. Infection was allowed to proceed for 1.5 hours at 37° C. After this, viral inoculums were aspirated and the cells were washed once with low pH sodium citrate buffer to inactivate unbound virus and virus particles remaining on the cell surface and then once with PBS buffer before adding fresh DMEM+10% FBS containing the indicated concentration of C75 or TOFA or an equivalent carrier (DMSO). Infected fibroblast cultures were harvested 72 hours post infection by collection of both cellular and supernatant materials and viral titer was determined by standard plaque assay (with plaques fluorescing green) on MRC-5 cells. As shown in FIG. 13, 10 µg/mL of both agents was adequate to produce a roughly one-log decrease in viral replication, with higher drug concentrations having yet more profound effects. Error bars in FIG. 13 show the standard deviation of duplicate measurements.

6.12 Example 12

Dose Response of TOFA in Inhibition of HCMV Replication

Primary fibroblasts (MRC-5 cells) were grown in DMEM (high glucose) containing 10% FBS and infected at a multiplicity of 3.0 plaque forming units per cell. The HCMV used was wild-type virus with the exception that it carried a green fluorescent protein reporter to facilitate determination of viral titers. Infection was allowed to proceed for 1.5 hours at 37° C. After this, viral inoculums were aspirated and the cells were washed once with PBS buffer before adding fresh DMEM+10% FBS containing the indicated concentration of TOFA or an equivalent carrier (DMSO). Infected fibroblast cultures were harvested 72 hours post infection by collection only of released virus (found in supernatant) and viral titer was determined by standard plaque assay (with plaques fluorescing green) on MRC-5 cells. As shown in FIG. 14, 20 µg/mL of TOFA produced a roughly two-log decrease in viral replication, with higher drug concentrations having yet more profound effects. Error bars in FIG. 14 show the standard deviation of duplicate measurements.

6.13 Example 13

Effect of C75 and TOFA on Replication of HCMV and Influenza A Virus

For growth of HCMV, MRC-5 fibroblasts (obtained from ATCC) were cultured in Dulbecco's modified Eagle medium (DMEM) containing 7.5% fetal calf serum and 4.5 g/L glucose. Infection with human cytomegalovirus was carried out with BADwt, which is derived from a bacterial artificial chromosome (BAC) clone of the AD169 strain of HCMV (see Giaever et al., *Nature* 418, 387 (Jul. 25, 2002)). The BAC was inserted into the genome of HCMV without deletion of any viral sequence and was excised by a co-transfected CRE recombinase that mediates recombination at the loxP sites, which flank the BAC, leaving just the loxP site in the viral clone. This clone has been tested in a diversity of assays and has always displayed a wild-type AD169 phenotype. Viral titers were determined by standard plaque assay on MRC-5 cells.

For growth of influenza A, Madin-darby canine kidney epithelial Cells (MDCK cells) were obtained from the ATCC and were cultured in DMEM containing 7.5% fetal calf serum and 4.5 g/L glucose. MDCK cells were infected with the A/WSN/33 Influenza strain (ATCC) in DMEM containing 0.2% BSA, 0.01% $CaCl_2$, 0.01% $MgCl_2$, 1 µg/ml trypsin (Worthington) and 0.1% FBS. Viral titers were determined by standard plaque assay on MDCK cells.

FIGS. 15A-B show the effect of TOFA (10 µg/mL), C75 (10 µg/mL) versus carrier only (DMSO) on replication of (A) HCMV (MOI=3.0) and (B) influenza A (MOI=0.1). In these assays, C75 or TOFA (10 µg/mL) was added simultaneously to addition of the virus to the host cells. Infection with HCMV proceeded for 96 hours and virions were then collected and counted by plaque assay (FIG. 15A). For influenza A, infection proceeded for 24 hours prior to collection and virions and their counting by plaque assay (FIG. 15B). FIG. 15A shows the production of infectious HCMV virions ninety-six hours after high multiplicity of infection (MOI=3.0) in the presence of carrier, TOFA (10 ug/mL) or C75 (10 ug/ml) (mean±standard error). FIG. 15B shows the production of infectious influenza A virions 24 hrs after infection (MOI=0.1) in the presence of carrier, TOFA (10 ug/mL) or C75 (10 ug/ml) (mean±standard error). As shown in FIGS. 15A-B, 10 µg/mL TOFA caused a greater than 1000-fold decrease in HCMV replication, and a greater than 1000-fold decrease in influenza A replication. 10 µg/mL C75 caused a greater than 100-fold decrease in HCMV replication and a greater than 10-fold effect decrease in influenza A replication.

6.14 Example 14

Integration of Experimentation and Computation to Obtain Quantitative Metabolite Concentration and Flux Estimates in Uninfected Versus Virally Infected Cells The present example builds upon the ability to collect a diversity of types of data regarding metabolite concentrations and isotope labeling patterns in uninfected and virally infected cells using methods described herein, and using analytical technologies including mass spectrometry and nuclear magnetic resonance spectroscopy. It begins by describing an exemplary computational framework, and then describes integration of data into the framework and the results that are obtained for HCMV infection. The general experimental and computational scheme can be used to investigate more and/or different elements in metabolism, as well as other host cells and viruses.

An ordinary differential equation (ODE) model of central carbon metabolism was constructed, based upon the diagram shown in FIG. 16, consisting of 68 differential equations, written so as to maintain flux balance. Equations of the model described the rates of loss of unlabeled forms of metabolites (and the creation of particular labeled forms) upon feeding of U-$^{13}$C-glucose or U-$^{13}$C glutamine medium. Separate equations were used to describe the glucose and glutamine labeling cases, although the fluxes were assumed to be identical in both instances. The labeled forms included explicitly in the model are citrate (with 2, 3, 4, or 5 $^{13}$C-atoms each treated separately), ketoglutarate and glutamate (with 1, 2, 3, or 4 $^{13}$C-atoms each treated separately), and malate, oxaloacetate, and aspartate (with 1, 2, or 3 $^{13}$C-atoms each treated separately). As glucose feeding yields more informative partial labeling of TCA components than glutamine feeding, the explicit treatment of partially labeled forms was limited to glucose feeding in the present example, although inclusion of glutamine labeling is also possible. Reactions between partially labeled forms were determined according to known action of relevant enzymes (Table 10).

The model consisted of 20 parameters: 12 intracellular fluxes, 2 nutrient uptake rates, 2 excretion rates, and 4 intracellular concentrations that were not directly experimentally measured herein (glucose, glutamine, and oxaloacetate, and the portion of the hexose-phosphate pool segregated from glycolysis). Additional intracellular fluxes shown in FIG. 11 reduced to linear combinations of the 16 fluxes described above.

Parameters (fluxes and unmeasured concentrations) were identified by a global inversion algorithm that seeks to find parameter values that minimize the difference between the experimental observations and simulated results, as measured by a cost function. The minimization is based on a genetic algorithm (GA) implemented in "GAlib," genetic algorithm package written by Matthew Wall at the Massachusetts Institute of Technology (Wall, 1995; Feng and Rabitz, Biophys. J. 86:1270-1281 (March, 2004)). Search ranges for each parameter (Table 11) were selected based on prior literature knowledge and initial searches using expansive ranges. The same search ranges were used for both the mock and viral models.

The GA operates by a mechanism similar to natural selection. First, a population of parameter sets was randomly generated. Each parameter set was then used to generate simulated results by integration of the system of ODEs using a stiff Gear integrator (See, e.g., Hindmarsh, A. C., and L. R. Petzold, "Algorithms and Software for Ordinary Differential Equations and Differential-Algebraic Equations," *Computers in Physics*, 9, (1995), pp. 34-41 and 148-155, also available as Lawrence Livermore National Lab Technical Report UCRL-JC-116619, April 1994). A fitness score was assigned to the parameter set based on how well the output data matched the laboratory data. The parameter sets that the best fit the lab data (50%) were then retained, and the remaining ones were replaced by the following mating process: pairs of parameter sets were chosen stochastically, based on their fitness score, to give pairs of offspring parameter sets (members of the next generation), such that each parameter value in the first offspring had a 56% chance of coming from the first parent, a 24% chance of coming from the second parent, and a 20% chance of receiving a random parameter value from the predetermined search range ("mutation"). The process then iterated.

The scoring function evaluated the agreement between laboratory results and the simulated data on the following dimensions: (1) the kinetic flux profiling data for U-$^{13}$C-glucose feeding; (2) the kinetic flux profiling data for U-$^{13}$C-glutamine feeding; (3) the measured uptake rates of glutamine and glucose; (4) the measured excretion rates of lactate, alanine, and glutamate; (5) the fraction of lactate with 1 versus 2 labeled carbons at steady state after 1,2-$^{13}$C-glucose feeding; and (6) the fraction of TCA intermediates labeled at steady state after 3-$^{13}$C-glucose feeding. In addition, a prohibitive cost was placed on fluxes that are known to be unidirectional taking on a negative value (although all parameter search ranges were limited to positive values, some fluxes were not themselves entered as parameters, but instead calculated as the difference between two or more parameterized fluxes based on flux balance constraints). Additional constraints were placed to limit drains on metabolism to physiologically reasonable rates: consumption of glucose-1-phosphate (into, e.g., glycoproteins or glycogen) was limited to 20% of the glycolytic rate, and consumption of amino acids was limited to 2 nmols protein/(plate of cells×h) (this limit was based on direct measurement of net changes in protein biomass during viral infection; specific amino acid rates were then estimated based on the fractional occurrence of the specific amino acid in total protein).

The functional forms of each of these components are listed in Table 12. The general approach was to apply a cost penalty only when the simulated results fell outside of the 95% confidence limits (+2 standard error, SE) of the experimental data. This was achieved by, for each experimental measurement, assessing whether the simulated data fell within the 95% confidence limits (in which case the score=1) or outside these limits (in which case the score=absolute magnitude of deviation/2 SE).

For kinetic flux profiling experiments, the SE used in the above formula was the average SE across all experimental time points for the given metabolite. This averaging of errors was performed in order to account for the small sample number. To prevent over fitting of low abundance species, a minimum error of 0.02 nmoles was set for all species. Error estimates for other experiments were set directly from experimental replicates. Metabolites for which dynamic labeling data were unavailable were eliminated from the scoring function. In the case of metabolites for which the model contained multiple species with the same number of labeled carbons, their concentrations were summed in order to compare to laboratory data.

The purpose of the experiments involving steady state TCA labeling after $3\text{-}^{13}\text{C}$-glucose feeding was to probe relative flux entering the TCA cycle through pyruvate carboxylase versus citrate synthase. The experimental data (specifically, for citrate and aspartate, which should be identical, and for malate) were compared to state-steady labeling fractions predicted for given flux parameters. These predictions were based on solving linear equations describing steady-state TCA activity. Mathematically, the fraction expected to be labeled for each species is described by the following:

$$PEP_{label}\left(f_3 + 2f_4 - f_5 - f_6 - lac_{out} - \frac{1.5}{6.75}X\right) + \quad \text{(Eqn 1)}$$

$$OAA_{label} = \frac{\left(f_6 + f_7 + Q_{in} - E_{out} - \frac{3.5}{6.75}X + f_{10}\right)Malate_{label}}{f_3 + 2f_4 - f_5 - f_6 - lac_{out} - \frac{1.5}{6.75} + f_6 + f_7 + Q_{in} - E_{out} - \frac{3.5}{6.75}X + f_{10}}$$

$$Malate_{label} = \frac{(10f_5 + f_{11} + f_{10})OAA_{label}}{f_6 + f_7 + Q_{in} - E_{out} - \frac{3.5}{6.75}X + f_{10} + f_{11}} \quad \text{(Eqn 2)}$$

$$Citrate_{label} = Asp_{label} = OAA_{label} \quad \text{(Eqn 3)}$$

Fluxes and X are as defined in FIG. 16. Labeling fractions are from experimental data.

A key challenge in accurately extracting fluxes is correctly determining flux through the first committed step of major pathways. This was facilitated, for most pathways, by specific data beyond the kinetic flux profiling data (e.g., for glycolysis, glucose uptake; for pentose phosphate pathway, $1,2\text{-}^{13}\text{C}$-glucose labeling in combination with glucose uptake). For entry into the TCA cycle, the $3\text{-}^{13}\text{C}$-glucose data gives fraction via pyruvate carboxylase versus citrate synthase; however, an absolute flux estimate is also needed. As total carbon entry to the TCA cycle cannot be directly measured, extra weight (4-fold additional) was placed on the 5 and 15 minute time points in decay of unlabeled citrate signal, as these time points were uniquely informative regarding overall flux from glucose into the TCA cycle. Other scoring functions and inclusion of other types of data are feasible and may have value in certain circumstances. The exact details here are merely exemplary.

The scores on each dimension were integrated by weighted averaging. Weights were such that each metabolite time profile (total 8 measurements) received equal weight to each other data input (e.g., glucose uptake measurement; $3\text{-}^{13}\text{C}$-glucose steady-state TCA labeling). The final score was normalized by the total number of inputs (and their weights), such that a perfect score is 1:

$$S = \frac{S_{KFP} + S_{flux} + S_{PPP} + S_{pyruvatecarboxylase} + S_{proteinout} + S_{hexoseout} + S_{citrate}}{\sum\limits_{data} weight} + S_{neg} \quad \text{(Eqn 4)}$$

The above approach was applied to the data types described above, collected as described herein for both mock-infected and HCMV-infected fibroblasts at 48 hpi.

Concentrations of metabolites were directly measured by HPLC-MS/MS. Fibroblasts in culture were fed U-$^{13}$C-glucose and U-$^{13}$C-glutamine for one week, and were HCMV- or mock-infected. Metabolism was quenched and metabolites extracted in 80:20 methanol:water at −80° C. at 48 hpi as described herein. Fractional labeling of endogenous metabolites is shown in Table 7. Similarly-labeled infected and mock-infected cells were also extracted with the solvent spiked with known concentrations of unlabeled forms of the metabolites shown in Table 8. The ratios of labeled peak heights (derived from the labeled cellular metabolites) to the unlabeled peak heights (derived largely from the spiked standards) were used, in combination with knowledge of the standard concentrations and extent of labeling of the cellular metabolites (Table 8), to determine the absolute quantities of metabolites in the infected and uninfected cells. Numerous cellular metabolites were markedly increased in concentration upon HCMV infection. The increases in certain of these metabolites (e.g., citrate) suggested enhancement of fatty acid biosynthesis-related processes by the virus.

Data from kinetic flux profiling (KFP) studies were converted to absolute concentrations of labeled and unlabeled species by multiplying the concentrations in Table 8 by the fractional labeling of the metabolites observed in the KFP work (e.g., absolute concentration unlabeled=absolute concentration of metabolite from Table 8×unlabeled peak magnitude from KFP study/(sum of peak magnitudes of unlabeled and all labeled forms from KFP study).

Using data from repeated KFP runs, repeated experiments determining metabolite influxes and effluxes, and repeated studies of $1,2\text{-}^{13}\text{C}$-glucose labeling and $3\text{-}^{13}\text{C}$-glucose labeling, intracellular metabolic fluxes were determined via GA as described above. A total of 20 independent GA runs were conducted for data from HCMV-infected cells, and a comparable number using data from mock-infected cells. The 100 flux sets best matching the experimental data were collected from these computational runs. The median, maximum, and minimum values for each flux in those sets are reported in Table 9. Notably, a diversity of fluxes are substantially upregulated by the virus. These include fluxes to nucleotide biosynthesis (pentose-P to ATP, GTP, UTP, or CTP; up ~2.5-fold) and to fatty acid synthesis (citrate to malonyl-CoA; up ~20-fold). The remarkable extent of up-regulation of the malonyl-CoA flux due to the virus indicated the unique value of therapeutics targeting fatty acid synthesis for the treatment of viral infection.

Thus, the fluxes presented in Tables 8 and 9 that are strongly up-regulated by the virus, may be desirable targets for anti-viral therapy, to the extent that these fluxes can be inhibited without adversely affecting uninfected cells. Inhibition of fatty acid synthesis and related processes (e.g., elongation, desaturation, cholesterol synthesis) is generally well tolerated in mammals. Accordingly, inhibition of these processes, alone or in combination, are valuable means of treating viral infections.

Table 7 below shows the percentage labeling of central carbon metabolites upon growth of fibroblasts in media containing $^{13}$C-glucose and $^{13}$C-glutamine. The fibroblasts were mock or HCMV infected for 48 hours.

TABLE 7

Percentage of Labeling of Central Carbon Metabolites
Metabolite penetrance of carbon-13
upon growth in $^{13}$C media

| Metabolite | Mock | HCMV |
|---|---|---|
| Glucose-6-Phosphate | 32% | 38% |
| Lactate | 94% | 98% |
| Glyceraldehyde-P | 33% | 40% |
| Ribose-P | 99% | 99% |
| DHAP | 100% | 100% |
| Pyruvate | 91% | 95% |
| Erythrose-4-P | 100% | 100% |
| Succinate | 50% | 93% |
| Malate | 96% | 99% |
| a-ketoglutarate | 83% | 97% |
| UDPG | 100% | 100% |
| 3-phospoglycerate | 96% | 98% |
| Citrate | 70% | 99% |
| FBP | 93% | 99% |
| Fumarate | 100% | 100% |

TABLE 7-continued

Percentage of Labeling of Central Carbon Metabolites
Metabolite penetrance of carbon-13
upon growth in $^{13}$C media

| Metabolite | Mock | HCMV |
|---|---|---|
| PEP | 100% | 100% |
| Aconitate | 56% | 95% |
| F6P + G1P | 39% | 49% |
| Ala | 12% | 32% |
| Glu | 99% | 99% |
| UTP | 95% | 100% |
| ATP | 97% | 99% |

Table 8 below shows the metabolite concentrations (nmols/10 cm plate of fibroblasts) in mock or HCMV infected fibroblast.

TABLE 8

Metabolite Flux Concentrations
Measured Metabolite Concentrations

| | Mock | HCMV |
|---|---|---|
| | (nMols/plate) | (nMols/plate) |
| G6P | 1.30 ± 0.11 | 4.28 ± 0.83 |
| Lactate | 175.51 ± 27.23 | 586.58 ± 96.79 |
| GAP | 0.70 ± 0.47 | −0.46 ± 0.04 |
| Pentose-P | 2.69 ± 0.97 | 1.92 ± 0.24 |
| DHAP | 8.90 ± 0.02 | 54.07 ± 8.02 |
| Pyruvate | 0.97 ± 0.07 | 1.59 ± 0.46 |
| Succinate | 0.39 ± 0.15 | 1.09 ± 0.11 |
| Malate | 2.33 ± 0.13 | 15.12 ± 2.10 |
| AKG | 0.65 ± 0.48 | 2.39 ± 1.62 |
| UDPG | 2.19 ± 0.18 | 8.20 ± 0.50 |
| 3PG | 0.26 ± 0.02 | 2.64 ± 1.09 |
| Citrate | 1.00 ± 0.14 | 15.15 ± 1.19 |
| FBP | 0.69 ± 0.18 | 6.63 ± 3.57 |
| Fumarate | 0.38 ± 0.02 | 3.34 ± 0.63 |
| PEP | 0.05 ± 0.01 | 0.57 ± 0.23 |
| Aconitate | 0.01 ± 0.00 | 0.17 ± 0.00 |
| Ala | 21.71 ± 0.75 | 133.41 ± 25.78 |
| Glu | 257.80 ± 11.17 | 1009.09 ± 73.58 |
| ATP | 103.29 ± 32.09 | 119.03 ± 4.35 |
| UTP | 29.28 ± 15.66 | 39.06 ± 12.21 |
| F6P + G1P | 0.83 ± 0.08 | 2.98 ± 0.84 |

Table 9 below shows the metabolic flux values of central carbon metabolism during mock and HCMV infection.

TABLE 9

Model Derived Metabolic Flux Values
Model Derived Flux values

| | | Mock (nMol/min/plate) | | | HCMV (nMol/min/plate) | | |
|---|---|---|---|---|---|---|---|
| Flux From: | Flux to: | Median | Min | Max | Median | Min | Max |
| extracellular | glucose | 12.057 | 10.174 | 13.412 | 29.427 | 28.265 | 30.113 |
| glucose | Hexose-P | 12.057 | 10.174 | 13.412 | 29.427 | 28.265 | 30.113 |
| Glycogen | Hexose-P | 2.413 | 1.357 | 3.090 | 2.645 | 2.427 | 3.090 |
| Hexose-P | macromolecules | 1.971 | 0.177 | 2.931 | 6.034 | 4.882 | 6.525 |
| Hexose-P | Pentose-P | 1.837 | 1.500 | 1.862 | 1.361 | 1.202 | 1.854 |
| Pentose-P | Hexose-P | 1.154 | 0.931 | 1.154 | 0.736 | 0.637 | 1.069 |
| Pentose-P | DHAP | 0.577 | 0.466 | 0.577 | 0.368 | 0.318 | 0.535 |
| Pentose-P | ATP | 0.034 | 0.019 | 0.051 | 0.078 | 0.072 | 0.089 |
| Pentose-P | GTP | 0.034 | 0.019 | 0.051 | 0.078 | 0.072 | 0.089 |
| Pentose-P | UTP | 0.022 | 0.002 | 0.035 | 0.047 | 0.038 | 0.052 |
| Pentose-P | CTP | 0.022 | 0.002 | 0.035 | 0.047 | 0.038 | 0.052 |
| Hexose-P | FBP | 11.847 | 11.334 | 12.201 | 25.728 | 24.344 | 26.158 |
| FBP | DHAP | 23.694 | 22.669 | 24.402 | 51.455 | 48.689 | 52.315 |
| DHAP | Lipids | 0.006 | 0.000 | 0.039 | 0.138 | 0.125 | 0.171 |
| DHAP | 3PG | 24.267 | 23.096 | 24.888 | 51.685 | 48.909 | 52.725 |

TABLE 9-continued

Model Derived Metabolic Flux Values
Model Derived Flux values

| | | Mock (nMol/min/plate) | | | HCMV (nMol/min/plate) | | |
|---|---|---|---|---|---|---|---|
| Flux From: | Flux to: | Median | Min | Max | Median | Min | Max |
| 3PG | PEP | 24.267 | 23.096 | 24.888 | 51.685 | 48.909 | 52.725 |
| PEP | Pyruvate | 24.267 | 23.096 | 24.888 | 51.685 | 48.909 | 52.725 |
| Pyruvate | Lactate | 23.497 | 22.274 | 23.824 | 46.538 | 43.713 | 47.754 |
| Lactate | extracellular | 23.497 | 22.274 | 23.824 | 46.538 | 43.713 | 47.754 |
| Pyruvate | extracellular | 0.370 | 0.350 | 0.375 | 0.732 | 0.688 | 0.751 |
| Pyruvate | Alanine | 0.286 | 0.261 | 0.515 | 0.656 | 0.588 | 0.709 |
| Alanine | extracellular | 0.122 | 0.116 | 0.124 | 0.242 | 0.227 | 0.248 |
| Alanine | protein | 0.164 | 0.139 | 0.391 | 0.414 | 0.354 | 0.461 |
| Pyruvate | Oxaloacetate | 0.089 | 0.070 | 0.134 | 0.387 | 0.357 | 0.440 |
| Pyruvate | AcCoA | 0.035 | 0.024 | 0.083 | 3.373 | 3.133 | 3.499 |
| non-pyruvate | AcCoA | 0.211 | 0.135 | 0.543 | 1.146 | 1.019 | 1.297 |
| AcCoA/OAA | Citrate | 0.245 | 0.161 | 0.625 | 4.511 | 4.166 | 4.797 |
| Citrate | Malonyl-CoA | 0.063 | 0.001 | 0.391 | 1.380 | 1.247 | 1.706 |
| Citrate | AKG | 0.166 | 0.027 | 0.280 | 3.130 | 2.743 | 3.381 |
| extracellular | glutamine | 5.728 | 5.035 | 6.592 | 8.492 | 7.112 | 9.572 |
| glutamine | protein | 0.110 | 0.092 | 0.261 | 0.276 | 0.236 | 0.307 |
| glutamine | glutamate | 5.627 | 4.916 | 6.343 | 8.214 | 6.876 | 9.310 |
| glutamate + proline | protein | 0.274 | 0.231 | 0.652 | 0.690 | 0.591 | 0.768 |
| glutamate | extracellular | 5.248 | 4.467 | 5.370 | 7.328 | 6.166 | 8.511 |
| glutamate | AKG | 151.164 | 10.152 | 8241.499 | 311.024 | 67.493 | 9862.987 |
| AKG | glutamate | 150.852 | 9.848 | 8241.263 | 310.696 | 67.102 | 9862.603 |
| AKG | Malate | 0.331 | 0.246 | 0.494 | 3.322 | 2.939 | 3.474 |
| Asp | Malate | 4.285 | 0.082 | 88.716 | 0.137 | 0.010 | 4.446 |
| OAA | Malate | 46.529 | 1.190 | 8329.913 | 682.370 | 15.149 | 9813.436 |
| OAA | Asp | 9.059 | 3.545 | 4372.567 | 11.601 | 6.803 | 8242.116 |
| Asp | OAA | 3.908 | 1.393 | 4325.138 | 10.814 | 6.252 | 8241.381 |

In Table 10 below, citrate, in the $3^{rd}$ column is produced from oxaloacetate (OAA) and acetyl-coenzyme A (AcCoA) listed in columns 1 and 2. Malonyl coenzyme A (MalCoA), in the $4^{th}$ column, and malate and OAA, in the 5th column, are produced from citrate in column 3 via citrate lyase. Ketoglutarate (KG) in the $6^{th}$ column is produced from citrate in column 3 via isocitrate dehydrogenase. Malate and OAA, in the $7^{th}$ column, are produced from ketoglutarate in column 6 via clockwise reactions of the TCA cycle. Numbers and Greek letters in the body of the table indicate positions of labeled carbons.

TABLE 11

Search Ranges for Model Parameters. (Fluxes are defined in FIG. 16.)

| Parameter | Minimum | Maximum |
|---|---|---|
| $F_0$ | $10^{1.5}$ | $10^{-1}$ |
| $F_1$ | $10^1$ | $10^{-1}$ |
| $F_2$ | $10^{-0.5}$ | $10^{0.3}$ |
| $F_3$ | $10^1$ | $10^{-2}$ |
| $F_4$ | $10^{1.6}$ | $10^{0.8}$ |

TABLE 10

Reactions Transferring $^{13}C$ Between Partially Labeled TCA Cycle Components.

| | | From OAA + AcCoA | | From citrate via citrate lyase | | From citrate via TCA cycle | From KG |
|---|---|---|---|---|---|---|---|
| OAA | AcCoA[a] | Citrate[b] | MalCoA[a] | Malate & OAA | KG | | Malate & OAA[c] |
| 1, 2 | — | 3, 6 | — | 1, 2 | 3 | | 2/3 |
| — | α, β | 1, 2 | α, β | — | 4, 5 | | 1, 2/3, 4 |
| 3, 4 | — | 4, 5 | — | 3, 4 | 1, 2 | | 1/4 |
| 1, 2 | α, β | 1, 2, 3, 6 | α, β | 1, 2 | 3, 4, 5 | | 1, 2, 3/2, 3, 4[d] |
| 3, 4 | α, β | 1, 2, 4, 5 | α, β | 3, 4 | 1, 2, 4, 5 | | 1, 3, 4/1, 2, 4[d] |
| 1, 2, 3[e] | — | 3, 4, 6 | — | 1, 2, 3 | 2, 3 | | 1, 2/3, 4 |
| 1, 2, 3[e] | α, β | 1, 2, 3, 4, 6 | α, β | 1, 2, 3 | 2, 3, 4, 5 | | 1, 2, 3, 4 |
| 1, 2, 3, 4 | — | 3, 4, 5, 6 | — | 1, 2, 3, 4 | 1, 2, 3 | | 1, 2/3, 4 |

[a]The α-carbon is designated as the one bonded to the sulfur of CoA, β is the carbon adjacent to α.
[b]We designate carbon 1 of citrate as the carboxylic acid originating from Acetyl-CoA. Carbons connected via the backbone linking it to the most distant carboxylic acid are numbered as 2, 3, 4, and (for the most distant carboxylic acid) 5. We refer to the carboxylic acid bonded to the carbon containing the alcohol as carbon 6.
[c]Due to scrambling of the label at succinate, malate and OAA produced from KG produce two different labeling patterns in a 1:1 ratio. Both are shown in this column, separated by a slash.
[d]These forms are assumed to accumulate in insignificant amounts over the length of time simulated, consistent with our experimental observations. Accordingly, products produced from them are not considered.
[e]This form of OAA is created by the reaction of labeled pyruvate and unlabeled carbonate via pyruvate carboxylase.

TABLE 11-continued

Search Ranges for Model Parameters. (Fluxes are defined in FIG. 16.)

| Parameter | Minimum | Maximum |
|---|---|---|
| $F_5$ | $10^0$ | $10^{-4}$ |
| $F_6$ | $10^1$ | $10^{-3}$ |
| $F_7$ | $10^{0.5}$ | $10^{-2.5}$ |
| $F_8$ | $10^4$ | $10^1$ |
| Partitioned Hexose-P | $10^{0.75}$ | $10^{0.75}$ |
| $F_{10}$ | $10^4$ | $10^0$ |
| $F_{11}$ | $10^2$ | $10^{-2}$ |
| $F_{12}$ | $10^4$ | $10^0$ |
| Glucose concentration | $10^{1.5}$ | $10^{-0.5}$ |
| OAA concentration | $10^{0.3}$ | $10^{-1.7}$ |
| Glutamine concentration | $10^3$ | $10^0$ |
| Glucose uptake (A) | $10^{1.75}$ | $10^{0.5}$ |
| Lactate excretion (B) | $10^{1.7}$ | $10^{1.3}$ |
| Glutamine uptake (C) | $10^{1.5}$ | $10^{0.5}$ |
| Glutamate excretion (D) | $10^{1.5}$ | $10^{0.5}$ |

TABLE 12

Functional Forms of the Components of the Scoring Function.

| Description | Equation | Variables |
|---|---|---|
| Kinetic flux profiling | $S_{KFP} = \sum_{i=1}^{N_{sp}} \sum_{t=1}^{N_t} \begin{cases} 1 : |M_{i,t}^{calc} - M_{i,t}^{lab}| \leq \varepsilon_{i,t} \\ \frac{|M_{i,t}^{calc} - M_{i,t}^{lab}|}{\varepsilon_i} : |M_{i,t}^{calc} - M_{i,t}^{lab}| > \varepsilon_{i,t} \end{cases}$ | $N_{sp}$ = Number of species (43, between both glucose and glutamine labeling) $N_t$ = Number of experimental time points (8 for both glucose and glutamine labeling) $M_{i,t}^{calc}$ = calculated value for the $i^{th}$ metabolite at the $t^{th}$ time point $X_{i,t}^{lab}$ = measured laboratory value for the $i^{th}$ metabolite at the $t^{th}$ time point $\varepsilon_i$ = average of 2 SE of the laboratory measurement for the $i^{th}$ metabolite across all time points |
| Uptake and excretion | $S_{flux} = 8 \times \sum_{1}^{4} \begin{cases} 1 : |F_i^{calc} - F_i^{lab}| \leq \varepsilon_i \\ \frac{|F_i^{calc} - F_i^{lab}|}{\varepsilon_i} : |F_i^{calc} - F_i^{lab}| > \varepsilon_i \end{cases}$ | 1: glucose uptake; 2: sum of lactate, alanine, and pyruvate excretion; 3: glutamine uptake; 4: glutamate excretion $F_i^{calc}$ = the calculated value for the $i^{th}$ flux $X_{i,t}^{lab}$ = the measured laboratory value for the $i^{th}$ flux $\varepsilon_i$ = 2 SE of the laboratory measurement for the $i^{th}$ flux |
| Glycolysis/ PPP ratio | $S_{PPP} = 8 \times \begin{cases} 1 : |R^{calc} - R^{lab}| \leq \varepsilon \\ \frac{|R^{calc} - R^{lab}|}{\varepsilon_i} : |R^{calc} - R^{lab}| > \varepsilon \end{cases}$ | $R^{cal} = \frac{3F_3}{F_3 + F_4}$ $R^{lab} = \frac{\text{lactate\_with\_1\_}^{13}\text{C\_atom}}{\text{lactate\_with\_1\_or\_2\_}^{13}\text{C\_atoms}}$ after 1,2-$^{13}$C-glucose feeding $\varepsilon$ = 2 SE of the laboratory measurement |
| Pyruvate carboxylase/ citrate synthase partitioning | $S_{pyruvatecarboxylase} = 8 \times \sum_{i=1}^{2} \begin{cases} 1 : |L_i^{calc} - L_i^{lab}| \leq \varepsilon_i \\ \frac{|L_i^{calc} - L_i^{lab}|}{\varepsilon_i} : |L_i^{calc} - L_i^{lab}| > \varepsilon_i \end{cases}$ | 1: average of citrate and aspartate labeling at steady state after 3-$^{13}$C-glucose feeding 2: malate labeling at steady state after 3-$^{13}$C-glucose feeding $L_i^{calc}$ = calculated value as per Eqn 1-3 $X_{i,t}^{lab}$ = measured laboratory value $\varepsilon_i$ = 2 SE of the $i^{th}$ laboratory measurement |
| Protein Synthesis | $S_{proteinout} = 8 \times \begin{cases} 1 : X - X_{max} \leq \varepsilon \\ \frac{X - X_{max}}{\varepsilon} : X - X_{max} > \varepsilon \end{cases}$ | $P^{lab}X$ as per FIG. 16 $P^{lab}X_{max}$ = 2 nmols/plate/h $\varepsilon$ = 1 nmols/plate/h |
| Hexose consumption | $S_{hexoseout} = 8 \times \begin{cases} 1 : G^{calc} - G^{max} \leq \varepsilon \\ \frac{G^{calc} - G^{max}}{\varepsilon} : G^{calc} - G^{max} > \varepsilon \end{cases}$ | $\frac{G^{max}}{G_{calc}} = 0.2 \times$ glucose uptake rate as FIG. 16 $\varepsilon = 0.02 \times$ glucose uptake rate |
| Citrate 5 and 15 min time points | $S_{cit} = 4 \times \sum_{i=1}^{2} \begin{cases} 1 : |M_i^{calc} - M_i^{lab}| \leq \varepsilon_i \\ \frac{|M_i^{calc} - M_i^{lab}|}{\varepsilon_i} : |M_i^{calc} - M_i^{lab}| > \varepsilon_i \end{cases}$ | 1: 5 min point after switch into U-$^{13}$C-glucose 2: 15 min point after switch into U-$^{13}$C-glucose Other symbols as per $S_{KFP}$ |

TABLE 12-continued

Functional Forms of the Components of the Scoring Function.

| Description | Equation | Variables |
|---|---|---|
| Penalty for negative fluxes | $S_{neg} = \sum_{i=1}^{5} \begin{Bmatrix} 0.5 : N_i^{calc} < 0 \\ 0 : N_i^{calc} \geq 0 \end{Bmatrix}$ | 1: glutamate → ketoglutarate<br>2: hexose phosphate efflux<br>3: assimilation of pentose phosphate into ATP<br>4: pyruvate → oxaloacetate<br>5: citrate → ketoglutarate<br>$N_i^{calc}$ = net flux |

6.15 Example 15

Inhibition of Hepatitis B Virus (HBV) Replication by ACC Inhibitors

As discussed in sections 5.4 and 5.5, a wide variety of assays can be employed to measure the potential therapeutic effect of a Compound on viral infection, including assay of individual viral processes, assay of the production of virus components, particles, or infectious progeny, assay of the spread of virus within cultured cells or animals, or assay of viral pathogenesis within an infected animal. HBV causes serious, life-threatening, chronic disease in humans. One, non-limiting example of an assay that could be performed to assess the effect of an ACC inhibitor on HBV replication follows. As noted in section 5.4, HepG2-2.2.15 (Sells et al., PNAS 84, 1005-9, 1987) is a stable cell line containing the HBV ayw strain genome. Compounds blocking any step of viral replication and release can be assayed in these cells (Korba & Milman, Antiviral Res. 15:217-28, 1991). The ACC inhibitor, e.g., TOFA, is added at various concentrations (1, 3, 10, 30, 90μ/ml) to HepG2-2.2.15 cell cultures maintained in serum-free medium or in medium containing serum. The medium with the ACC inhibitor is replaced every 24 hours, and media samples are removed after drug treatment for 24, 48, 72 or 96 hours and assayed for the presence of extracellular viral DNA by real-time quantitative PCR. A reduction in the amount extracellular viral DNA or a delay in its accumulation during the treatment period with the ACC inhibitor is indicative of anti-HBV activity. Uptake of neutral red dye is used to determine the relative level of toxicity in duplicate cultures at each time a sample is harvested. Lamivudine (3TC) is used as a positive assay control for inhibition of the production of extracellular HBV DNA (Korba & Gerin, Antivir. Res. 19:55-70, 1992). In an exemplary assay, lamivudine produces its typical anti-HBV effects. Carrier (DMSO) does not alter production of extracellular HBV DNA. TOFA at 3 μg/mL produces a small but statistically significant reduction in extracellular HBV DNA. TOFA at 10 μg/mL produces an ~10-fold reduction (range ~3 to ~30-fold) in production of extracellular HBV DNA. TOFA at 30 μg/mL markedly impairs production of extracellular HBV DNA, with a greater than 10-fold effect, reaching greater than 100-fold in some cases. TOFA at 90 μg/mL almost completely blocks production of extracellular HBV DNA but also negatively impacts some uninfected host cell lines.

6.16 Example 16

Inhibition of Hepatitis C Virus (HCV) Replication by ACC Inhibitors

As discussed in sections 5.4 and 5.5, a wide variety of assays can be employed to measure the potential therapeutic effect of a drug on viral infection, including assay of individual viral processes, assay of the production of virus components, particles, or infectious progeny, assay of the spread of virus within cultured cells or animals, or assay of viral pathogenesis within an infected animal. HCV causes serious, life-threatening, chronic disease in infected humans. HCV is a member of the Flavivirus family, and it packages a positive RNA strand (the sense of mRNA) into its virions. Many positive-strand RNA viruses have been shown to replicate their genomes at distinctive cellular membrane sites within infected cells (Sagan et al., Biochem. Cell Biol. 84, 67-79, 2006 and references therein), and could be expected to be sensitive to drugs that modulate lipid biosynthesis and composition within the cell. Of note, however, a positive-strand RNA virus has been tested (coxsackie B3 virus) and reported to be insensitive to the ACC inhibitor TOFA (Rassmann et al., Antiviral Res. 76, 150-8, 2007). TOFA has been reported to inhibit HCV replication to only a modest extent (about 3-fold) in Huh-7 cells containing an HCV replicon (Kapadia & Chisari, PNAS 102, 2561-6, 2004), a level of inhibition that does not suggest TOFA would provide a therapeutic effect in HCV disease. Importantly, however, only a single, low dose of TOFA (5 microg/ml) was tested. One, non-limiting example of an assay that could be performed to assess the effect of higher TOFA doses, which would more completely inhibit ACC activity, on HCV replication follows. As noted in section 5.4, Huh7 ET cells, which contain an HCV RNA replicon with a stable luciferase (LUC) reporter, can be used to assay for compounds with antiviral activity against HCV (Krieger et al. Virol., 2001, 75, 4614-24). The activity of the LUC reporter is directly proportional to HCV RNA levels, and positive control antiviral compounds behave comparably using either LUC or RNA endpoints. TOFA is added at various concentrations (1, 3, 10, 30, 90 μg/ml) to Huh7 ET cell cultures maintained in serum-free medium or in medium containing serum. The medium with drug is replaced every 24 hours, and cell extracts are prepared and LUC activity assayed at 24, 48, 72 and 96 hours after the initiation of TOFA treatment. Reduced LUC activity in drug-treated as compared to cells that do not receive drug is indicative of antiviral activity. A positive control, such as human interferon-alpha 2b, is employed to confirm that the LUC assay responds to inhibition of the HCV replicon; and uptake of neutral red dye is used to determine the relative level of toxicity in duplicate cultures at each time a sample is harvested. TOFA at 10 μg/mL results in an ~10-fold reduction in LUC activity, a greater effect than seen in prior literature which suggested that TOFA would not provide a therapeutic effect in HCV disease. TOFA at 30 μg/mL results in a marked reduction in LUC activity, reaching 100-fold or greater in some experiments. TOFA at 10 μg/mL or 30 μg/mL does not result in cellular uptake of neutral red dye, indicating the absence of host cell toxicity. Treatment with other ACC inhibitors at

6.17 Example 17

Inhibition of West Nile Virus (WNV) or Dengue Virus (DV) Replication by ACC Inhibitors As discussed in sections 5.4 and 5.5, a wide variety of assays can be employed to measure the potential therapeutic effect of a drug on viral infection, including assay of individual viral processes, assay of the production of virus components, particles, or infectious progeny, assay of the spread of virus within cultured cells or animals, or assay of viral pathogenesis within an infected animal. WNV and DV, members of the Flavivirus family of positive-strand RNA viruses, cause severe disease in humans. One, non-limiting example of an assay that could be performed to assess the effect of an ACC inhibitor on WNV and DV replication follows. The ACC inhibitor TOFA is added at various concentrations (1, 3, 10, 30, 90 microg/ml) to WNV-infected or DV-infected Vero monkey kidney cell cultures maintained in serum-free medium or in medium containing serum. The medium with drug is replaced every 24 hours, and media samples are removed after drug treatment for 24, 48, 72 or 96 hours and assayed for the presence of extracellular viral RNA by real-time quantitative RT-PCR. A reduction in the amount extracellular viral RNA or a delay in the accumulation of extracellular viral RNA during the drug treatment period will be indicative of anti-WNV or anti-DV activity. Uptake of neutral red dye is used to determine the relative level of toxicity in duplicate cultures at each time a sample is harvested. TOFA at 20 µg/mL results in ~10-fold reduction, sometime greater, in accumulation of extracellular viral RNA. The accumulation of extracellular viral RNA is also delay compared to untreated cells.

6.18 Example 18

Inhibition of Human Immunodeficiency Virus Type 1 (HIV-1) by ACC Inhibitors As discussed in sections 5.4 and 5.5, a wide variety of assays can be employed to measure the potential therapeutic effect of a drug on viral infection, including assay of individual viral processes, assay of the production of virus components, particles, or infectious progeny, assay of the spread of virus within cultured cells or animals, or assay of viral pathogenesis within an infected animal. HIV-1 is the causative agent of the AIDS syndrome. One, non-limiting example of an assay that could be performed to assess the effect of an ACC inhibitor on HIV-1 replication follows. The ACC inhibitor TOFA is added at various concentrations (1, 3, 10, 30, 90 µg/ml) to HIV-1 strain IIIB (Popovic et al., *Science* 224, 497-500, 1984)-infected C8166 cells, a lymphoid cell line permissive for replication of HIV-1 (Somasundaran & Robinson, *Science* 242, 1554-7, 1988), maintained in medium containing 10% fetal calf serum. The medium with drug is replaced every 24 hours, and media samples are removed after drug treatment for 24, 48, 72, 96, 120 or 144 hours and assayed for the presence of extracellular viral RNA by real-time quantitative RT-PCR or for the presence of HIV p24 antigen by ELISA. A reduction in the amount extracellular viral RNA or p24 antigen or a delay in the accumulation of extracellular viral RNA or p24 during the drug treatment period will be indicative of anti-HIV-1 activity. Uptake of neutral red dye is used to determine the relative level of toxicity in duplicate cultures at each time a sample is harvested.

6.19 Example 19

Inhibition of Poxvirus and Vaccinia Virus (VV) Replication by ACC Inhibitors As discussed in sections 5.4 and 5.5, a wide variety of assays can be employed to measure the potential therapeutic effect of a drug on viral infection, including assay of individual viral processes, assay of the production of virus components, particles, or infectious progeny, assay of the spread of virus within cultured cells or animals, or assay of viral pathogenesis within an infected animal. VV is a member of the orthopox family of viruses, and it is studied as a model for variola virus (small pox virus). Although natural variola infections have been eliminated by vaccination, concerns have arisen about the use of variola as a biological weapon. One, non-limiting example of an assay that could be performed to assess the effect of an ACC inhibitor on VV replication, which would be predictive of its effect on variola replication, follows. The ACC inhibitor TOFA is added at various concentrations (1, 3, 10, 30, 90 microg/ml) to VV (modified vaccinia virus Ankara strain)-infected BHK-21 hamster kidney cell cultures maintained in serum-free medium or in medium containing serum. The medium with drug is replaced every 24 hours; and media plus cell samples are removed after drug treatment for 24, 48, 72 or 96 hours, cells are lysed in the media and lysates are assayed for the presence of viral DNA by real-time quantitative RT-PCR. A reduction in the amount of viral DNA during the drug treatment period or a delay in the accumulation of viral DNA will be indicative of anti-VV activity. Uptake of neutral red dye is used to determine the relative level of toxicity in duplicate cultures at each time a sample is harvested.

6.20 Example 20

Enhanced Inhibition of HCMV, Influenza A, HIV-1, HBV or HCV by a Combination of an ACC Inhibitor and an HMG-CoA Reductase Inhibitor Statins are competitive inhibitors of 3-hydroxy-3-methylglutary-CoA (HMG-CoA) reductase, which functions in the synthesis of mevalonate and cholesterol. Various statins have been found to partially interfere with the replication cycles of specific viruses. For example, Fluvastatin can partially inhibit HCMV replication in cultured endothelial cells (Potena et al., Circulation 109, 532-6, 2004); Lovastatin can partially inhibit replication of HCV replicons in Huh-7 cells (Kapadia and Chisari, PNAS 102, 2561-6, 2005; Sagan et al., Biochem. Cell Biol. 84, 67-79, 2006). Lovastatin does not block production of infectious HBV particles, but inhibits secretion of the HBV surface antigen, HBsAg, which is produced in large amounts in infected individuals and might influence HBV pathogenesis (Lin et al., Virology 314, 253-60, 2003). Intriguingly, although the potential for statins to impair influenza A virus growth and/or replication has not been previously suggested, patients on statins appear less likely to develop respiratory disease or die during influenza epidemics (Hak et al. 16*th European Congress of Clinical Microbiology and Infectious Diseases*, Nice, abstr.; http://www.blackwellpublishing.com/eccmid16/abstract.asp?id=49073, 2006). As described above, one embodiment of the present invention involves use of HMG-CoA reductase inhibitors to treat influenza A and other viruses that had not been previously recognized to be sensitive to statin therapy. The present example concerns the combined use of statins and ACC inhibitors to antagonize viral replication and spread. There are multiple rationales for such a combination. Non-limiting examples of such rationales include the following. Both enzymes function in lipid metabolism: ACC catalyzes the rate-limiting reaction for fatty acid synthesis, and HMG-CoA reductase catalyzes a key step in the mevalonate pathway. Both enzymes utilize acetyl-CoA as a substrate for lipid synthesis, both enzymes play key roles in pathways that produce lipids for modification of proteins (e.g., ACC:palmitoylation; HMG-CoA reductase:prenylation), and both enzymes are phosphorylated and inactivated by AMP-activated protein kinase. Non-limiting examples of assays that could be performed to assess the effect of a combination of an ACC inhibitor plus statin on HCMV, influenza A, HBV, or HCV replication follow. Assays for TOFA-mediated antiviral activity using HCMV-infected human fibroblasts, influenza A-infected MDCK cells, HIV-1-infected C8166 cells, HBV-producing HepG2-2.2.15 cells, and Huh7 ET cells that contain an HCV RNA replicon have been described in herein. In each assay, various concentrations of TOFA can be combined with various concentrations of lovastatin and assayed for their effect on virus replication. Lovastatin must be activated before use in this assay by conversion from its lactone prodrug form to its active form. In one preferred embodiment, a physiological concentration of lovastatin will be held constant as the dose of TOFA is increased. Control cultures are treated with no drug, lovastatin alone or the various concentrations of TOFA alone. Samples are taken at 24, 48, 72 and 96 hours after initiation of drug treatment. The antiviral effect of lovastatin plus each concentration of TOFA is then compared to the activity of lovastatin alone or the various concentrations of TOFA alone. Uptake of neutral red dye can be used to determine the relative level of toxicity in duplicate cultures at each time a sample is harvested. The concentration of TOFA required to reduce viral growth and/or replication by 10-fold is reduced by 2-fold, and sometime more, by the presence of a therapeutically effective concentration of the active form of lovastatin.

6.21 Example 21

Enhanced Inhibition of HCMV Replication by a Combination of an ACC Inhibitor and a Cox Inhibitor Cyclooxygenase 2 (Cox2) is strongly induced after infection of fibroblasts with HCMV, prostaglandin E2 synthesis is strongly induced after infection, and supraphysiological concentrations of Cox inhibitors can inhibit HCMV replication (Zhu et al., PNAS 99, 3932-3937, 2002). Cox inhibitors block the production of prostaglandins, lipid compounds that serve as second messages and elicit a wide range of physiological responses in cells and tissues. A non-limiting example of a rationale for a beneficial antiviral effect of a combination of ACC inhibitor and Cox inhibitor follows from the fact that eicosinoids are synthesized by COX action on arachidonic acid. Arachidonic acid is derived from diet and fatty acid synthesis, and, consequently, its availability is influenced by ACC activity. A non-limiting example of an assay that can be performed to assess the effect of a combination of an ACC inhibitor plus Cox inhibitor on HCMV replication follows. Assays for TOFA-mediated antiviral activity using HCMV-infected human fibroblasts have been described in this document. In each assay, various concentrations of TOFA can be combined with various concentrations of indomethacin and assayed for their effect on virus replication. In one preferred embodiment, a physiological concentration of indomethacin is held constant as the dose of TOFA is increased. Control cultures are treated with no drug, indomethacin alone or the various concentrations of TOFA alone. Samples are taken at 24, 48, 72 and 96 hours after initiation of drug treatment. The antiviral effect of indomethacin plus each concentration of TOFA is then compared to the activity of indomethacin alone or the various concentrations of TOFA alone. Uptake of neutral red dye is used to determine the relative level of toxicity in duplicate cultures at each time a sample is harvested. In the presence of a pharmacologically acceptable concentration of indomethacin (equal to the typical plasma level achieved in patients using the FDA-approved dosage of the drug for the treatment of pain), the concentration of TOFA required to produce a 10-fold reduction in HCMV replication is markedly reduced, from ~10 µg/mL to ≤5 µg/mL. At 10 µg/mL of TOFA, the magnitude of the therapeutic effect is increased from ~10-fold in the absence of indomethacin to ~100-fold in its presence. The combined use of TOFA and indomethacin does not increase host cell toxicity as measured by the neutral red dye assay. Similar results are obtained for other Cox2 inhibitors and other ACC inhibitors.

6.22 Example 22

Effect of TOFA on the Metabolome of HCMV-Infected Fibroblasts Indicates Effective Blockade of Acetyl-CoA Carboxylase (ACC) and Thereby Fatty Acid Synthesis Primary fibroblasts (MRC-5 cells) were grown in DMEM (high glucose) containing 7.5% FBS and infected at a multiplicity of 3.0 plaque forming units per cell (control cells were mock infected instead of virally infected). After 2 hours of viral adsorption at 37° C., the viral inoculums were aspirated and the cells were washed once with low pH sodium citrate buffer (40 mM sodium citrate, 10 mM KCl, 135 mM NACl, pH 3.0) to inactivate unbound virus and then once with PBS buffer. Mock-infected cells were then returned to growth medium (+DMSO vehicle) for 48 h. HCMV-infected cells were returned to either growth medium (+DMSO vehicle) or to growth medium containing TOFA (20 µg/mL) for 48 h. At the end of the 48 h culture period (the time of maximal viral replication in the HCMV-infected cells), growth medium was aspirated and replaced immediately with −70° C. 80:20 methanol:water. Metabolites were extracted into the methanol:water and samples analyzed by LC-MS/MS for a diversity of metabolites as described herein. Results for four highly informative intracellular metabolites are shown in FIG. 17.

Malonyl-CoA is the direct product of ACC. Its concentration is increased ~8-fold by HCMV infection. Addition of TOFA to HCMV-infected cells reduced malonyl-CoA concentration to below the limit of detection. This large drop in malonyl-CoA is consistent with effective inhibition of ACC by TOFA.

Fatty acid synthase uses malonlyl-CoA as a substrate to add two-carbon units to growing fatty acid chains. Once added, these two carbon units must be reduced twice with NADPH. As shown in Figure A, NADPH levels in HCMV-infected cells were below those in mock-infected cells, consistent with rapid NADPH consumption by virally-induced fatty acid biosynthesis. TOFA markedly increased the NADPH concentration in the virally infected cells, consistent with its indirectly blocking NADPH consumption by stopping fatty acid biosynthesis upstream of the NADPH-consuming reductive steps. $NADP^+$ levels followed the opposite trend from NADPH, rising during viral infection and falling with TOFA treatment, consistent with TOFA's indirectly blocking the utilization of NADPH (and thereby generation of $NADP^+$).

Citrate plays a role in shuttling two-carbon units from the mitochondrion to the cytosol, where they are used by ACC. Citrate concentrations were increased by HCMV-infection, consistent with HCMV increasing activity of the citrate shuttle. TOFA, by impairing ACC and thereby citrate utilization, resulted in yet greater increases in citrate concentration in the virally infected cells.

6.23 Example 23

Structurally Diverse Acetyl-coA Carboxylase (ACC) Inhibitors Block HCMV Replication Dual ACC1/ACC2 inhibitors such as CP-640186 (see structure VI in section 5.2), CP-610431 (see structure VI in section 5.2), and Compound 8a (see structure XXIVb in section 5.2) presented in FIG. 18 can also inhibit HCMV replication by approximately 50 fold, 50 fold, and 100 fold, respectively. See, e.g., Harwood et al., J. Biol. Chem. 2003 278:37099-37111; Clark et al., Bioorg. Med. Chem. Lett. 2007 17:1961-1965; and Gu et al., J. Med. Chem. 2006 49:3770-3773.

Selective ACC2 inhibitors, such as Compound 7a (see structure XXIVa3 in section 5.2), Compound 8b (see structure XXIVb in section 5.2), and Compound 9c (see structure XXIVa1 in section 5.2) presented in FIG. 19 can also inhibit HCMV replication by approximately 40 fold, 100 fold, and greater than 100 fold, respectively. See, e.g., Harwood et al., J. Biol. Chem. 2003 278:37099-37111; Clark et al., Bioorg. Med. Chem. Lett. 2007 17:1961-1965; and Gu et al., J. Med. Chem. 2006 49:3770-3773.

FIG. 20 shows a bar graph of the actual results obtained with ACC inhibitors Compounds 7b, 8a, 8b and 9c presented in FIGS. 18 and 19. The raw data used to generate the bar graph in FIG. 20 are shown in Table 13.

TABLE 13

ACC inhibitors block viral replication in HCMV-infected cells

| Treatment | Dose (µg/mL) | Viral yield (pfu/mL) | Fold inhibition of viral replication |
|---|---|---|---|
| Media control | n/a | 3100000 | 0.0 |
| Vehicle control (DMSO 2 µL/mL) | n/a | 3700000 | −0.2 |
| Compound 7b | 10 | 76000 | 39.8 |
| Compound 7b | 3.3 | 1500000 | 1.1 |
| Compound 7b | 1.1 | 1700000 | 0.8 |
| Compound 7b | 0.33 | 2300000 | 0.3 |
| Compound 7b | 0.11 | 4400000 | −0.3 |
| Compound 8a | 10 | 7700 | 401.6 |
| Compound 8a | 3.3 | 490000 | 5.3 |
| Compound 8a | 1.1 | 820000 | 2.8 |
| Compound 8a | 0.33 | 1700000 | 0.8 |
| Compound 8a | 0.11 | 2600000 | 0.2 |
| Compound 8b | 10 | 32000 | 95.9 |
| Compound 8b | 3.3 | 1200000 | 1.6 |
| Compound 8b | 1.1 | 1600000 | 0.9 |
| Compound 8b | 0.33 | 2100000 | 0.5 |
| Compound 8b | 0.11 | 2600000 | 0.2 |
| Compound 9c | 10 | 1400 | 2213.3 |
| Compound 9c | 3.3 | 1200000 | 1.6 |
| Compound 9c | 1.1 | 2000000 | 0.6 |
| Compound 9c | 0.33 | 2600000 | 0.2 |
| Compound 9c | 0.11 | 4200000 | −0.3 |

TABLE 14

Results from 2 viral replication inhibition experiments

| Treatment | Dose (µg/mL) | Viral yield (pfu/mL) | Fold inhibition of viral replication |
|---|---|---|---|
| Media control | n/a | 1450000 | 0.0 |
| Vehicle control (DMSO 6 µL/mL) | n/a | 480000 | 2.0 |
| Compound CP31 | 30 | 7700 | 187.3 |
| Compound CP86 | 30 | 16000 | 89.6 |
| Media control | n/a | 3300000 | 0.0 |
| Vehicle control (DMSO 6 µL/mL) | n/a | 1500000 | 1.2 |
| TOFA | 30 | 7700 | 427.6 |
| TOFA | 60 | 40 | 82499.0 |

Briefly, the experiments described in FIG. 20 and Tables 13 and 14 were carried out as follows. Primary fibroblasts (MRC-5 cells) were grown in DMEM (high glucose) containing 7.5% FBS and infected at a multiplicity of 3.0 plaque forming units per cell in the presence of ACC inhibitor or vehicle control (DMSO). After 2 hours of viral adsorption at 37° C., the viral inoculums were aspirated and the cells were washed once with low pH sodium citrate buffer (40 mM sodium citrate, 10 mM KCl, 135 mM NACl, pH 3.0) to inactivate unbound virus and then once with PBS buffer before adding growth medium containing ACC inhibitor or vehicle control. Infected fibroblast cultures were harvested 72 hours post infection and viral titer was determined by standard plaque assay on MRC-5 cells. As shown in Tables 13 and 14, all tested ACC inhibitors, including compounds specific to the ACC2 isozyme, were effective in blocking HCMV replication. In Table 13, all results were collected in a single experiment. In Table 14, results are from two independent experiments (separated by a blank line), with separate media control and vehicle control results reported for each experimental day.

The toxicity of the diverse ACC inhibitors on host cells was determined by visual inspection of cell lawns and neutral red viability assay. No evidence of toxicity was found for any of the inhibitors at the above-tested concentrations by neutral red assay. Visual inspection indicated no evidence of drug-induced alterations in cell morphology, except for the CP compounds, with CP31 (CP610431) having a somewhat greater effect than CP86 (CP640186) (neutral red assay for these compounds was indistinguishable from DMSO control at the tested concentrations).

6.24 Example 24

Identification of Metabolites Up-Regulated by HCMV Infection Using High Resolution Mass Spectrometry Another nonlimiting approach to finding metabolic pathways up-regulated by viral infection is based on unbiased high resolution mass spectrometry analysis. For example, such analysis was employed as described below.

Primary fibroblasts (MRC-5 cells) were grown to confluence in DMEM (high glucose) containing 7.5% FBS. The cells were then switched to DMEM (high glucose) without serum and maintained in culture for 3-5 days. Thereafter, the cells were infected at a multiplicity of 3.0 plaque forming units per cell (control cells were mock infected instead of virally infected). After 2 hours of viral adsorption at 37° C., the viral inoculums were aspirated and the cells were washed once with low pH sodium citrate buffer (40 mM sodium citrate, 10 mM KCl, 135 mM NaCl, pH 3.0) to inactivate unbound virus and then once with PBS buffer. Cells were then returned to DMEM (high glucose) and metabolome samples were collected at various time points by quenching and extraction in cold methanol:water as described herein. The resulting extracts were then analyzed by liquid chromatography-high mass-resolution mass spectrometry in full scan mode on an Orbitrap instrument (similar results can also be obtained using a TOF instrument). The resulting raw data were examined for LC-MS/MS peaks that increased markedly in viral infection. Such peaks indicate metabolites whose production is likely increased by the virus, and accordingly for which inhibition of their production pathway is likely to have antiviral efficacy. As presented in FIG. 21, one such peak was found at m/z 174. Analysis of the accurate mass identified a molecular formula of $C_6H_8NO_5$— which corresponded to the de-protonated molecular ion of $C_6H_9NO_5$. The formula $C_6H_9NO_5$ was found to match compounds including N-acetyl-aspartate, a derivative of aspartic acid formed by reaction of aspartate with acetyl-CoA (which also plays a key role in the fatty acid biosynthesis induced by HCMV). The identity as N-acetyl-aspartate was confirmed based on LC retention time match to purified standard and MS/MS analysis. N-acetyl-aspartate is the second most abundant compound in the brain (after glutamate) and plays a key role in fluid balance and energy metabolism. N-acetyl-aspartate may play a role in the cytomegaly induced by HCMV and inhibition of its production might impair this process and HCMV replication. N-acetyl-aspartate might also play an essential role in 2-carbon transfer reactions or energy metabolism in HCMV-infected cells.

6.25 Example 25

Inhibitors of Phosphoinositide 3-Kinases as Antiviral Agents 6.25.1 Inhibition of HCMV Replication by 3-Methyladenine, a Class III Phosphoinositide 3-Kinase.

Phosphatidic acid is comprised of a glycerol backbone, with a saturated fatty acid bonded to carbon-1, an unsaturated fatty acid bonded to carbon-2, and a phosphate group bonded to carbon-3. Phosphatidylinositol [PI] is a phospholipid that in essence consists of a phosphatidic acid backbone, linked via its phosphate group to inositol. Importantly, the production of PI is dependent on fatty acid availability.

Phosphoinositide 3-kinases [PI(3)Ks] are a family of kinases that phosphorylate the inositol ring of phosphoinositides. Class III PI(3)K, also known as human vaculolar protein sorting 34 [hVps34], phosphorylates the 3'-hydroxyl group on the inositol ring of PI to produce PI(3)P.

3-methyladenine inhibits class III PI(3)K (Petiot et al., J Biol Chem 275, 992-998, 2000), and it also inhibits the replication of human cytomegalovirus (FIG. 22). This observation indicates that the enzyme, class III PI(3)K, and its product, PI(3)P, are important for the efficient production of human cytomegalovirus progeny. Thus, inhibitors of class III PI(3)K can be novel antiviral agents. In specific embodiments, a method of treating viral infection described herein comprises inhibiting a class III PI(3)K in a mammal suffering from a viral infection. A nonlimiting example of a Compound that inhibits a class III PI(3)K is 3-methyladenine.

The results presented in FIG. 22 were obtained from an experiment described briefly as follows: fibroblasts were infected with HCMV at a multiplicity of 0.01 pfu/cell in the presence or absence of 3-methyladenine (5 mM), and medium was assayed for infectious virus at the indicated times after infection.

6.25.2 Inhibition of Viral Replication by Sequestering Inositol-Containing Chemical Species.

PI(3)P regulates multiple intracellular processes, including membrane trafficking, through interactions with proteins containing FYVE (SEQ ID NO: 55) domains. A polypeptide containing tandem FYVE (SEQ ID NO: 55) domains (Gillooly et al., EMBO J. 19:4577-4588, 2000) was introduced into cells and was found to block the formation of cytoplasmic vesicles, which are produced during the late phase of human cytomegalovirus infection. The appearance of these vesicles correlates with the production of infectious virus. Without being bound by any particular theory, one interpretation is that the FYVE domains are sequestering PI(3)P, preventing its interaction with proteins and the formation of vesicles required for the formation of infectious virus. This observation indicates that agents that bind to, and thereby block the normal function of, PI(3)P may act as novel antiviral agents. Thus, in certain embodiments, a method of treating viral infection described herein involves sequestering PI(3)P. Non-limiting examples of PI(3)P sequestering agents include peptides or chemically modified peptides containing one or more FYVE (SEQ ID NO: 55) motifs, including peptides that containing the FYVE (SEQ ID NO: 55) motif with a cell transduction domain such as the cell-membrane transduction domain of the human immunodeficiency virus type 1 (HIV-1) Tat protein (amino acid sequence: YGRKKRRQRRR (SEQ ID NO: 56) or a subset or extended version thereof). Other cell-membrane transduction domains are well known in the art and can be combined with the FYVE (SEQ ID NO: 55) sequence (including multiple repeats or variants thereof) or with other PI(3)P-sequestering sequence(s) in the design of antiviral therapeutics. The FYVE (SEQ ID NO: 55) motif (with or without a cell membrane transduction domain) can be combined with other chemical moieties to increase the plasma half-life of the FYVE (SEQ ID NO: 55) motif (e.g., by protecting the FYVE (SEQ ID NO: 55) motif from hydrolysis by circulating and/or cellular proteases).

Those skilled in the art will recognize or be able to ascertain, using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The present invention is further described by the embodiments set forth in the following numbered subparagraphs.

1. A method for treating or preventing viral infection in a mammal, comprising administering to a mammalian subject in need thereof a therapeutically effective amount of one or more compound or prodrug thereof, or pharmaceutically acceptable salt of said compound or prodrug, wherein the compound is:

i) a compound of Formula I:

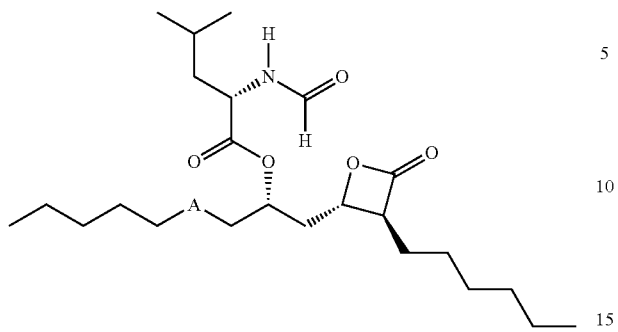

as defined in paragraphs [00101]-[00108] hereinabove;
ii) a compound of Formula II:

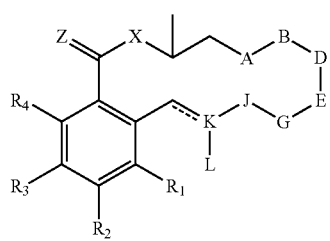

as defined in paragraphs [00109]-[00125] hereinabove;
iii) a compound of Formula III:

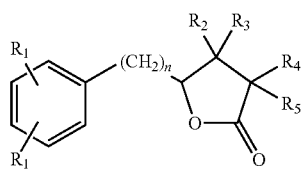

as defined in paragraphs [00126]-[00132] hereinabove;
iv) a compound of Formula IV:

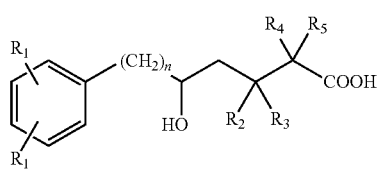

as defined in paragraphs [00123]-[00141] hereinabove;
v) a compound of Formula V:

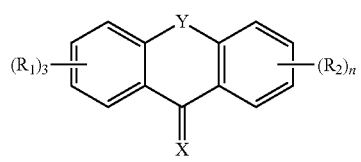

as defined in paragraphs [00142]-[00151] hereinabove;

vi) a compound of Formula VI:

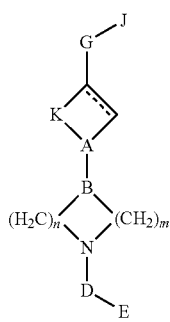

as defined in paragraphs [00152]-[00166] hereinabove;
vii) a compound of Formula VII:

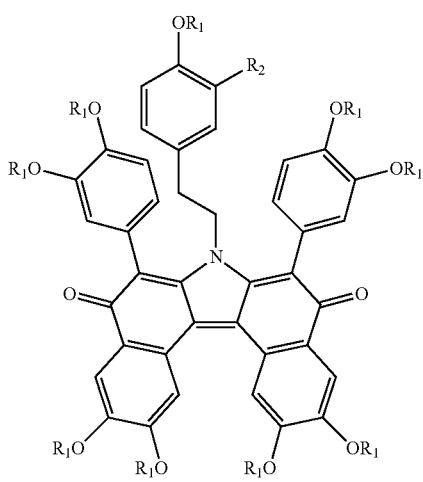

as defined in paragraphs [00167]-[00179] hereinabove;
viii) a compound of Formula VIII:

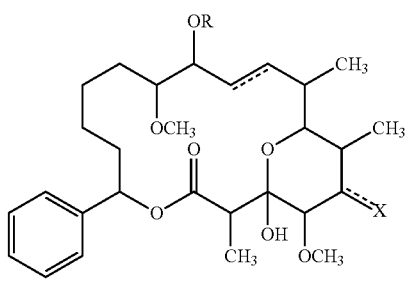

as defined in paragraphs [00180]-[00195] hereinabove;
ix) a compound of Formula IX:

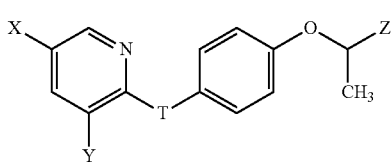

as defined in paragraphs [00196]-[00210] hereinabove;

x) a compound of Formula X:

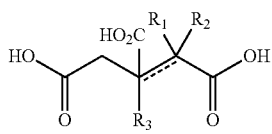

as defined in paragraphs [00211]-[00229] hereinabove;
xi) a compound of Formula XI:

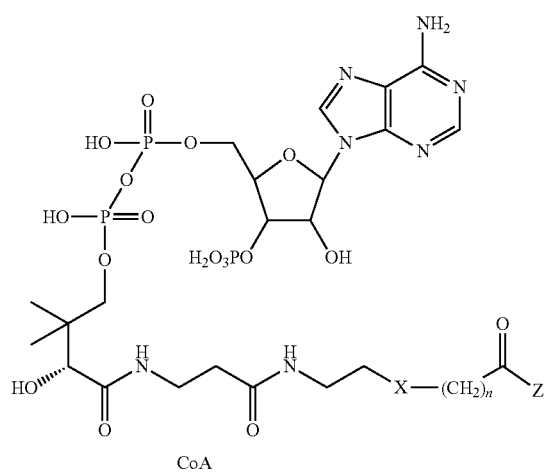

as defined in paragraphs [00230]-[00240] hereinabove;
xii) a compound of Formula XII:

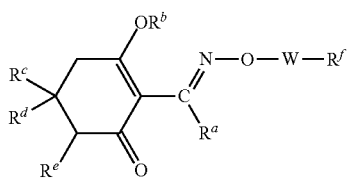

as defined in paragraphs [00241]-[00258] hereinabove;
xiii) a compound of Formula XIII:

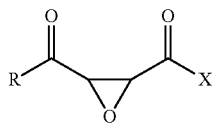

as defined in paragraphs [00259]-[00269] hereinabove;
xiv) a compound of Formula XIV:

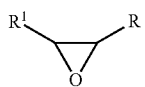

as defined in paragraphs [00270]-[00279] hereinabove;

xv) a compound of Formula XV:

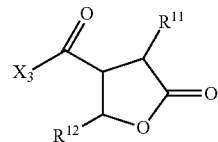

as defined in paragraphs [00280]-[00289] hereinabove;
xvi) a compound of Formula XVI:

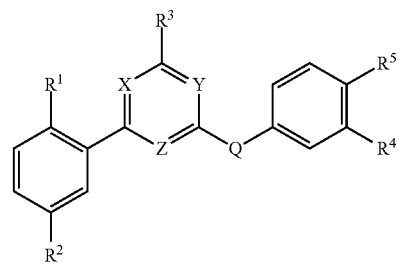

as defined in paragraphs [00290]-[00299] hereinabove;
xvii) a compound of Formula XVII:

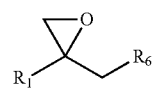

as defined in paragraphs [00300]-[00307] hereinabove;
xviii) a compound of Formula XVIII:

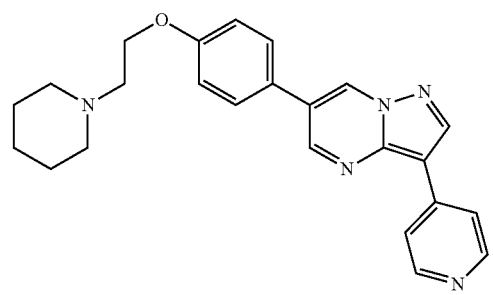 [SMILES: c1cc(-c2cnn3cc(-c4ccc(OCCN5CCCCC5)cc4)cnc23)ccn1]

as defined in paragraphs [00308]-[00309] hereinabove;
xix) a compound of Formula XIX:

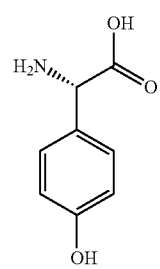

as defined in paragraphs [00310]-[00311] hereinabove;

xx) a compound of Formula XX:

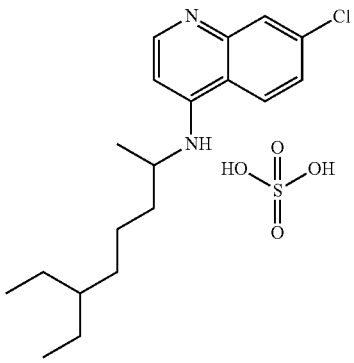

as defined in paragraphs [00312]-[00313] hereinabove;
xxi) a compound of Formula XXI:

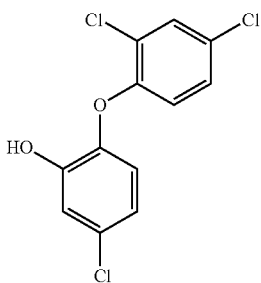 [SMILES: Oc1cc(Cl)ccc1Oc1ccc(Cl)cc1Cl]

as defined in paragraphs [00314]-[00315] hereinabove;
xxii) a compound of Formula XXII:

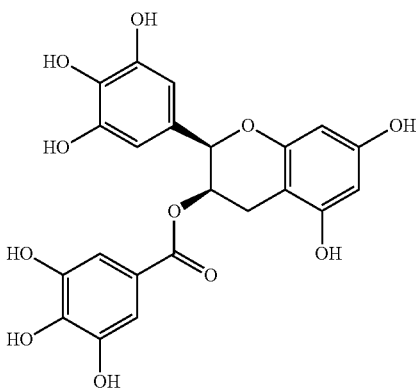 [SMILES: O=C(O[C@@H]1Cc2c(O)cc(O)cc2O[C@@H]1c1cc(O)c(O)c(O)c1)c1cc(O)c(O)c(O)c1]

as defined in paragraphs [00316]-[00323] hereinabove;
xxiii) a compound of Formula XXIII:

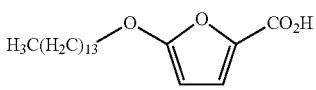

as defined in paragraph [00452] hereinabove;

xxiv) a compound of Formula XXIV:

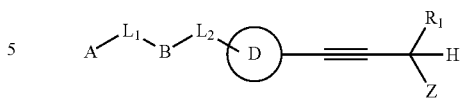

as defined in paragraphs [00324]-[00348] hereinabove;
xxv) a compound of Formula XXV:

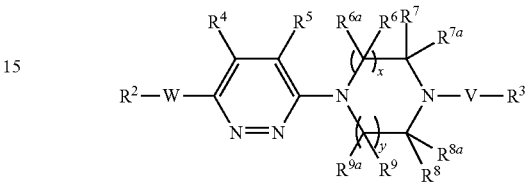

as defined in paragraphs [00349]-[00364] hereinabove;
xxvi) a compound of Formula XXVI:

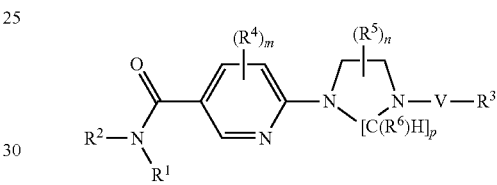

as defined in paragraphs [00365]-[00380] hereinabove;
xxvii) a compound of Formula XXVII:

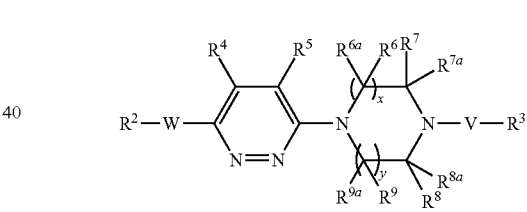

as defined in paragraphs [00381]-[00395] hereinabove;
xxviii) a compound of Formula XXVIII:

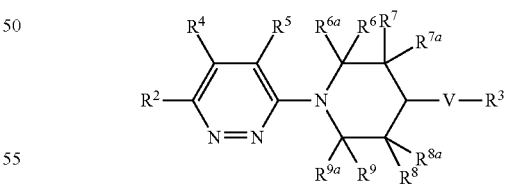

as defined in paragraphs [00396]-[00421] hereinabove;
xxix) a compound of Formula XXIX:

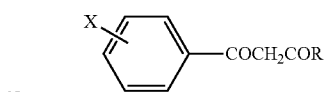

as defined in paragraphs [00422]-[00425] hereinabove;

xxx) a compound of Formula XXX:

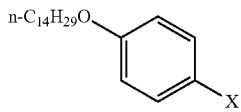

as defined in paragraphs [00426]-[00428] hereinabove;
xxxi) a compound of Formula XXXI:

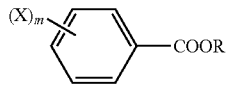

as defined in paragraphs [00429]-[00433] hereinabove;
xxxii) a compound of Formula XXXII:

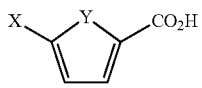

as defined in paragraphs [00447]-[00451] hereinabove;
xxxiii) a compound of Formula XXXIII:

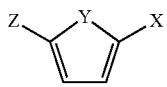

as defined in paragraphs [00434]-[00446] and [00452]-[00453] hereinabove;
xxxiv) a compound of Formula XXXIV:

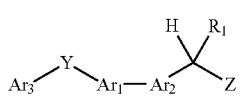

as defined in paragraphs [00454]-[00477] hereinabove;
xxxv) a compound of Formula XXXV:

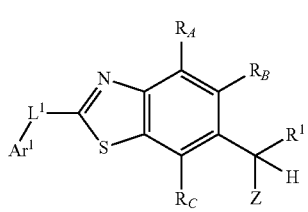

as defined in paragraphs [00478]-[00492] hereinabove;
xxxvi) a compound of Formula XXXVI:

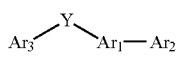

as defined in paragraphs [00493]-[00521] hereinabove;

xxxvii) a compound of Formula XXXVII:

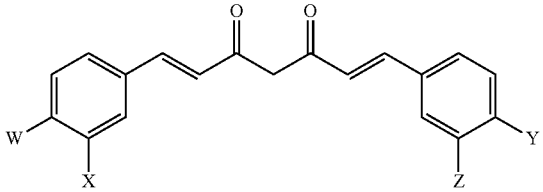

as defined in paragraphs [00522]-[00529] hereinabove;
xxxviii) a compound of Formula XXXVIII:

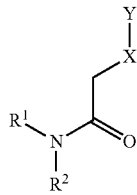

as defined in paragraphs [00530]-[00548] hereinabove;
xxxix) a compound of Formula XXXIX:

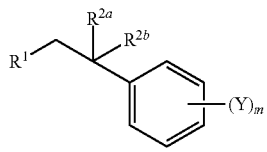

as defined in paragraphs [00549]-[00562] hereinabove;
xl) a compound of Formula XL:

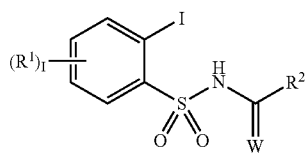

as defined in paragraphs [00563]-[00573] hereinabove;
xli) a compound of Formula XLI:

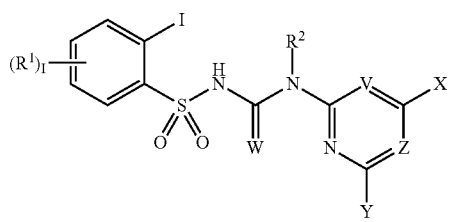

as defined in paragraphs [00574]-[00584] hereinabove;
xlii) a compound of Formula XLII:

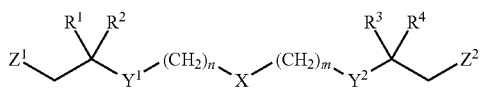

as defined in paragraphs [00585]-[00591] hereinabove;

xliii) a compound of Formula XLIII:

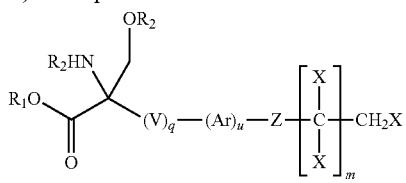

as defined in paragraphs [00592]-[00607] hereinabove;
xliv) a compound of Formula XLIV:

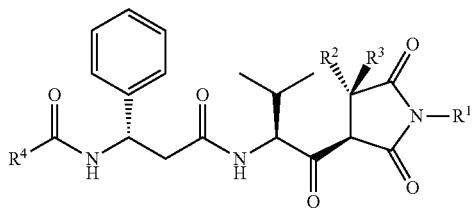

as defined in paragraphs [00608]-[00618] hereinabove;
xlv) a compound of Formula XLV:

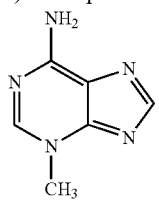

as defined in paragraphs [00619]-[00620] hereinabove;
xlvi) a compound of Formula XLVI:

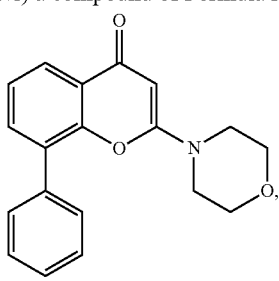

as defined in paragraphs [00621]-[00622] hereinabove; or
xlvii) a compound of Formula XLVII:

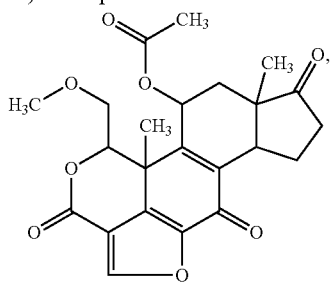

as defined in paragraphs [00623]-[00624] hereinabove.

2. A method for treating or preventing viral infection in a mammal, comprising administering to a mammalian subject in need thereof a therapeutically effective amount of one or more compound or prodrug thereof, or pharmaceutically acceptable salt of said compound or prodrug, wherein the compound is a compound of the Formula XXXIII:

wherein:
a) X is —COOH, —CO$_2$(C$_1$-C$_6$)alkyl, —CONH$_2$, —H, —CO(C$_1$-C$_6$)alkyl, —COC(halo)$_3$, or a moiety that can form an adduct with coenzyme A;
b) Y is O or S; —NH or N(C-1-C6)alky; and
c) Z is —(C$_5$-C$_{20}$)alkyl, —O(C$_5$-C$_{20}$)alkyl or —(C$_5$-C$_{20}$)alkoxy, —(C$_5$-C$_{20}$)haloalkyl, —O—(C$_5$-C$_{20}$)haloalkyl or —(C$_5$-C$_{20}$)haloalkoxy, -halo, —OH, —(C$_5$-C$_{20}$)alkenyl, —(C$_5$-C$_{20}$)alkynyl, —(C$_5$-C$_{20}$)alkoxy-alkenyl, —(C$_5$-C$_{20}$)hydroxyalkyl, —O(C$_1$-C$_6$)alkyl, —CO$_2$(C$_1$-C$_6$)alkyl, —O(C$_5$-C$_{20}$)alkenyl, —O(C$_5$-C$_{20}$)alkynyl, —O(C$_5$-C$_{20}$)cycloalkyl; —S(C$_5$-C$_{20}$)alkyl, —NH(C$_5$-C$_{20}$)alkyl, —NHCO(C$_5$-C$_{20}$)alkyl, —N(C$_1$-C$_6$)alkylCO(C$_5$-C$_{20}$)alkyl or —O(C$_5$-C$_{20}$)alkoxy.

3. The method of paragraph Error! Reference source not found., wherein the X of the compound of Formula XXXIII is a moiety that can form an ester linkage with coenzyme A.

4. The method of subparagraph number 2, wherein the X of the compound of Formula XXXIII is a moiety that allows for the formation of compounds of the formula:

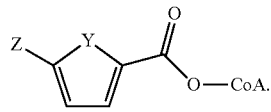

5. The method of subparagraph number 2, wherein the X of Formula XXXIII is —COOH.
6. The method of subparagraph number 2, wherein the Y of Formula XXXIII is O.
7. The method of subparagraph number 2, wherein the Z of Formula XXXIII is —O(C$_5$-C$_{20}$)alkyl, —O(C$_5$-C$_{20}$)haloalkyl, —O(C$_5$-C$_{20}$)alkenyl, —O(C$_5$-C$_{20}$)alkynyl or —O(C$_5$-C$_{20}$)alkoxy.
8. The method of subparagraph number 2, wherein the Y of Formula XXXIII is O, X is —COOH and Z is —O(C$_5$-C$_{20}$)alkyl, —O(C$_5$-C$_{20}$)haloalkyl, —O(C$_5$-C$_{20}$)alkenyl, —O(C$_5$-C$_{20}$)alkynyl or —O(C$_5$-C$_{20}$)alkoxy.
9. The method of subparagraph number 2, wherein the compound of Formula XXXIII has the structure:

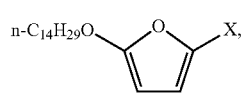

wherein
X is —COOH, —CO$_2$(C$_1$-C$_6$)alkyl, —CONH$_2$, —H, —CO(C$_1$-C$_6$)alkyl, —COC(halo)$_3$, or

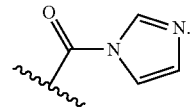 [SMILES: *C(=O)n1ccnc1]

10. The method of subparagraph number 2, wherein the compound of Formula XXXIII has the structure:

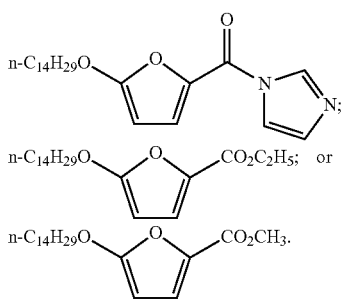

11. The method of subparagraph number 2, wherein the compound of Formula XXXIII has the structure:

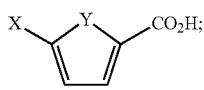

wherein:
  i) X is —($C_5$-$C_{20}$)alkyl, —O($C_5$-$C_{20}$)alkyl or —($C_5$-$C_{20}$)alkoxy, —($C_5$-$C_{20}$)haloalkyl, —O($C_5$-$C_{20}$)haloalkyl or —($C_5$-$C_{20}$)haloalkoxy, -halo, —OH, —($C_5$-$C_{20}$)alkenyl, —($C_5$-$C_{20}$)alkynyl, —($C_5$-$C_{20}$)alkoxy-alkenyl, —($C_5$-$C_{20}$)hydroxyalkyl, —O($C_1$-$C_6$)alkyl, —$CO_2$($C_1$-$C_6$)alkyl, —O($C_5$-$C_{20}$)alkenyl, —O($C_5$-$C_{20}$)alkynyl, —O($C_5$-$C_{20}$)cycloalkyl, —S($C_5$-$C_{20}$)alkyl, —NH($C_5$-$C_{20}$)alkyl, —NHCO($C_5$-$C_{20}$)alkyl, —N($C_1$-$C_6$)alkylCO($C_5$-$C_{20}$)alkyl or —O($C_5$-$C_{20}$)alkoxy; and
  ii) Y is O, S, —NH or N($C_1$-$C_6$)alkyl.

12. The method of subparagraph number 2, wherein the compound of Formula XXXIII has the structure:

13. The method of subparagraph number 2, wherein the compound is 5-(tetradecyloxy)-2-furoic acid [TOFA].

14. The method of subparagraph number 2, wherein the compound is not TOFA.

15. A method for treating or preventing a viral infection in a mammal, comprising administering to a mammalian subject in need thereof a therapeutically effective amount of a compound that inhibits the activity of an enzyme in the fatty acid biosynthesis pathway.

16. The method of subparagraph number Error! Reference source not found. wherein the host enzyme is:
  i) an Acetyl CoA carboxylase;
  ii) an ATP citrate lyase;
  iii) an HMG-CoA synthase;
  iv) a domain of Fatty Acid Synthase;
  v) a Fatty Acid Synthase keto-acyl synthase domain;
  vi) a Fatty acid synthase thioesterase domain;
  vii) a Lysophosphatidic acid acyltransferase;
  viii) a Lysophosphatidic acid acyltransferase-beta;
  ix) a Malonyl-CoA decarboxylase;
  x) an AMP-activated protein kinase (AMPK);
  xi) a Fatty acid elongase;
  xii) a ELOVL (elongation of very long chain fatty acid);
  xiii) a Stearoyl-CoA desaturases 1-5;
  xiv) a Delta-6-desaturase; or
  xv) a Delta-5-desaturase.

17. A method for treating or preventing a viral infection in a mammal, comprising administering to a mammalian subject in need thereof a therapeutically effective amount of a compound that inhibits the activity of a host enzyme in the fatty acid metabolic pathway.

18. The method of subparagraph number Error! Reference source not found. wherein the host enzyme is:
  i) a methylmalonyl Coenzyme A mutase;
  ii) an acyl-Coenzyme A carboxylase beta;
  iii) a Acyl-Coenzyme A oxidase 2, branched chain;
  iv) a putative acyl-CoA dehydrogenase;

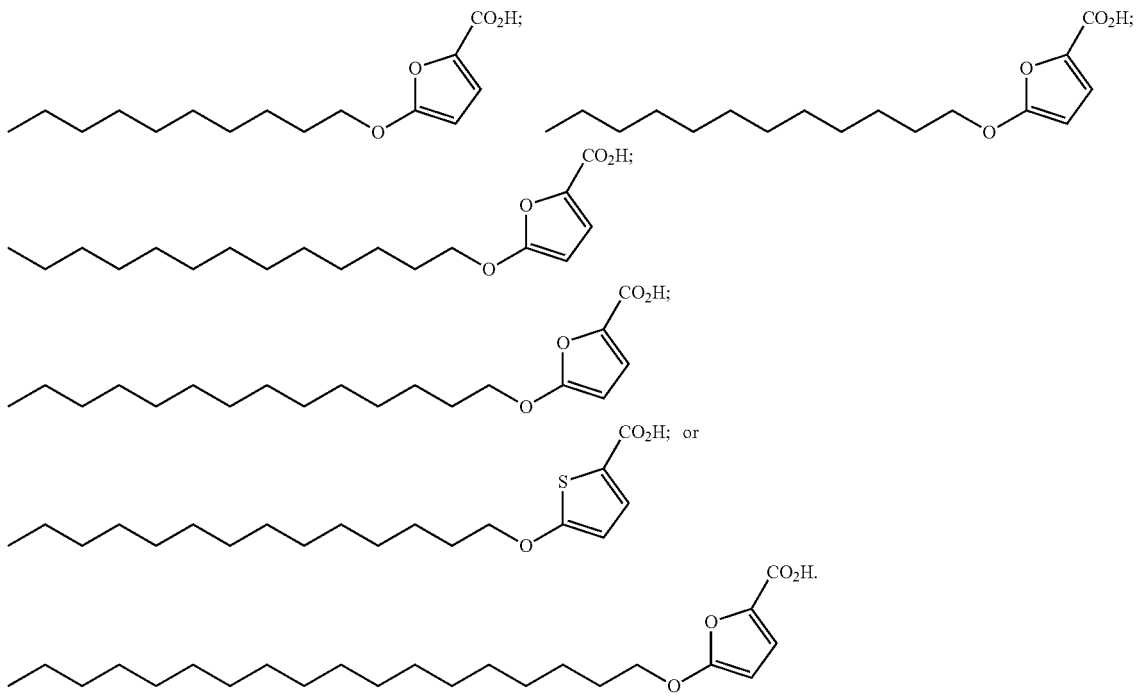

v) a short-branched chain acyl-Coenzyme A dehydrogenase;
vi) a xenobiotic/medium-chain fatty acid:CoA ligase;
vii) an enoyl Coenzyme A hydratase domain containing 3;
viii) a phospholipid scramblase 1;
ix) a phospholipid scramblase 2;
x) a phospholipid scramblase 4;
xi) a fatty acid desaturase 1;
xii) a Carnitine Palmitoyl transferase (CPT);
xiii) a fatty acid binding protein 5 (psoriasis-associated); or
xiv) a fatty acid binding protein 3, muscle and heart (mammary-derived growth inhibitor).

19. A method for treating or preventing a viral infection in a mammal, comprising administering to a mammalian subject in need thereof a therapeutically effective amount of a compound that inhibits the activity of a host enzyme in the glucose transport pathway.

20. The method of subparagraph number 19 wherein the enzyme is GLUT4.

21. A method for treating or preventing a viral infection in a mammal, comprising administering to a mammalian subject in need thereof a therapeutically effective amount of a compound that inhibits the activity of a host enzyme in the glycolytic pathway.

22. The method of subparagraph number 21 wherein the enzyme is:
   i) a glucose phosphate isomerase;
   ii) a triosephosphate isomerase 1;
   iii) a phosphoglycerate kinase 1;
   iv) an enolase 1 (alpha); or
   v) a pyruvate kinase, muscle.

23. A method for treating or preventing a viral infection in a mammal, comprising administering to a mammalian subject in need thereof a therapeutically effective amount of a compound that inhibits the activity of a host enzyme in the Tricarboxylic Acid (TCA) cycle.

24. The method of subparagraph number 23 wherein the enzyme is:
   i) an isocitrate dehydrogenase;
   ii) a succinate-CoA ligase;
   iii) a succinate dehydrogenase;
   iv) a malate dehydrogenase;
   v) a malic enzyme; or
   vi) a TCA aconitase.

25. A method for treating or preventing a viral infection in a mammal, comprising administering to a mammalian subject in need thereof a therapeutically effective amount of a compound that inhibits the activity of a host Proton ATPase enzyme.

26. The method of subparagraph number 25 wherein the enzyme is a:
   i) a F0 complex, subunit b, isoform 1;
   ii) a F0 complex, subunit c (subunit 9) isoform 3;
   iii) a F0 complex, subunit c (subunit 9), isoform 1;
   iv) a F0 complex, subunit e;
   v) a F0 complex, subunit F6;
   vi) a F0 complex, subunit g;
   vii) a F1 complex, alpha subunit, isoform 1;
   viii) a F1 complex, beta polypeptide;
   ix) a F1 complex, epsilon subunit; or
   x) an F1 complex, O subunit.

27. A method for treating or preventing a viral infection in a mammal, comprising administering to a mammalian subject in need thereof a therapeutically effective amount of a compound that inhibits the activity of a host enzyme involved in cholesterol synthesis or metabolism.

28. The method of subparagraph number 27 wherein the enzyme is a:
   i) an acetyl-CoA acetyltransferase;
   ii) an HMG-CoA synthase;
   iii) an HMG-CoA reductase;
   iv) an isopentyldiphosphate isomerase;
   v) a mevalonate kinase;
   vi) a phosphomevalonate kinase;
   vii) a geranyl-diphosphate synthase;
   viii) a farnesyl-diphosphate synthase;
   ix) a farnesyl-diphosphate farnesyltransferase;
   x) a squalene monooxigenase;
   xi) a lanosterol synthase;
   xii) a squalene epoxidase; or
   xiii) a squalene oxidocyclase.

29. A method for treating or preventing a viral infection in a mammal, comprising administering to a mammalian subject in need thereof a therapeutically effective amount of one or more compounds that inhibit the activity of a host metabolic or biosynthetic enzyme.

30. The method of subparagraph number 29 wherein the enzyme is:
   i) a lactate dehydrogenase B;
   ii) a dicarbonyl/L-xylulose reductase;
   iii) a hydroxyprostaglandin dehydrogenase 15-(NAD);
   iv) a ribulose-5-phosphate-3-epimerase;
   v) a glutamate dehydrogenase;
   vi) a glutaminase;
   vii) a phospholipase A2;
   viii) a cyclooxygenase 1; or
   ix) a cyclooxygenase 2.

31. A method for treating or preventing a viral infection in a mammal, comprising administering to a mammalian subject in need thereof a therapeutically effective amount of a a fatty acid biosynthesis inhibitor and a cholesterol biosynthesis inhibitor, or prodrug thereof, or pharmaceutically acceptable salt of said inhibitor or prodrug.

32. The method of subparagraph number 31 wherein the fatty acid biosynthesis inhibitor an ACC[Acetyl-CoA Carboxylase] inhibitor and the cholesterol biosynthesis inhibitor is an HMGCoA (3-hydroxy-3-methyl-glutaryl-CoA) reductase inhibitor.

33. A method for treating or preventing a viral infection in a mammal, comprising reducing the activity of a host enzyme the fatty acid biosynthesis pathway in a mammalian subject in need thereof 34. The method of subparagraph number 33 wherein the host enzyme is a:
   i) an Acetyl CoA carboxylase;
   ii) an ATP citrate lyase;
   iii) an HMG-CoA synthase;
   iv) a domain of Fatty Acid Synthase;
   v) a Fatty Acid Synthase keto-acyl synthase domain;
   vi) a Fatty acid synthase thioesterase domain;
   vii) a Lysophosphatidic acid acyltransferase;
   viii) a Lysophosphatidic acid acyltransferase-beta;
   ix) a Malonyl-CoA decarboxylase;
   x) an AMP-activated protein kinase (AMPK);
   xi) a Fatty acid elongase;
   xii) an ELOVL (elongation of very long chain fatty acid);
   xiii) a Stearoyl-CoA desaturases 1-5;
   xiv) a Delta-6-desaturase; or
   xv) a Delta-5-desaturase.

35. A method for treating or preventing a viral infection in a mammal, comprising reducing the activity of a host enzyme in the fatty acid metabolic pathway in a mammalian subject in need thereof 36. The method of subparagraph number 35 wherein the host enzyme is:
  i) a methylmalonyl Coenzyme A mutase;
  ii) an acyl-Coenzyme A carboxylase beta;
  iii) an Acyl-Coenzyme A oxidase 2, branched chain;
  iv) a putative acyl-CoA dehydrogenase;
  v) a short-branched chain acyl-Coenzyme A dehydrogenase;
  vi) a xenobiotic/medium-chain fatty acid:CoA ligase;
  vii) an enoyl Coenzyme A hydratase domain containing 3;
  viii) a phospholipid scramblase 1;
  ix) a phospholipid scramblase 2;
  x) a phospholipid scramblase 4;
  xi) a fatty acid desaturase 1;
  xii) a Carnitine Palmitoyl transferase (CPT);
  xiii) a fatty acid binding protein 5 (psoriasis-associated); or
  xiv) a fatty acid binding protein 3, muscle and heart (mammary-derived growth inhibitor).

37. A method for treating or preventing a viral infection in a mammal, comprising reducing the activity of a host enzyme in the glucose transport pathway in a mammalian subject in need thereof.

38. The method of subparagraph number 37 wherein the enzyme is GLUT4.

39. A method for treating or preventing a viral infection in a mammal, comprising reducing the activity of a host enzyme in the glycolytic pathway in a mammalian subject in need thereof 40. The method of subparagraph number 39 wherein the enzyme is:
  i) a glucose phosphate isomerase;
  ii) a triosephosphate isomerase 1;
  iii) a phosphoglycerate kinase 1;
  iv) an enolase 1 (alpha); or
  v) a pyruvate kinase, muscle.

41. A method for treating or preventing a viral infection in a mammal, comprising reducing the activity of a host enzyme in the Tricarboxylic Acid (TCA) cycle in a mammalian subject in need thereof 42. The method of subparagraph number 41 wherein the enzyme isn:
  i) an isocitrate dehydrogenase;
  ii) a succinate-CoA ligase;
  iii) a succinate dehydrogenase;
  iv) a malate dehydrogenase;
  v) a malic enzyme; or
  vi) a TCA aconitase.

43. A method for treating or preventing a viral infection in a mammal, comprising reducing the activity of a host Proton ATPase enzyme in a mammalian subject in need thereof.

44. The method of subparagraph number 43 wherein the enzyme is:
  i) a F0 complex, subunit b, isoform 1;
  ii) a F0 complex, subunit c (subunit 9) isoform 3;
  iii) a F0 complex, subunit c (subunit 9), isoform 1;
  iv) a F0 complex, subunit e;
  v) a F0 complex, subunit F6;
  vi) a F0 complex, subunit g;
  vii) a F1 complex, alpha subunit, isoform 1;
  viii) a F1 complex, beta polypeptide;
  ix) a F1 complex, epsilon subunit; or
  x) a F1 complex, 0 subunit.

45. A method for treating or preventing a viral infection in a mammal, comprising reducing the activity of a host enzyme involved in cholesterol synthesis or metabolism in a mammalian subject in need thereof.

46. The method of subparagraph number 45 wherein the enzyme is:
  i) an acetyl-CoA acetyltransferase;
  ii) an HMG-CoA synthase;
  iii) an HMG-CoA reductase;
  iv) an isopentyldiphosphate isomerase;
  v) an mevalonate kinase;
  vi) an phosphomevalonate kinase;
  vii) an geranyl-diphosphate synthase;
  viii) an farnesyl-diphosphate synthase;
  ix) an farnesyl-diphosphate farnesyltransferase;
  x) an squalene monooxigenase;
  xi) a lanosterol synthase;
  xii) a squalene epoxidase; or
  xiii) squalene oxidocyclase.

47. A method for treating or preventing a viral infection in a mammal, comprising reducing the activity of a host metabolic or biosynthetic enzyme in a mammalian subject in need thereof.

48. The method of subparagraph number 47 wherein the enzyme is:
  i) a lactate dehydrogenase B;
  ii) a dicarbonyl/L-xylulose reductase;
  iii) a hydroxyprostaglandin dehydrogenase 15-(NAD);
  iv) a ribulose-5-phosphate-3-epimerase;
  v) a glutamate dehydrogenase;
  vi) a glutaminase;
  vii) a phospholipase A2;
  viii) a cyclooxygenase 1; or
  ix) a cyclooxygenase 2.

49. The method of subparagraph numbers 1, 2, 15, 17, 19, 21, 23, 25, 27, 29, 31, 32, 33, 34, 35, 37, 39, 41, 43, 45, or 47 wherein the viral infection is caused by: a Hepadnavirus, including hepatitis B virus (HBV), woodchuck hepatitis virus, ground squirrel hepatitis virus, duck hepatitis B virus, and heron hepatitis B virus; a Herpesvirus, including herpes simplex virus (HSV) types 1 and 2, varicella-zoster virus, cytomegalovirus (CMV), human cytomegalovirus (HCMV), Epstein-Barr virus (EBV), human herpesvirus 6 (variants A and B), human herpesvirus 7, human herpesvirus 8, Kaposi's sarcoma-associated herpes virus (KSHV), and B virus; a Poxvirus (Poxyiridae); a Vaccinia virus, including variola virus, smallpox virus, monkeypox virus, cowpox virus, camelpox virus, mousepox virus, raccoonpox viruses, molluscum contagiosum virus, orf virus, milker's nodes virus, bovine papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, and Yabapox virus; a Flavivirus (Flaviviridae), including dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, and Kyasanur Forest disease virus; a Togavirus (Togaviridae), including Venezuelan equine encephalitis virus, chikungunya virus, Ross River virus, Mayaro virus, Sindbis virus, and rubella virus; a Retrovirus (Retroviridae), including human immunodeficiency virus (HIV) types 1 and 2, human T cell leukemia virus (HTLV) types 1, 2, and 5, mouse mammary tumor virus (MMTV), Rous sarcoma virus (RSV), lentiviruses; a Coronavirus (Coronaviridae), including severe acute respiratory syndrome (SARS) virus; a Filovirus (Filoviridae), including Ebola virus, Marburg virus; a Rhabdovirus (Rhabdoviridae), including rabies virus, and vesicular stomatitis virus; a Bunyavirus (Bunyaviridae) including Crimean-Congo hemorrhagic fever virus, Rift Valley fever virus, La Crosse virus, and Hantaan virus; an Orthomyxovirus (Orthomyxoviridae), including influenza virus (types A, B, and C); a Paramyxovirus (Paramyxoviridae), including parainfluenza virus, respiratory syncytial virus (types A and B), measles virus, and mumps virus; an Arenavirus (Arenaviridae), including lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Tacaribe virus, and Tamiami virus; a Parvovirus (Parvoviridae), including canine parvovirus, and parvovirus B19; a Circovirus (Circoviridae), including porcine circovirus type 1 and 2, BFDV (Beak and Feather Disease Virus), and chicken anaemia virus; Polyomavirus (Polyomaviridae), including simian virus 40 (SV40), JC virus, BK virus, and Budgerigar fledgling disease virus; a Papillomavirus (Papillomaviridae), including human papillomavirus, and bovine papillomavirus (BPV) type 1; an Adenovirus (Adenoviridae), including human adenovirus (HAdV-A, HAdV-B, HAdV-C, HAdV-D, HAdV-E, and HAdV-F), fowl adenovirus A, ovine adenovirus D, and frog adenovirus; a Reovirus (Reoviridae), including human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, and mycoreovirus 1; a Birnavirus (Birnaviridae), including bursal disease virus, pancreatic necrosis virus; a Calicivirus (Caliciviridae), including swine vesicular exanthema virus, rabbit hemorrhagic disease virus, Norwalk virus, and Sapporo virus; or a Picornavirus (Picornaviridae), including human polioviruses (1-3), human coxsackieviruses A1-22, 24 (CA1-22 and CA24, CA23=echovirus 9), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardioviruses, aphthoviruses, and echoviruses.

50. The method of subparagraph numbers 1, 2, 15, 17, 19, 21, 23, 25, 27, 29, 31, 33, 35, 37, 39, 41, 43, 45, or 47, wherein the mammal is a human subject.

51. A pharmaceutical composition for the treatment or prevention of viral infections comprising a therapeutically effective amount of a composition comprising (i) one or more compound, prodrug thereof, or pharmaceutically acceptable salt of said compound or prodrug; and (ii) a pharmaceutical acceptable carrier, wherein the compound is:

i) a compound of Formula I:

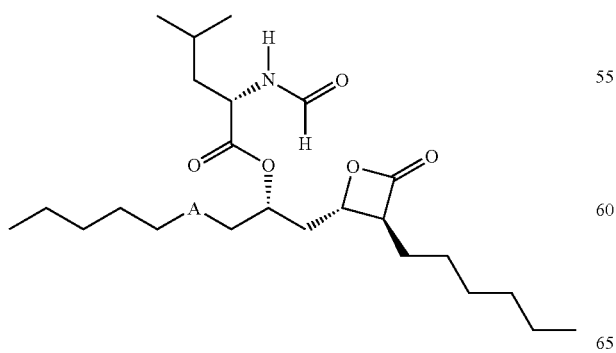

as defined in paragraphs [00101]-[00108] hereinabove;

ii) a compound of Formula II:

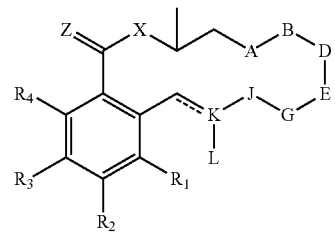

as defined in paragraphs [00109]-[00125] hereinabove;

iii) a compound of Formula III:

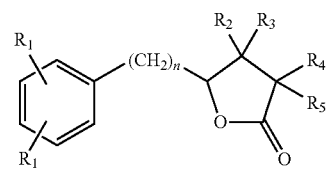

as defined in paragraphs [00126]-[00132] hereinabove;

iv) a compound of Formula IV:

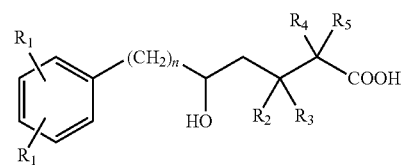

as defined in paragraphs [00123]-[00141] hereinabove;

v) a compound of Formula V:

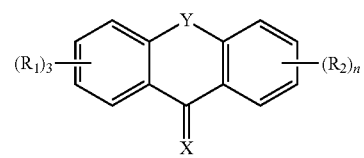

as defined in paragraphs [00142]-[00151] hereinabove;

vi) a compound of Formula VI:

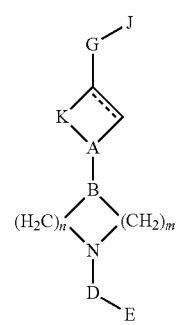

as defined in paragraphs [00152]-[00166] hereinabove;

vii) a compound of Formula VII:

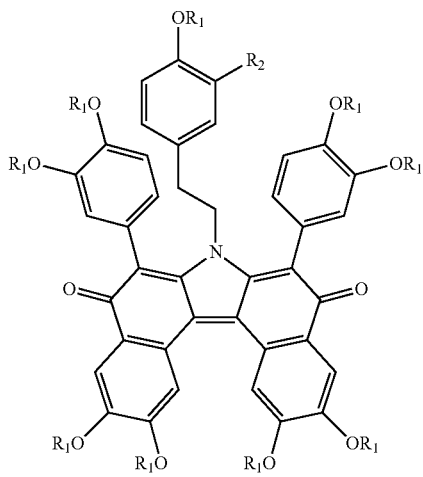

as defined in paragraphs [00167]-[00179] hereinabove;
viii) a compound of Formula VIII:

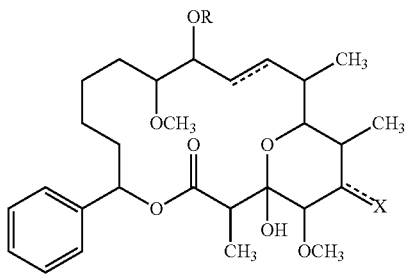

as defined in paragraphs [00180]-[00195] hereinabove;
ix) a compound of Formula IX:

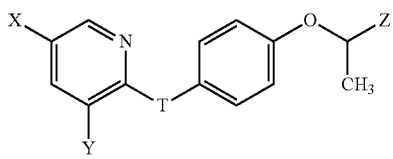

as defined in paragraphs [00196]-[00210] hereinabove;
x) a compound of Formula X:

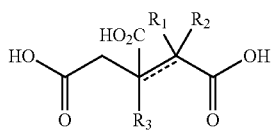

as defined in paragraphs [00211]-[00229] hereinabove;

xi) a compound of Formula XI:

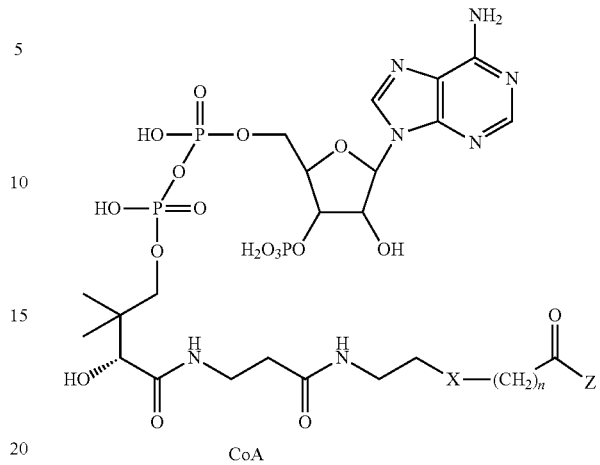

as defined in paragraphs [00230]-[00240] hereinabove;
xii) a compound of Formula XII:

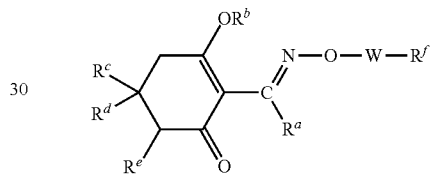

as defined in paragraphs [00241]-[00258] hereinabove;
xiii) a compound of Formula XIII:

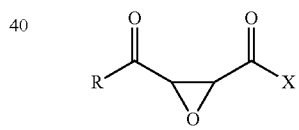

as defined in paragraphs [00259]-[00269] hereinabove;
xiv) a compound of Formula XIV:

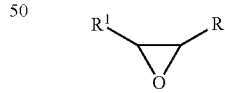

as defined in paragraphs [00270]-[00279] hereinabove;
xv) a compound of Formula XV:

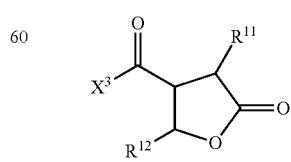

as defined in paragraphs [00280]-[00289] hereinabove;

xvi) a compound of Formula XVI:

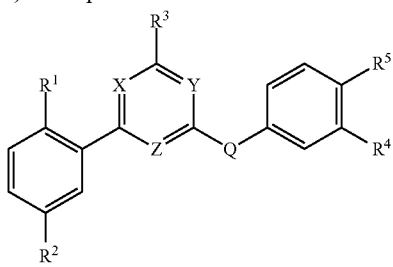

as defined in paragraphs [00290]-[00299] hereinabove;
xvii) a compound of Formula XVII:

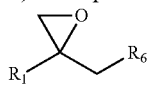

as defined in paragraphs [00300]-[00307] hereinabove;
xviii) a compound of Formula XVIII:

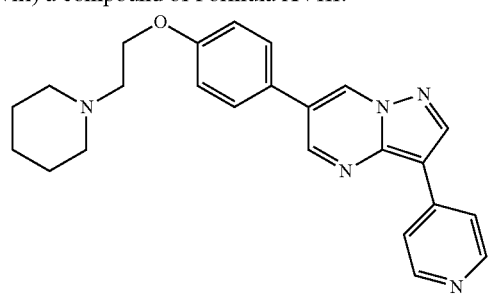

as defined in paragraphs [00308]-[00309] hereinabove;
xix) a compound of Formula XIX:

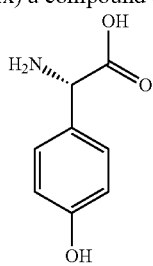

as defined in paragraphs [00310]-[00311] hereinabove;
xx) a compound of Formula XX:

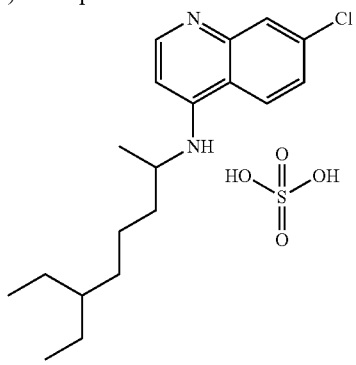

as defined in paragraphs [00312]-[00313] hereinabove;

xxi) a compound of Formula XXI:

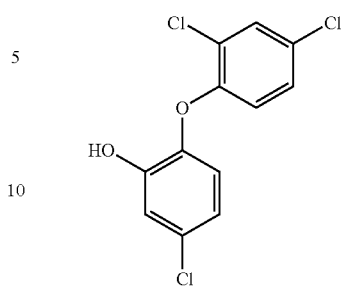

as defined in paragraphs [00314]-[00315] hereinabove;
xxii) a compound of Formula XXII:

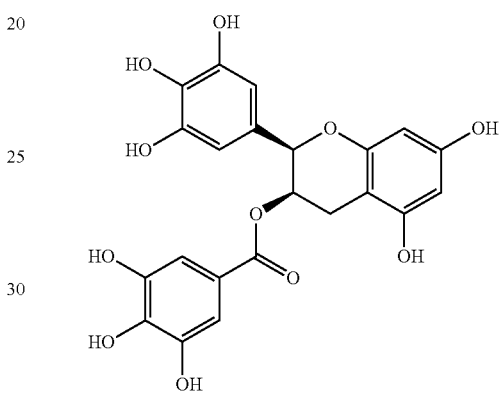

as defined in paragraphs [00316]-[00323] hereinabove;
xxiii) a compound of Formula XXIII:

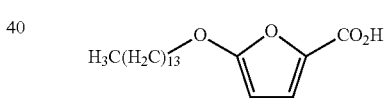

as defined in paragraph [00452] hereinabove;
xxiv) a compound of Formula XXIV:

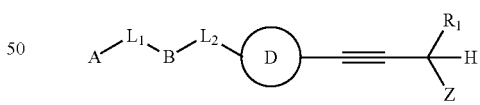

as defined in paragraphs [00324]-[00348] hereinabove;
xxv) a compound of Formula XXV:

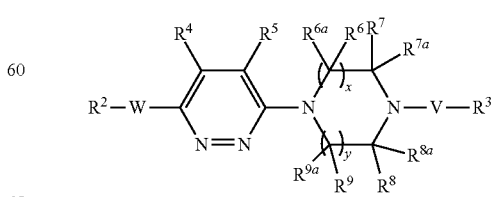

as defined in paragraphs [00349]-[00364] hereinabove;

xxvi) a compound of Formula XXVI:

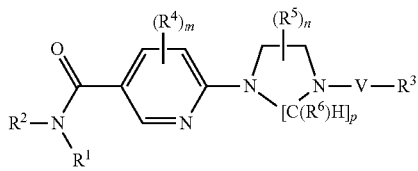

as defined in paragraphs [00365]-[00380] hereinabove;
xxvii) a compound of Formula XXVII:

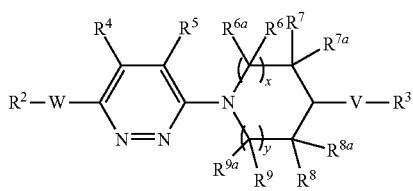

as defined in paragraphs [00381]-[00395] hereinabove;
xxviii) a compound of Formula XXVIII:

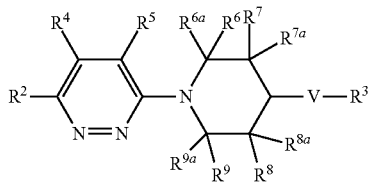

as defined in paragraphs [00396]-[00421] hereinabove;
xxix) a compound of Formula XXIX:

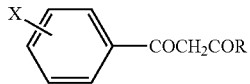

as defined in paragraphs [00422]-[00425] hereinabove;
xxx) a compound of Formula XXX:

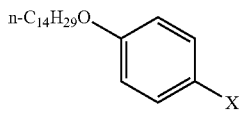

as defined in paragraphs [00426]-[00428] hereinabove;
xxxi) a compound of Formula XXXI:

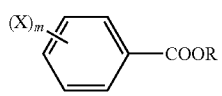

as defined in paragraphs [00429]-[00433] hereinabove;

xxxii) a compound of Formula XXXII:

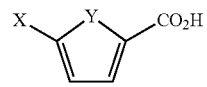

as defined in paragraphs [00447]-[00451] hereinabove;
xxxiii) a compound of Formula XXXIII:

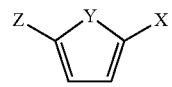

as defined in paragraphs [00434]-[00446] and [00452]-[00453] hereinabove;
xxxiv) a compound of Formula XXXIV:

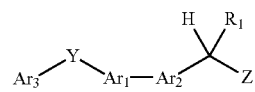

as defined in paragraphs [00454]-[00477] hereinabove;
xxxv) a compound of Formula XXXV:

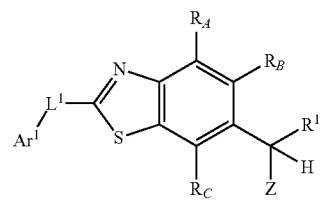

as defined in paragraphs [00478]-[00492] hereinabove;
xxxvi) a compound of Formula XXXVI:

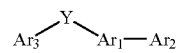

as defined in paragraphs [00493]-[00521] hereinabove;
xxxvii) a compound of Formula XXXVII:

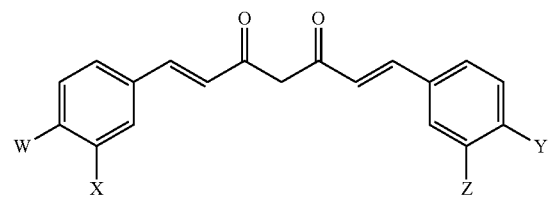

as defined in paragraphs [00522]-[00529] hereinabove;

xxxviii) a compound of Formula XXXVIII:

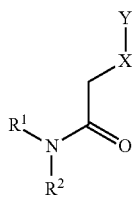

as defined in paragraphs [00530]-[00548] hereinabove;
xxxix) a compound of Formula XXXIX:

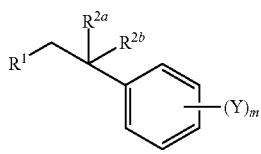

as defined in paragraphs [00549]-[00562] hereinabove;
xl) a compound of Formula XL:

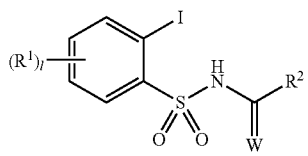

as defined in paragraphs [00563]-[00573] hereinabove;
xli) a compound of Formula XLI:

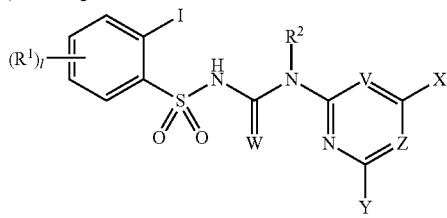

as defined in paragraphs [00574]-[00584] hereinabove;
xlii) a compound of Formula XLII:

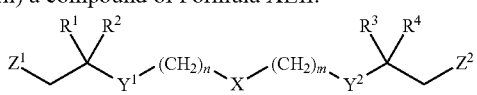

as defined in paragraphs [00585]-[00591] hereinabove;
xliii) a compound of Formula XLIII:

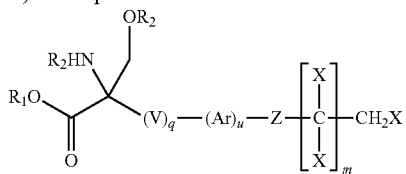

as defined in paragraphs [00592]-[00607] hereinabove;

xliv) a compound of Formula XLIV:

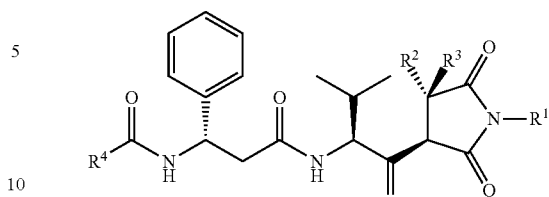

as defined in paragraphs [00608]-[00618] hereinabove;
xlv) a compound of Formula XLV:

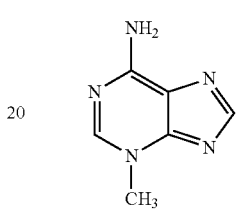

as defined in paragraphs [00619]-[00620] hereinabove;
xlvi) a compound of Formula XLVI:

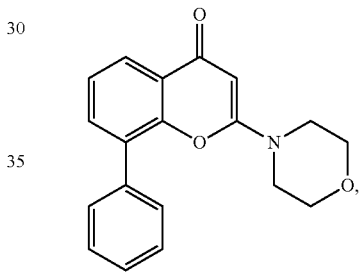

as defined in paragraphs [00621]-[00622] hereinabove; or
xlvii) a compound of Formula XLVII:

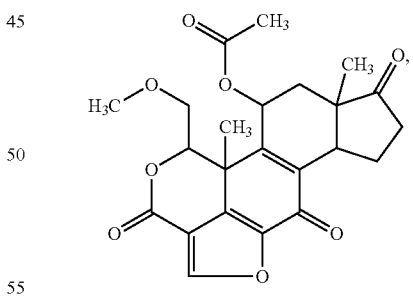

as defined in paragraphs [00623]-[00624] hereinabove.

52. A pharmaceutical composition for the treatment or prevention of viral infections comprising a therapeutically effective amount of a fatty acid biosynthesis inhibitor and a cholesterol biosynthesis inhibitor and a pharmaceutical acceptable carrier.

53. The pharmaceutical composition of subparagraph number 52 wherein the fatty acid biosynthesis inhibitor is an ACC [Acetyl-CoA Carboxylase] inhibitor and the cholesterol biosynthesis inhibitor is an HMGCoA (3-hydroxy-3-methyl-glutaryl-CoA) reductase inhibitor.

54. A method for treatment or prevention of a virus infection in a human subject, comprising administering an effective amount of 4S-hydroxycitrate, 2,2-difluorocitrate, thiol-citrate, sb201076, sb204990, 2-chloro-1,3,8-trihydroxyl-6-methyl-9-anthrone, 3-oxobutylsulfoxyl-CoA, purpurone, CP610431, CP640186, soraphen-A, sethoxydim, orlistat or CT32228, or a pharmaceutically acceptable salt thereof to a human subject in need thereof.

REFERENCES

Bajad et al., (2006) J Chromatogr A 1125, 76-88.
Bolling, C., and Fiehn, O. (2005) Plant Physiol. 139:1995-2005.
Clark et al., (2007) Bioorg. Med. Chem. Lett. 17:1961-1965.
Clayton et al., (2006) Nature. 440:1073-1077.
Coulier et al., (2006) Anal Chem. 78:6573-6582.
Feng, X. J., and Rabitz, H. (2004) Biophys. J. 86:1270-1281.
Feng et al., (2006). J. Phys. Chem. A. Mol. Spectrosc. Kinet. Environ. Gen. Theory 110:7755-7762.
Fiehn, O., (2002) Plant Mol. Biol. 48:155-171.
Giaever et al., (2002) Nature 418:387-391.
Gibson et al., (1981) Fundam. Appl. Toxicol. 1:19-25.
Gillooly et al., EMBO J. 19:4577-4588, 2000.
Gu et al., (2006) J. Med. Chem. 49:3770-3773.
Harwood et al., (2003) J. Biol. Chem. 278:37099-37111.
Holmes et al., (2006) PLoS Med. 3:e327.
Kapadia et al., (2007) J. Virol. 81, 374-383.
Kapadia et al., (2005) Proc Natl Acad Sci USA 102:2561-2566.
Kariya et al., (1978) Biochem Biophys Res Commun 80, 1022-1024.
Kind et al., (2007) Anal Biochem. 363:185-195.
Kimball, E., and Rabinowitz, J. D. (2006) Anal Biochem. 358:273-280.
Landini, M. P., (1984) J. Gen. Virol. 65 (Pt 7):1229-1232.
Lee et al., (1998) Am J Physiol 274:E843-E851.
Lu, W., Kimball, E., and Rabinowitz, J. D. (2006) J. Am. Soc. Mass Spectrom. 17:37-50.
Lu, W., Kwon, Y. K., and Rabinowitz, J. D. (2007) J Am Soc Mass Spectrom. 18:898-909.
Luo et al., (2007) J. Chromatogr. A 1147:153-164.
Maharjan, R. P., and Ferenci, T. (2003) Anal Biochem 313: 145-154.
Milne et al., (2006) Methods 39:92-103.
Munger et al., (2006) PLoS Pathog. 2:e132.
Nicholson et al., (2002) Nat. Rev. Drug Discov. 1:153-161.
Olsson et al., (2004) Anal Chem. 76:2453-2461.
Petiot et al., (2000) J. Biol. Chem. 275, 992-998.
Pizer et al., (1998) Cancer Res 58:4611-4615.
Rabinowitz, J. D., and Kimball, E. K. (2007). Anal Chem. 79:6167-73.
Reed et al., (2003) Genome Biol. 4:R54.
Rezzi et al., (2007) J. Proteome Res. 6:4469-4477.
Sabatine et al., (2005) Circulation 112:3868-3875.
Sauer, U. (2006) Mol. Syst. Biol. 2:62.
Schaub et al., (2006) Biotechnol. Prog. 22:1434-1442.
Schilling and Palsson, (1998) Proc. Natl. Acad. Sci. USA 95:4193-4198.
Stephanopoulos, G. (1999) Metab. Eng. 1:1-11.
Szyperski et al., (1999) Metab. Eng. 1:189-197.
van Winden et al., (2005) FEMS Yeast Research 5:559-568.
Villas-Boas et al., (2005) Yeast 22:1155-1169.
Wikoff et al., (2007) Clin. Chem. 53:2169-2176.
Wittmann et al., (2004) Anal Biochem. 327:135-139.
Wu et al., (2005) Anal Biochem. 336:164-171.
Yuan et al., (2006) Nat. Chem. Biol. 2:529-530.
Zupke et al., (1995) Appl Microbiol Biotechnol 44:27-36.

What is claimed:

1. A method for treating or impeding the onset of infection by a herpesvirus, comprising administering to a subject in need thereof a therapeutically effective amount of the Formula XXXII:

(Formula XXXII)

or a prodrug thereof, or a pharmaceutically acceptable salt or ester of said compound or prodrug, wherein:

(a) X is —$O(C_5$-$C_{20})$alkyl, —$O(C_5$-$C_{20})$alkenyl, or —$S(C_5$-$C_{20})$alkyl; and (b) Y is O, or S; and wherein the prodrug comprises a biohydrolyzable ester, a biohydrolyzable amine, or biohydrolyzable carbonate.

2. The method of claim 1, wherein X is —$O(C_{10}$-$C_{20})$alkyl or —$O(C_{10}$-$C_{20})$alkenyl.

3. The method of claim 1, wherein Y is O.

4. The method of claim 1, wherein the compound of the Formula XXXII is 5-(tetradecyloxy)-2-furoic acid (TOFA).

5. The method of claim 1, wherein the compound of Formula XXXII has the structure:

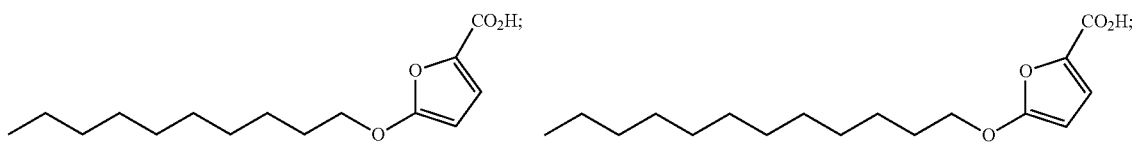

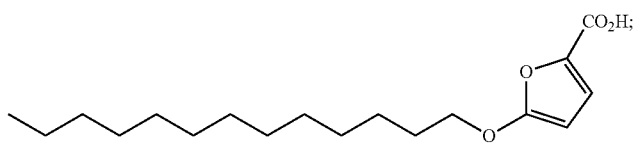

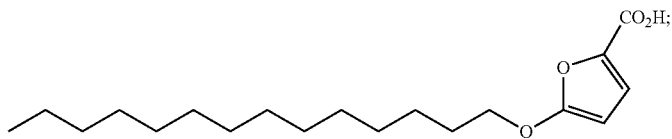

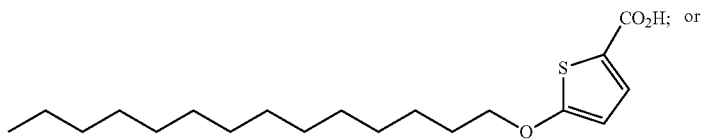

-continued

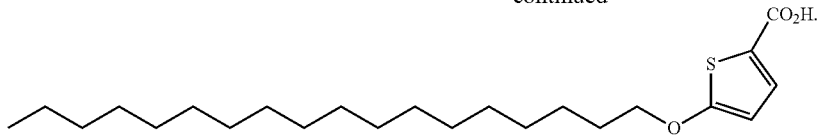

6. The method of claim 1, wherein the compound of Formula XXXII is administered at a dose of about 500 mg/day to about 1000 mg/day.

7. The method of claim 1, wherein the compound of Formula XXXII is administered at a dose of about 1000 mg/day to about 1500 mg/day.

8. The method of claim 1, wherein the compound of Formula XXXII is administered at a dose of about 1000 mg/day to about 1500 mg/day.

9. The method of claim 1, wherein the compound of Formula XXXII is administered at a dose of about 1500 mg/day.

10. The method of any one of claims 1 to 9, wherein the method is for treating an infection by a herpesvirus.

11. The method of any one of claims 1 to 9, wherein the compound is administered to the subject prophylactically.

12. The method of any one of claims 1 to 9, wherein the compound is co-administered with a cholesterol biosynthesis inhibitor, or pharmaceutically acceptable salt of said inhibitor.

13. The method of claim 12, wherein the cholesterol biosynthesis inhibitor is an 3-hydroxy-3-methyl-glutaryl-CoA (HMGCoA) reductase inhibitor.

14. The method of claim 13, wherein the HMG-CoA reductase inhibitor is mevastatin, lovastatin, pravastatin, simvastatin, fluvastatin, cerivastatin, atorvastatin, or itavastatin.

15. The method of any one of claims 1 to 9, wherein the compound is co-administered with foscarnet or a nucleoside analog.

16. The method of claim 15, wherein the nucleoside analog is gancyclovir, cidofovir, acyclovir, famciclovir, penciclovir, valaciclovir, trifluridine, idoxuridine, vidarabine, ribavirin.

17. A method for treating or impeding the onset of infection by an influenza virus, comprising administering to a subject in need thereof a therapeutically effective amount of the Formula XXXII:

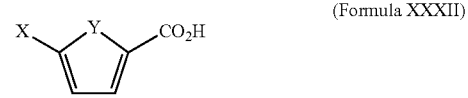

(Formula XXXII)

or a prodrug thereof, or a pharmaceutically acceptable salt or ester of said compound or prodrug, wherein:
(c) X is —O($C_5$-$C_{20}$)alkyl, —O($C_5$-$C_{20}$)alkenyl, or —S($C_5$-$C_{20}$)alkyl; and
(d) Y is O, or S; and
wherein the prodrug comprises a biohydrolyzable ester, a biohydrolyzable amine, or biohydrolyzable carbonate.

18. The method of claim 17, wherein X is —O($C_{10}$-$C_{20}$)alkyl or —O($C_{10}$-$C_{20}$)alkenyl.

19. The method of claim 17, wherein Y is O.

20. The method of claim 17, wherein the compound of the Formula XXXII is 5-(tetradecyloxy)-2-furoic acid (TOFA).

21. The method of claim 17, wherein the compound of Formula XXXII has the structure:

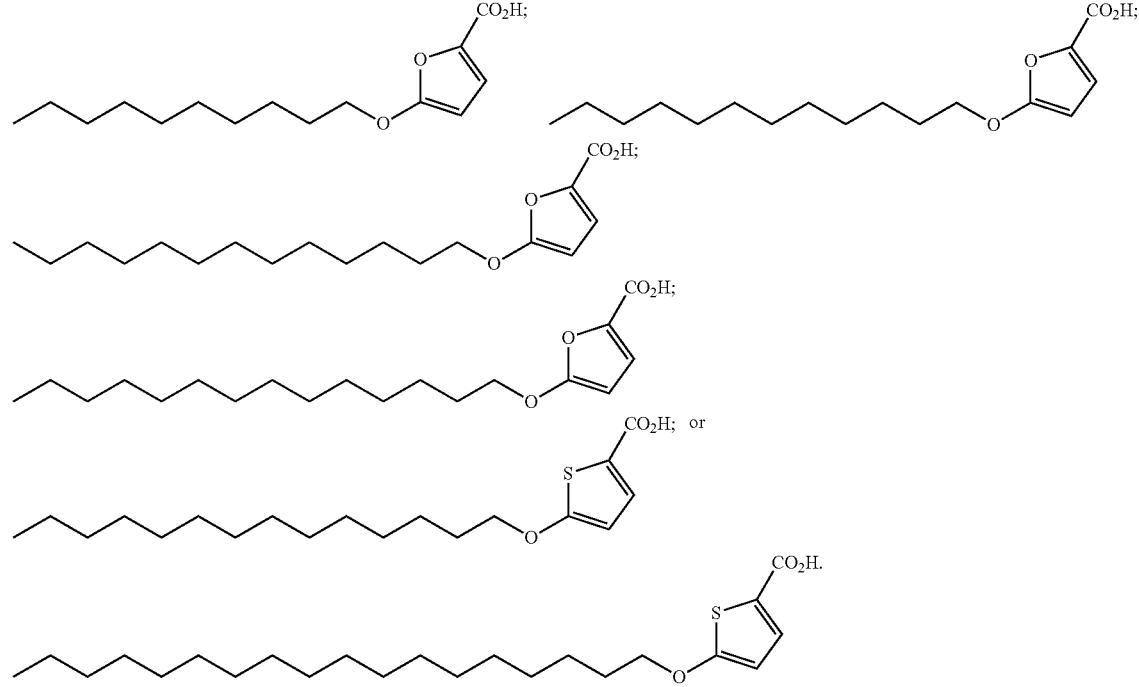

22. The method of claim 17, wherein the compound of Formula XXXII is administered at a dose of about 500 mg/day to about 1000 mg/day.

23. The method of claim 17, wherein the compound of Formula XXXII is administered at a dose of about 1000 mg/day to about 1500 mg/day.

24. The method of claim 17, wherein the compound of Formula XXXII is administered at a dose of about 1000 mg/day to about 1500 mg/day.

25. The method of claim 17, wherein the compound of Formula XXXII is administered at a dose of about 1500 mg/day.

26. The method of any one of claims 17 to 25, wherein the method is for treating an infection by an influenza virus.

27. The method of any one of claims 17 to 25, wherein the compound is administered to the subject prophylactically.

28. The method of any one of claims 17 to 25, wherein the compound is co-administered with a cholesterol biosynthesis inhibitor, or pharmaceutically acceptable salt of said inhibitor.

29. The method of claim 28, wherein the cholesterol biosynthesis inhibitor is an 3-hydroxy-3-methyl-glutaryl-CoA (HMGCoA) reductase inhibitor.

30. The method of claim 29, wherein the HMG-CoA reductase inhibitor is mevastatin, lovastatin, pravastatin, simvastatin, fluvastatin, cerivastatin, atorvastatin, or itavastatin.

31. The method of any one of claims 17 to 25, wherein the compound is co-administered with amantadine, oseltamavir, rimantadine, or zanamivir.

* * * * *